(12) United States Patent
Zhou et al.

(10) Patent No.: US 9,096,890 B2
(45) Date of Patent: Aug. 4, 2015

(54) SELF-CONTAINED BIOLOGICAL ASSAY APPARATUS, METHODS, AND APPLICATIONS

(71) Applicant: RHEONIX, INC., Ithaca, NY (US)

(72) Inventors: Peng Zhou, Newtown, PA (US); Lincoln C. Young, Ithaca, NY (US); Benjamin Thomas, Freeville, NY (US); Zongyuan Chen, Claymont, DE (US); Greg Mouchka, Brooktondale, NY (US); Todd Roswech, Ithaca, NY (US); Gwendolyn Spizz, Ithaca, NY (US); Rubina Yasmin, Ithaca, NY (US)

(73) Assignee: RHEONIX, INC., Ithaca, NY (US)

( * ) Notice: Subject to any disclaimer, the term of this patent is extended or adjusted under 35 U.S.C. 154(b) by 140 days.

(21) Appl. No.: 13/770,521

(22) Filed: Feb. 19, 2013

(65) Prior Publication Data

US 2014/0065598 A1    Mar. 6, 2014

Related U.S. Application Data

(62) Division of application No. 13/033,165, filed on Feb. 23, 2011, now Pat. No. 8,383,039.

(60) Provisional application No. 61/444,952, filed on Feb. 21, 2011, provisional application No. 61/445,125, (Continued)

(51) Int. Cl.
*C12Q 1/68* (2006.01)
*G01N 35/10* (2006.01)
*C12Q 1/70* (2006.01)

(52) U.S. Cl.
CPC .............. *C12Q 1/6806* (2013.01); *C12Q 1/686* (2013.01); *C12Q 1/6846* (2013.01); *C12Q 1/6883* (2013.01); *C12Q 1/708* (2013.01); *G01N 35/1002* (2013.01)

(58) Field of Classification Search
CPC .. C12Q 1/6806; C12Q 1/6846; C12Q 1/6825; C12Q 1/686; C12Q 1/6883; G01N 35/1002
USPC ............... 436/43, 54, 89, 180, 807, 809, 811, 436/812; 422/500–505, 507–509, 518, 422/62–67, 68.1; 435/287.7
See application file for complete search history.

(56) References Cited

U.S. PATENT DOCUMENTS

| 5,304,487 A | 4/1994 | Wilding et al. |
| 5,498,392 A | 3/1996 | Wilding et al. |
| 5,731,212 A | 3/1998 | Gavin et al. |

(Continued)

*Primary Examiner* — Brian R Gordon
(74) *Attorney, Agent, or Firm* — William Greener; Bond, Schoeneck & King, PLLC

(57) ABSTRACT

A self-contained, fully automated, biological assay-performing apparatus includes a housing; a dispensing platform including a controllably-movable reagent dispensing system, disposed in the housing; a reagent supply component disposed in the housing; a pneumatic manifold removably disposed in the housing in a space shared by the dispensing platform, removably coupled to a fluidic transport layer and a plurality of reservoirs, wherein the fluidic transport layer, the reservoirs, and a test sample to be introduced therein are disposed in the housing in the space separate from the dispensing platform; a pneumatic supply system removably coupled to the pneumatic manifold in the housing in a space separate from the dispensing platform; and a control system coupled to at least one of the dispensing platform and the pneumatic supply system, disposed in the housing.

13 Claims, 89 Drawing Sheets

Related U.S. Application Data filed on Feb. 22, 2011, provisional application No. 61/445,130, filed on Feb. 22, 2011, provisional application No. 61/346,202, filed on May 19, 2010, provisional application No. 61/355,773, filed on Jun. 17, 2010, provisional application No. 61/405,339, filed on Oct. 21, 2010, provisional application No. 61/307,186, filed on Feb. 23, 2010, provisional application No. 61/307,121, filed on Feb. 23, 2010, provisional application No. 61/393,237, filed on Oct. 14, 2010, provisional application No. 61/374,302, filed on Aug. 17, 2010.

(56) References Cited

U.S. PATENT DOCUMENTS

| | | | |
|---|---|---|---|
| 6,083,763 A * | 7/2000 | Balch | 506/9 |
| 6,331,441 B1 * | 12/2001 | Balch et al. | 506/15 |
| 6,335,166 B1 | 1/2002 | Ammann et al. | |
| 6,399,023 B1 | 6/2002 | Chow | |
| 6,867,050 B2 * | 3/2005 | Peck et al. | 506/40 |
| 7,238,323 B2 * | 7/2007 | Knapp et al. | 422/68.1 |
| 7,297,313 B1 | 11/2007 | Northrup et al. | |
| 8,030,080 B2 * | 10/2011 | Spence et al. | 436/43 |
| 8,597,594 B2 * | 12/2013 | Posner et al. | 422/505 |
| 2004/0151629 A1 * | 8/2004 | Pease et al. | 422/68.1 |
| 2007/0292941 A1 | 12/2007 | Handique et al. | |
| 2008/0280285 A1 * | 11/2008 | Chen et al. | 435/5 |
| 2009/0137029 A1 * | 5/2009 | Breidenthal et al. | 435/287.2 |
| 2009/0253181 A1 | 10/2009 | Vangbo et al. | |
| 2010/0173394 A1 * | 7/2010 | Colston et al. | 435/287.2 |
| 2011/0293489 A1 | 12/2011 | Zhou et al. | |
| 2012/0115214 A1 * | 5/2012 | Battrell et al. | 435/287.2 |
| 2012/0164036 A1 * | 6/2012 | Stern et al. | 422/502 |
| 2012/0270305 A1 * | 10/2012 | Reed et al. | 435/287.2 |

* cited by examiner

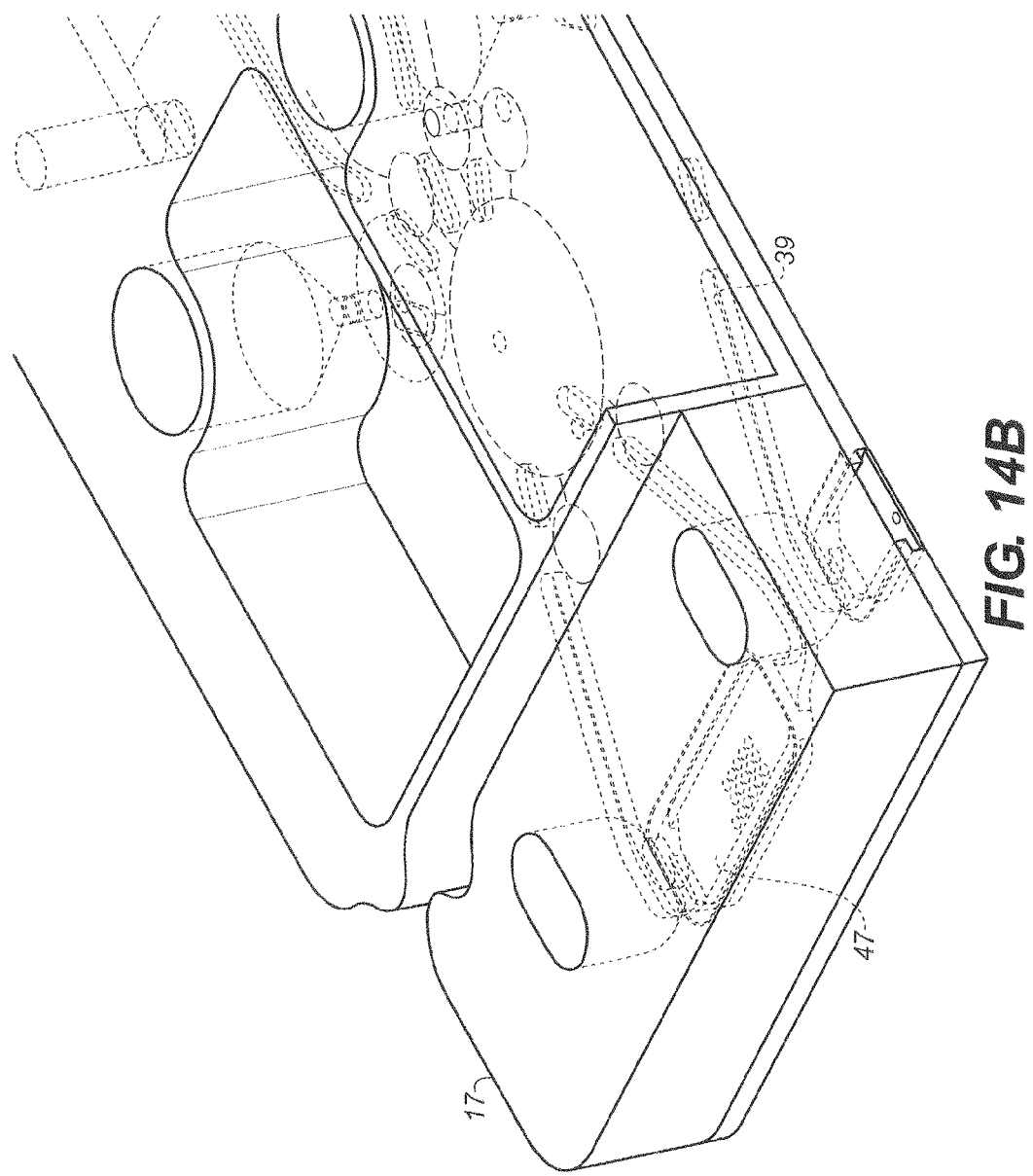

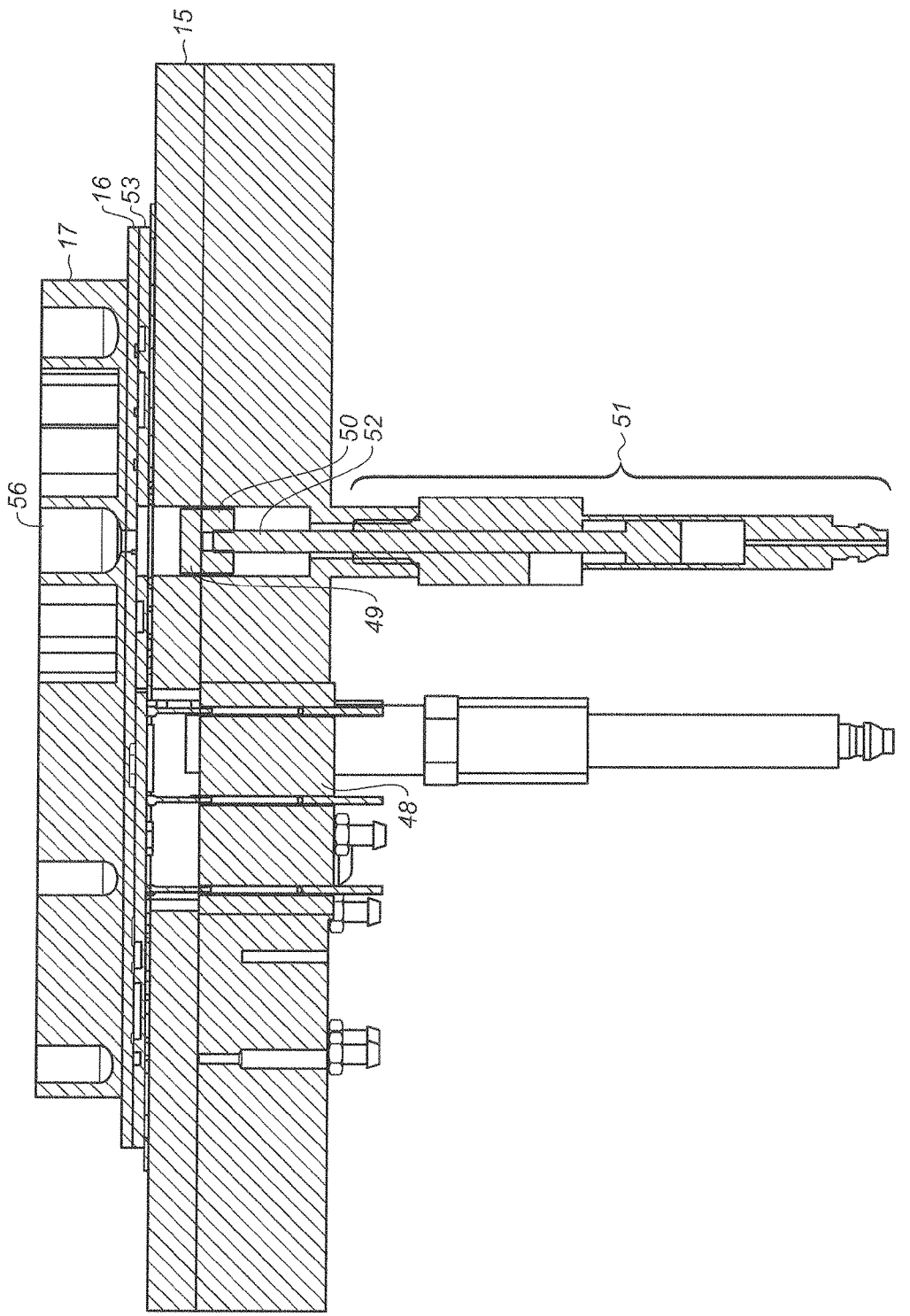

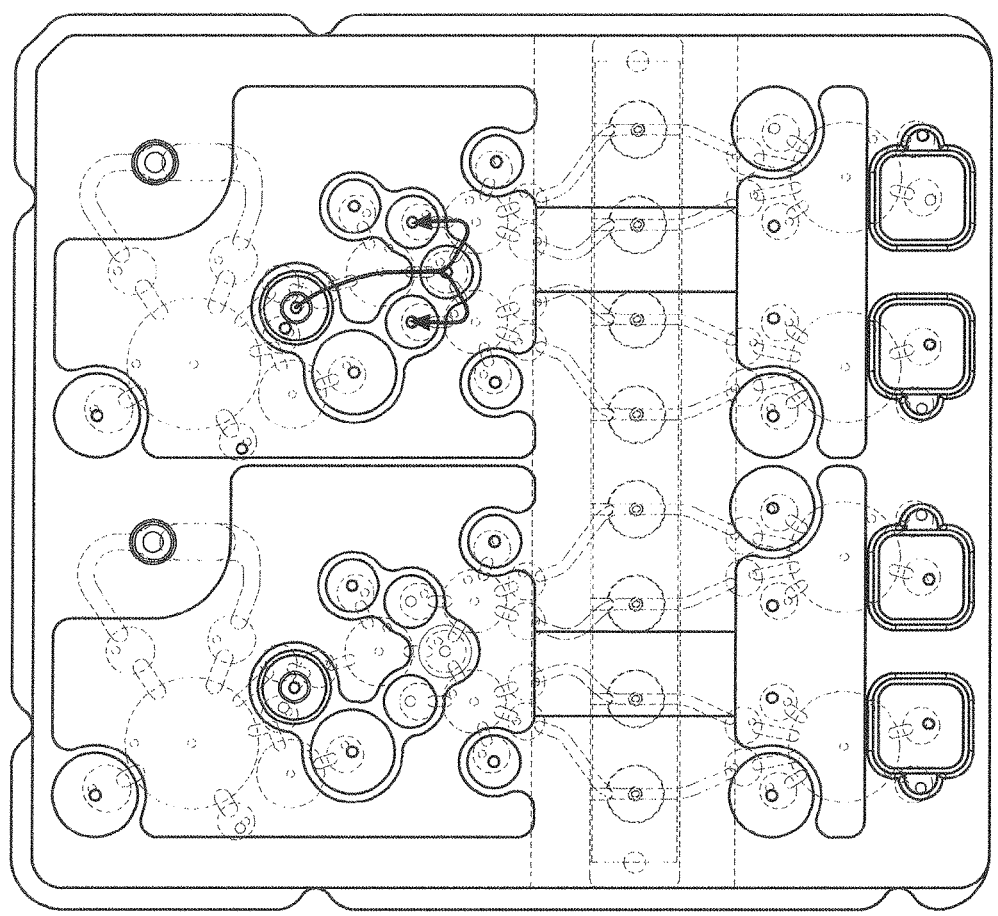

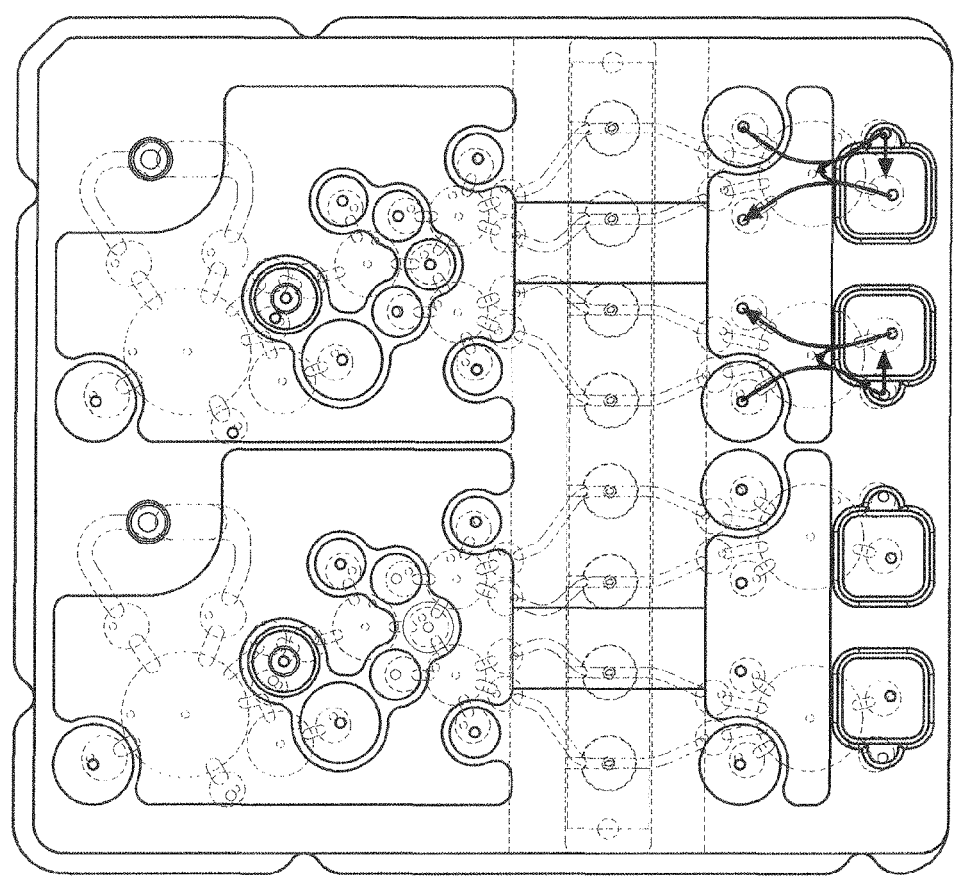

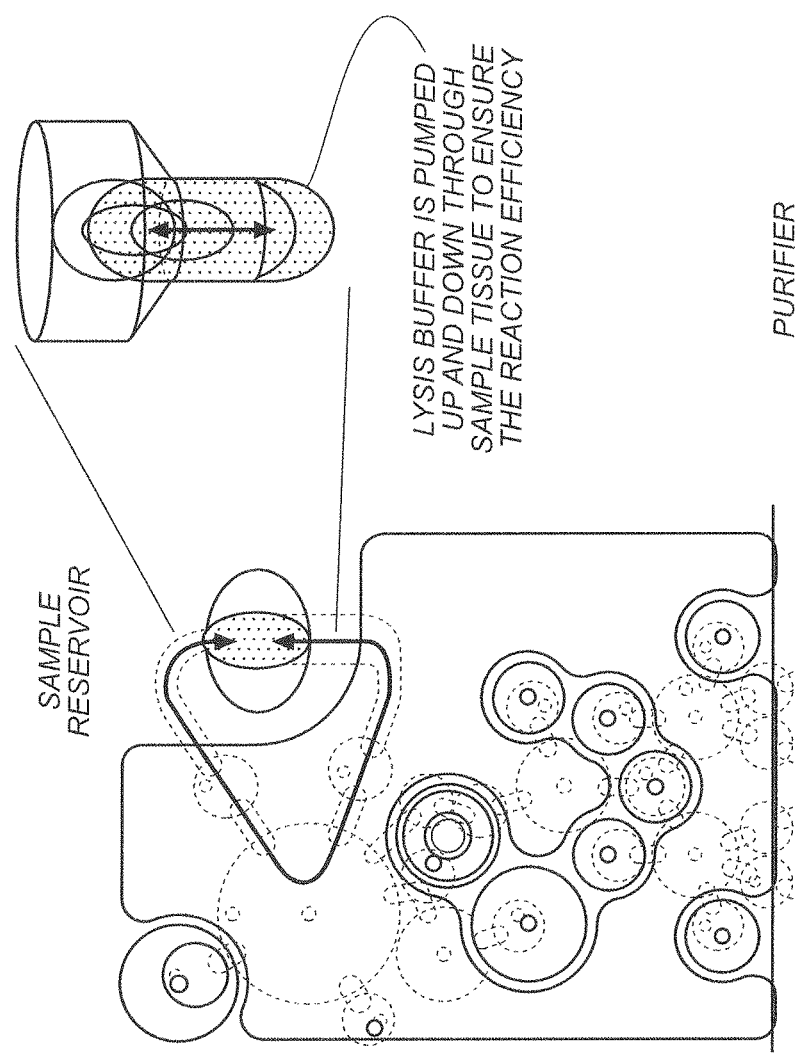

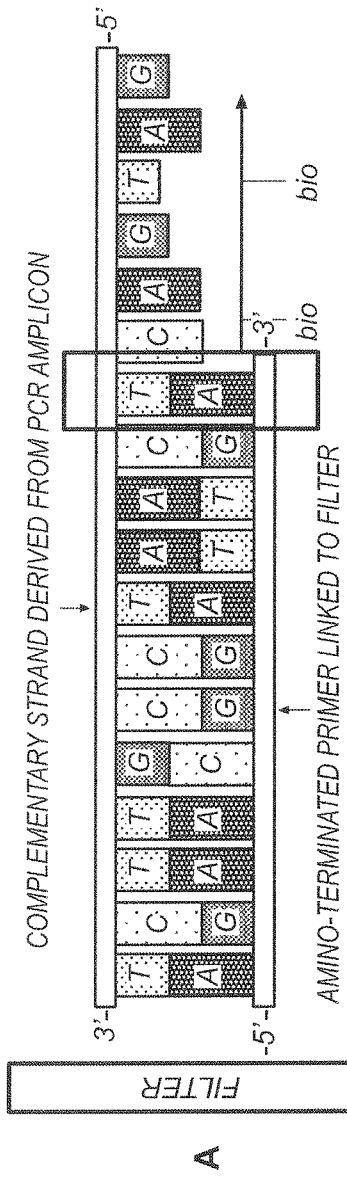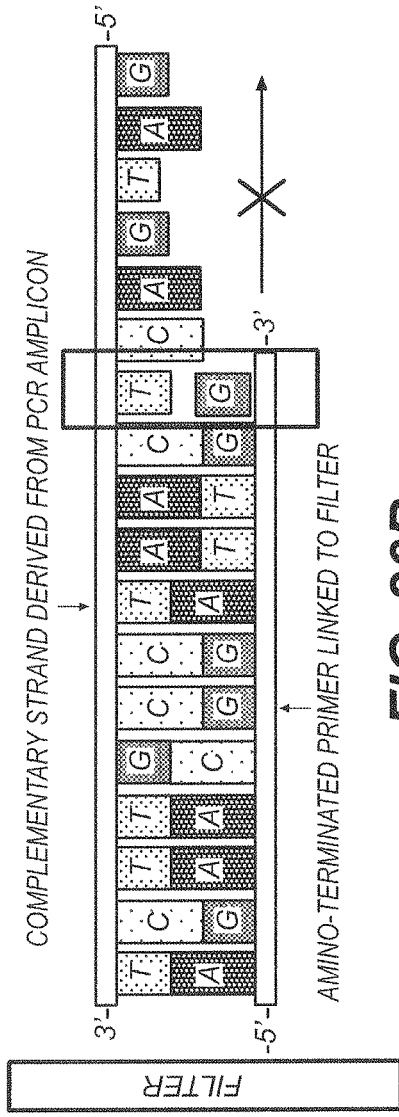
FIG. 26A
FIG. 26B

|         | 1   | 2   | 3   | 4   |
|---------|-----|-----|-----|-----|
| CYP2C9*2 | C/C | C/T | C/C | T/T |
| CYP2C9*3 | A/A | A/C | C/C | A/A |
| VKORC1  | A/A | G/G | A/G | A/G |

| FILTER KEY | | |
|---|---|---|
| SC | SC | SC |
| CYP2C9*2 WT/C | CYP2C9*2 WT/C | VKORC1 WT/G |
| CYP2C9*2 MUT/T | CYP2C9*2 MUT/T | VKORC1 MUT/A |
| CYP2C9*3 WT/A | CYP2C9*3 WT/A | VKORC1 WT/G |
| CYP2C9*3 MUT/C | CYP2C9*3 MUT/C | VKORC1 MUT/A |
|  |  | SC |

| SEQ ID NO: | HPV TYPE | PROBE SEQUENCE (5' - 3') |
|---|---|---|
| 1 | 6 | TTC CAT AAA ACG GGC TAA CAA A |
| 2 | 11 | ACT CTA TCA AAA AAG TTA ACA A |
| 3 | 16 | AAA CCT AAC AAT AAC AAA ATA TTA |
| 4 | 18 | GGT GGC AAT AAG CAG GAT A |
| 5 | 31 | AAA TCT GAC AAT CCT AAA AA |
| 6 | 33 | AAA AAT CCT ACT AAC GCT AAA AAA |
| 7 | 35 | AAA ACA AGA TTC TAA TAA AAT AGC A |
| 8 | 39 | TAA AGT GGG TAT GAA TGG TGG T |
| 9 | 42 | CAA AAA GGC CAA ATA AGA CA |
| 10 | 43 | CCT TAA AAA TTC CTC TGG TAA AA |
| 11 | 44 | ATA CGA CCA GCA AAC AAG AC |
| 12 | 45 | ACC TAA TGG TGC AGG TAA TA |
| 13 | 51 | TAA AAC CTC AAC GCG TGC T |
| 14 | 52 | AAA ACA CCA GTA GTG GTA ATG G |
| 15 | 53 | CAT TTC TAA ATC TGG TAA AGC A |
| 16 | 56 | AAG GAC AAT ACC AAA ACA AAC A |
| 17 | 58 | CCA TCA AAA GTC CCA ATA AC |
| 18 | 59 | GGT GGT AAT GGT AGA CAG GA |
| 19 | 66 | CAA ATC TGG TAC CAA AAC AAA |
| 20 | 68 | TTA AGG TTC CTA TGT CTG GG |

TABLE 1

FIG. 30

| SEQ ID NO: | HPV | FORWARD |
|---|---|---|
| 23 | 6 | gcttggatccCGTAAACGTATTCCCTTATTTTTT |
| 24 | 11 | gcttggatccCGTAAACGTATTCCCTTATTTTTT |
| 25 | 16 | gcttggatccCGTAAACGTTTACCATATTTTTTT |
| 26 | 18 | gcttggatccCGTAAACGTGTTCCCTATTTTTTT |
| 27 | 31 | gcttggatccCGTAAACGTGTATCATATTTTTTT |
| 28 | 33 | gcttggatccCGTAAACGTTTTCCATATTTTTTT |
| 29 | 39 | gcttggatccCGTAAACGTATTCCCTATTTTTTT |
| 30 | 42 | gcttggatccCGTAAACCTGTACCATATTTTTTT |
| 31 | 51 | gcttggatccCGTAAACGTATACCCTATTTTTTT |
| 32 | 53 | gcttggatccCGTAAACGTATTCCCTATTTTCTT |
| 33 | 56 | gcttggatccCGTAAACGTATTCCCTATTTTTTT |
| 34 | 66 | gcttggatccCGTAAACGTATTCCCTATTTTTTT |

| SEQ ID NO: | HPV | REVERSE |
|---|---|---|
| 35 | 6 | aagcgaattcACCTTAAATACCCTGTATTG |
| 36 | 11 | aagcgaattcACCTTAAACACTCTATATTG |
| 37 | 16 | aagcgaattcATTCTAAATACCCTGTATTG |
| 38 | 18 | aagcgaattcACCCTAAATACTCTATATTG |
| 39 | 31 | aagcgaattcACCCTAAATACCCTATATTG |
| 40 | 33 | aagcgaattcACCCTAAAAACCCTATATTG |
| 41 | 39 | aagcgaattcACGCGAAATACCCTATATTG |
| 42 | 42 | aagcgaattcACTCTAAATACTCTGTACTG |
| 43 | 51 | aagcgaattcACCCTAAATACCCTGTATTG |
| 44 | 53 | aagcgaattcACTCTAAACACCCTATACTG |
| 45 | 56 | aagcgaattcACCCTAAATACCCTATATTG |
| 46 | 66 | aagcgaattcACCCTAAACACTCTATACTG |

TABLE 2

FIG. 31

| FORWARD PRIMERS ||||
| SEQ ID NO: | TYPE & PRIMER | SEQUENCE | # PRIMERS |
|---|---|---|---|
| 50 | 33 | CGTAAACGTTTTCCATATTTTTTT | |
| 51 | 52 | CGTAAACGTTTTCCATATTTTTTT | |
| 52 | 58 | CGTAAACGTTTTCCATATTTTTTT | 2 |
| 53 | 16 | CGTAAACGTTTACCATATTTTTTT | |
| 54 | L1FGS2 | CGTAAACGTTTWCCATATTTTTTT | |
| 55 | 66 | CGTAAACGTATTCCCTATTTTTTT | |
| 56 | 56 | CGTAAACGTATTCCCTATTTTTTT | |
| 57 | 45 | CGTAAACGTATTCCCTATTTTTTT | 2 |
| 58 | 39 | CGTAAACGTATTCCCTATTTTTTT | |
| 59 | 51 | CGTAAACGTATCCCTATTTTTTT | |
| 60 | L1FGS1 | CGTAAACGTATWCCCTATTTTTTT | |
| 61 | 31 | CGTAAACGTGTATCATATTTTTTT | |
| 62 | 43 | CGTAAACGCTTTTCATATTTTTTT | 4 |
| 63 | 42 | CGTAAACCTGTACCATATTTTTTT | |
| 64 | L1FGS5 | CGTAAACGYGTWTCATATTTTTTT | |
| 65 | 59 | CGTAAACGTGTTCCCTATTTTTTT | |
| 66 | 18 | CGTAAACGTGTTCCCTATTTTTTT | 1 |
| 67 | L1FGS4 | CGTAAACGTGTTCCCTATTTTTTT | |
| 68 | 44 | CGTAAACGTGTTTCCTTGTTTTTT | |
| 69 | 6B | CGTAAACGTATTCCCTTATTTTTT | 1 |
| 70 | 11 | CGTAAACGTATTCCCTTATTTTTT | |
| 71 | L1FGS3 | CGTAAACGTATTCCCTTATTTTTT | |
| 72 | 68 | CGTAAACACCTTCCTTATTTTTTT | 1 |
| 73 | L1F68 | CGTAAACACCTTCCTTATTTTTTT | |
| 74 | 35 | CGTAAAGCTATCCCATATTTTTTT | 1 |
| 75 | L1F35 | CGTAAAGCTATCCCATATTTTTTT | |
| 76 | 53 | CGTAAACGTATTCCCTATTTTCTT | 1 |
| 77 | L1F53 | CGTAAAGCTATTCCCTATTTTCTT | |
| | | TOTAL PRIMERS IN SET | 13 |
| | | KEY: W=A/T; Y=C/T ||

TABLE 3A

FIG. 32

| BIOTINYLATED REVERSE PRIMERS ||||
|---|---|---|---|
| SEQ ID NO: | TYPE & PRIMER | SEQUENCE | # PRIMERS |
| 78 | 31 | ACCCTAAATACCCTATATTG | |
| 79 | 39 | ACGCGAAATACCCTATATTG | 4 |
| 80 | L1RGS5 | ACSCKAAATACCCTATATTG | |
| 81 | 44 | ATCTTAAAAACCCTATATTG | |
| 82 | 56 | ACCCTAAATACCCTATATTG | |
| 83 | 18 | ACCCTAAATACTCTATATTG | 6 |
| 84 | 11 | ACCTTAAACACTCTATATTG | |
| 85 | 33 | ACCCTAAAAACCCTATATTG | |
| 86 | L1RGS4 | ACCCTAAAHACYCTATATTG | |
| 87 | 16 | ATTCTAAATACCCTGTATTG | |
| 88 | 52 | ATTCTAAATACCCTGTATTG | 1 |
| 89 | L1RGS6 | ATTCTAAATACCCTGTATTG | |
| 90 | 51 | ACCCTAAATACCCTGTATTG | |
| 91 | 6B | ACCTTAAATACCCTGTATTG | 2 |
| 92 | L1RGS3 | ACCYTAAATACCCTGTATTG | |
| 93 | 68 | ACCCTAAACACTCTGTATTG | |
| 94 | 59 | ACCCTAAATACTCTGTATTG | |
| 95 | 43 | ACTCTAAATACTCTGTATTG | 4 |
| 96 | 35 | ACTCTAAATACTCTGTATTG | |
| 97 | L1RGS2 | ACYCTAAAYACTCTGTATTG | |
| 98 | 66 | ACCCTAAACACTCTATACTG | |
| 99 | 53 | ACTCTAAACACCCTATACTG | |
| 100 | 45 | ACTCTAAACACCCTATACTG | 2 |
| 101 | L1RGS1 | ACTCTAAACACYCTATACTG | |
| 102 | 58 | ACCCTAAAGACCCTATACTG | 1 |
| 103 | L1RGS58 | ACCCTAAAGACCCTATACTG | |
| 104 | 42 | ACTCTAAATACTCTGTACTG | 1 |
| 105 | L1RGS42 | ACTCTAAATACTCTGTACTG | |
| | | TOTAL PRIMERS IN SET | 21 |
| | | KEY: S=G/C; K=G/T; H=A/C/T; Y=C/T ||

*TABLE 3B*

FIG. 33

| | |
|---|---|
| TOTAL SAMPLES | 117 |
| HPV PIXEL POSITIVE | 88 |
| HPV SPOT POSITIVE | 40 |
| MULTIPLE INFECTIONS | 12 |
| HIGH RISK SINGLE INFECTION | 21 |
| LOW RISK SINGLE INFECTION | 7 |
| HIHG RISK ONLY MULTIPLE INFECTION | 5 |
| LOW RISK ONLY MULTIPLE INFECTION | 2 |
| MIXED MULTIPLE INFECTION (LOW AND HIGH RISK) | 5 |

TABLE 4

| SAMPLE # | DIGENE RESULT | HPE PIXELS | HPV TYPE (RDB) |
|---|---|---|---|
| 9036 | 0.10 | 1772.86 | 53 |
| 9040 | 0.12 | 1498.37 | 18 |
| 9032 | 0.16 | 514.51 | 18 |
| 9014 | 0.20 | 539.04 | 58 |
| 9053 | 0.28 | 2965.64 | 66 |
| 9029 | 0.48 | 8123.85 | 51,42 |
| 9055 | 0.50 | 6613.20 | 31 |

FIG. 41B

```
AGTATCAGGTCCTGATATACCCATTAATATAACTGACCAAGCTCCTTCATTAATTCCTATAGTTCCAGGGT
CTCCACAATATACAATTATTGCTGATGCAGGTGACTTTATTACATCCTAGTTATTACATGTTACGAAAA
CGACGTAAACGTTTACCATATTTTTTCAGATGTCTCTTGGCTGCCTAGTGAGGCCACTGTCTACTTGC
CTCCTGTCCCAGTATCTAAGGTTGTAAGCACGGATGAATATGTTGCACGCACAACATATATTATCATGCA
GGAACATCCAGACTACTTGCAGTTGGACATCCCTATTTCCTATTAAAAAACCTAACAATAACAAATATT
AGTTCCTAAAGTATCAGGATTACAATACAGGGTATTTAGAATACATTTACCTGACCCCAATAAGTTTGGTT
TTCCTGACACCTCATTTTATAATCCAGATACACAGCGGCTGGTTTGGGCCTGTGTGTAGGTGTTGAGGTAGGT
CGTGGTCAGCCATTAGGTGTGGGCATTAGTGGCCATCCTTTATTAAATAAATTGGATGACACAGAAAATGC
TAGTGCTTATGCAGCAAATGCAGGTGTGGATAATAGAGAATGTATATCTATGGATTACAAACAAACACAAT
TGTGTTTAATTGGTTGCAAACCACCTATAGGGGAACACTGGGCAAAGGATCCCCATGTGGTGATATGTTGCA
GTAAATCCAGGTGATTGTCCACCATTTACTACATTAAACACAGTTATTCAGGATGGTTCCACTGATATTGTACAT
TGGCTTTGGTGCTATGACTTTACCAGATTATATATTAAAAAGTGTCAGAACCATATGGCAACAGCTTATTTTATTTA
CTATTTGCAAATATCCAGATTATATTTAGACATTTATTTAATAGGGCTGTGTTGGTGAAAATGTACCAGACGA
CGAAGGAACATTAAAGGCTCTGGGTCCAAATTAGCACCTTATTGGTTACAACGACAGTTGGATAATATG
TTTATACATTAAAGGCTCTGATGATGTAACCAACTATTTGTTTACTGTTGATACTGTTGAAAATGTCATTATG
CTATGGTTACCTGTGATGATGTAACCAACTATTTGTTTACTGTTGATACTGTTGATATGTCATTATG
GGCATTTGTTGGGTAACCAACTATTTGTTTACTGTTGATACTGTTAAGGAGTACCTAGACATGGGAGG
TGCTGCCATATCTACTTCAGAAACTACATATAAAAATACTAACTTAAGGAGTACCTAGACATGGGAGG
AATATGATTTACAGTTTATTTTTCAACTGTCAAATAACCTTAACTGCAGACGTTATGACATACATAGAAGA
TCTATGAATTTCCACTATTTTGTAACCAGGACTCAAATTTGGTCTCAAAACATACACCTCCCCAGGAGGCACACTAGAAGA
TACTTATAGGTTTGTAACCAGGACTCAAATTGCTTGTCAAAAACATACACCTCCCCAGGAGGCACACTAGAAGA
CCCTTAAAAATACACTTTTTGGGAAGTAAATTTAAAGGAAGTTTTCTGCAGACCTAAGATCAGTTCCT
TTAGGAGCAAATTTTACTACAAGCAGGATTGAAGGCCAAACCAAATTTACATTAGGAAAACGAAAGC
TACACCCACCACCTCATCTACCTCTACAACTGCTAAACGCAAAAAAACGTAAGCTGTAAGTATTGTATGTAT
GTTGAATTAGTGTTGTTT
```

FIG. 42

| SAMPLE | SIGNAL |
|---|---|
| NEGATIVE | - |
| POSITIVE | + |
| BENCH POSITIVE | + |
| BENCH POSITIVE | + |
| CARD IMS & HS W/MIX | + |
| CARD IMS & HS W/MIX | + |

FIG. 44

SELF-CONTAINED BIOLOGICAL ASSAY APPARATUS, METHODS, AND APPLICATIONS

CROSS-REFERENCE TO RELATED APPLICATIONS

The instant application is a divisional application of U.S. application Ser. No. 13/033,165 filed on Feb. 23, 2011, now U.S. Pat. No. 8,383,039 issued Feb. 26, 2013 and claims priority to the following U.S. provisional Applications: Ser. No. 61/444,952 filed on Feb. 21, 2011; Ser. No. 61/445,125 filed on Feb. 22, 2011; Ser. No. 61/445,130 filed on Feb 23, 2011; Ser. No. 61/346,202 filed on May 19, 2010; Ser. No. 61/355,773 filed on Jun. 17, 2010; Ser. No. 61/405,339 filed Oct. 21, 2010; Ser. No. 61/307,186, filed on Feb. 23, 2010; Ser. No. 61/307,121 filed on Feb. 23, 2010; Ser. No. 61/393,237 filed on Oct. 14, 2010; 61/374,302 filed on Aug. 17, 2010, the subject matter of all of which are incorporated herein by reference in their entireties.

BACKGROUND OF THE INVENTION

1. Field of the Invention

Embodiments of the present invention relate generally to the field of microfluidics and, more particularly to a self-contained, microfluidic-based biological assay apparatus and associated methods and applications.

2. Technical Background

Biochemical assays are generally used in research, clinical, environmental and industrial settings to detect or quantify the presence or amount of certain gene sequences, antigens, diseases, and pathogens. The assays are often used to identify organisms including parasites, fungi, bacteria and viruses present in a host organism or a sample. Under certain conditions assays may provide a measure of quantification which may be used to calculate the extent of infection or disease and to monitor the state of a disease over time. In general, biochemical assays either detect antigens (immunoassays) or nucleic acids (nucleic acid-based or molecular assays) extracted from samples derived from research, clinical, environmental or industrial sources.

Molecular biology, which includes nucleic acid-based assays, can be broadly defined as the branch of biology that deals with the formation, structure and function of macromolecules such as nucleic acids and proteins and their role in cell replication and the transmission of genetic information, as well as the manipulation of nucleic acids, so that they can be sequenced, mutated, and further manipulated into the genome of an organism to study the biological effects of the mutation.

The conventional practice of biochemistry and molecular biology can require physical process resources on a scale that are frequently inversely proportional to the size of the subject being studied. For example, the apparatus and process chemistry associated with the preparation and purification of a biological sample such as a nucleic acid fragment for prospective analysis may easily require a full scale bio-laboratory with sterile facilities. Furthermore, an environmentally isolated facility of similar scale may typically be required to carry out the known nucleic acid amplification procedures such as polymerase chain reaction (PCR) for amplifying the nucleic acid fragment.

"Microfluidics" generally refers to systems, devices, and methods for processing small volumes of fluids. Microfluidic systems can integrate a wide variety of operations for manipulating fluids. Such fluids may include chemical or biological samples. These systems also have many application areas, such as biological assays (for, e.g., medical diagnoses, drug discovery and drug delivery), biochemical sensors, or life science research in general as well as environmental analysis, industrial process monitoring and food safety testing.

One type of microfluidic device is a microfluidic chip. Microfluidic chips may include micro-scale features (or "microfeatures"), such as channels, valves, pumps, reactors and/or reservoirs for storing fluids, for routing fluids to and from various locations on the chip, and/or for reacting reagents. However, existing microfluidic systems lack adequate mechanisms for allowing controlled manipulation of multiple fluids except via prescribed flow patterns, hence limiting the practicality with which the systems can be utilized in various chemical or biological assays. This is because real-world assays often require repetitive manipulation of different reagents for various analytical purposes.

Moreover, many existing microfluidic devices are restricted for one specific use and cannot be easily adapted or customized for other applications without being completely redesigned. These devices lack modularity, and therefore cannot share common device components that allow one design to perform multiple functions. This lack of flexibility leads to increased production costs as each use requires the production of a different system.

Furthermore, many existing microfluidic systems lack any means for straightforward end-point assays that are able to easily detect interactions or existence of analytes resulting from the assays. By way of example, visual detection of sample color changes after an assay is often used to evaluate the assay results.

Thus there exists a need for improved microfluidic systems for processing fluids for analysis of biological or chemical samples, and in particular, in the detection and analysis of biologically active macromolecules derived from such samples such as DNA, RNA, amino acids and proteins. It is desired that the systems are mass producible, inexpensive, and preferably disposable. It is desired that the systems be simple to operate and that many or substantially all of the fluid processing steps be automated. It is desired that the systems be customizable, and be modular such that the system can be easily and rapidly reconfigured to suit various applications in which the detection of macromolecules is desired. It is also desired that the systems be able to provide straightforward and meaningful assay results.

When performing a nucleic acid-based assay, preparation of the sample is the first and most critical step to release and stabilize target nucleic acids that may be present in the sample. Sample preparation can also serve to eliminate nuclease activity and remove or inactivate potential inhibitors of nucleic acid amplification or detection of the target nucleic acids. The method of sample preparation can vary and will depend in part on the nature of the sample being processed. Various lysis procedures are well known in the art and are designed to specifically isolate nucleic acids from cells or viruses suspended in the original sample.

Following lysis, the released nucleic acids in the sample need to be purified so that the potential inhibitors for the amplification reaction are removed from the nucleic acids. Generally, purification is a cumbersome and repetitive set of tasks consuming large amounts of reagents, capital equipment, and labor and it is often the step most associated with failure of down-steam amplification reactions.

Following purification it is generally desirable to amplify specific nucleic acid sequences using any of several nucleic acid amplification procedures which are well known in the art. Specifically, nucleic acid amplification is the enzymatic synthesis of nucleic acid amplicons (copies) which contain a sequence that is homologous to a nucleic acid sequence being amplified. Examples of nucleic acid amplification procedures practiced in the art include the polymerase chain reaction (PCR), strand displacement amplification (SDA), ligase chain reaction (LCR), Nucleic Acid Sequence Based Amplification (NASBA), transcription-associated amplification (TAA), Cold PCR, and Non-Enzymatic Amplification Technology (NEAT). Nucleic acid amplification is especially beneficial when the amount of target sequence present in a sample is very low. By amplifying the target sequences and detecting the amplicon synthesized, the sensitivity of an assay can be vastly improved, since fewer target sequences are needed at the beginning of the assay to better ensure detection of nucleic acid in the sample belonging to the organism or virus of interest.

Detection of a targeted nucleic acid sequence requires the use of a nucleic acid probe having a nucleotide base sequence that is substantially complementary to the targeted sequence or, alternatively, its amplicon. Under selective assay conditions, the probe will hybridize to the targeted sequence or its amplicon in a manner permitting a practitioner to detect the presence of the targeted sequence in a sample. Effective probes are designed to prevent nonspecific hybridization with any nucleic acid sequence that will interfere with detecting the presence of the targeted sequence. Probes and/or the amplicons may include a label capable of detection, where the label is, for example, a radiolabel, fluorescent dye, biotin, enzyme, electrochemical or chemiluminescent compound.

When performed manually, the complexity and shear number of processing steps associated with a nucleic acid-based assay introduce opportunities for practitioner-error, exposure to pathogens, and cross-contamination between assays, and others. Following a manual format, the practitioner must safely and conveniently juxtapose the test samples, reagents, waste containers, assay receptacles, pipette tips, aspirator device, dispenser device, while being especially careful not to confuse racks, test samples, assay receptacles, and associated tips, or to knock over any tubes, tips, containers, or instruments. In addition, the practitioner must carefully perform aspirating and dispensing steps with handheld, non-fixed instruments in a manner requiring precise execution to avoid undesirable contact between assay receptacles, aerosol formation, or aspiration of magnetic particles or other substrates used in a target-capture assay.

A need exists for an automated analyzer that addresses many of the concerns associated with manual approaches to performing nucleic acid-based assays. In particular, significant advantages can be realized by automating the various process steps of a nucleic acid-based assay, including greatly reducing the risk of user-error, pathogen exposure, contamination and spillage. Automating the steps of a nucleic acid-based assay will also reduce the amount training required for practitioners and virtually eliminate sources of physical injury attributable to high-volume manual applications.

SUMMARY OF THE INVENTION

Embodiments and aspects of the present invention address the needs described above by providing a self-contained, microfluidic-based biological assay apparatus, associated methods, and applications thereof.

According to a non-limiting, exemplary embodiment, a self-contained, fully automated, biological assay-performing apparatus includes a housing; a dispensing platform including a controllably-movable reagent dispensing system, disposed in the housing; a reagent supply component disposed in the housing; a pneumatic manifold removably disposed in the housing in a space shared by the dispensing platform, removably coupled to a fluidic transport layer and a plurality of reservoirs, wherein the fluidic transport layer, the reservoirs, and a test sample to be introduced therein are disposed in the housing in the space separate from the dispensing platform; a pneumatic supply system removably coupled to the pneumatic manifold in the housing in a space separate from the dispensing platform; and a control system coupled to at least one of the dispensing platform and the pneumatic supply system, disposed in the housing.

According to a non-limiting aspect, the dispensing platform further includes a motion control system operatively coupled to the reagent dispensing system, wherein the reagent dispensing system includes a reagent dispenser component having a distal dispensing end; and a camera connected to the reagent dispensing system having a field of view that includes at least a selected region of interest of the reservoirs.

According to a non-limiting aspect, the pneumatic manifold is interfaced with a microfluidic system having at least one assay capacity. The microfluidic system may further comprise a multi-layer, monolithic, polymeric, non-elastomeric microfluidic component having a given configuration of microfeatures including a plurality of pneumatically-activated diaphragms. The pneumatic manifold may have one or more pneumatic only (i.e., absence of 'fluidic') ports on an underside thereof, and one or more pneumatic only channels disposed therein in fluid connection with one or more valves in the fluidic transport layer and the one or more pneumatic only ports, wherein the one or more pneumatic only ports have a fixed configuration, and the one or more pneumatic only channels have a given configuration specifically corresponding to a given configuration of the one or more pneumatically-activated diaphragms in the fluidic transport layer. The pneumatic supply system may further include one or more aperture tubes that provide a passage of the pneumatic signal there through, in fluid connection with the one or more pneumatic only ports, wherein the one or more aperture tubes have a fixed configuration specifically corresponding to the fixed configuration of the one or more pneumatic only ports of the pneumatic manifold, removably connected to the pneumatic manifold. Each multi-layer, monolithic microfluidic component may further include a polymeric, non-elastomeric substrate having one or more fluid channels disposed therein, each of the fluid channels having an inlet end and an outlet end; at least one reagent reservoir of a type capable of holding a reagent material; at least one bi-directional diaphragm pump comprising at least three non-elastomeric membrane-based diaphragm valve structures; and a valve disposed in fluid coupling with the at least one reagent reservoir and at least one of the inlet ends, wherein the valve is adapted to controllably direct a flow of the material from the at least one reagent reservoir to one or more reservoirs via at least one of the channels coupled to the valve, further wherein each multi-layer, monolithic microfluidic component consists of a non-elastomeric, polymeric material. Each substrate may further include one or more analysis reservoirs, each analysis reservoir including an analysis system disposed therein. The analysis system may be one of colorimetric, fluorescent colorimetric, chemiluminescent, electrochemical, electrophoretic, lateral flow, protein microarray, nucleic acid microarray, or fluorescent. The apparatus may further include a securing-ring structure having one or more indentations or channels in the perimeter thereof, wherein the analysis membrane is operatively engaged with the securing-ring structure. The securing-ring structure may comprise two opposing ring structures each having one or more perimeter indentations, further wherein the analysis membrane is disposed intermediate the two opposing ring structures. The apparatus may further include one or more heaters disposed in different locations to effect heating of the test sample or portions thereof in the analysis process. A heater may be disposed in proximity to a magnetically-engageable reservoir. The apparatus may further include a tube mounting layer attached to a bottom surface of the substrate including one or more tubes each having a proximal end that is fluidly connected to a respective fluidic channel and a distal end projecting downwardly perpendicularly from the substrate; and one or more respective amplification/reaction chambers attached at a top region thereof to the tube mounting layer such that the distal end of each tube is disposed substantially near a bottom region thereof. The apparatus may further include a magnetic assembly operably disposed under a reservoir or channel, wherein the magnetic assembly further comprises a magnet, a magnet holder, a piston rod, and a pneumatic piston assembly (alternatively the piston assembly may be motor or electromagnetically activated). A heater assembly may be operably connected to the magnetic assembly.

Another non-limiting, exemplary embodiment of the invention is directed to an automated process for isolating, amplifying, and analyzing a target nucleic acid sequence that may be present in a fluid test sample. The process includes the steps of providing a pneumatic manifold that operates a microfluidic system having a fluidic transport layer and a fluidic channel disposed therein, and reservoirs attached thereto; introducing the fluid test sample into the fluidic channel; providing at least one reagent to the channel from at least one respective reservoir that is in fluid connection with the fluidic transport layer; combining the fluid test sample and the at least one reagent in a region of the fluidic transport layer, reservoir or amplification reactor; transporting the fluid test sample to a temperature-controlled amplification/reaction reactor that is in operative communication with the fluidic transport layer; incubating the fluid test sample in the amplification/reaction reactor under conditions sufficient to permit the target nucleic acid sequence to be amplified; transporting the fluid test sample to an analysis reservoir; and analyzing the amplified target nucleic acid sequence from the test sample, wherein the test sample is transported from a starting location in the fluidic transport layer to the analysis reservoir separately from any other samples and separately from the pneumatic manifold and the dispensing system.

In an aspect, the transporting and combining steps are accomplished by pumping the fluid test sample and the volume of at least one reagent through the fluidic transport layer via at least one multi-valve diaphragm pump that is operated by the pneumatic manifold. According to an aspect, the analyzing step may further include performing a microarray analysis in a microarray analysis reservoir in the microfluidic system. The automated process may further involve providing a microarray analysis membrane in the microarray analysis reservoir; flowing a fluid over a top surface of the microarray analysis membrane; and removing the fluid substantially through a fluid exit route along a periphery of the microarray analysis membrane. The automated process may further involve providing a microarray analysis membrane in the microarray analysis reservoir; and, flowing a fluid alternatively back and forth over a top surface of the microarray analysis membrane. The automated process may further involve providing heat to the of the microarray analysis membrane.

In another non-limiting embodiment of the automated process for isolating, amplifying, and analyzing a target nucleic acid sequence that may be present in a fluid test sample, the target nucleic acid sequence is associated with a disease or disorder of interest, an infectious agent, a pathogen, a predisposition for cancer, or a predisposition for sensitivity to a drug, pharmaceutical composition, chemical or compound of interest.

In another non-limiting embodiment of the automated process for isolating, amplifying, and analyzing a target nucleic acid sequence that may be present in a fluid test sample, the target nucleic acid sequence comprises a SNP.

In another non-limiting embodiment of the automated process for isolating, amplifying, and analyzing a target nucleic acid sequence that may be present in a fluid test sample, the disease or disorder is HPV or sepsis.

In another non-limiting embodiment of the automated process for isolating, amplifying, and analyzing a target nucleic acid sequence that may be present in a fluid test sample, the target nucleic acid sequence is associated with predisposition for
warfarin sensitivity or predisposition for anticoagulation in response to warfarin treatment.

In another non-limiting embodiment of the automated process for isolating, amplifying, and analyzing a target nucleic acid sequence that may be present in a fluid test sample, the analyzing step comprises detecting an interaction between the amplified target nucleic acid sequence and a probe for the target nucleic acid sequence.

In another non-limiting embodiment of the automated process for isolating, amplifying, and analyzing a target nucleic acid sequence that may be present in a fluid test sample, the analyzing step comprises determining presence of, or predisposition for: the disease or disorder of interest, the infectious agent, the pathogen, cancer, or sensitivity to the drug, pharmaceutical composition, chemical or compound of interest.

In another non-limiting embodiment of the automated process for isolating, amplifying, and analyzing a target nucleic acid sequence that may be present in a fluid test sample, an automated process wherein the analyzing step comprises determining an amount or level of the amplified target nucleic acid sequence and wherein the method further comprises comparing the amount or level with a preselected amount or level of the target nucleic acid sequence.

A method wherein a difference between the amount or level and the preselected amount or level is indicative of presence of, or predisposition for: a disease or disorder of interest, an infectious agent, a pathogen, cancer, or sensitivity to a drug, pharmaceutical composition, chemical or compound of interest. These, as well as additional features and advantages of the invention will be set forth in the detailed description that follows and will be readily apparent to those skilled in the art from that description or, recognized by practicing the invention as described in the detailed description, the drawing figures, and the appended claims.

It is to be understood that both the foregoing general description and the following detailed description are merely exemplary of the embodiments of the invention and are intended to provide an overview or framework for understanding the nature and character of the invention as it is claimed. The accompanying drawings are included to provide a further understanding of the various claimed embodiments and aspects of the invention, and are incorporated in and constitute a part of this specification.

BRIEF DESCRIPTION OF THE DRAWINGS

FIG. 14B shows a close up perspective view of the covered and vented analysis reservoir feature including a model of the analysis membrane and the step feature used to retain the analysis membrane, according to an exemplary aspect of the invention.

FIG. 18 shows a cross sectional side view of the pneumatic manifold and the microfluidic system of a single assay unit showing functional features of the manifold incorporating pneumatically activated magnets including a non-heated magnetic assembly and multiple heated reaction sites, according to an exemplary aspect of the invention;

FIGS. 21A-K show layered, top views of exemplary process stages using the channels, reactors, and reservoirs in the combined fluidic transport layer and the reservoir layer when operated by the pneumatic manifold, according to illustrative aspects of the invention;

FIG. 25 schematically illustrates an on-CARD sample lysis process, to a non-limiting, illustrative aspect of the invention;

FIGS. 26A-B: Primer Extension Protocol. Amino-terminated capture probes containing the 3' interrogating nucleotide are covalently linked to a membrane filter. Following amplification, the amplicon product is denatured and the complementary strand anneals to the probe. If there is a perfect match between the 3' nucleotide of the probe and the amplicon (A), DNA synthesis will occur incorporating biotinylated (bio) nucleotides. If there is a mismatch between the 3' nucleotide of the probe and the amplicon (B), DNA synthesis will not occur and thus no incorporation of biotin. See Example 2 for further details;

FIG. 30, Table 1: Capture probe sequences, SEQ ID NOS: 1-20. See Example 4 for details;

FIG. 31, Table 2: Forward and reverse primers with type specific L1 sequences, SEQ ID NOS:23-46. See Example 4 for details;

FIG. 32, Table 3A: Forward primers for amplifying the HPV L1 gene, SEQ ID NOS:50-77. See Example 4 for details;

FIG. 33, Table 3B: Biotinylated reverse primers for amplifying the HPV L1 gene, SEQ ID NOS:78-105. See Example 4 for details;

FIG. 40, Table 4: Summary of results of PCR and RDB of the clinical samples. As shown in the table, 75% (88/117) of the samples demonstrated an HPV amplified band following PCR and 45% (40/88) of the HPV amplicon positives were captured by an HPV-specific probe on RDB. See Example 4 for details;

FIGS. 41A-B: A: Comparison of samples positive for HPV high risk using the Digene system versus the HPV result obtained with the embodiment described in Example 4; B: 6 high risk samples were detected by the embodiment described in Example 4 that were read as negative by the Digene system, demonstrating the superiority of the Example 4 embodiment with respect to sensitivity and specificity of the assay. See Example 4 for details;

FIG. 42: The sequence of the L1 gene of HPV 16 (SEQ ID NO:106) containing highlighted sequences corresponding to the various target regions for amplification (SEQ ID NOS: 107-112). See Example 4 for details;

FIG. 44 shows results obtained from the CARD-based detection of a sparse target with lateral flow assay described in Example 5. Heat shock mRNA from *Cryptosporidium parvum* was detected. IMS=immunomagnetic separation. HS=heat shock.

DETAILED DESCRIPTION

Figure 1:
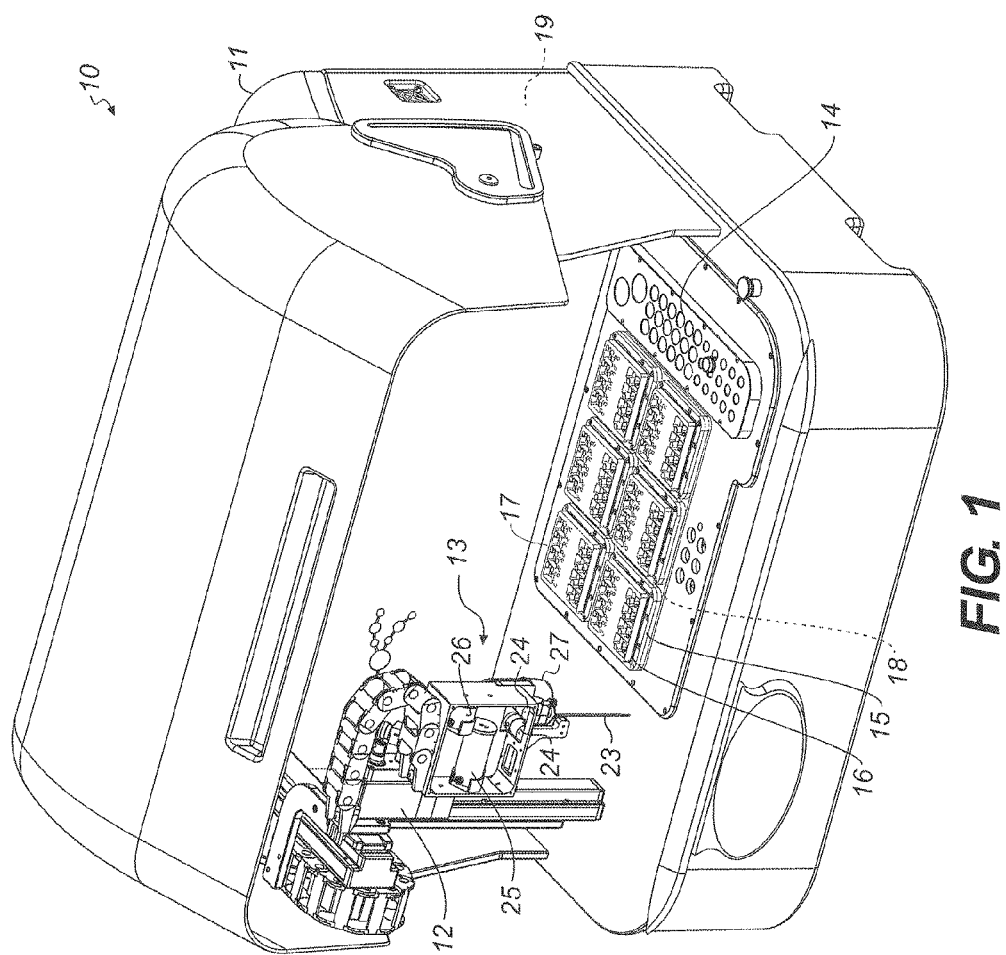
FIG. 1 shows a perspective view of a self-contained biological assay apparatus, according to an exemplary embodiment of the invention.
Figure 2:
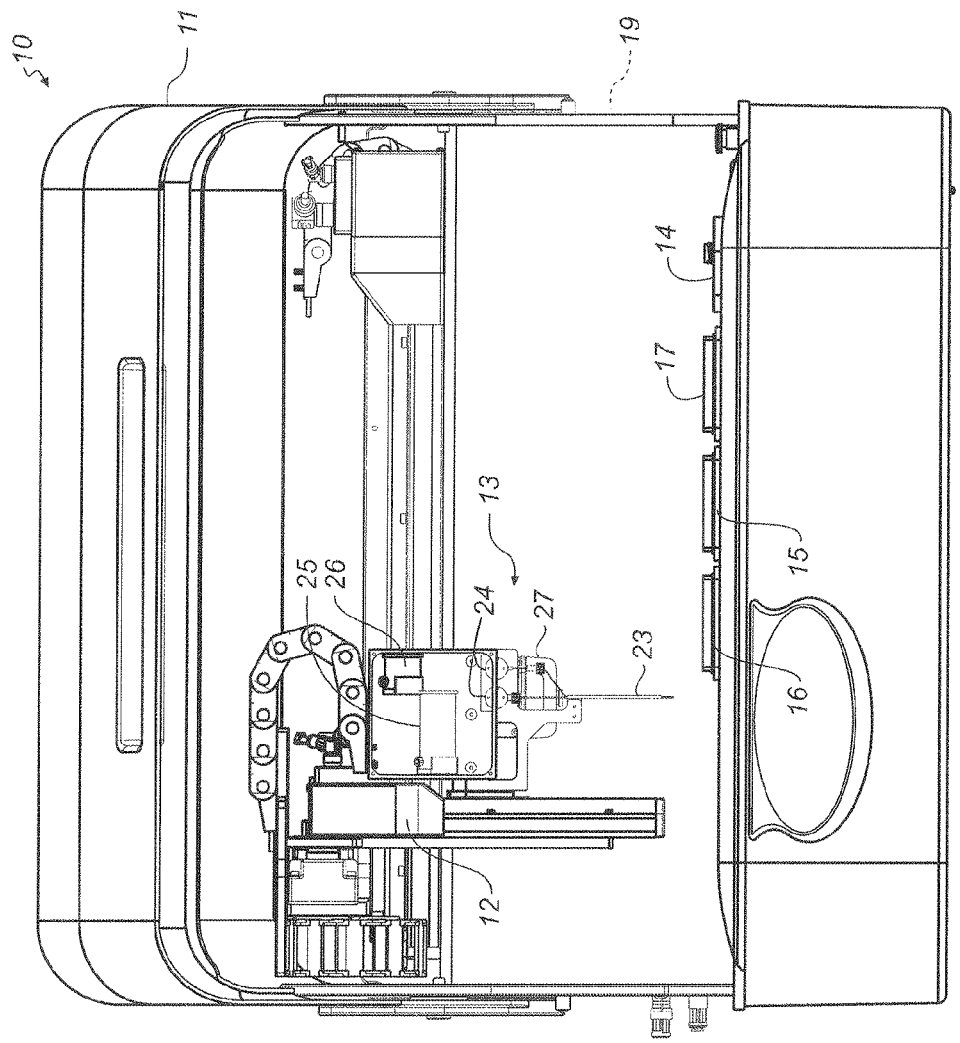
FIG. 2 shows a front elevational view of the self-contained biological assay apparatus shown in FIG. 1.
Figure 3:
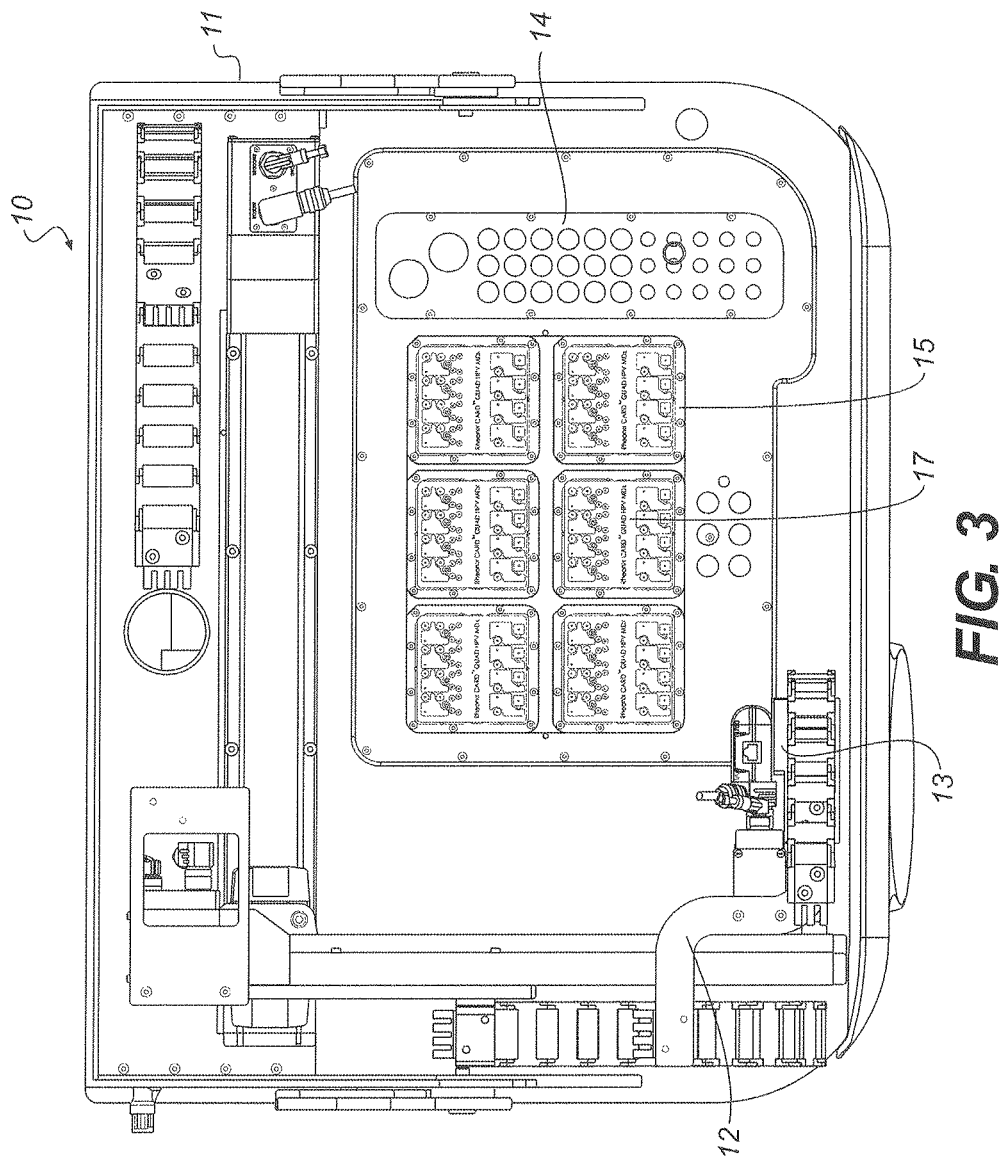
FIG. 3 shows a top plan view of the self-contained biological assay apparatus shown in FIG. 1.

Reference will now be made in detail to the present exemplary embodiments of the invention, examples of which are described below and further illustrated in the accompanying drawing figures. Wherever possible, the same reference numbers will be used throughout the figures to refer to the same or like parts.

FIGS. 1-4, illustrate a self-contained, fully automated, biological assay apparatus 10 according to an embodiment of the invention. The apparatus includes a housing 11; a dispensing platform 12 including a controllable, movable reagent dispensing system 13 disposed in the housing; a reagent supply component 14 that can hold a supply of one or more reagents, in operative connection with the dispensing system, disposed in the housing; a pneumatic manifold 15 that operates to affect the transport of fluid in a fluidic transport layer 16 and a plurality of reservoirs 17 attached to the fluidic transport layer 16 opposite the pneumatic manifold 15, that is removably disposed in the housing 11 in a space shared by the dispensing platform 12, wherein the fluidic transport layer 16, reservoirs 17 and a test sample to be introduced therein are disposed in a space separate from the dispensing platform 12; a pneumatic supply system 18, which functions to provide pneumatic signals (positive and negative (vacuum) pressure) routed through the pneumatic manifold 15 to affect the transport of the test sample and the reagents in the fluidic transport layer 16, and its plurality of reservoirs 17, disposed on the pneumatic manifold 15 and in operative connection with the pneumatic supply system 18 in the housing 11 in a space separate from the dispensing platform 12; and a control system 19 that is used to control the dispensing platform 12, the heating systems (29, 48, and 48a), the cooling system (accomplished by directing a jet of compressed air, that may or may not be actively cooled, from the pneumatic supply system 18 at the heater, or supplying airflow from a fan) and the pneumatic supply system 18, disposed in the housing 11.

With reference to FIGS. 1-4, 5, 6, 9, 10-13, 16 and 20, a self-contained, biological assay apparatus 10 is designed to require an operator of the assay apparatus 10 only to introduce a biological sample of interest into a specific sample input port 33 of a plurality of such ports $33_n$ on the reservoir layer 17, which covers the fluidic transport layer 16 (with attached film layer 30) and, which altogether are managed by the pneumatic manifold 15, and then initiate a start sequence of the control system 19, whereby the sample is completely and automatically processed through an assay to the assay's end point. As depicted in the figures, there are 24 separate exemplary sample assay units arranged in a "six by four" pattern, where each sample is separate, within its assay unit, from all other samples, and from the biological assay apparatus throughout the processing sequence. Although 24 assay units are depicted in the exemplary embodiment, the lower limit is one assay unit and there is no particular upper limit.

In operation, once a sample to be analyzed has been introduced into the sample input reservoir 33 of reservoir layer 17, the sample is automatically drawn from the sample input reservoir into the fluidic transport layer 16, or reagents are transported by the fluidic transport layer 16 from a separate reservoir to the sample input reservoir 33. All of the processing steps required to analyze the sample are then carried out within either the reservoir layer 17 and/or the fluidic transport layer 16 including amplification via appropriate reactors (e.g., 31, FIGS. 11, 12) disposed in the fluidic layer 16 or communicating with the fluidic layer 16 via a lumen 44 of the system, without the intervention of an operator. In completing all of the series of processing steps required to analyze the sample automatically, the system maintains separation of the sample from the reagent dispensing system 13, the pneumatic manifold 15, and the pneumatic supply system 18. This separation feature eliminates cross-contamination problems that inevitably increase the costs and decrease the reliability of current systems that perform similar tasks but that require the sample move from station to station within an apparatus while it is being processed or that require the dispensing system to impart movement of fluids within a microfluidic system.

The apparatus 10 includes a housing 11 that is designed to enclose the interior of the system during operation so that the fully automated processing can proceed to completion uninterrupted by an operator. The housing 11 also encloses the control system 19, the dispensing platform 12, the reagent supply component 14, and the pneumatic supply system 18, which operates the pneumatic manifold 15.

FIGS. 1-4 also depict the reagent dispensing system 13. The reagent dispensing system is attached to the X-Y-Z motion control system and together is the dispensing platform 12. The dispensing system 13 is comprised of a dispenser needle 23, a large storage loop 25, a small storage loop 26, a solenoid valve 24 for each storage loop 25, 26, and a camera 27. The dispenser needle 23 is comprised of a double barrel tube or elongate needle structures of length, L, having different respective, selected bore sizes. The smaller barrel (bore) is attached to the small storage loop 26 through a dedicated solenoid valve 24 and the larger barrel is attached to the large storage loop 25 through a dedicated solenoid valve 24. The purpose of the dissimilar size is to facilitate precise metering of reagents delivered by the reagent dispensing system 13. The smaller the bore of the barrel of the needle, the easier it is to meter smaller amounts of reagent. In an illustrative aspect, one of the reagent dispenser needles has a bore diameter $b_1$, where $0.003 \leq b_1 \leq 0.018$ inches (in) and the other reagent dispenser needle has a bore diameter $b_2$, where $0.015 \leq b_2 \leq 0.030$ in.

The camera 27 may have various functions for the self-contained biological analysis system 10. One function may be to coordinate the location of the dispenser needle 23 of the dispensing system 13 with the reagent supply component 14 and the reservoir layer 17 attached to the fluidic transport layer 16 so the reagents in the reagent supply component 14 are dispensed into the proper reservoir on the reservoir layer 17. Another function is to provide sample and/or analysis information to the control system 19. When an operator provides a sample to the sample input port 33 of reservoir layer 17 of a particular assay unit the camera 27 can record the sample's information from an optical source such as a bar code or other distinct optical marking systems known in the art. The information from the sample can then inform the control system 19 of proper sample loading and later it may be combined with the resulting analysis. The identified and properly loaded sample then is processed by the self-contained biological assay apparatus 10 and the end result recorded by the same camera 27. The information can then be communicated to the operator through a control system operator interface.

The small and large control loops 25, 26 are coils of tubing attached through the solenoid valves 24 to their particular barrel of the double barrel dispensing needle 23. When a particular reagent is required by an assay the dispensing needle 23 is moved by the X-Y-Z motion control system to the particular reagent in the reagent supply component 14. The needle is inserted into the reagent's container and negative pressure is supplied through the small or large storage loop 25, 26 and through an open solenoid valve 24. The desired amount of the particular reagent is withdrawn from the reagent's container. The X-Y-Z motion control system then transports the dispensing system 13 to the location of a reservoir requiring the reagent. Positive pressure is then supplied to the large or small storage loop and the appropriate solenoid valve is opened for it to dispense a metered amount of reagent into the reservoir. The dispensing system 13 may then be repositioned to another reservoir requiring the same reagent and the dispensing process repeated until all of the reservoirs requiring a particular reagent are supplied. The dispensing needle 23 and the storage loop 25 or 26 used are then cleaned by repeated flushing of the dispensing needle 23 and the tubing of the storage loop 25 or 26 with the appropriate washing fluid. The dispensing system 13 is then prepared to transport and supply another reagent when the assay requires it.

The proper metering of reagents is accomplished by active controlling through control system 19 of the positive or negative pressure supplied to the storage loops 25, 26 and timing the opening and closing of the solenoid valves 24 of the dispensing system 13 while either withdrawing or dispensing reagents.

The deployment of a single dispensing needle 23 that is automatically cleaned is an advantage since alternative methods of reagent dispensing generally require the use of a pipetter and large numbers of disposable pipette tips. The self-contained biological assay apparatus 10 uses a fluidic transport layer 16 that separates the sample from the reagent input reservoirs in the reservoir layer 17 thus avoiding the potential for cross contamination that occurs in alternative systems. Therefore the single dispensing needle system 23 is employed and the need for a pipetter system is not required. Alternatively, the dispenser system may be configured as a pipetter system and operate in a similar manner although incorporating disposable pipette tips instead of cleaning the dispenser needle between reagent applications. In the case where a pipette system is employed the sample may also be automatically dispensed into the sample input port 33 by the pipette and the pipette tip disposed to avoid cross contamination.

As variously illustrated in FIGS. 5-14, the pneumatic manifold 15, which is comprised of two subunits 15a and 15b where subunit 15a receives the pneumatic supply from the pneumatic supply system 18 and splits the signals through its integrated pneumatic channels 32 to deliver the pneumatic signals to subunit 15b's pneumatic channels that in turn supply the pneumatic signals to the diaphragms on the underside of the fluidic transport layer, interfaces with a plurality of microfluidic systems (16, 16a, and 17 in combination, referred to hereinafter as an assay unit or, commercially, as a CARD® (Chemistry and Reagent Device)), each CARD having a singular or plural assay capacity. Each CARD further includes a multi-layer, monolithic, polymeric, non-elastomeric microfluidic chip (microfluidic transport layer) 16 that has a given configuration of microfeatures including a plurality of pneumatic signal-actuated diaphragm valves. The system further includes a separate, replaceable pneumatic manifold including a plurality of pneumatic ports there through and a plurality of pneumatic channels disposed therein in fluid connection with both the plurality of diaphragm valves and the plurality of pneumatic ports. The plurality of pneumatic ports and pneumatic channels have a given configuration specifically corresponding to the given configuration of the plurality of diaphragm valves on the fluidic transport layer 16. The fluidic transport layer 16 is removably connected to the pneumatic manifold 15. The pneumatic supply system 18 further comprises a plurality of pneumatic connections that provide pneumatic signals to the pneumatic manifold 15, in fluid connection with the plurality of pneumatic ports. The plurality of pneumatic connections have a configuration corresponding to the configuration of the plurality of pneumatic ports of the pneumatic manifold 15. The pneumatic manifold 15 is removably connected to the pneumatic supply system 18.

Each multi-layer, monolithic fluidic transport layer 16 further includes a polymeric, non-elastomeric substrate 16a having a plurality of fluid channels 39 disposed therein, each of the fluid channels 39 having an inlet end and an outlet end, and at least one bi-directional diaphragm pump comprising at least three non-elastomeric membrane-based valve structures that are constructed from a single, non-elastomeric, polymeric film layer 30. In various aspects, each fluidic transport layer 16 may include an integral or component reservoir layer 17 including at least a sample input reservoir 33 capable of holding a sample and at least reagent reservoir (34) that is capable of holding a reagent material.

The reservoir layer 17 and its attached fluidic transport layer 16 (including transport layer substrate 16a) are removably disposed on the pneumatic manifold 15 so that upon completion of an analysis the combined reservoir layer 17 and fluidic transport layer 16 may be removed and replaced with a different combined reservoir layer 17 and fluidic transport layer 16 that is either unused or has been cleaned and prepared for re-use. The pneumatic manifold 15 is also removably disposed on the pneumatic supply system 18 in the housing. The pneumatic manifold 15 may also then be replaced with another pneumatic manifold 15 that is complimentary to another arrangement of combined reservoir layer 17 and fluidic transport layer 16 designed for alternative assays or greater or lesser numbers of assay units of any particular assay.

Figure 23:
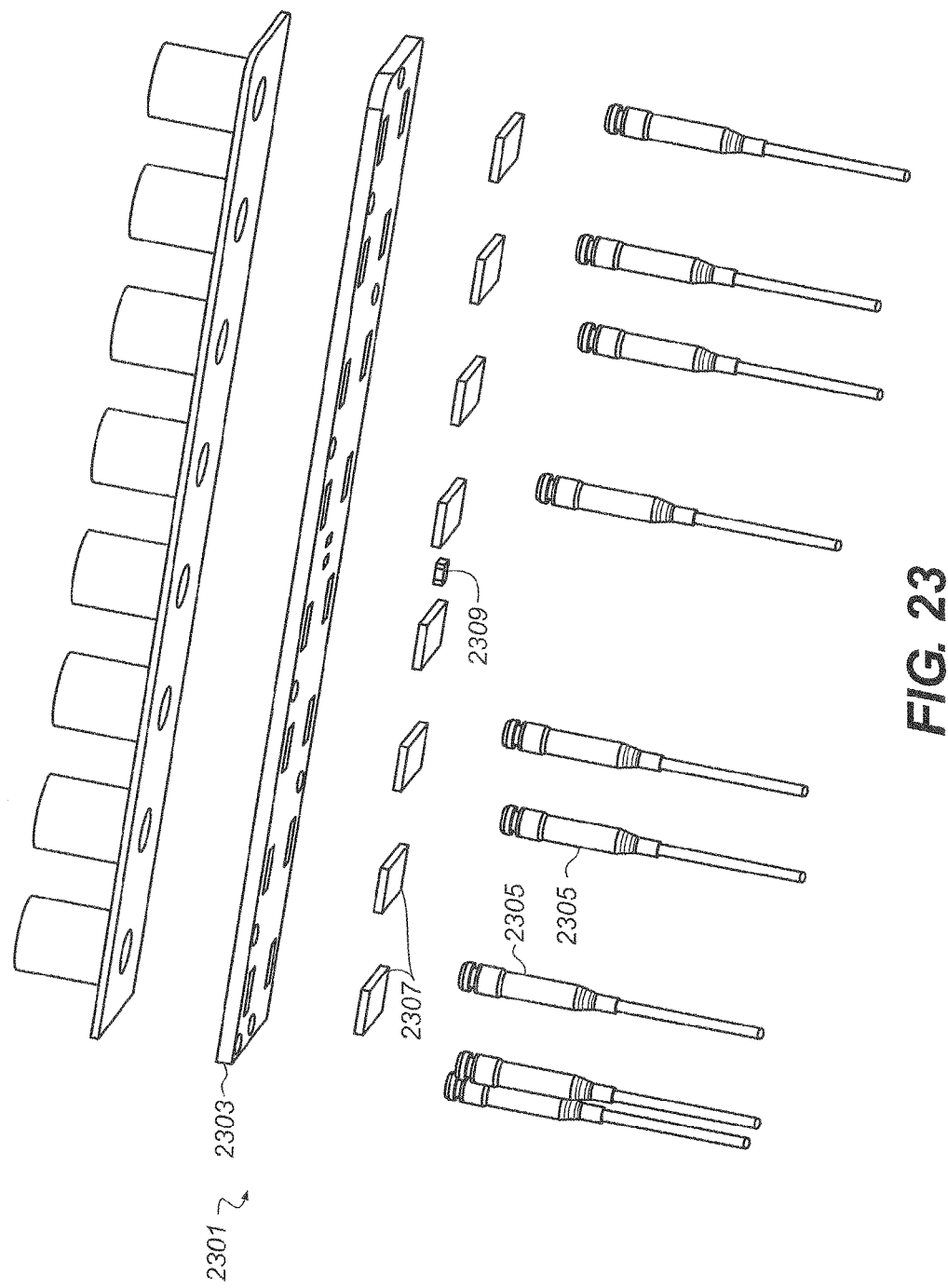
FIG. 23 is an exploded view of a multipurpose heater according to a non-limiting, illustrative aspect of the invention.

As illustrated in FIGS. 7, 14C, 15A, 15B, 18 and 19, the pneumatic manifold 15 may include multi-purpose and/or specific purpose heaters (29, 48 and 48a) used, e.g., to heat the amplification/reaction reactors 31 and/or other reservoirs or channels. In a non-limiting aspect as illustrated in an exploded view in FIG. 23, the multipurpose heater 2301 may be in the form of a laminated copper/aluminum structure 2303 that is mounted on spring-loaded electrical contact pins 2305, which provide electrical contact for resistors 2307 that generate heat that is then conducted through the laminated heater body. The contact pins also provide a connection to a temperature sensing device 2309 used to modulate the heater. The spring-mounted electrical contacts also provide uniform contact between the heater surfaces and the object to be heated. The laminated heater apparatus may be a commercially available metal core (laminated copper/aluminum; e.g., Thermally Conductive PCB Substrate, Laird Technologies, Chesterfield, Mo.) board. The metal core board provides excellent thermal conductivity, which further provides good temperature uniformity with a temperature sensor component built into the circuit layout. One of the challenges of microfluidic systems is being able to accurately measure the temperature of the heated area. The pogo contact pins (e.g., Spring Contact Probes, Interconnect Devices Incorporated, Kansas City, Kans.) provide electrical and mechanical interface. The fluidic transport layer 16 interfaces with the pneumatic ports and the heaters 29, 48 and 48*a*. When the diaphragm pumps disposed on the fluidic layer 16 are operated by positive and negative pneumatic pressure supplied to the pneumatic manifold 15 from the pneumatic supply system 18, the sample and/or reagents are drawn into the fluidic transport layer 16 and transported there through to undergo various processing steps and analysis steps, involving the reservoir layer 17, amplification reactor(s) 31, and other components such as the heaters 29, 48 and 48*a* and magnets 49 disposed on the pneumatic manifold 15. Throughout the process the sample and any intermediary reactions performed in the fluidic transport layer 16, the reservoir layer 17, or an amplification reactor 31 are separated in their particular assay unit from the other assay units. The separation prevents cross contamination of the sample with or from any other assay units, the reagent dispensing system 13, the pneumatic manifold 15, or the pneumatic supply system 18, thereby providing greater analytical reliability and decreased operation costs since the system's cleaning requirements are greatly reduced. The pneumatic supply system 18 functions to provide pneumatic signals (positive and negative pressure) routed through the pneumatic manifold 15 to affect the transport of the test sample and the reagents within the fluidic transport layer 16. Its operation is coordinated with the dispensing platform 12 so that when reagents are delivered to particular or common reservoirs on reservoir layer 17 by the dispensing system 13 from the reagent supply component 14 the proper processing procedures occur. The pneumatic manifold 15 also may incorporate areas where heating, cooling (accomplished by directing a jet of compressed air, that may or may not be actively cooled, from the pneumatic supply system 18 at the heater, or supplying air flow from a fan), or magnetism may be applied to facilitate a reaction. The pneumatic supply system 18 is disposed in operative connection with the pneumatic manifold 15 in the housing 11 in a space separate from the dispensing platform 12 and a control system 19 that is used to control the dispensing platform 12, the pneumatic supply system 18, and any heating, cooling (accomplished by directing a jet of compressed air, that may or may not be actively cooled, from the pneumatic supply system 18 at the heater or supplying air flow from a fan), or magnetism performed by the pneumatic manifold 15 reaction occurring in the fluidic transport layer 16, the reservoir layer 17 or the amplification reactors 31.

Figure 4:
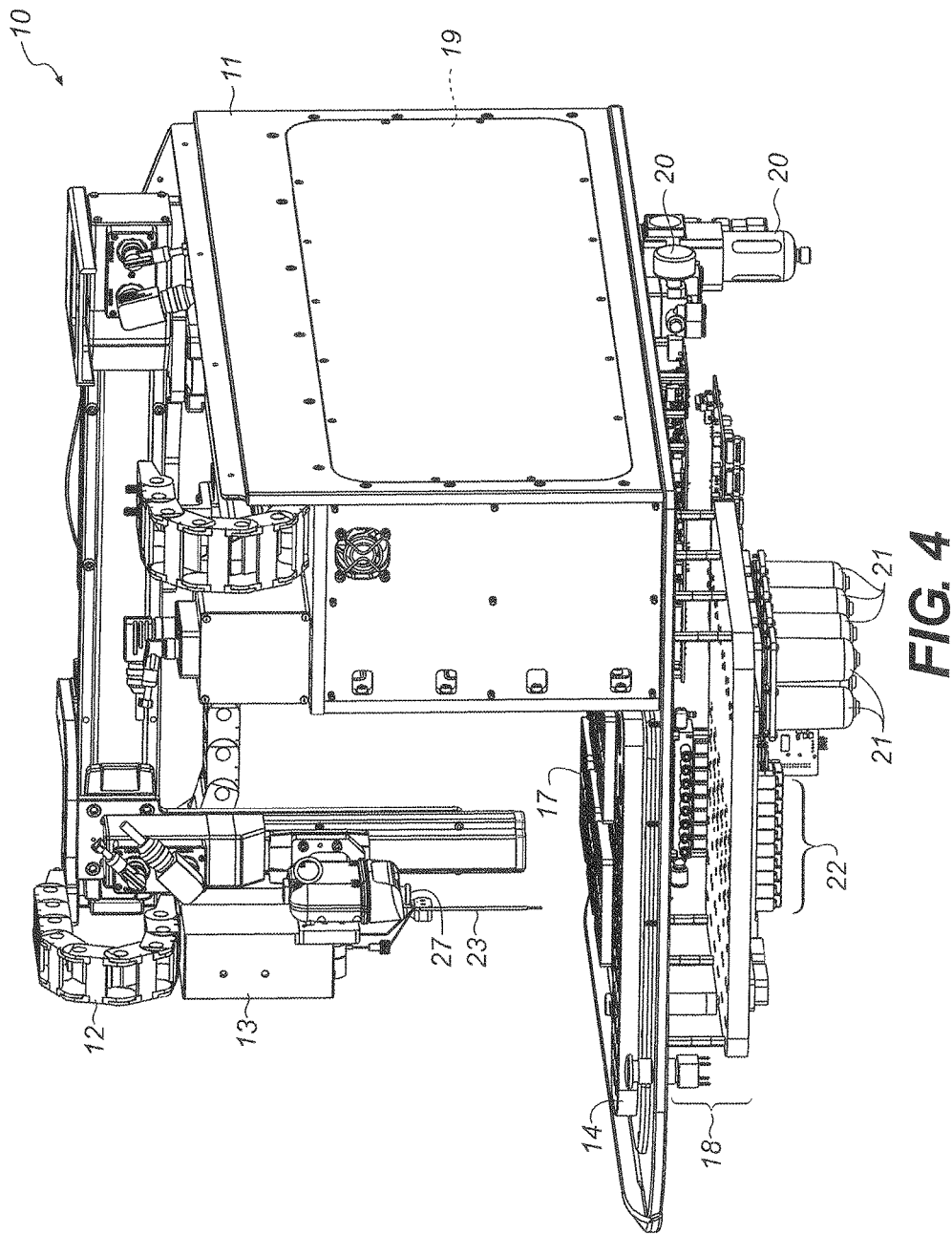
FIG. 4 shows a perspective view of the self-contained biological assay apparatus shown in FIG. 1.

FIG. 4 is a perspective view of the self-contained biological assay apparatus 10, which more clearly shows the location of the pneumatic supply system 18 beneath the pneumatic manifold 15. The pneumatic supply system 18 is located within the lower portion of the housing 11. The pneumatic manifold 15 is removably attached to the pneumatic supply system 18 in order to facilitate easy reconfiguration of the self-contained biological assay unit 10 for assays that require different designs of the fluidic transport layer 16. The pneumatic supply system 18 is comprised of a number of subcomponents designed to store, meter and route pneumatic pressure under the direction of the control system 19 through the pneumatic manifold 15 to operate the diaphragms located on the fluidic transport layer 16 of an assay unit. Positive and negative pressure is supplied to the positive and negative pressure storage reservoirs 21 through positive and negative pressure regulators 20. Positive and negative pressure are in turn metered and supplied to the channels of the pneumatic manifold 15 from the positive and negative pressure storage reservoirs 21 through pneumatic supply solenoids 22 (the tubes leading from the pneumatic supply solenoids 22 to the undersurface of the pneumatic manifold 15 are not shown for clarity (the configuration may also be configured without tubes by having a tubeless solid state interface between the pneumatic supply system 18 and the pneumatic manifold 15)). The pressure metering and the opening and closing of the solenoids is managed by control system 19 and supplies the metered pneumatic force to the pneumatic manifold 15, thereby operating the diaphragm pumps located on the fluidic transport layer 16.

Figure 5:
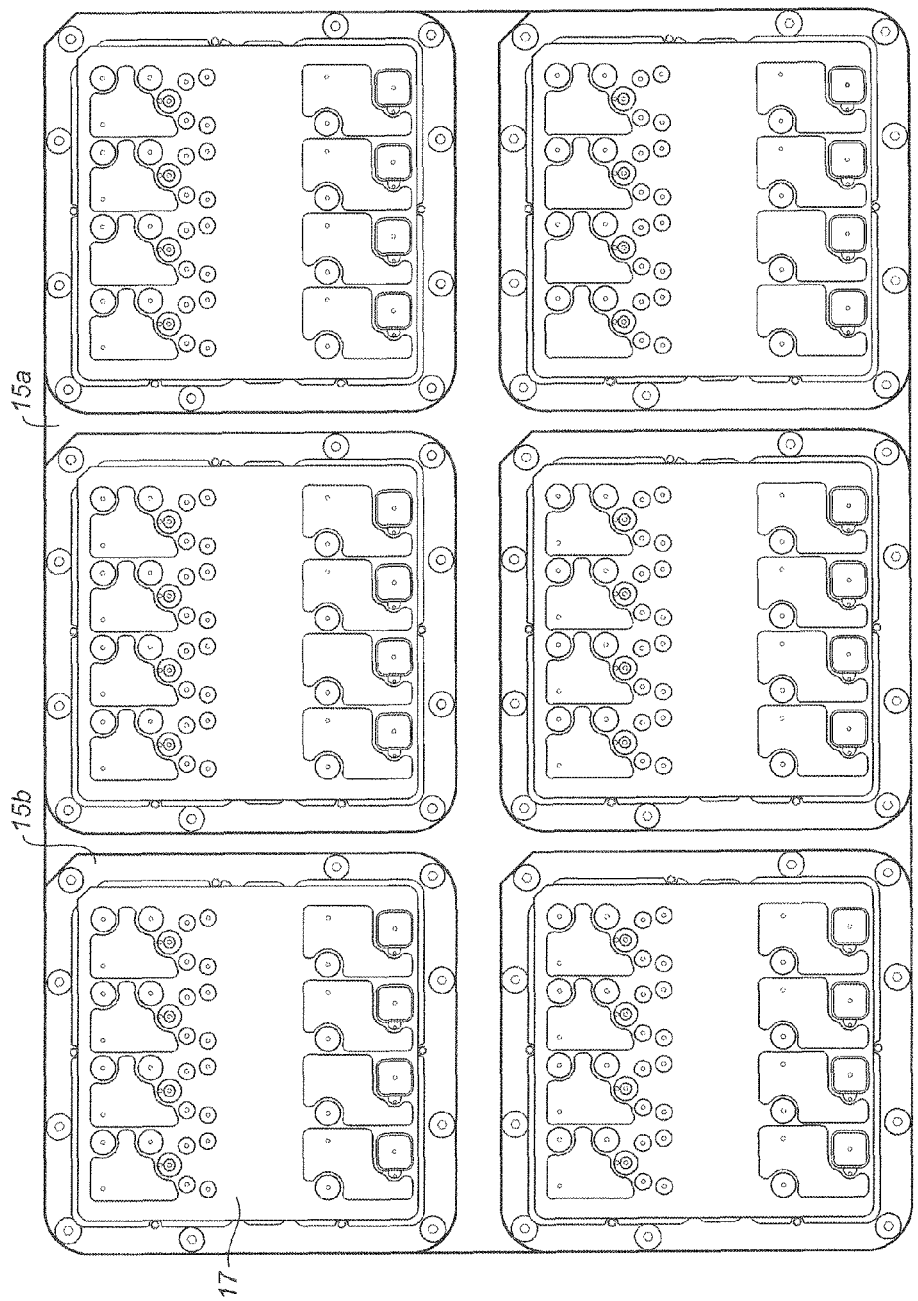
FIG. 5 shows a top plan view of a "six by four" arrangement of reservoirs, according to an exemplary aspect of the invention.

FIG. 5 illustrates an array of six CARDs depicting a "six by four" arrangement of reservoirs, each four assay unit CARD being removably disposed on the pneumatic manifold 15. In operation, the reservoir layer 17 is covered by a film (not shown) to protect its contents from potential cross contamination by samples in process in adjacent assay units and to prevent the contents of the reservoirs 17 from contaminating the dispensing platform 12, the pneumatic manifold 15, the pneumatic supply system 18, the control system 19, or the housing 11.

Figure 6:
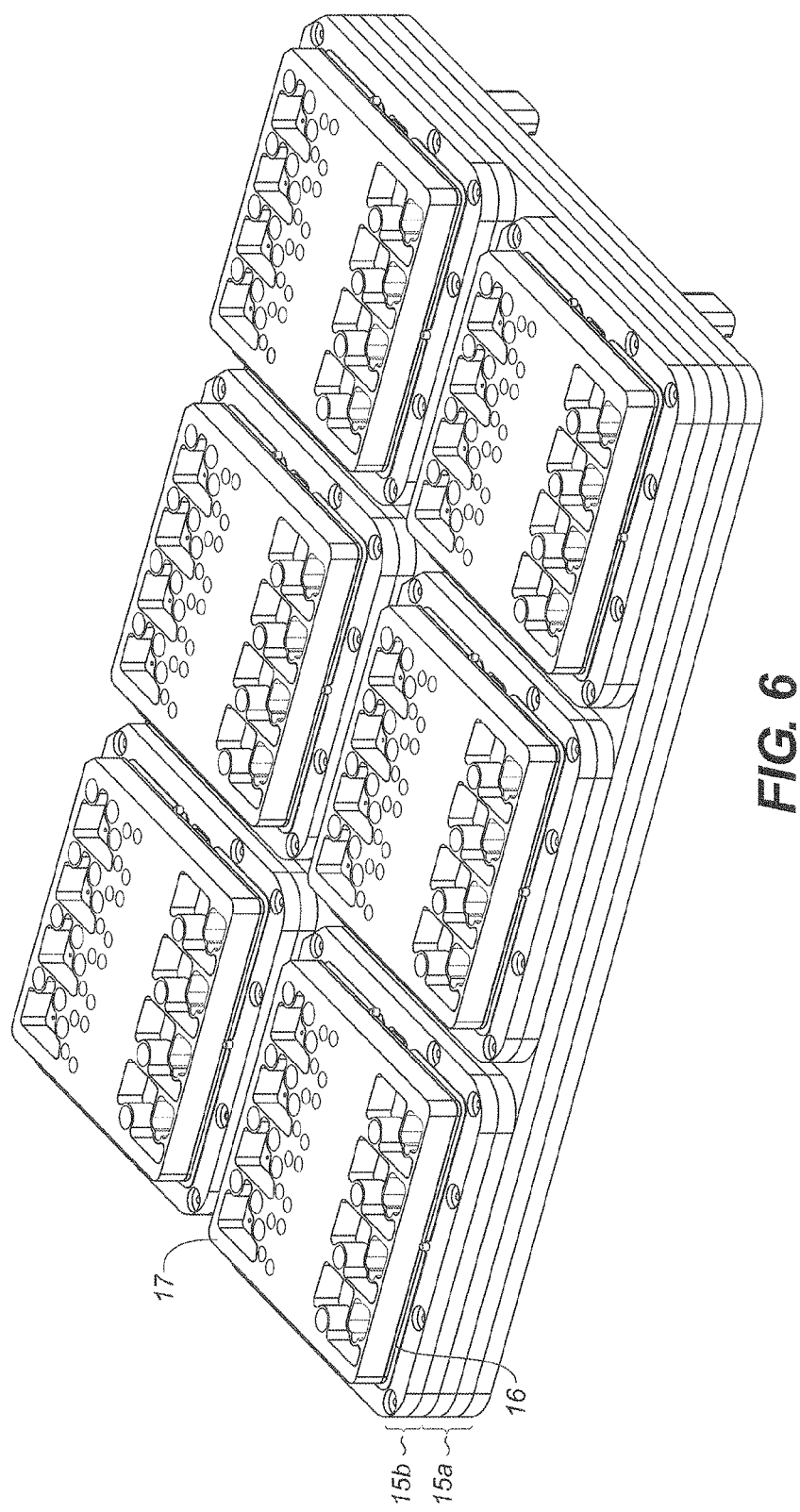
FIG. 6 shows a perspective view of a "six by four" arrangement of reservoirs attached to fluidic transport layers and mounted on the pneumatic manifold, according to an exemplary aspect of the invention.

FIG. 6 further illustrates a "six by four" CARD arrangement removably attached to the fluidic transport layer 16 on the pneumatic manifold 15.

Figure 7:
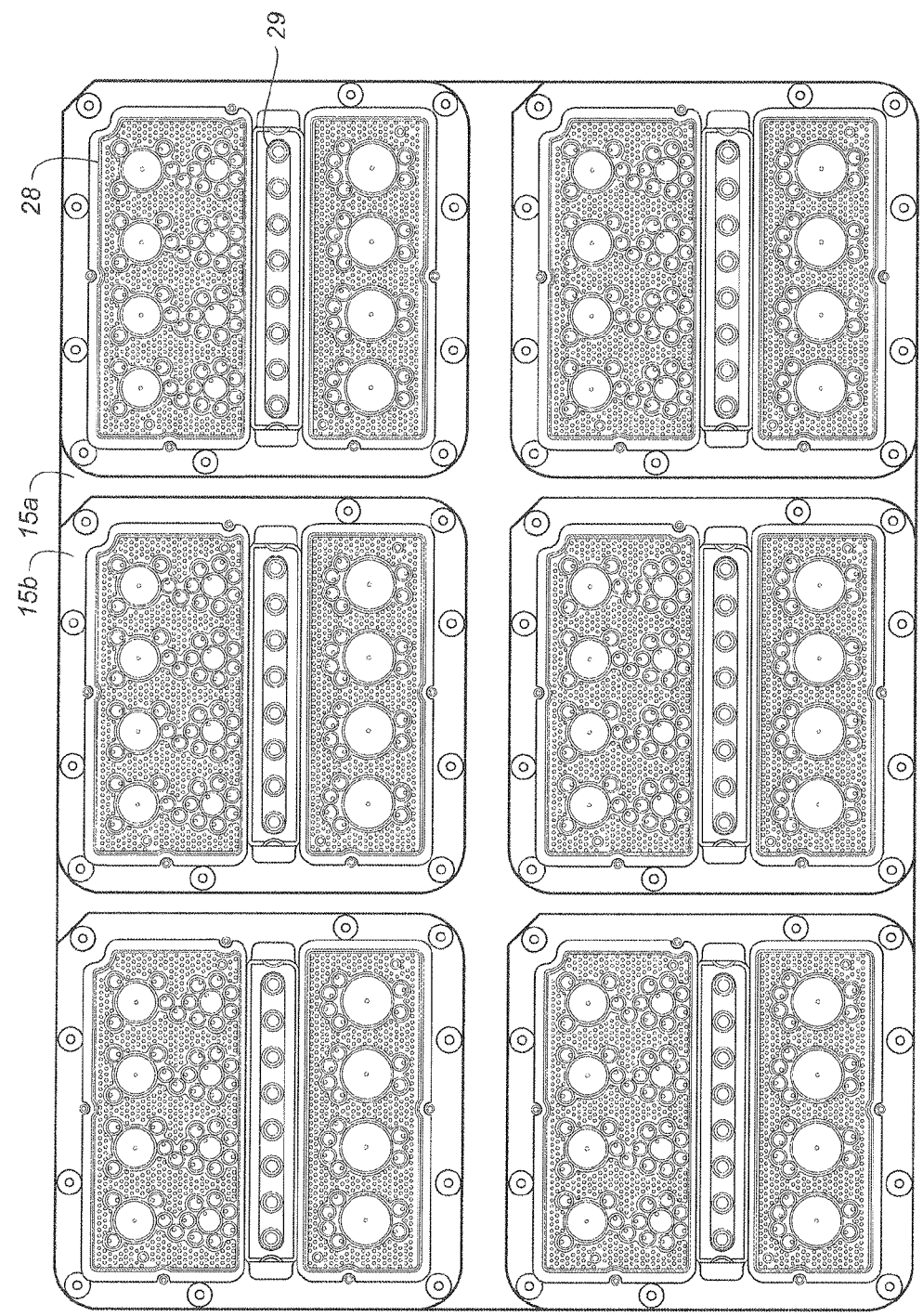
FIG. 7 shows a cross sectional top plan view of a "six by four" arrangement of the top gasket layer of the pneumatic manifold and the heaters that engage the amplification reactors, according to an exemplary aspect of the invention.

FIG. 7 is a top view of the interface between the fluidic transport layer 16 and the pneumatic manifold 15. Gaskets 28 are attached to the top of the pneumatic manifold 15 and are designed to isolate the pneumatic forces applied to the film layer 30 (FIG. 15B) of the fluidic transport layer 16. Terminating within each gasket void is a channel routed through the pneumatic manifold 15 from the pneumatic supply system 18. When a fluidic transport layer 16 is placed on top of the gasket 28, the unbonded portion of the film layer 30 of the fluidic transport layer 16 is then able to be flexed into or out of the gasket void by applied positive and/or negative pressure routed through the pneumatic manifold 15 from the pneumatic supply system 18 and controlled by control system 19. The control system 19 can apply the positive or negative pressure sequentially to selected locations, which creates a diaphragm pumping system as described in commonly assigned U.S. Pat. No. 7,832,429. By using such a system of actuated pumping, the pneumatic manifold supply system 18 and the pneumatic manifold 15 remain separated from the fluids transported through the fluidic transport layer 16, which eliminates cross-contamination between assay units and contamination of the pneumatic supply system 18 and the pneumatic manifold 15.

As mentioned above, heaters 29 may be located within the pneumatic manifold 15 that the amplification reactors 31 fit into when the CARD is placed onto the pneumatic manifold 15. At the appropriate time during the processing of a sample, the amplification reactor 31 is filled with the appropriate reagents and processed sample transported through the fluidic transport layer 16 from various reservoirs in reservoir layer 17. The contents of the amplification reactor are then heated and cooled (accomplished by directing a jet of compressed air, that may or may not be actively cooled, from the pneumatic supply system 18 at the heater or supplying air flow from a fan) in a controlled manner through instructions from the control system 19.

Figure 8A:
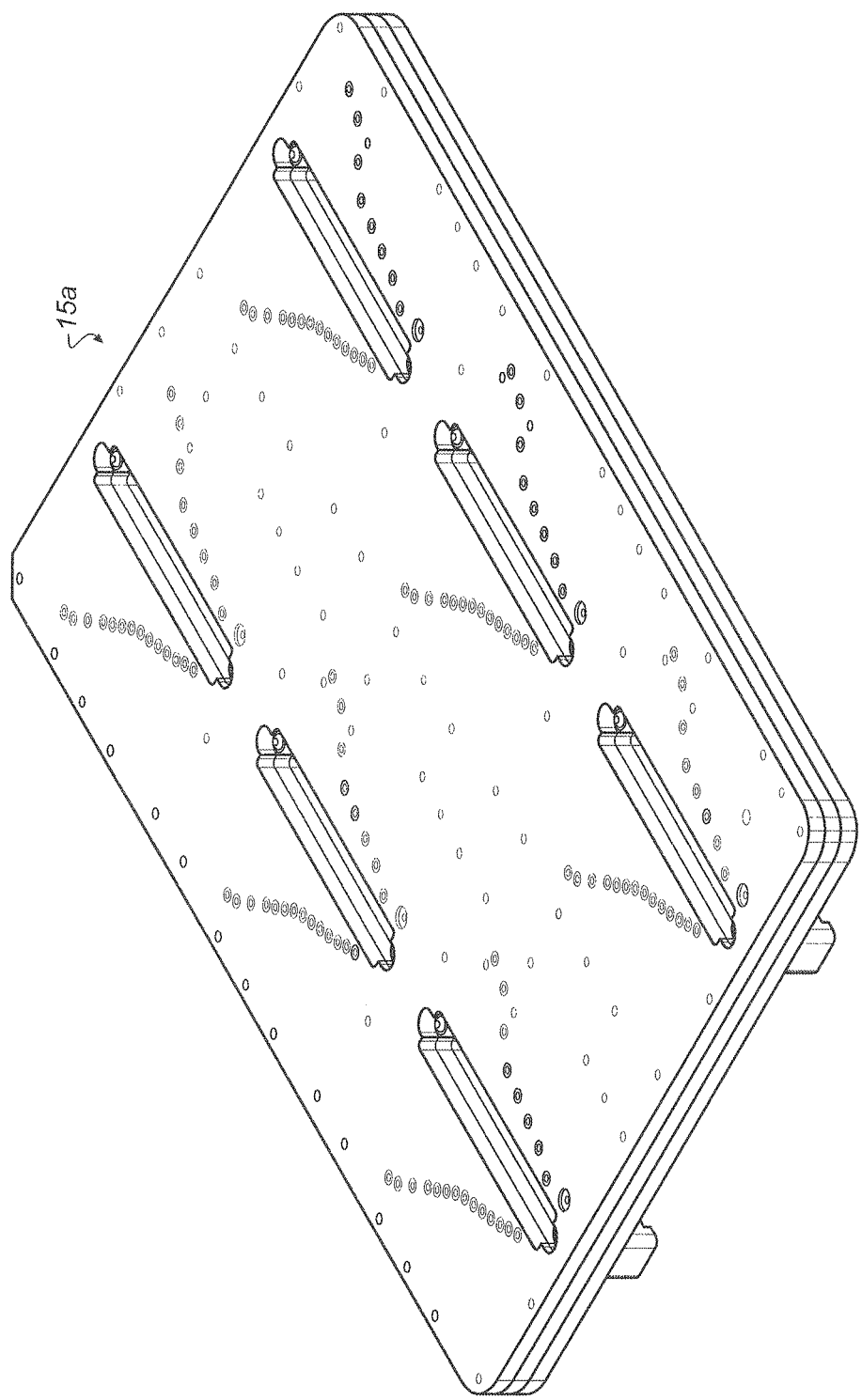
FIGS. 8A-C show, respectively, a top perspective view, a top plan view, and a bottom perspective view of a "six by four" arrangement of the bottom portion of the pneumatic manifold of the self-contained biological assay apparatus, according to an exemplary aspect of the invention.

FIG. 8A illustrates a perspective view of the layer 15*a* of a "six by four" arrangement of the pneumatic manifold 15 of the self-contained biological assay apparatus 10. The orifices through which the pneumatic signals are routed to higher layers 15*b* of the pneumatic manifold 15 and the bays where the heaters are located.

Figure 8B:
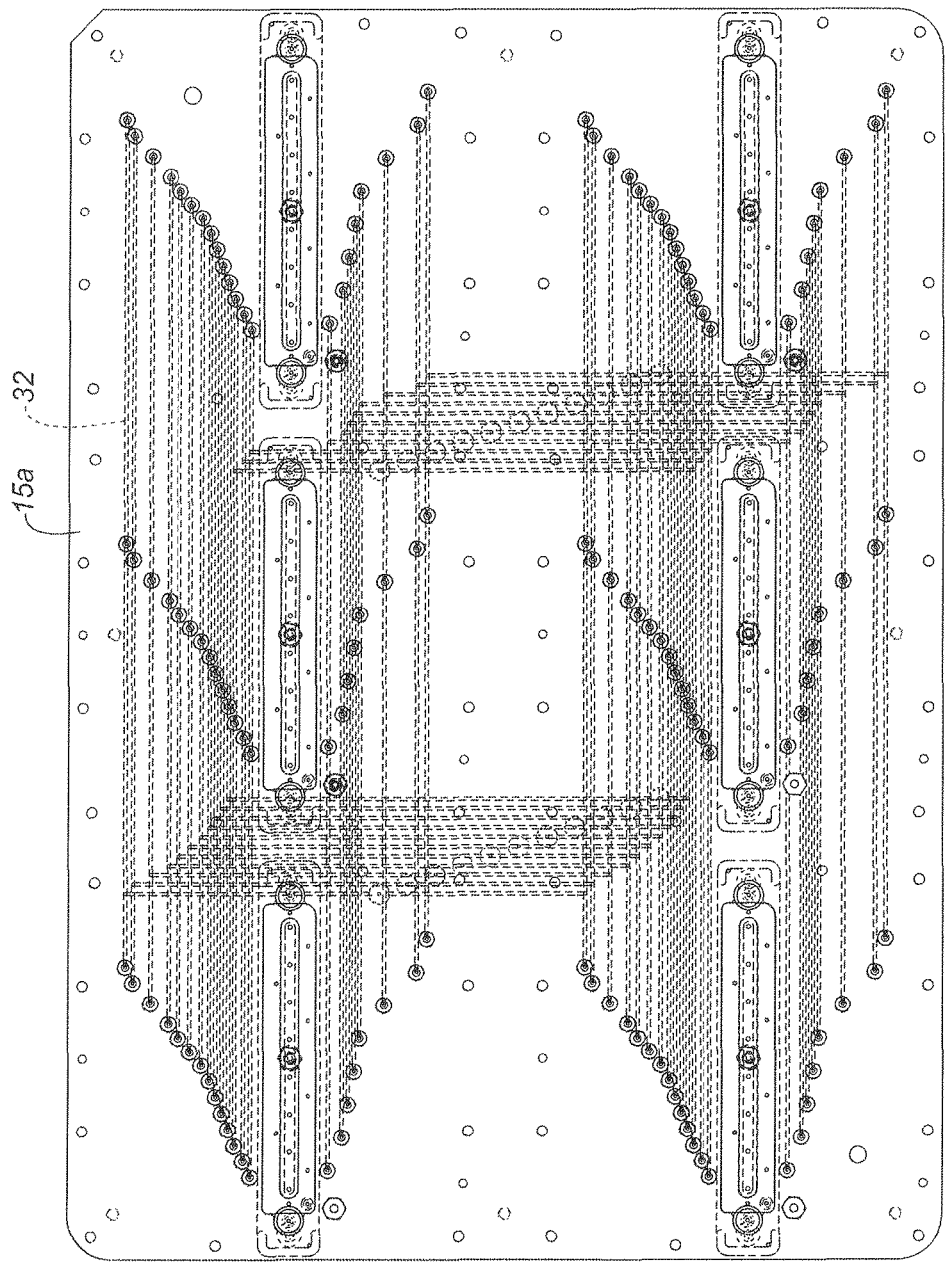

FIG. 8B illustrates a top layered view of a "six by four" arrangement of the pneumatic manifold 15a of the self-contained biological assay apparatus 10. The channels 32 through which the pneumatic signals are routed from the orifices on the bottom of the pneumatic manifold 15 form the pneumatic supply system 18 and the orifices on the layer depicted in 8A.

Figure 8C:
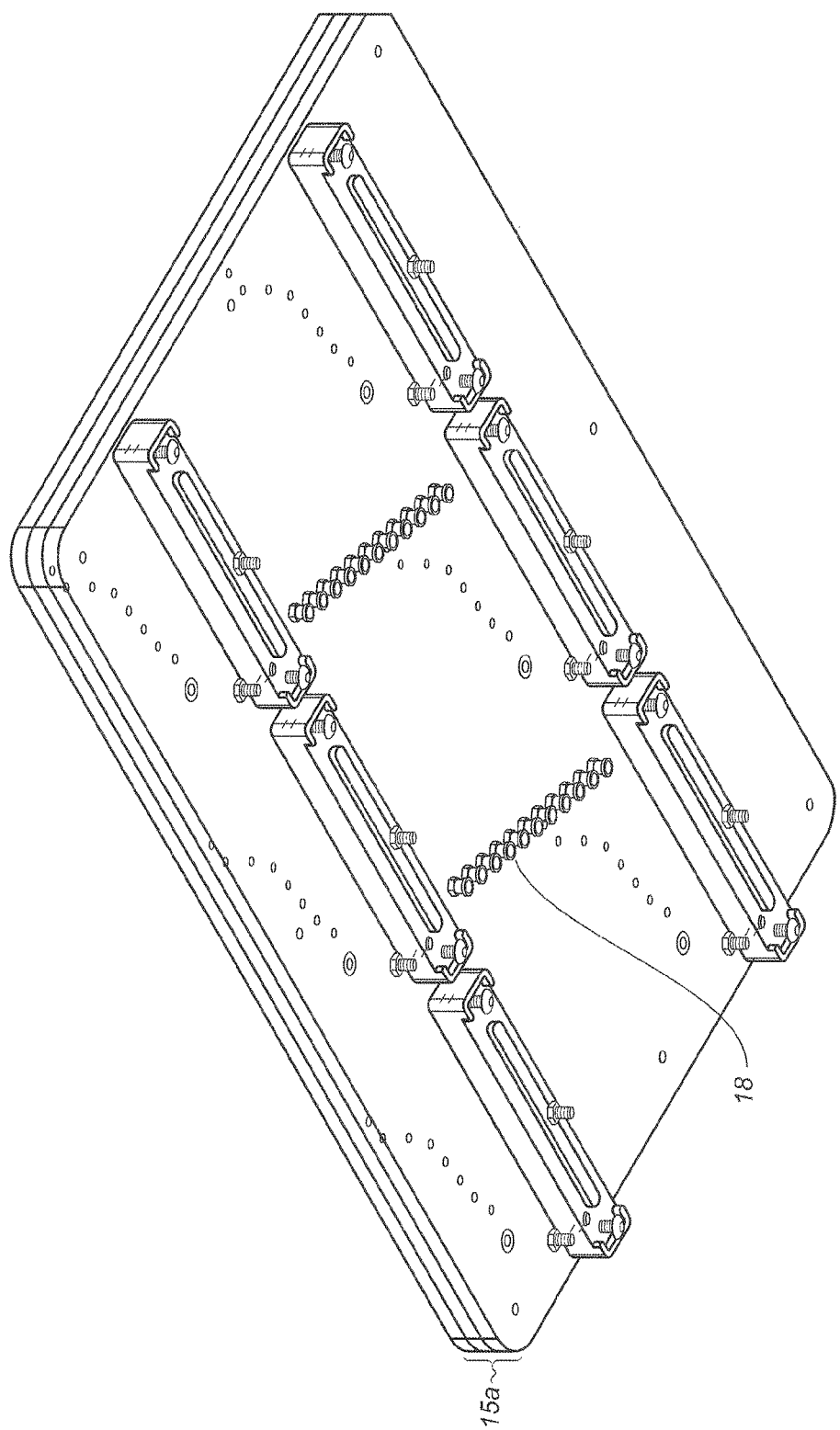

FIG. 8C illustrates a perspective bottom view of a "six by four" arrangement of the pneumatic manifold 15 of the self-contained biological assay apparatus 10. The pneumatic solenoids 22 and the pressure storage reservoirs 21 depicted in FIG. 4 supply pneumatic pressure or vacuum to the orifices located on the bottom of the pneumatic manifold 15. The pressure storage reservoirs 21 supply metered positive and negative pressure to the pneumatic channels 32 shown in FIG. 8B that are fabricated in the pneumatic manifold 15. When the control system 19 opens a pneumatic supply solenoid 22, a pneumatic channel 32 is either supplied with metered negative or metered positive pressure depending upon which pressure storage reservoir 21 is attached to the specific pneumatic supply solenoid 22 opened or closed by the control system 19. The metering of the pressure is accomplished by adjusting the pressure of pressure storage reservoirs 21, modulating the opening of pneumatic supply solenoids 22 or a combination of both under the management of control system 19 The pressure supplied to the channel then operates the fluidic transport layer 16 through the gasket interface 28 of the pneumatic manifold 15.

Figure 9:
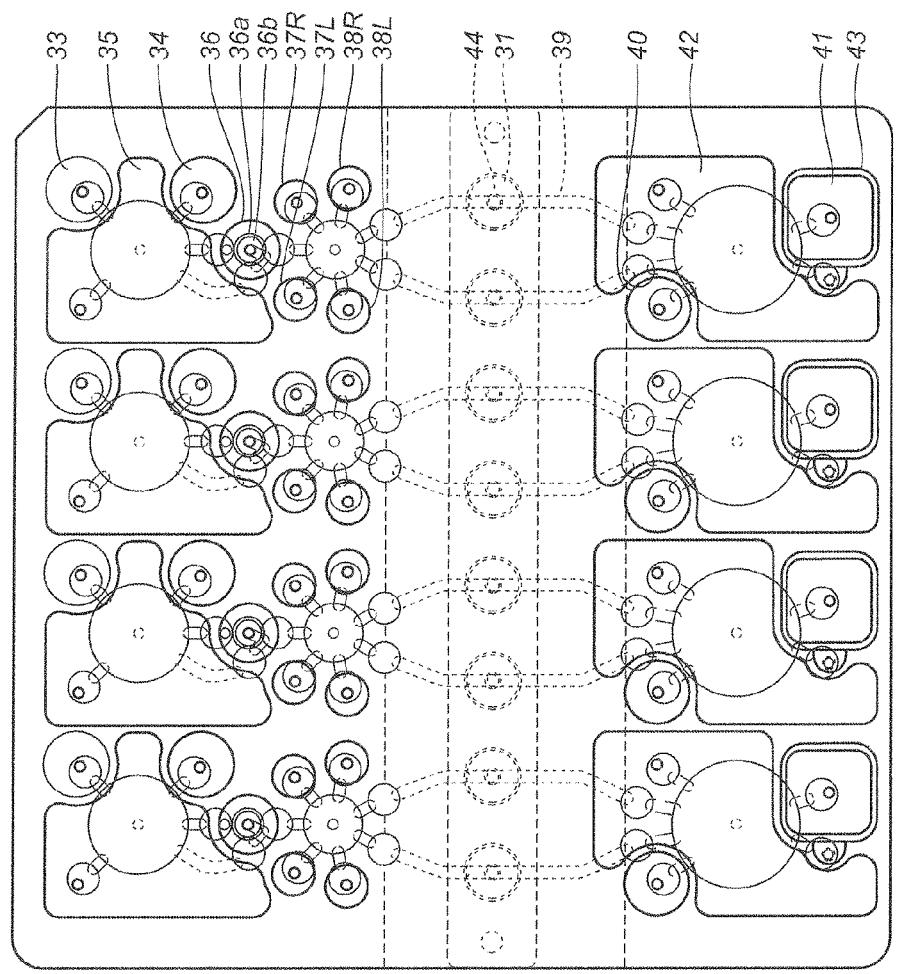
FIG. 9 shows a layered, cross sectional top plan view of a "four assay unit" arrangement of the reservoirs, fluidic channels and amplification reactors, which are a combination of the fluidic transport layer and the reservoir layer, according to an exemplary aspect of the invention.

FIG. 9 illustrates a layered top view of a "four assay unit" CARD, with fluidic channels 39 of the fluidic transport layer 16 and amplification reactors 31. The figure shows sample input reservoir 33, common preparative and purification reagent reservoir 34, waste reservoir 35, and silica filter reservoir 36 including silica filter retaining ring 36a, which would hold silica filter 36b (not shown for clarity) in the preparation and purification area of a single assay portion of a CARD. It also shows elution reservoirs 37 (left and right), amplification master mix reservoirs 38 (left and right), and amplification reactors 31 (left and right) attached underneath the fluidic transport layer 16 and accessed through a lumen 44. It also shows common reagent input reservoir 40, analysis reservoir 41, and waste reservoir 42 and the perforated ring system 43 used to support the analysis membrane 43 (not shown for clarity) of the analysis portion of a single assay unit of a four assay unit CARD.

FIGS. 10A through 10K generally illustrate a non-limiting, exemplary method of using the device to process and analyze a sample. A description of a single assay unit is provided here though there is no particular upper limit to the number of assay units that can process samples either in parallel or serially as samples are provided to the self-contained biological assay apparatus 10. The order that individual samples are processed are based upon the capabilities of the control system 19 to manage the pneumatic supply system 18 and the particular arrangement of the pneumatic manifold 15, and the specific reagents supplied by the reagent supply component 14 and delivered by the dispensing system 13. In particular, a specific assay may require a design of a reservoir layer 17 and its matching fluidic transport layer 16 that interfaces with the pneumatic manifold 15. When all of the matching elements are combined, the process will generally proceed as follows.

Figure 10A:
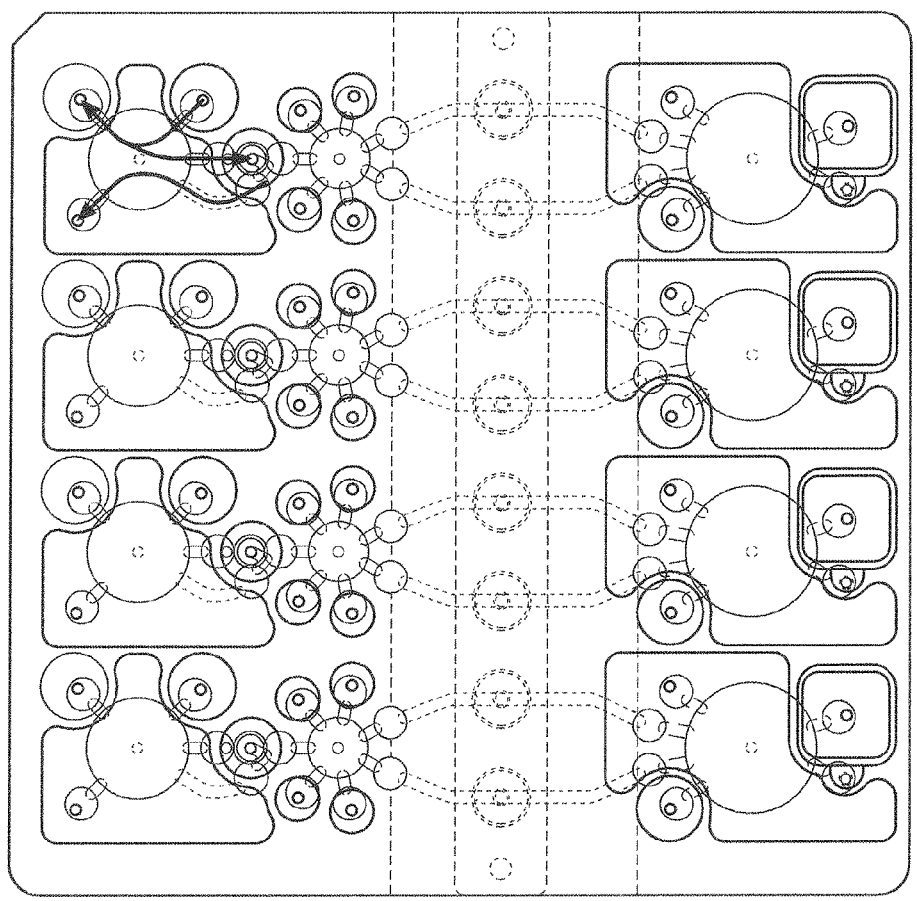
FIGS. 10A-K show layered, cross sectional top plan views of exemplary process stages using the channels, reactors, and reservoirs in the combined fluidic transport layer and the reservoir layer when operated by the pneumatic manifold, according to illustrative aspects of the invention.

In FIG. 10A, a sample is input into sample input reservoir 33 and the dispensing system 13 provides a cell lysing reagent into common reservoir 34. The cell lysing reagent is then pumped to the sample input reservoir 33 and incubated either with or without gentle agitation as described in co-pending application Ser. No. 12/249,872 as "fluffing" (i.e., the repeated actuation of a diaphragm accessing a reservoir to alternatively withdraw and then inject fluid into a reservoir to cause turbulence and mixing), as required by the assay. While the sample is incubating in sample input reservoir 33, an organic alcohol (e.g., ethanol) is dispensed by the dispensing system 13 into common reservoir 34 and pumped to sample input reservoir 33 further increasing the volume in sample input reservoir 33; the larger mixture continues to incubate. Upon completion of the incubation period the contents of sample input reservoir 33 are pumped onto the top of the silica filter 36b in silica filter reservoir 36 and pulled through the silica filter 36b and the contents pumped to waste reservoir 35.

Figure 10B:
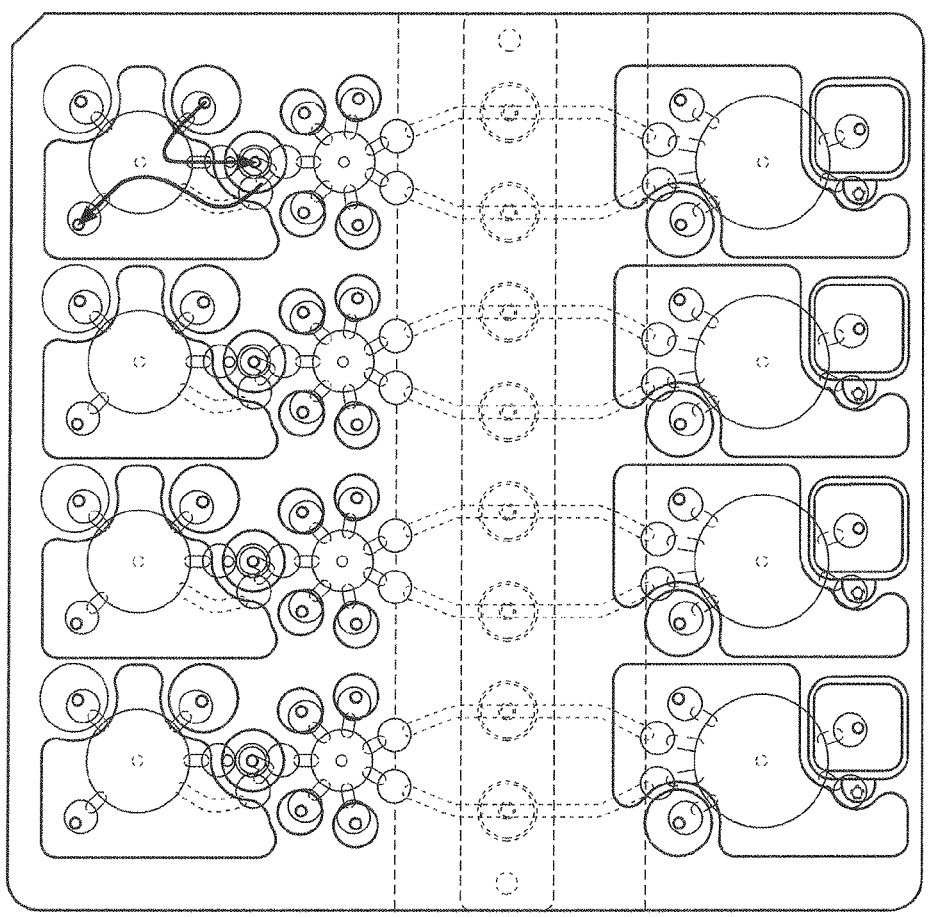

Per FIG. 10B, an organic alcohol (e.g., ethanol) is dispensed into common reservoir 34 and pumped on top of the silica filter 36b in silica filter reservoir 36, pulled through the silica filter and pumped to waste reservoir 35. A wash buffer is dispensed into common reservoir 34 and pumped on top of the silica filter 36b in silica filter reservoir 36, pulled through the silica filter 36b and pumped to waste reservoir 35. The same or another wash buffer is dispensed into common reservoir 34 and pumped on top of the silica filter 36b in silica filter reservoir 36, pulled through the silica filter 36b and pumped to waste reservoir 35.

Figure 10C:
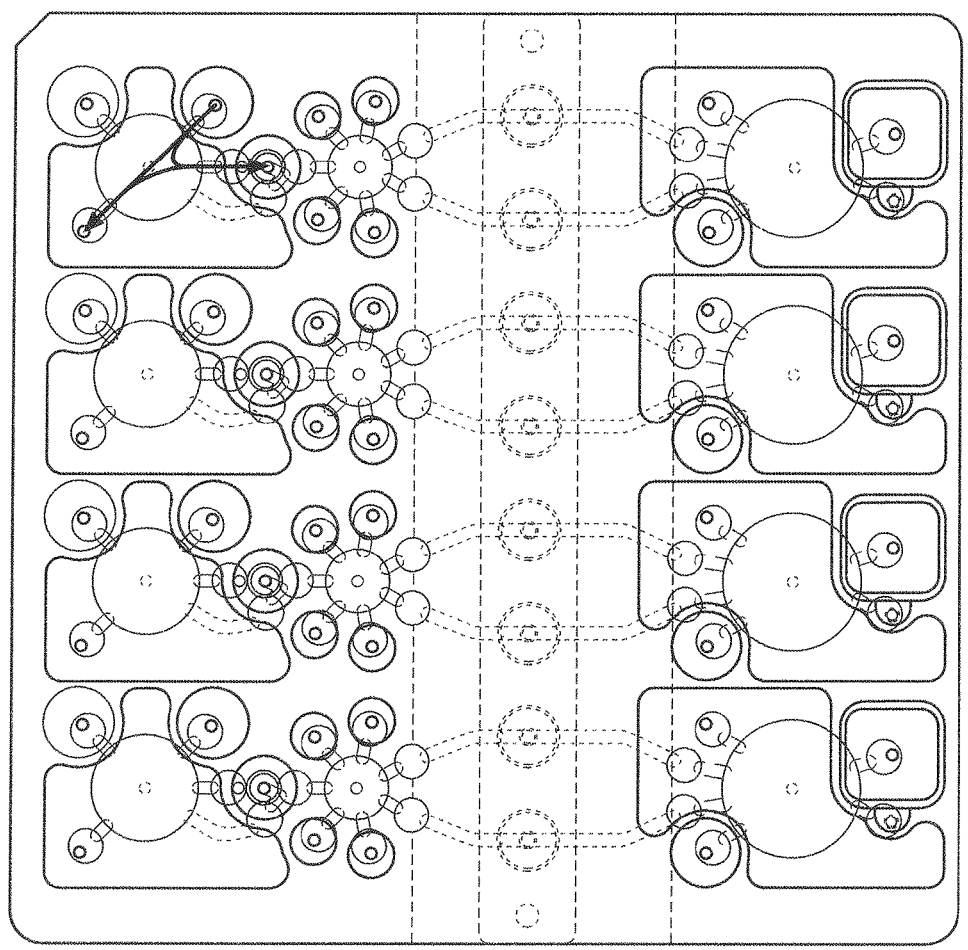

In FIG. 10C, an elution buffer is then dispensed into common reservoir 34 and pumped directly to waste reservoir 35 to clear the channel of residual lysate, the organic alcohol, and wash buffer. Fresh elution buffer is dispensed into common reservoir 34 and pumped on top of the silica filter 36b in silica filter reservoir 36 to clean the reservoir, then it is pumped from the top of the silica filter 36b to waste reservoir 35.

Figure 10D:
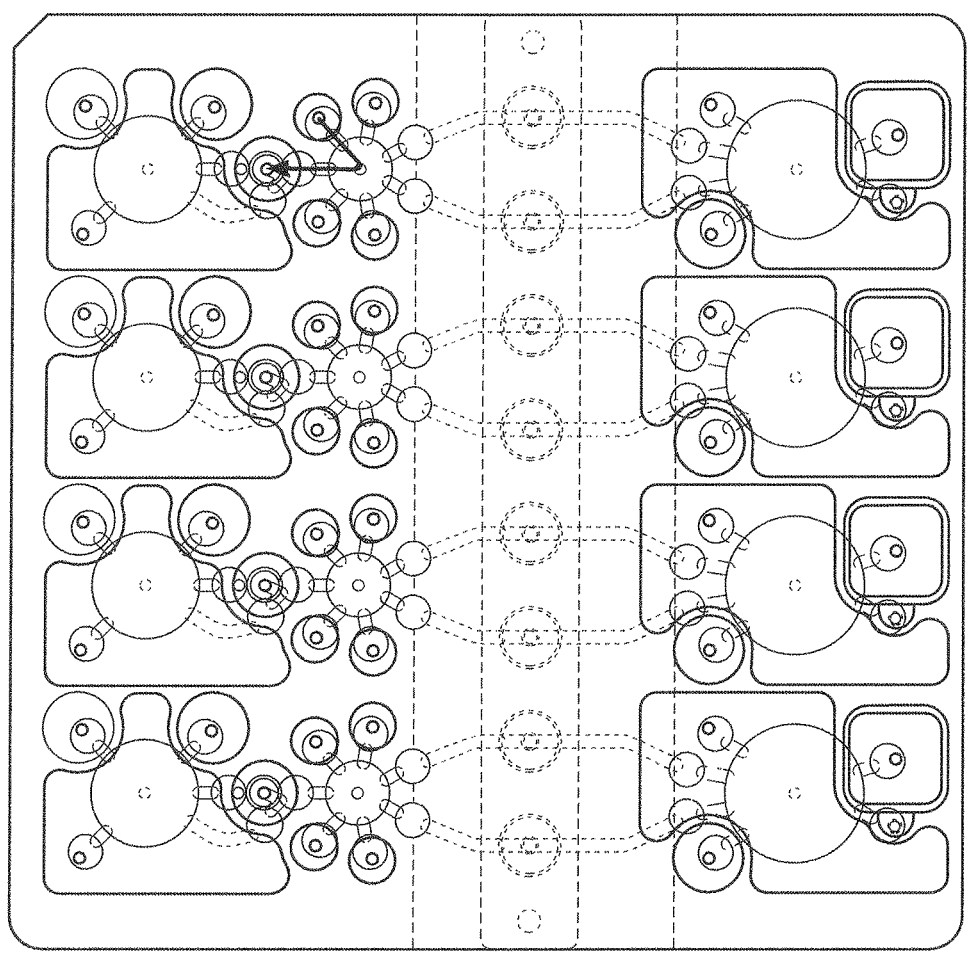

In FIG. 10D, elution buffer is then dispensed into elution reservoir 37 (right) and pumped up through the bottom of the silica filter 36b in reservoir 36.

Figure 10E:
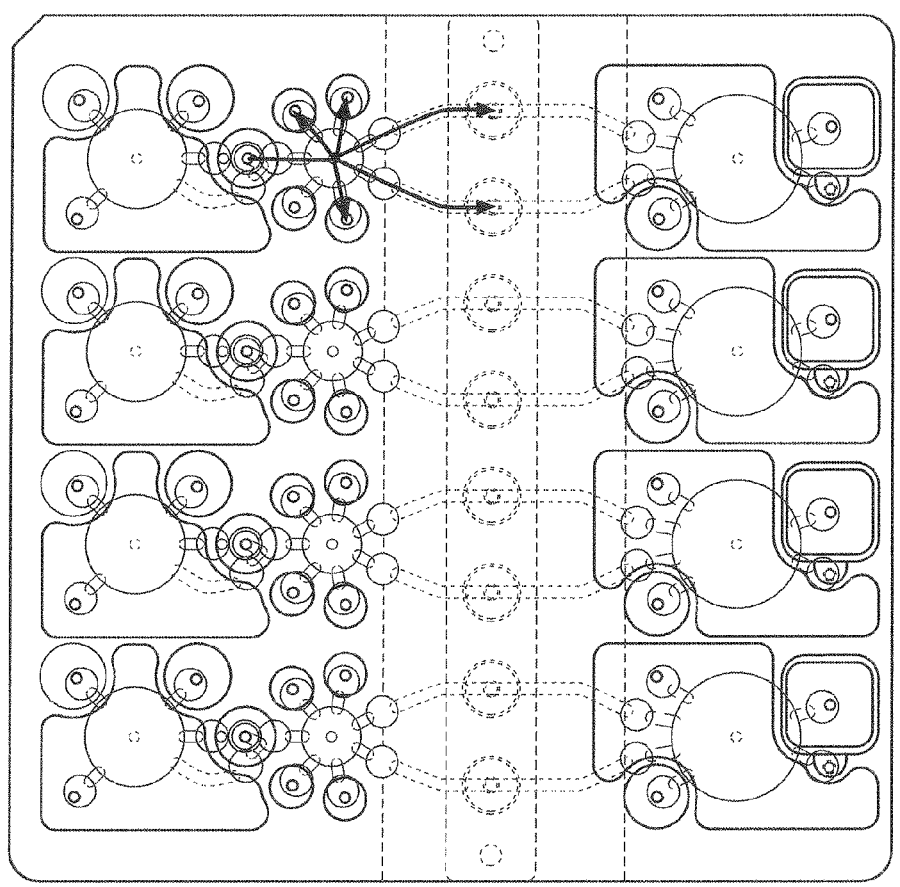

In FIG. 10E, amplification master mix is then dispensed into amplification master mix reservoirs 38 (left and right). An initial volume from silica filter reservoir 36 is pumped into elution reservoir 37 (right), then a single pump of material is pumped from silica filter reservoir 36 to amplification master mix reservoir 38 (right). The contents of amplification master mix reservoir 38 (right) are then emptied into amplification reactor 31 (right). The same process is repeated on the left side. Then the contents of amplification reactors 31 (left and right) are thermocycled under the control of control system 19 in accordance with the protocols of the particular assay in process.

Figure 10F:
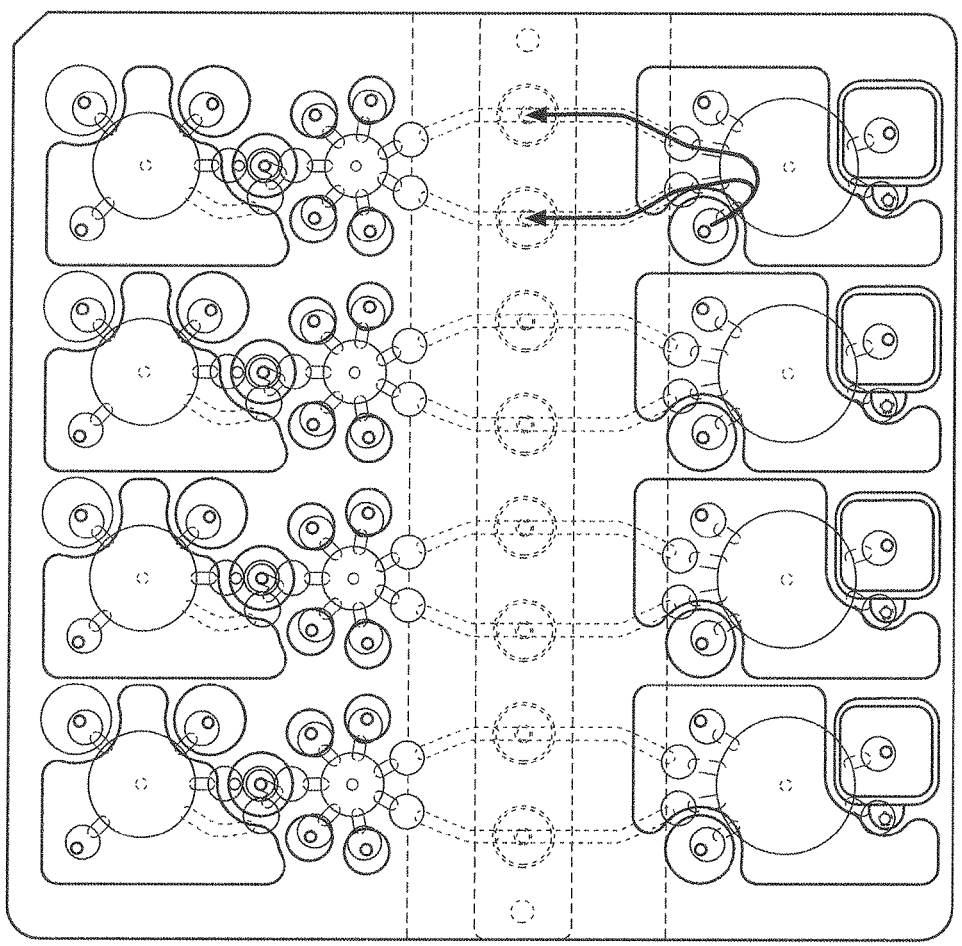

Next, per FIG. 10F following thermocycling, a pre-hybridization buffer is dispensed into common reagent reservoir 40 and pumped into amplification reactor 31 (right), then repeated to provide pre-hybridization buffer to amplification reactor 31 (left). The temperature in the amplification reactors is then increased to denature the amplicons produced from the earlier thermocycling.

Figure 10G:
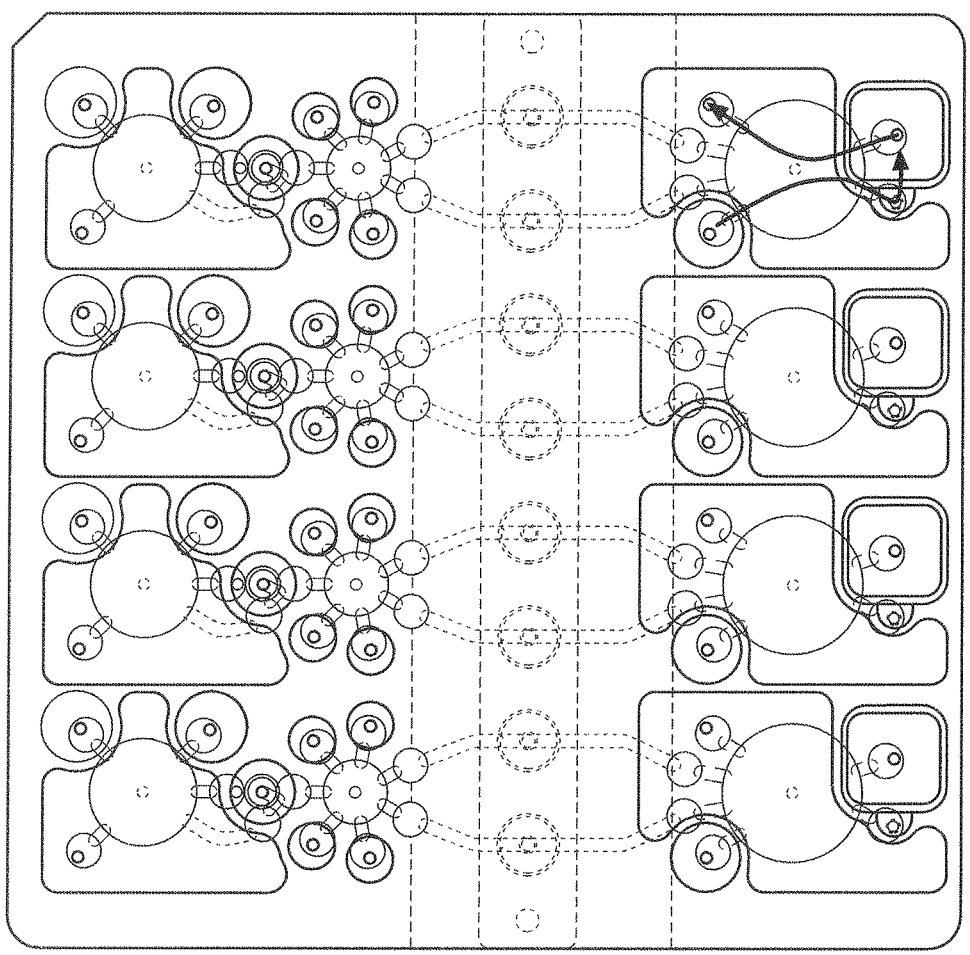

In FIG. 10G, in order to prepare the microarray on analysis membrane 47 to properly hybridize with the amplicons produced from the earlier thermocycling, while the amplicons are denaturing, dispense the same or another pre-hybridization buffer into common reagent reservoir 40 and pump it on top of the analysis membrane 47 (not shown for clarity) suspended in analysis reservoir 41, then pump it to waste reservoir 42; dispense wash buffer into common reagent reservoir 40, pump it over the analysis membrane 47 in analysis reservoir 41, and pump to waste reservoir 42 (repeat multiple times).

Figure 10H:
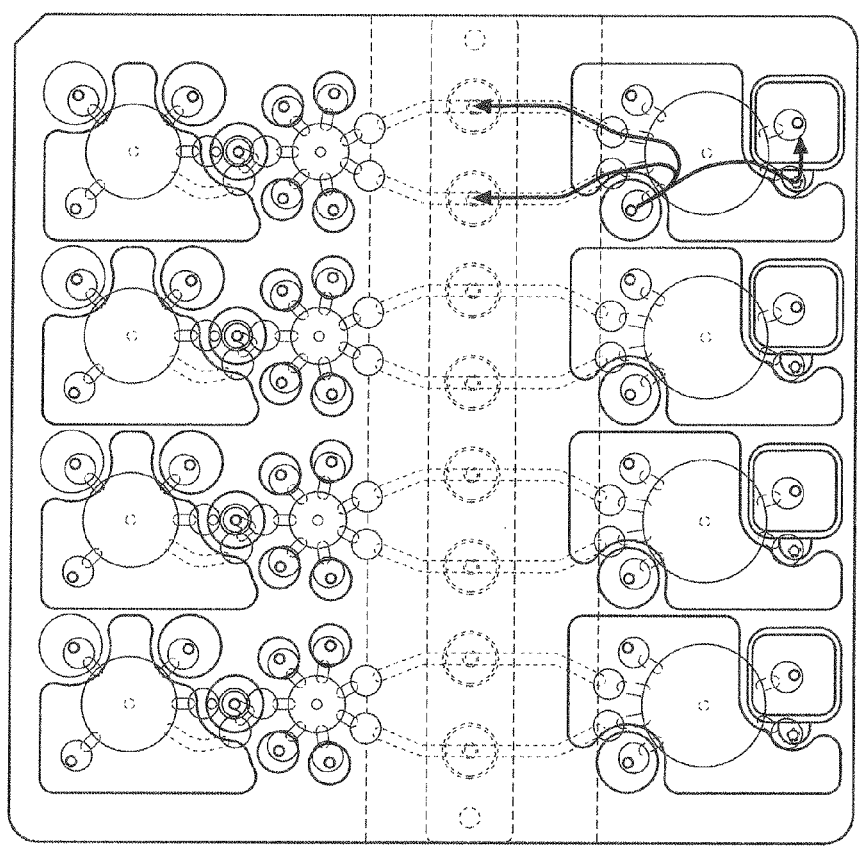

In FIG. 10H, the same or another pre-hybridization buffer is dispensed into common reagent reservoir 40 and from there into amplification reactors 31 (left and right) and on top of the analysis membrane 47 in analysis reservoir 41.

Figure 10I:
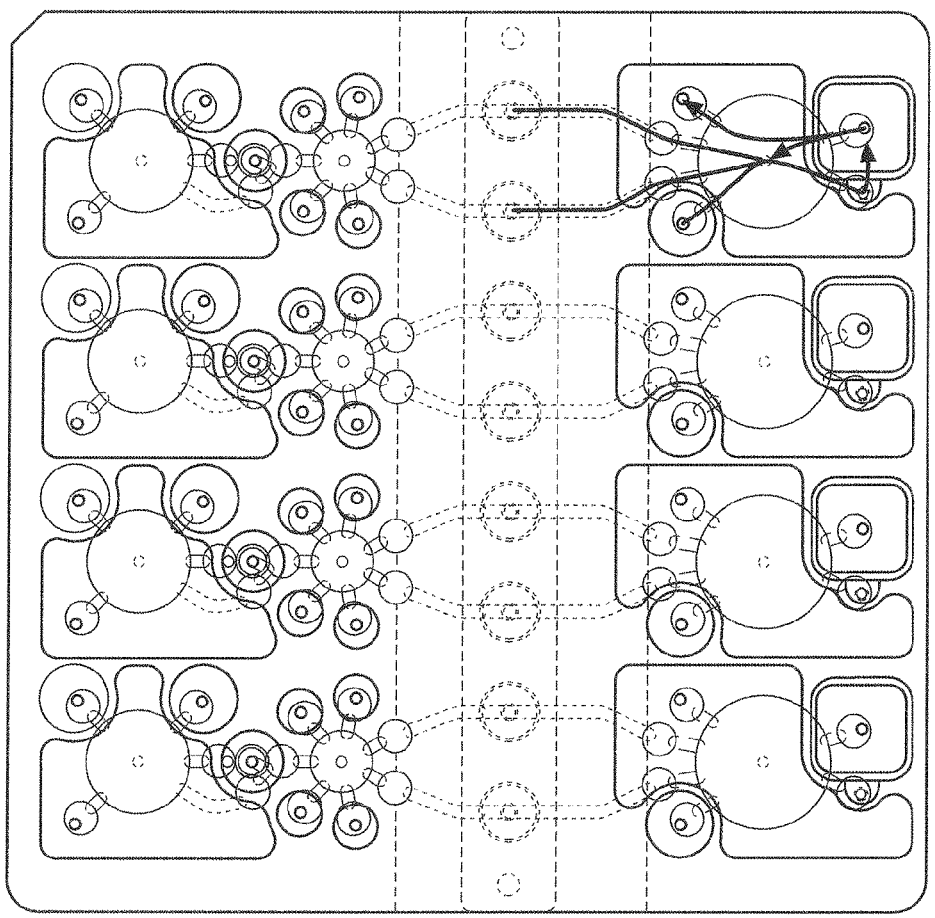

In FIG. 10I, the contents of amplification reactors 31 (left and right) are pumped on top of the analysis membrane 47 in analysis reservoir 41 and circulated multiple times, which provides sufficient contact between the amplicons and the targets attached to the analysis membrane 47. When satisfactory hybridization has occurred, the contents are pumped to waste reservoir 42. Wash buffer is dispensed into common reagent reservoir 40 and pumped on top of the analysis membrane 47 suspended in analysis reservoir 41, then pumped to waste reservoir 42 (repeat multiple times).

Figure 10J:
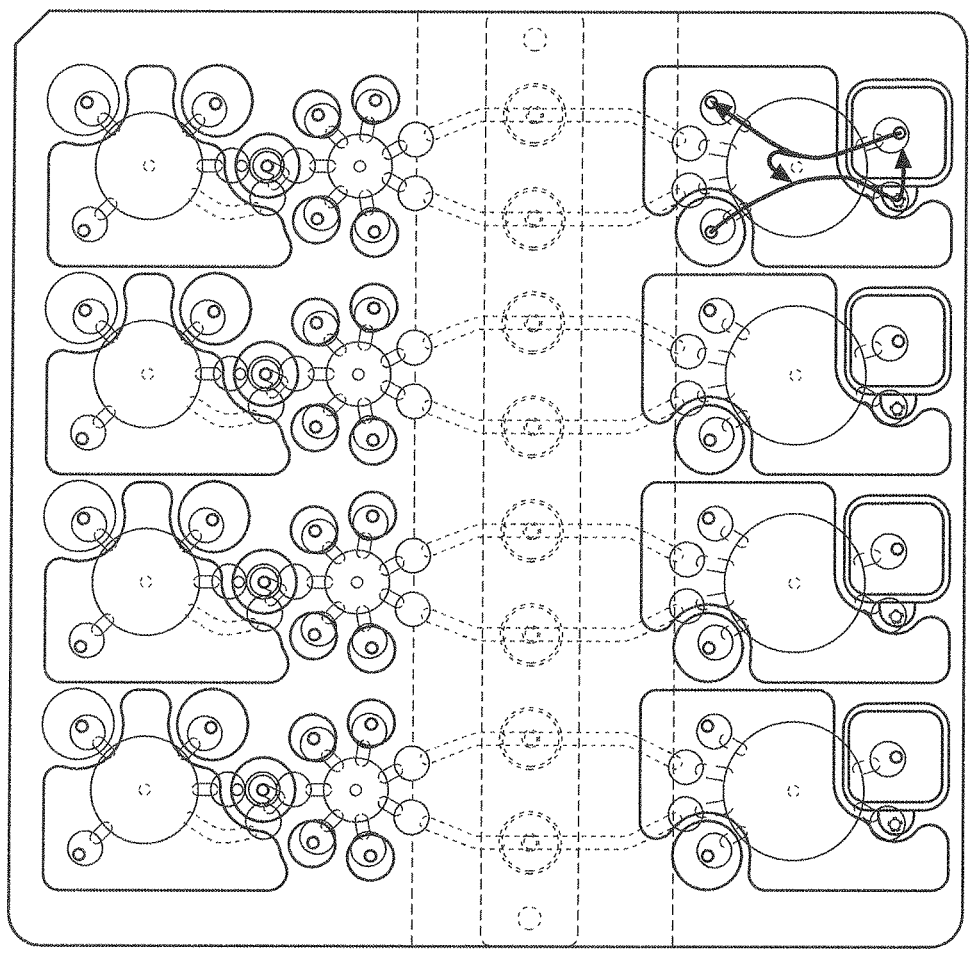

Next per FIG. 10J, dispense an appropriate amplicon visualization reagent (e.g., horseradish peroxidase ("HRP")) into common reagent reservoir 40 and pump on top of analysis membrane 47 suspended in analysis reservoir 41 and circulate until the reaction is satisfactorily complete; then pump the contents to waste reservoir 42. Dispense wash buffer into common reagent reservoir 40 and pump on top of the analysis membrane 47 suspended in analysis reservoir 41, and pump to waste reservoir 42 (repeat multiple times).

Figure 10K:
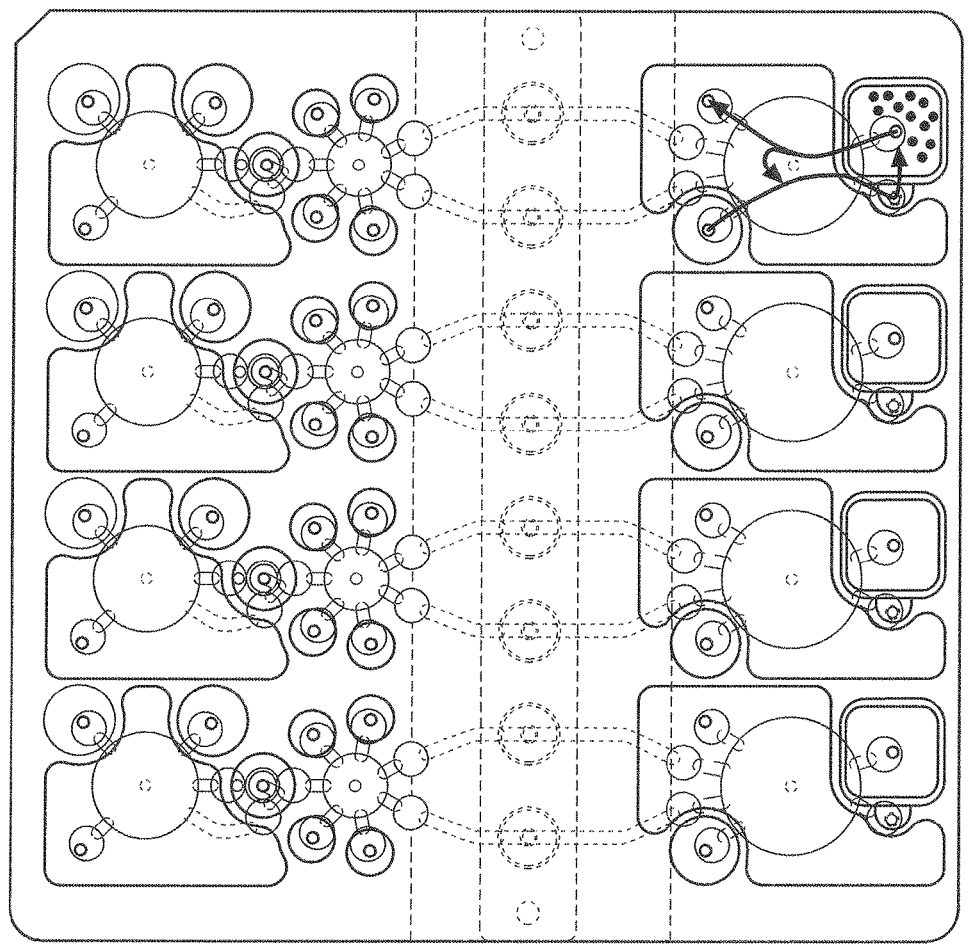

Per FIG. 10K, dispense a visualization reagent reactant (e.g., tetramethyl benzidine "TMB") into common reagent reservoir 40 and pump on top of the analysis membrane 47 suspended in analysis reservoir 41; circulate as described above to completely react the reagents (e.g., TMB with the HRP), and pump the contents to waste reservoir 42. Dispense wash buffer into common reagent reservoir 40 and pump on top of the analysis membrane 47 suspended in analysis reservoir 41, and pump to waste reservoir 42 (repeat multiple times). Finally, position the camera 27 on dispensing system 13 over the analysis membrane 47 suspended in analysis reservoir 41 and record the image. The image data is then processed by control system 19 and the results communicated to the operator.

Figure 11:
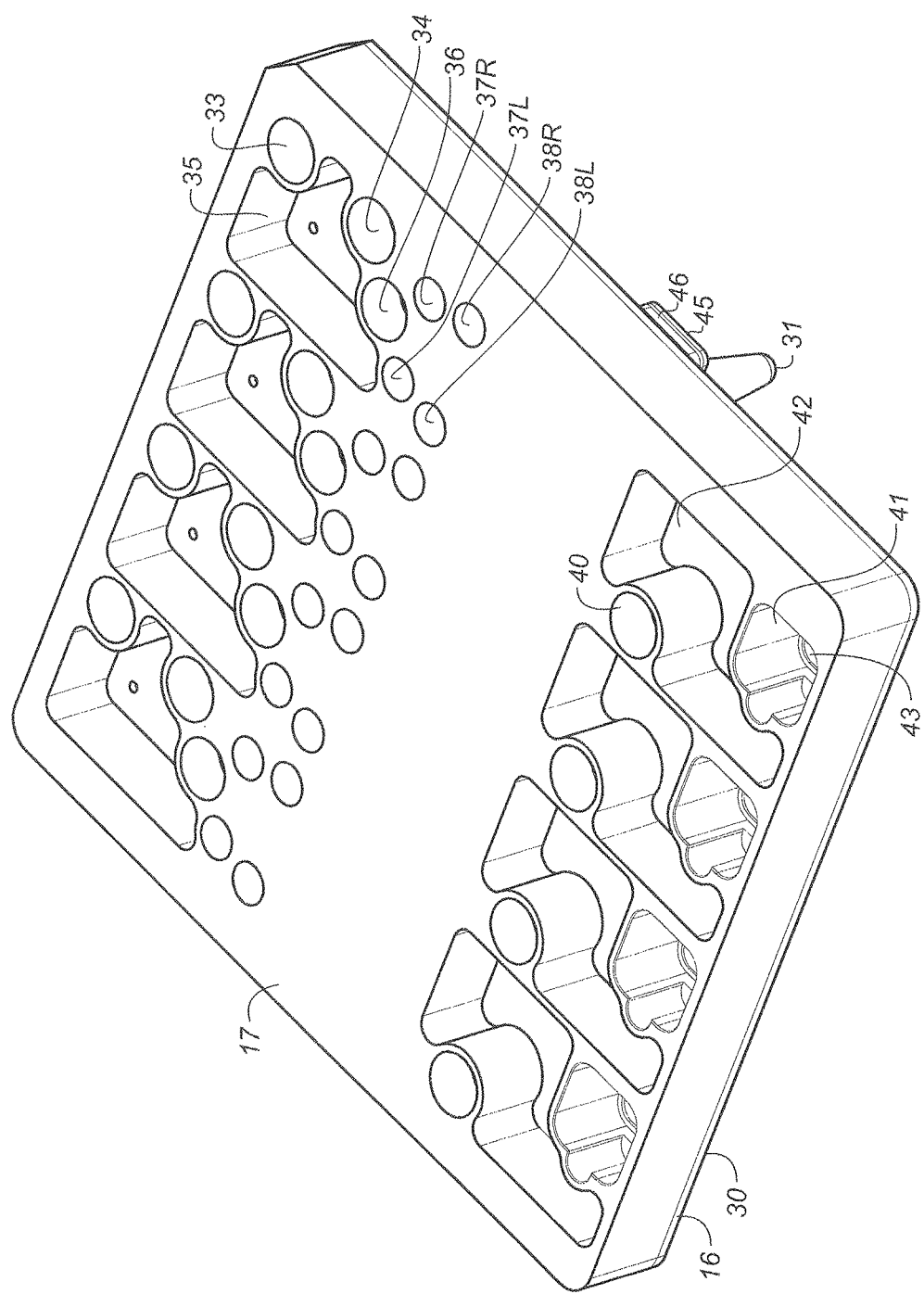
FIG. 11 shows a perspective view of a "four assay unit" component including the reservoir layer, the fluidic transport layer including a film layer, and an amplification reactor, according to an exemplary aspect of the invention.

FIG. 11 illustrates a perspective view of a "four assay unit" arrangement of a CARD including the reservoir layer 17, the fluidic transport layer 16 including the film (non-elastomeric membrane or diaphragm) layer 30, and one of the amplification reactors 31 with its attachment system 45, 46 as well as a portion of a perforated securing ring 43 used to suspend the analysis membrane 47 in analysis reservoir 41. More particularly, each exemplary 'quad' CARD has four microarray analysis reservoirs 41 (FIGS. 9, 11), which include a microarray analysis membrane 47 removeably disposed therein. An exemplary analysis membrane 47 is made of nylon, nitrocellulose, PVDF or any other appropriate material known in the art. The analysis reservoir 41 has a support platform on the bottom of the reservoir or a shelf or shoulder extending about the bottom inner perimeter thereof. A perforated, segmented, or indented securing ring may be used to secure the membrane in the analysis chamber. FIG. 13B shows an exemplary perforated securing ring 43 having channels 1708 for transporting fluid from within the analysis reservoir over the perimeter of the membrane to the bottom of the reservoir and then to outside of the reservoir. In an aspect, two securing rings 43 may be used to sandwich the membrane 47 therebetween or as illustrated a support platform slightly smaller than the membrane but not smaller than the inner dimension of the perforated ring 43 may be used to hold the membrane.

Figure 12:
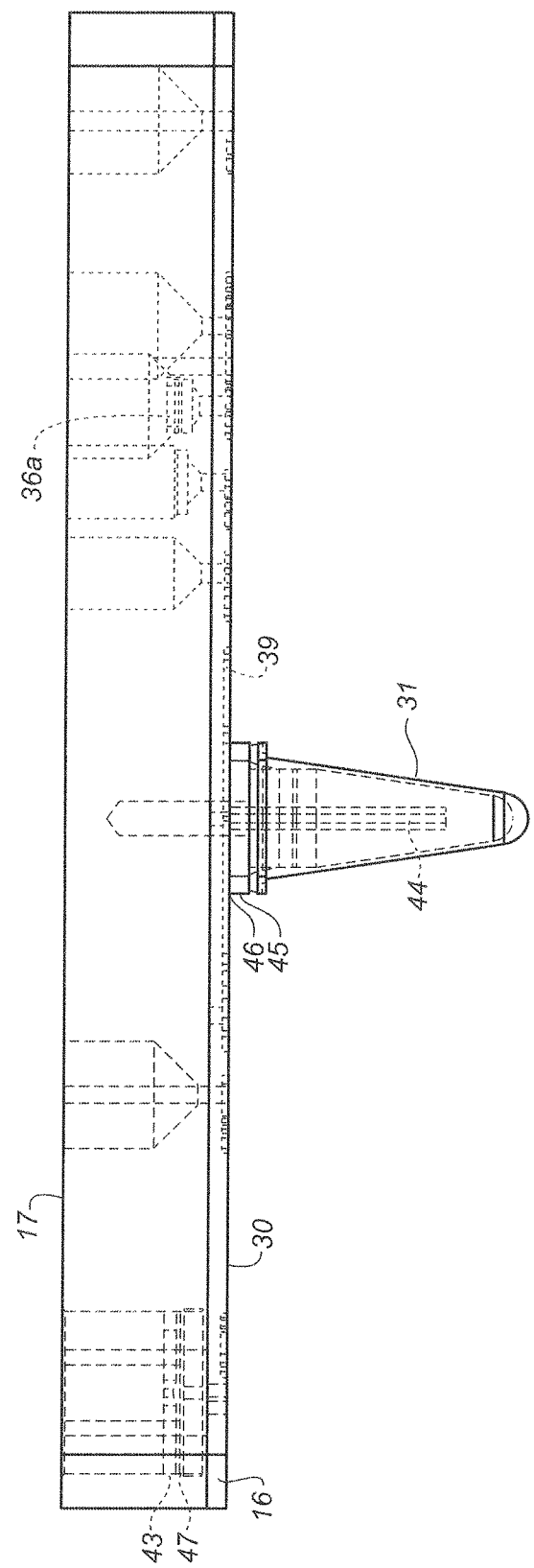
FIG. 12 shows a cross sectional side view of the "four assay unit" component shown in FIG. 11, according to an exemplary aspect of the invention.

FIG. 12 illustrates a side view of an "assay unit" including the reservoir layer 17, the fluidic transport layer 16 including the film layer 30 bounding the channels 39, and one of the amplification reactors 31, which includes a lumen 44 used to fill and empty the amplification reactor.

During a PCR reaction, for e.g., an aqueous solution may be repeatedly (20-50 times) cycled from low temperatures of approximately 30° C. to higher temperatures of approximately 95° C. In order to prevent the aqueous solution from losing volume due to evaporation or condensation, for e.g., on the tube's side above the bulk solution, it is advantageous to seal the exposed surface of the solution so that the reaction does not fail due to lack of sufficient solution volume or changes in reaction concentration from an unsealed environment.

To prevent the evaporation or uncontrolled condensation, wax, silicone, mineral oil, or some other substance may typically be introduced over the top of the solution to prevent evaporation; however, the use of these materials has certain disadvantages. For example, mineral oil is a liquid at room temperature and, therefore, for certain automatic systems it produces handling problems. Wax is a solid at room temperature and for automatic systems its melting temperature is very controllable, but wax often impedes the more desirable complex PCR reactions. Silicone, like mineral oil, is a liquid at room temperature, so it has similar handling problems but it does not impede PCR reactions.

For automatic PCR systems, it would be particularly advantageous to have a substance that could cover the solution automatically when the PCR reaction tube (e.g., 31, FIG. 11, 12) is filled. For example, a controlled mixture of high purity silicone oil with a small amount (a few %) of wax as an additive may be used. In an exemplary aspect, the mixture consists of wax=1% to 20% and silicone oil=99%-80%. According to an aspect, the mixture consists of approximately 5% wax and 95% silicone oil. The wax may be standard PCR wax (e.g., Sigma Aldrich paraffin wax with melting point of 58-62 degrees C.). The mixture is a solid at room temperature and expected storage temperatures. The mixture may be placed as a layer of material on the upper inside surface of the PCR tube (31) just below the opening of the tube and above the bottom opening of the lumen 44. When the temperature increases during the first thermocycle is performed after the analyte is introduced to the tube, the mixture melts and covers the surface of the solution preventing evaporation while at the same time it does not have an impeding effect on the reaction. Upon completion of the reaction the reactants can be removed from underneath the seal via the lumen (44, FIG. 12) either before or after the mixture re-hardens upon reducing the temperature in the amplification reactor below the melting point of the mixture. In an aspect, the mixture is allowed to cool forming a solid cap over the solution and the lumen 44 withdraws the solution from below the solidified layer.

Figure 13A:
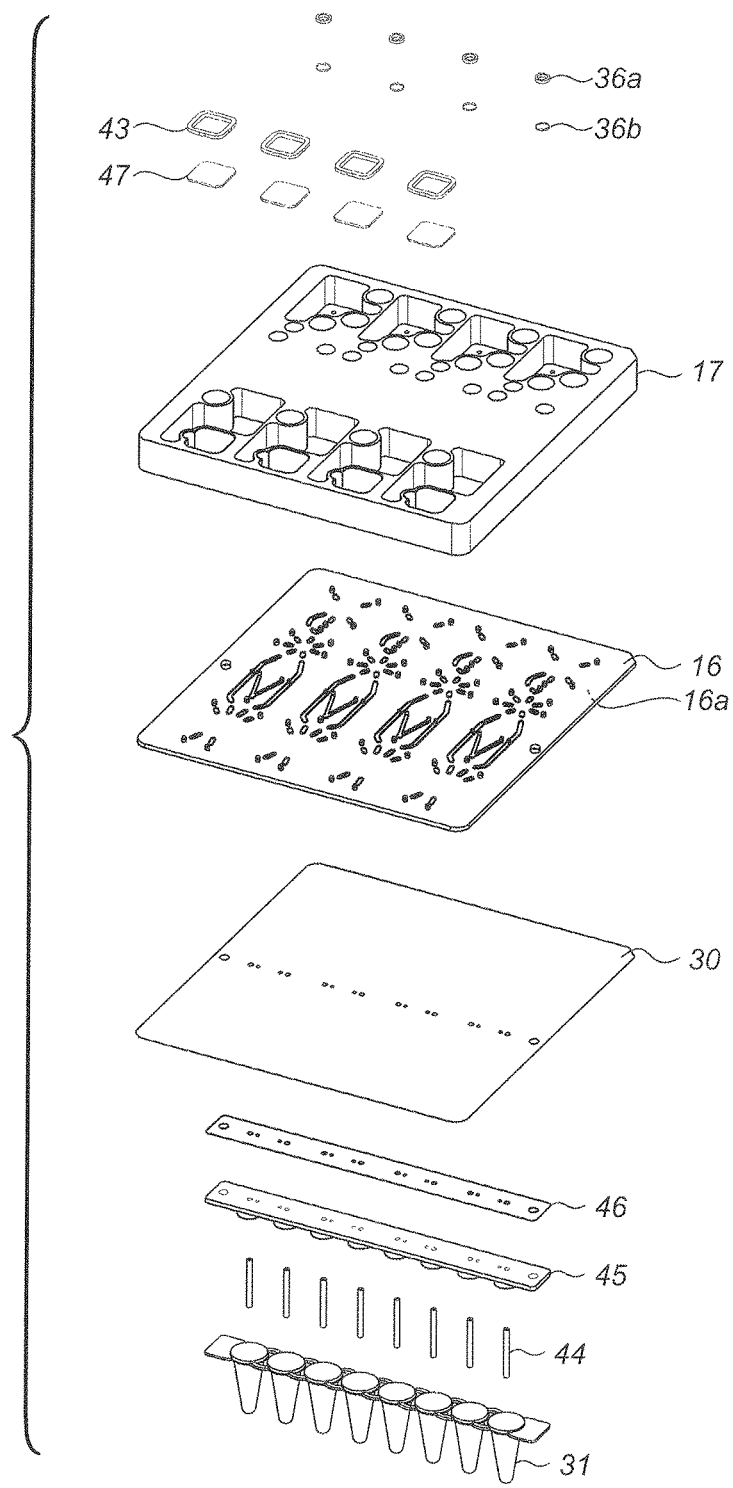
FIG. 13A shows an exploded view of an exemplary "four assay unit" component including the reservoir layer, the fluidic layer, the film layer, the amplification reactors including lumens which are used to fill and empty the amplification reactors, a perforated ring and membrane system for the analysis reservoir, a silica filter and a perforated retaining ring, according to an exemplary aspect of the invention.
Figure 13B:
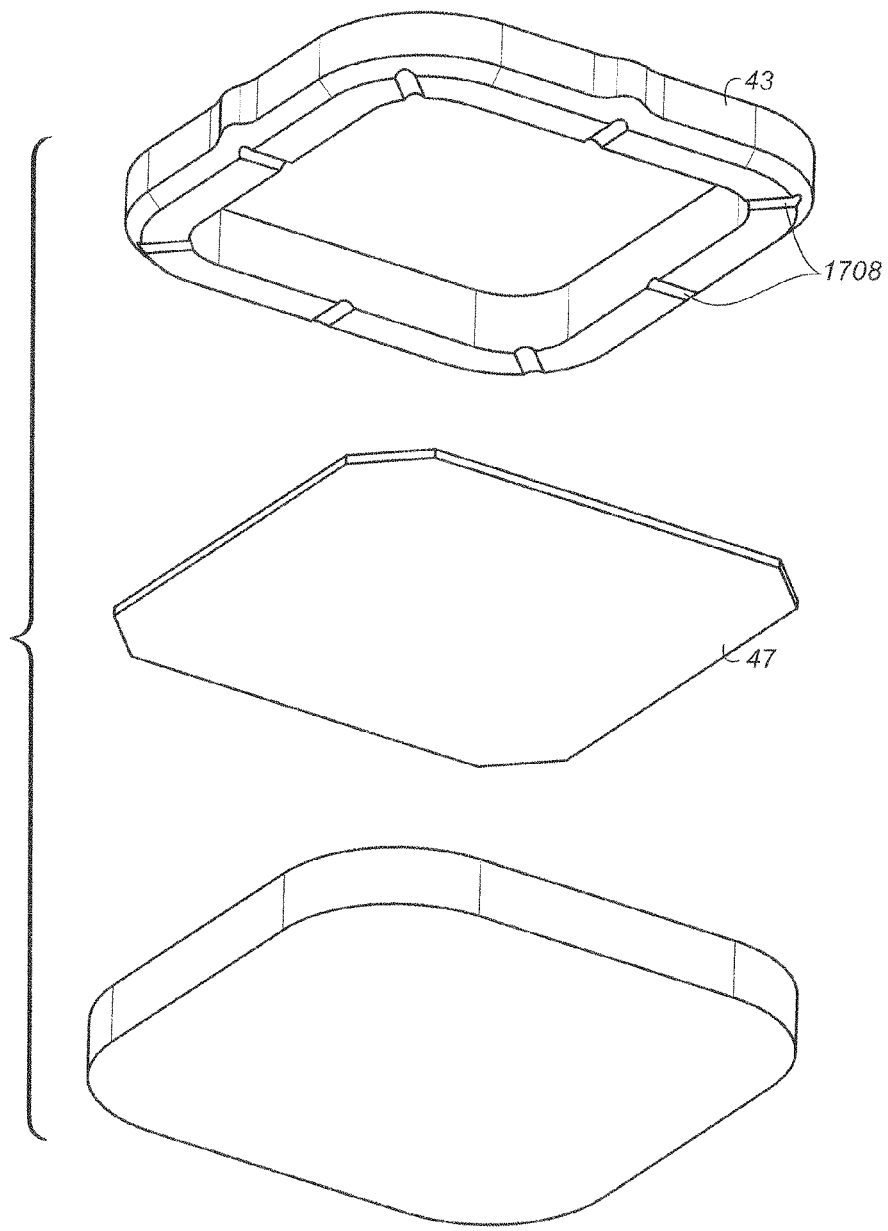
FIG. 13B shows an exemplary perforated ring with its flow channels, an analysis membrane and a membrane support structure; according to an exemplary aspect of the invention.

FIG. 13A illustrates an exploded view of a "four assay unit" CARD including the reservoir layer 17, the fluidic transport layer 16 including its film layer 30, and the amplification reactors 31, which include lumens 44 used to fill and empty the amplification reactors. The illustration also shows silica filter holders 36a, the silica filters 36b for the silica filter reservoirs 36 and the perforated securing rings 43 used to suspend the analysis membranes 47 in the analysis chambers.

Figure 14A:
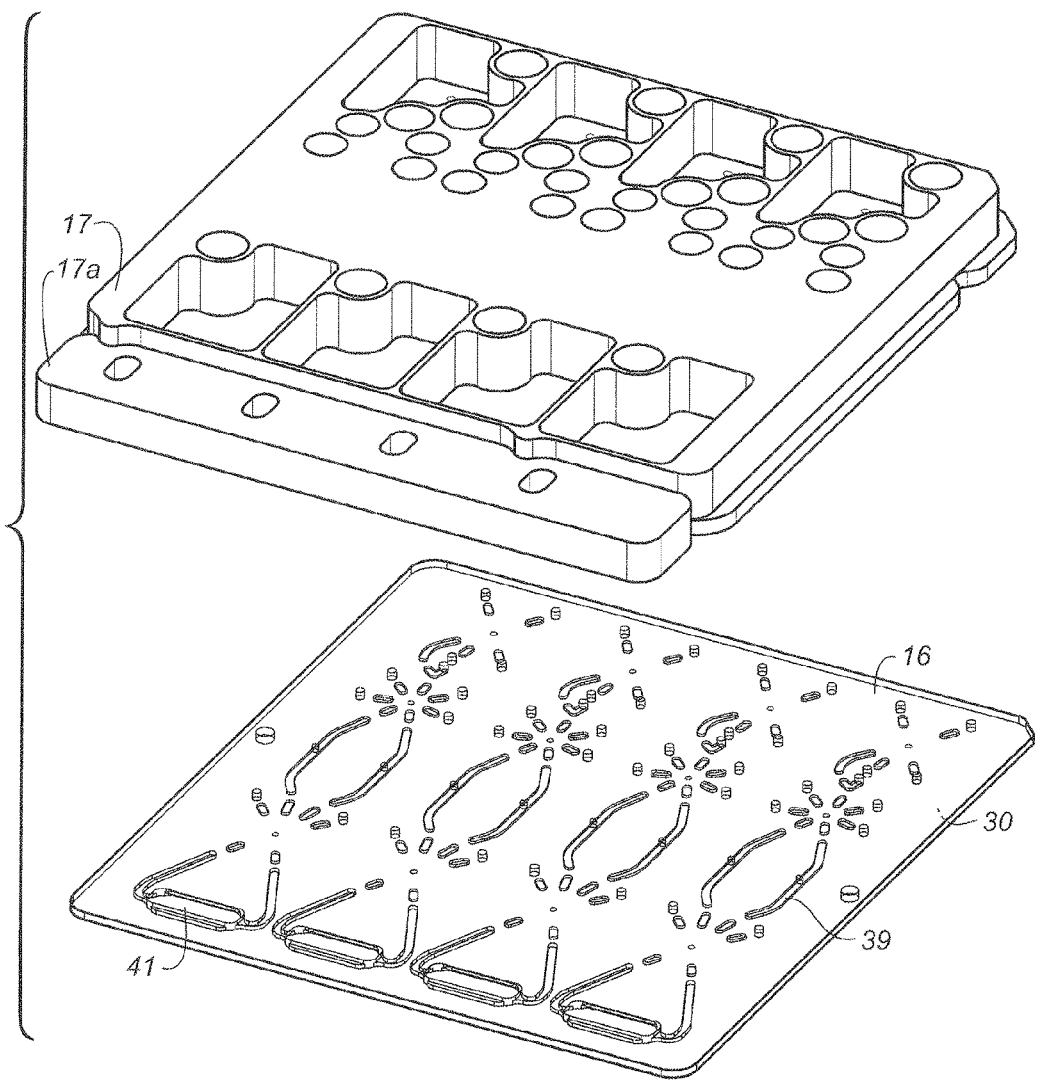
FIG. 14A shows a perspective view of an alternative embodiment of the reservoir layer for the analysis area of a "four assay unit" component including a covered and vented component for the analysis reservoirs that does not employ the perforated ring assembly to hold the analysis membrane, according to an exemplary aspect of the invention.
Figure 14C:
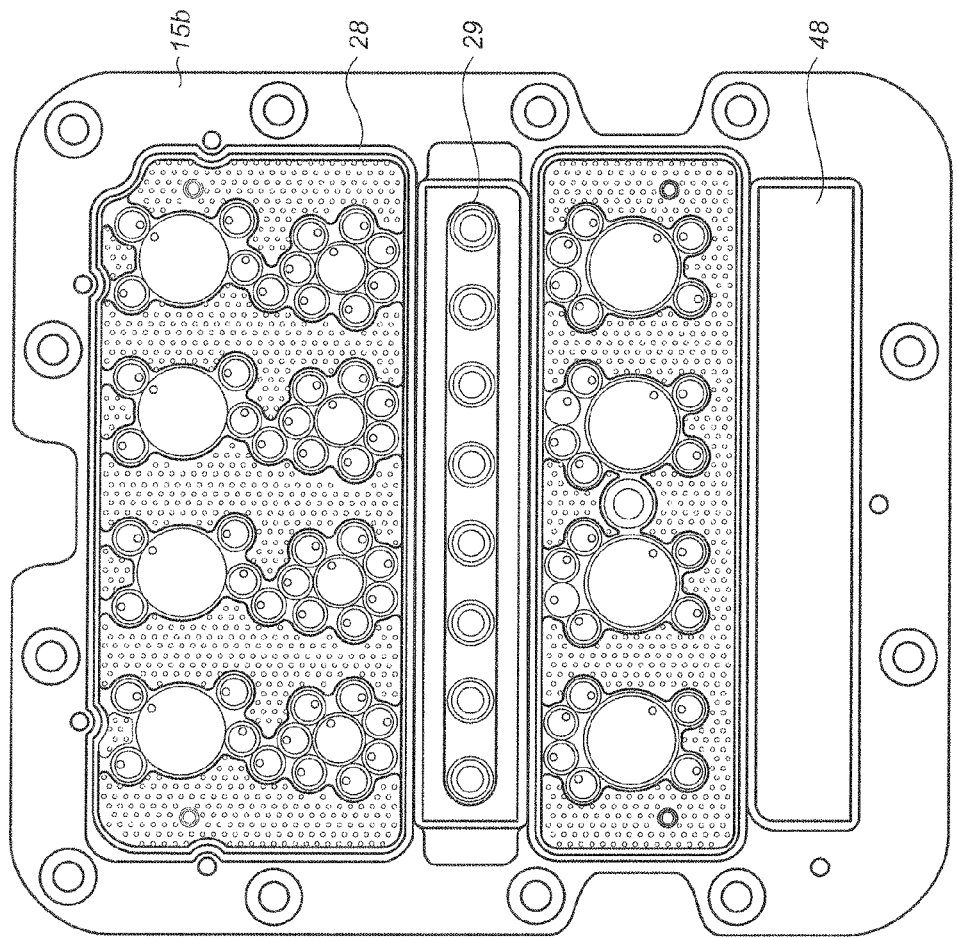
FIG. 14C shows a cross sectional top plan view of a four assay unit arrangement of the top gasket layer of the pneumatic manifold, the heaters that engage the amplification reactors and the heaters that engage the under surface of the analysis reservoirs, according to an exemplary aspect of the invention.

FIG. 14A-D illustrate an alternative arrangement of a portion of the analysis area of reservoir layer 17 and the fluidic transport layer 16 to which it is attached. The alternative arrangement is used to cover the analysis membrane 47 in order to improve contact between the circulating amplicons and the target molecules on the analysis membrane 47 in the analysis reservoir 41. The cover may be vented to allow air bubbles to escape from analysis reservoir 41. The arrangement also allows for efficient heating of the analysis reservoir 41 by eliminating the step or platform used in the perforated ring arrangement 43 previously illustrated. In the alternative arrangement the analysis membrane sits directly on the film layer 30 which in turn is disposed directly over a heating element 48*a*. Heat applied during an analysis reaction is often an important step in an assay. The covered system also allows for a different arrangement of the channels supplying and emptying the analysis reservoir. In the alternative arrangement since the membrane is on the very bottom of the reservoir the fluid can be washed over the top of the membrane 47 in an alternating pattern. In order to keep the membrane settled on the film layer that constitutes the bottom of the reservoir an overhang is fabricated in substrate layer 16*a* of analysis reservoir 41 and as shown in FIG. 14B channel openings are fabricated under the overhang at each end of the analysis reservoir 41. The analysis reservoir 41 is also fabricated so that it is longer than it is wide which combined with the channel openings onto each end allows for an efficient flow over the length of the analysis membrane and further combined with the cover allows for improved contact of the fluid with the surface of the analysis membrane allowing the amplicons in the fluid to more efficiently hybridize with their targets attached to the analysis membrane. The arrangement is further improved by allowing for alternating directions that the fluid can pass over the membrane by circulating the fluid alternatively clockwise and then counterclockwise using the pumps and channels of the fluidic transport layer 16. FIG. 14C illustrates an exemplary four assay unit alternative pneumatic manifold 15 and gasket layer 28 that corresponds to the alternative arrangement of the analysis area describe in 14A and 14B. Note the second heater 48*a* located on the pneumatic manifold 15 underneath the analysis reservoir 41.

Figure 14D:
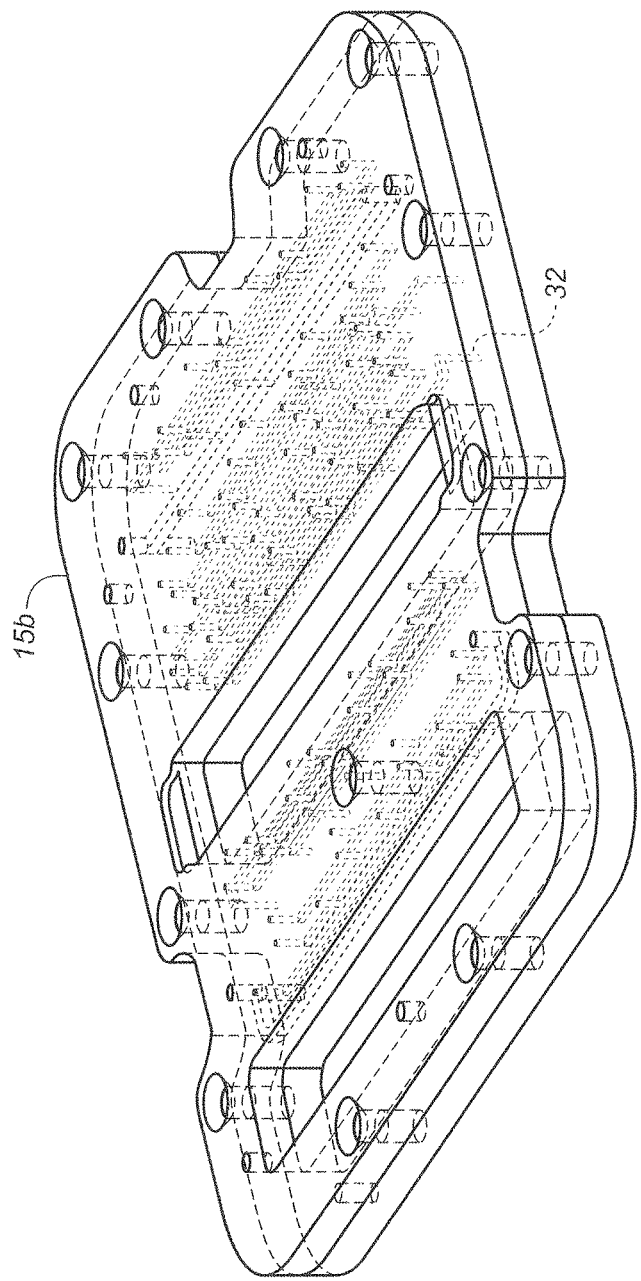
FIG. 14D shows the internal pneumatic channels of the upper layers of the pneumatic manifold showing how the pneumatic signals introduced into the bottom layer of the pneumatic manifold from the pneumatic supply system are further split and addressed to particular gasket layer voids on the surface of the pneumatic manifold.

FIG. 14D illustrates the internal pneumatic channels 32 of pneumatic manifold layer 15*b* showing how the pneumatic signals introduced into the bottom layer of 15*a* from the pneumatic supply system 18 are further split and addressed to particular gasket layer 28 voids on the surface of 15*b*.

Figure 15A:
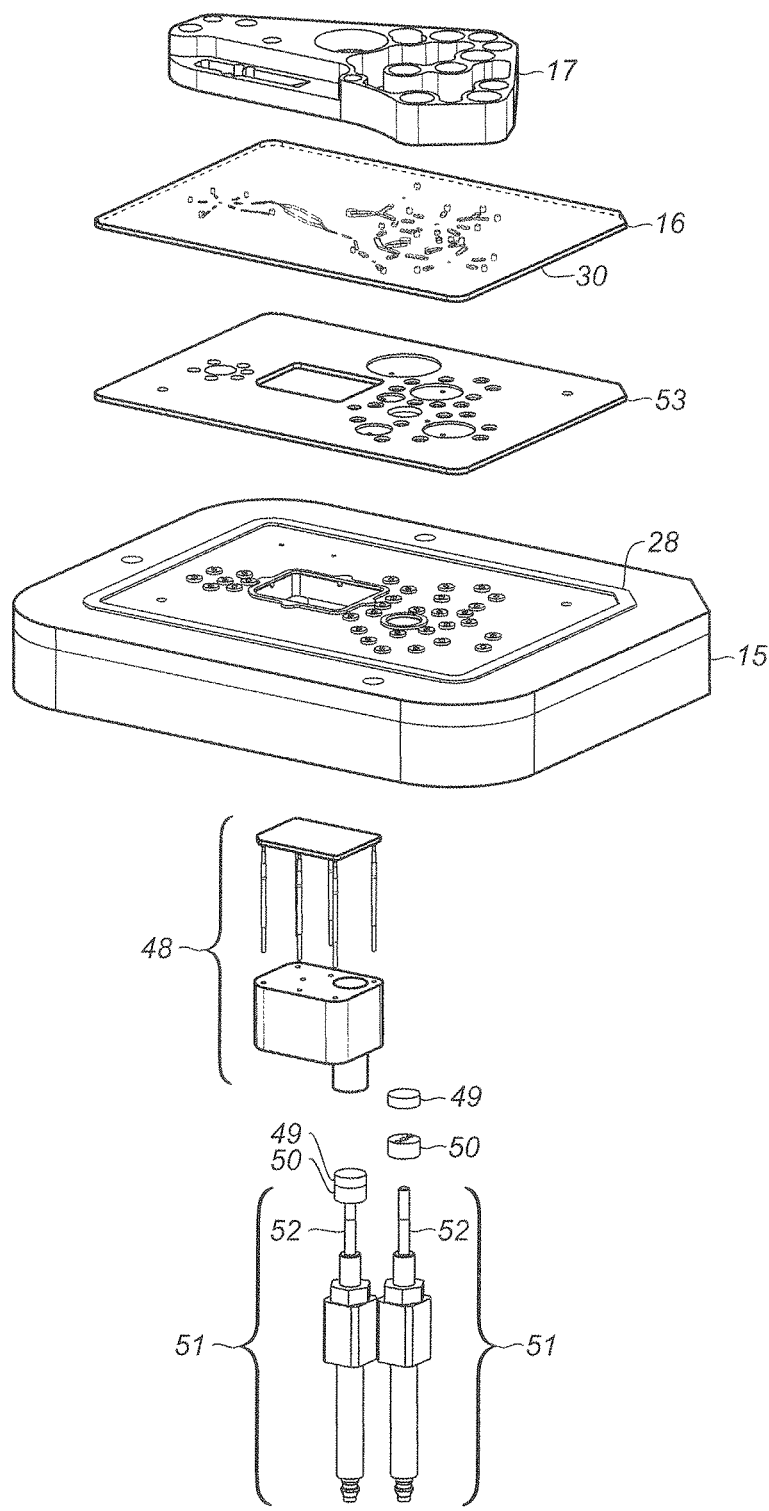
FIG. 15A shows an exploded perspective view of a single assay unit of a pneumatic manifold, incorporating pneumatically-activated magnets and a multipurpose heater, as well as an optional diaphragm layer for the interface between the fluidic layer and the pneumatic manifold, according to an exemplary aspect of the invention.

FIG. 15A illustrates an exploded perspective view of an exemplary single assay unit of a pneumatic manifold 15, incorporating pneumatically activated magnet assemblies 51 and a multi-purpose heater 48 coupled thereto, for preparative, amplification, and analysis reaction needs. The figure also includes an optional diaphragm layer 53 for the interface between the fluidic transport layer 16 and the pneumatic manifold 15. The illustrated system can be "numbered up" (e.g., "Quad CARD®") and attached to a pneumatic supply system 18 to operate multiple assay units in parallel or in random order as instructed by the control system 19. The illustrated system provides for the use of magnetism when required during an assay for the manipulation of ferrous, magnetic, or paramagnetic particles as required by any particular assay. In practice the particle required may be introduced into a particular reservoir on reservoir layer 17 by the dispenser system 13 and combined with the sample during certain steps of the assay. Alternatively, the particles may be included with the sample prior to its loading into the sample input reservoir 33 or, alternatively still, the particles may be pre-loaded into a reservoir or a channel during the manufacture of the fluidic transport layer 16 or the reservoir layer 17.

The sample with the particles in mixture may be pre-loaded in a reservoir or a channel located over a pneumatic piston assembly (alternatively the piston assembly may be motor or electromagnetically activated) 51 or the sample/particle mixture may be pumped to a reservoir or channel located over a pneumatic piston assembly (alternatively the piston assembly may be motor or electromagnetically activated) 51. In either case, the reservoir or channel over the pneumatic piston assembly (alternatively the piston assembly may be motor or electromagnetically activated) 51 may be subjected to a magnet 49, located on a magnet holder 50 fixed on the end of a piston rod 52 of the pneumatic piston assembly (alternatively the piston assembly may be motor or electromagnetically activated) 51 by providing positive pressure to the cylinder of the pneumatic piston assembly (alternatively the piston assembly may be motor or electromagnetically activated) 51, which then directs the magnet into place just under heated reservoir 55, or non-heated reservoir 56, or a channel containing the sample/particle mixture. When magnetism is delivered to the site with the sample/particle mixture, the assay then takes advantage of the particles' magnetic properties to carry out particular assay requirements; e.g., using the particles for a particular concentration step of biological material attracted to the particle or other common particle dependent assay step known in the art.

Alternatively or in combination, the pneumatically-actuated magnet systems 51 may be incorporated into a region of the pneumatic manifold 15 so that the particles and sample in progress may undergo a heating event in conjunction with a magnetism event. An example of such a case is to use the particles to concentrate an organism out of a larger sample volume. In the case where the organism is alive when it is captured, it can then be subjected to a heating event to cause the organism to express RNA that it would not normally express or that it could not express if it were dead. After the heating event, the magnetism is removed by subjecting the cylinder of the pneumatic piston assembly (alternatively the piston assembly may be motor or electromagnetically activated) 51 to negative pressure, thus withdrawing the magnet 49 from a location underneath heated magnetic reservoir 55, and pumping the solution with the particles and the concentrated sample with the organism to another location in order to proceed with extracting the RNA from the organism, and further amplifying the extracted RNA and analyzing the resulting amplicons in a manner consistent with the process described above.

FIG. 15A also illustrates the opportunity to provide heat in a reservoir 54 separate from the amplification reactor 31 in order to denature amplicons prior to analyzing the amplicons, incubate a labeling reaction or otherwise improve the process of a particular reaction. It further illustrates an alternative manner for locating the amplification reactor. Although this illustration does not provide an amplification reactor in a tube and lumen 44 arrangement as earlier described, there is no reason that such a tube and lumen 44 arrangement cannot be utilized with the pneumatic piston assemblies 51 described above. As shown, the interface between the pneumatic manifold 15 and the fluidic transport layer 16 includes an optional diaphragm layer 53 in place of the gasket layer 28 discussed above. The diaphragm layer serves the same function of providing an isolated space for the film layer 30 to deflect into when negative pressure is applied to the unbonded region of the film layer 30 by the pneumatic manifold 15 from pneumatic signals routed through the pneumatic channels 32 of the pneumatic manifold 15 attached to the pneumatic supply system 18 under the instructions of control system 19.

Figure 15B:
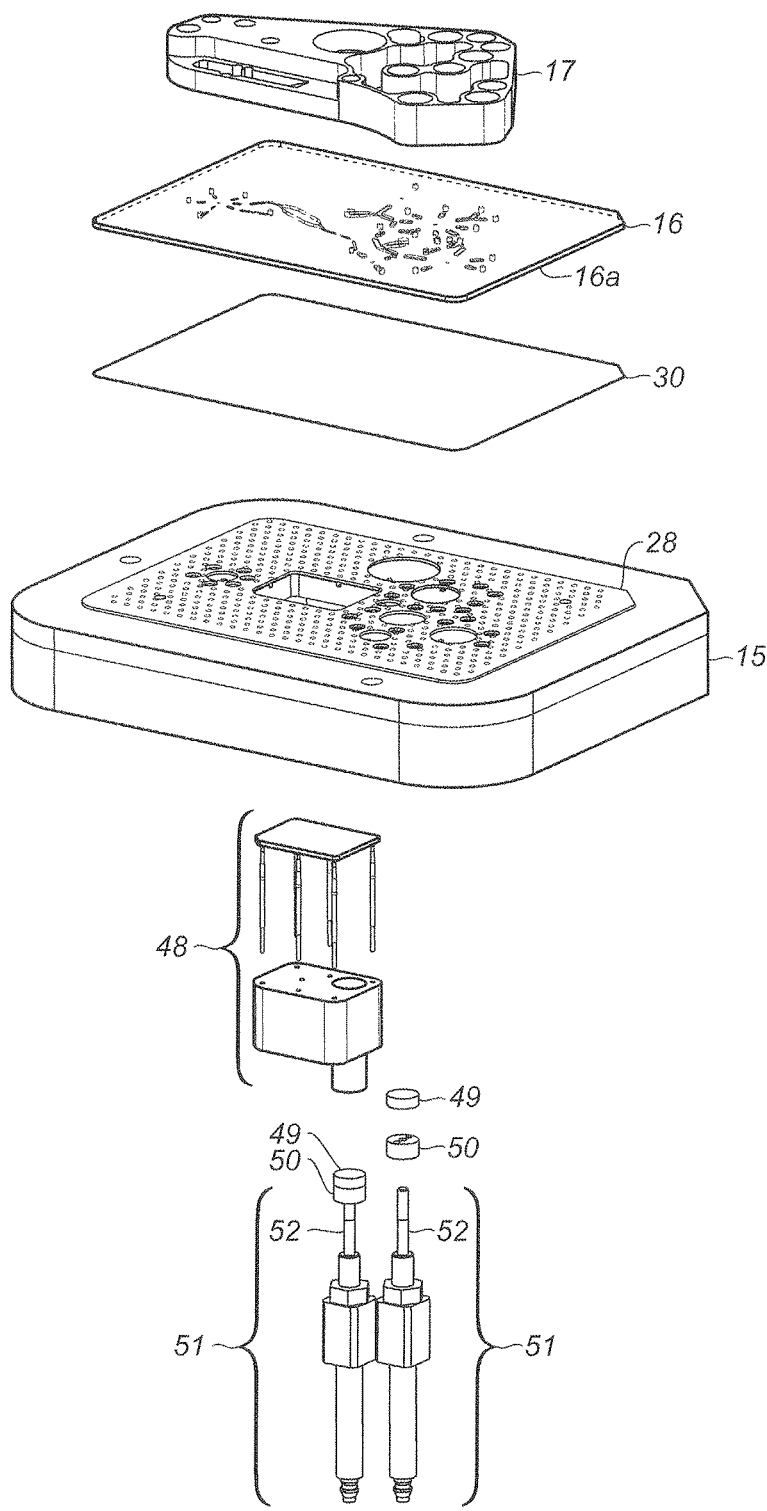
FIG. 15B shows an exploded perspective view of the single assay unit shown in FIG. 15A including a thin film layer of the fluidic transport layer and a gasket layer on the pneumatic manifold, according to an exemplary aspect of the invention.

FIG. 15B illustrates the same elements as FIG. 15A although without the diaphragm layer. Therefore the gasket layer 28 serves the function as described in FIG. 7 above and the fluidic transport layer 16 interfaces directly with the pneumatic manifold 15. The arrangement without the diaphragm layer is advantageous since the manufacturing and the material costs in both cases are lower in the absence of the diaphragm layer while the performance of assays on the system is no different.

Figure 16:
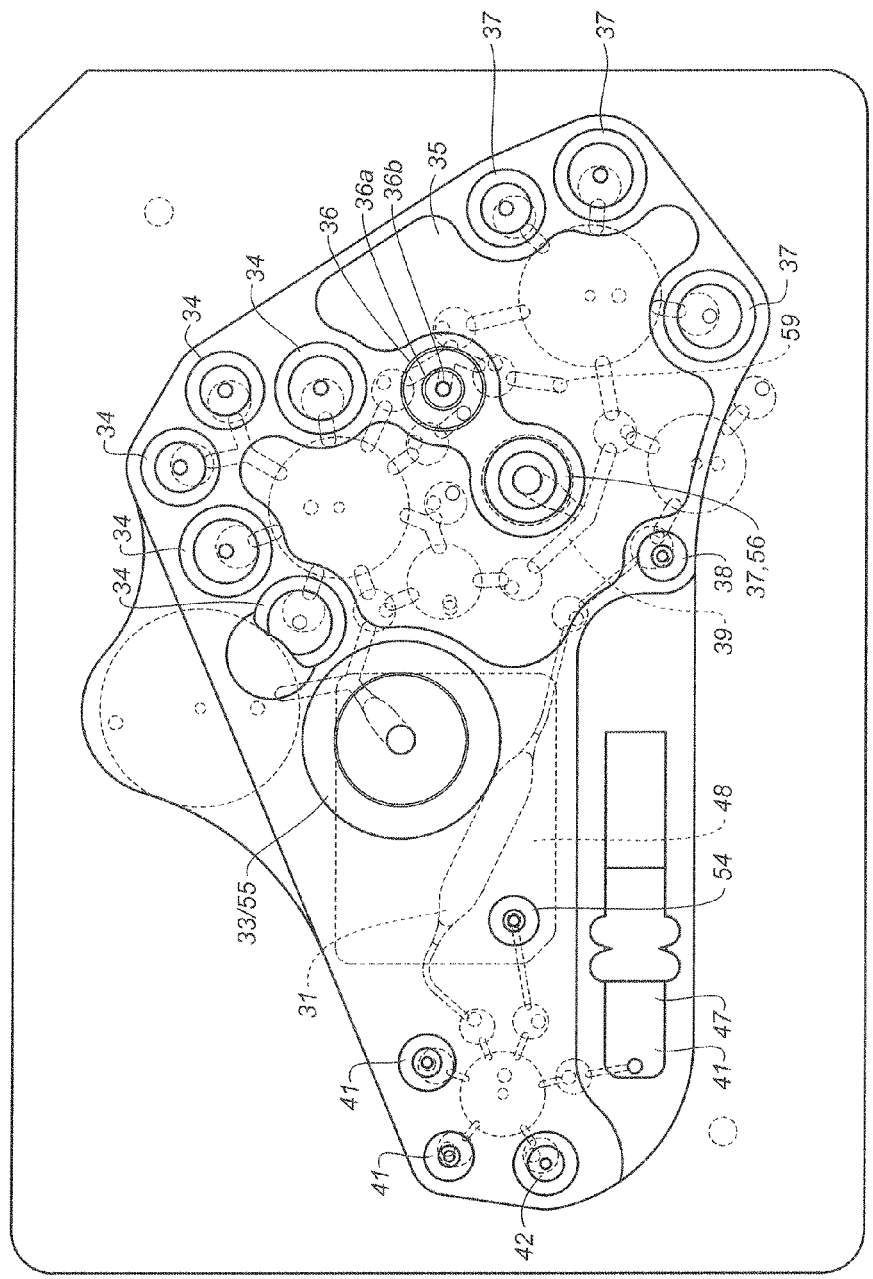
FIG. 16 shows a layered, cross sectional top plan view of a "single assay unit" arrangement of the reservoirs, fluidic channels and amplification reactor, which are a combination of the fluidic transport layer and the reservoir layer, according to an exemplary aspect of the invention.

FIG. 16 illustrates a view of a single assay unit for improved rapid detection of sparse targets, non-viable and viable water-borne organisms, and shows functional structures including pneumatically activated magnets 51 and multiple heated reaction sites, as well as the arrangement of reservoirs and channels employed by the system. In particular, the system illustrates how the pneumatic manifold 15 can be arranged in combination with the fluidic transport layer 16 and its attached reservoir layer 17 so that heat can be delivered to different steps of an assay. In the specific case, heat can be employed in a preparative step in heated magnetic separation/concentration/reaction reservoir 55 (where magnetism can also be selectively employed as desired in conjunction with heating in reservoir 55). Following optional heating, the sample is transported through the fluidic transport layer 16 for further preparative steps of an assay. Following the extraction of DNA or RNA as required by an assay, the extracted DNA or RNA is then combined with the amplification master mix and transported through the fluidic transport layer 16 to the amplification reactor 31. As illustrated in FIG. 16, the reactor is in the plane of the fluidic transport layer 16, though it may also employ a reactor configured as in FIGS. 11, 12 and 13 out of the plane of the fluidic transport layer 16. After the amplicons are produced in the amplification reactor 31, they can be transported to the heated analysis reactor 54 where they can be heated in order to denature and/or label them, or a combination of requirements that may require heating. The amplicons are then transported to the analysis reservoir 41 (which also can be configured for heating) for completion of the assay.

Figure 17A:
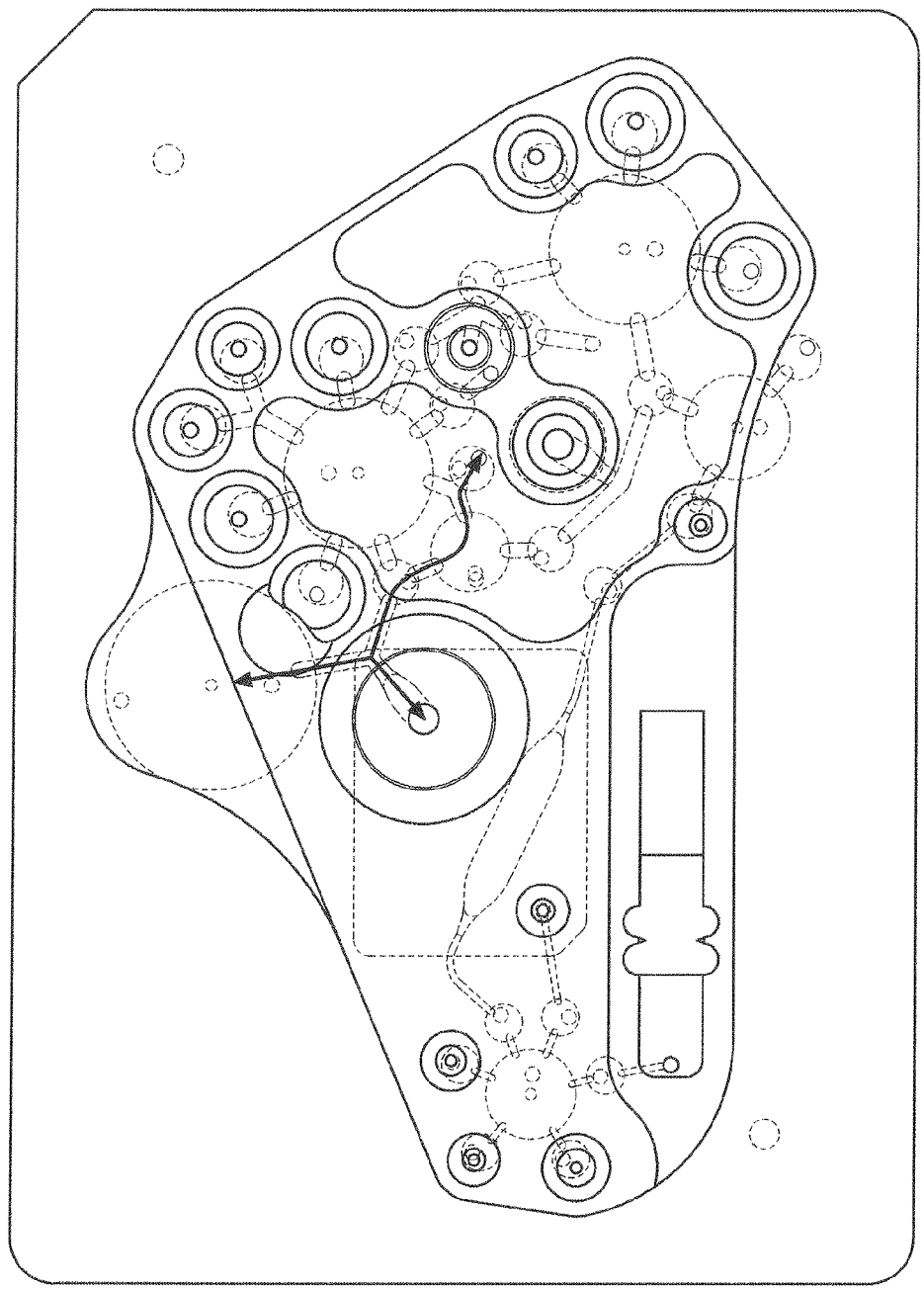
FIGS. 17A-O show layered, top views of exemplary process stages using the channels, reactors, and reservoirs in the combined fluidic transport layer and the reservoir layer when operated by the pneumatic manifold, according to illustrative aspects of the invention.
Figure 17B:
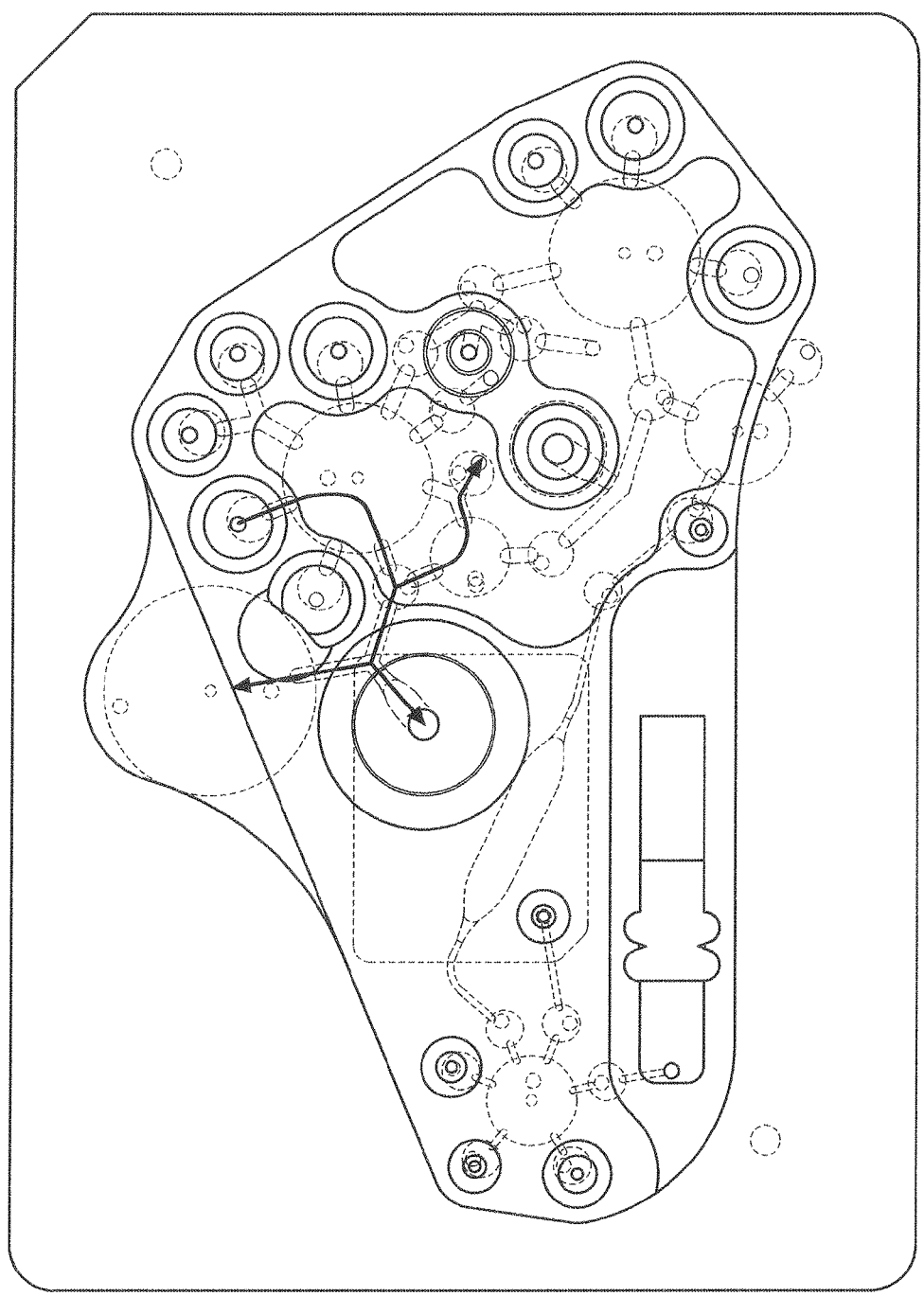
Figure 17C:
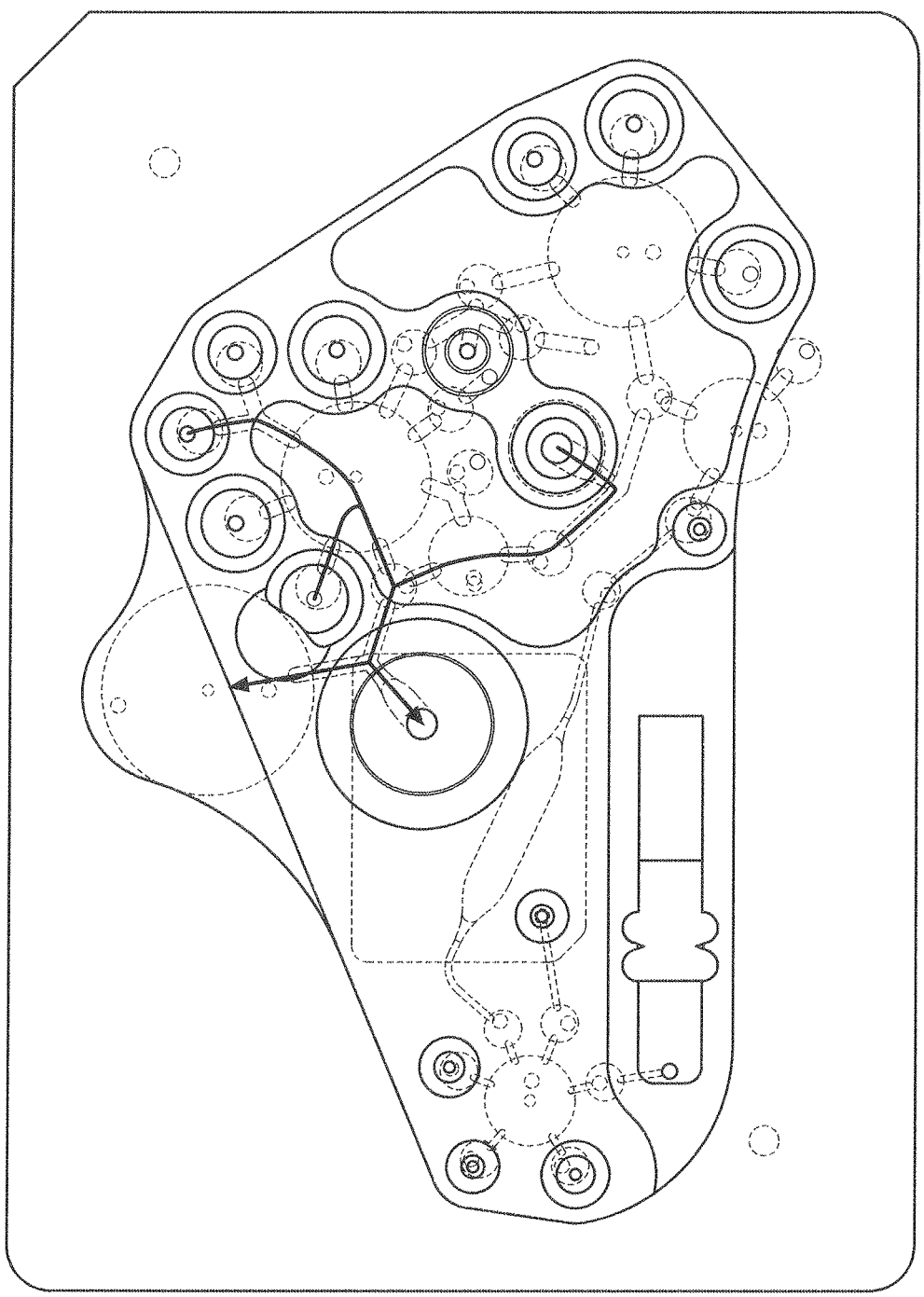
Figure 17D:
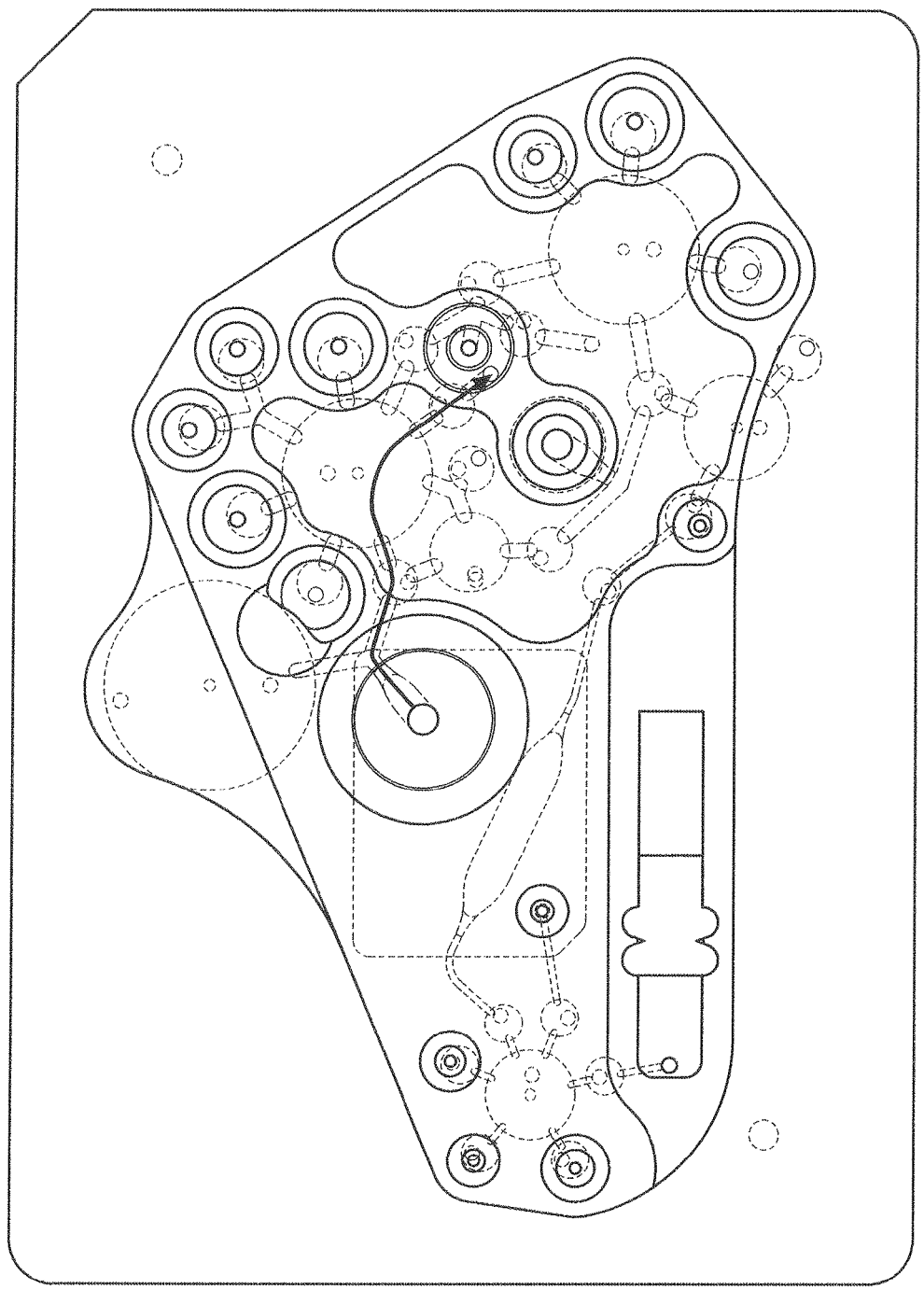
Figure 17E:
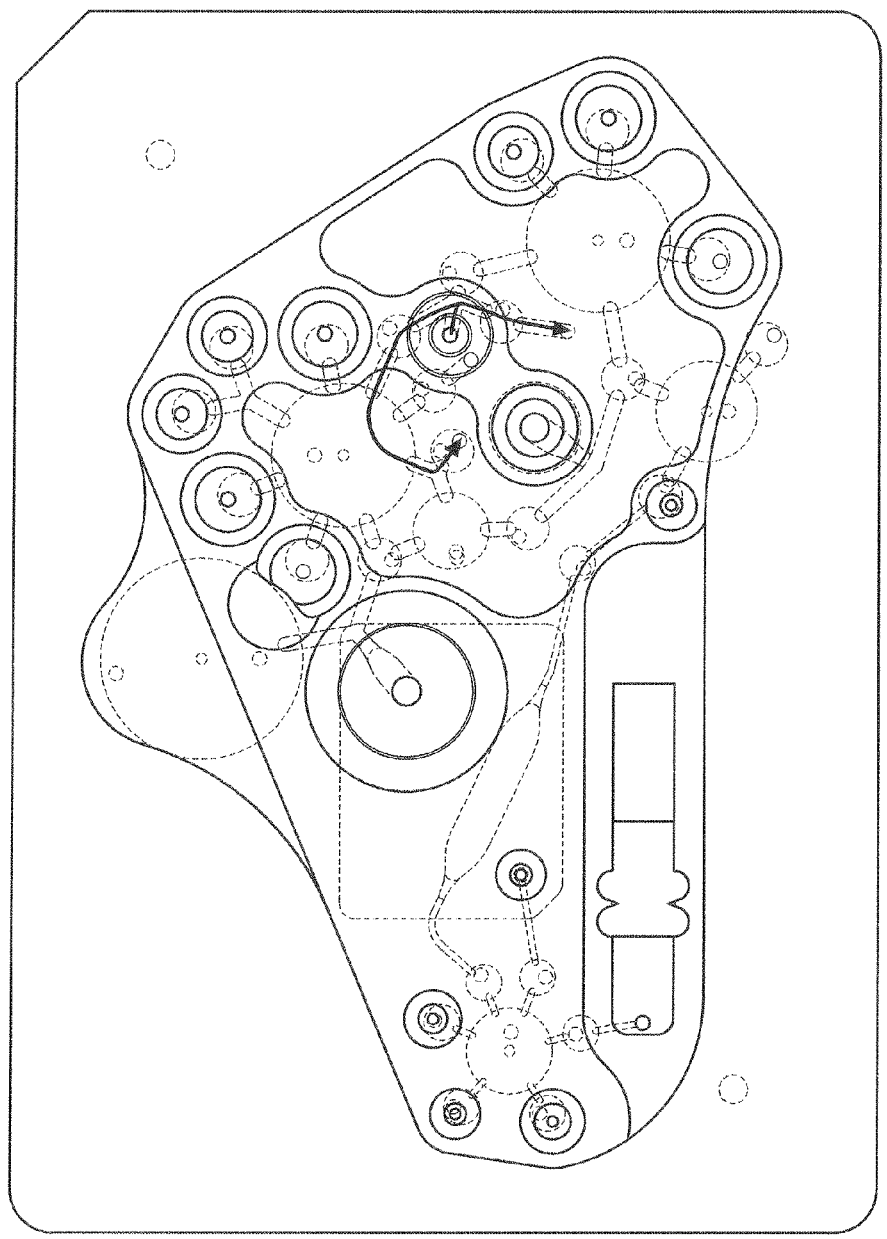
Figure 17F:
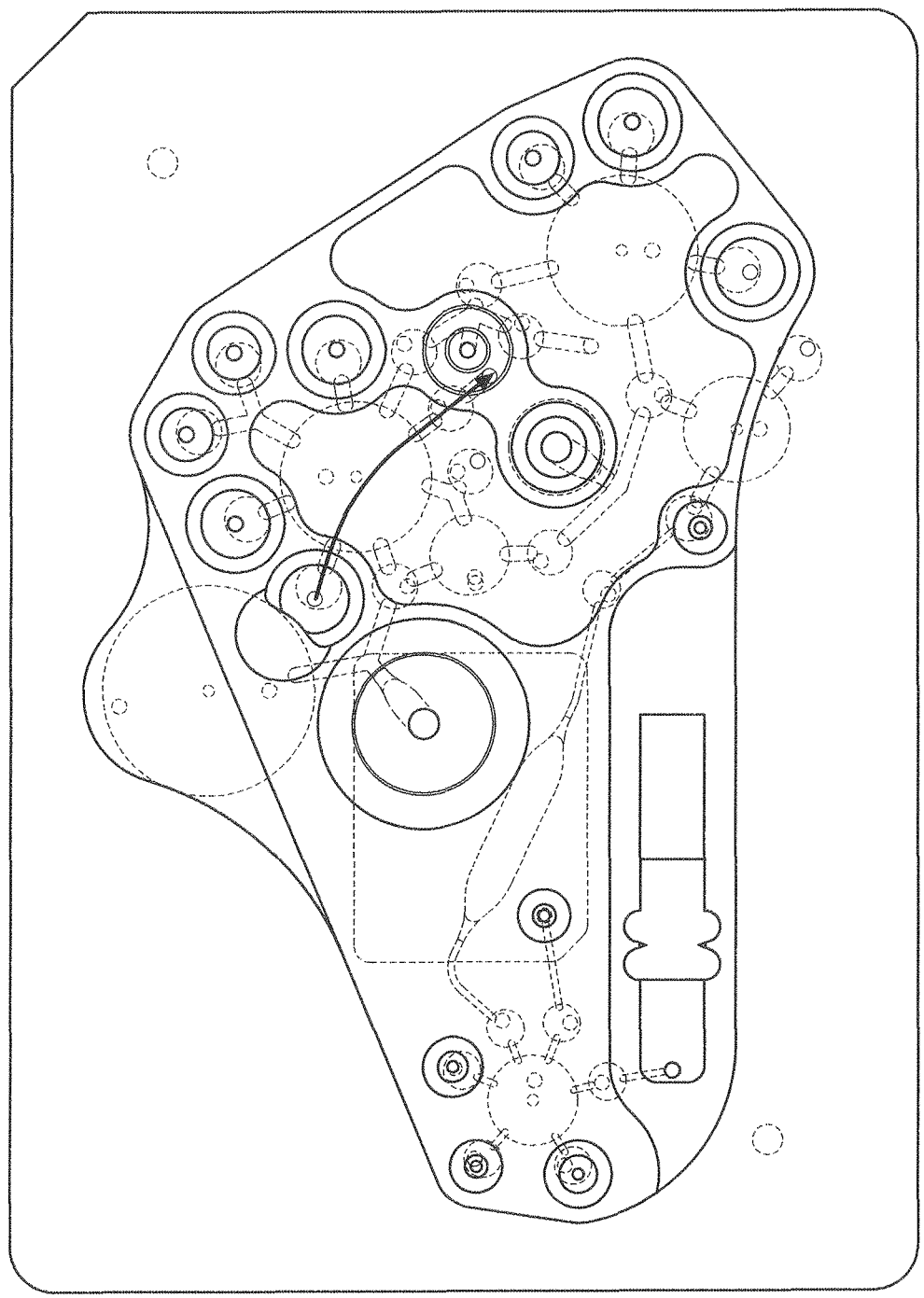
Figure 17G:
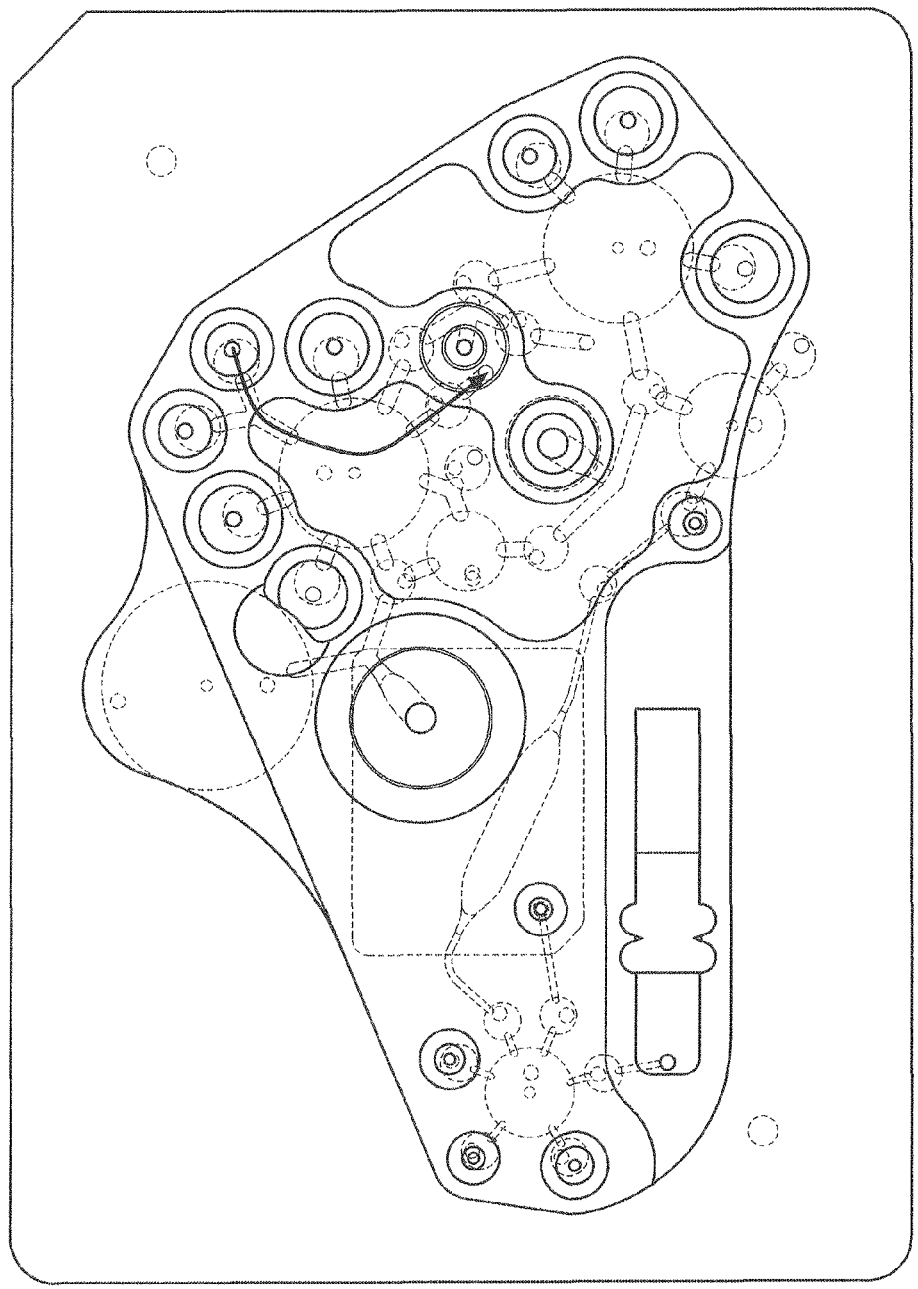
Figure 17H:
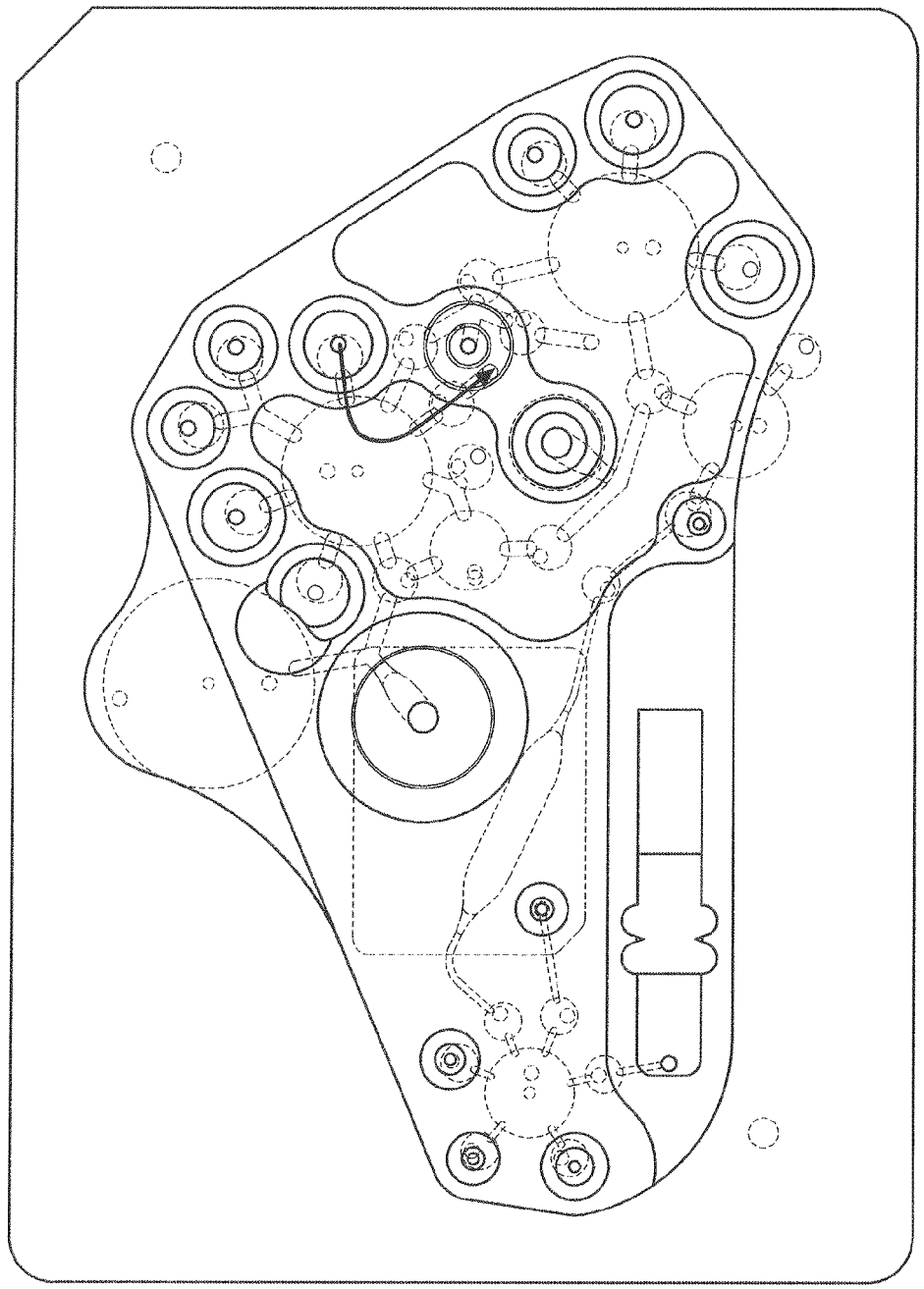
Figure 17I:
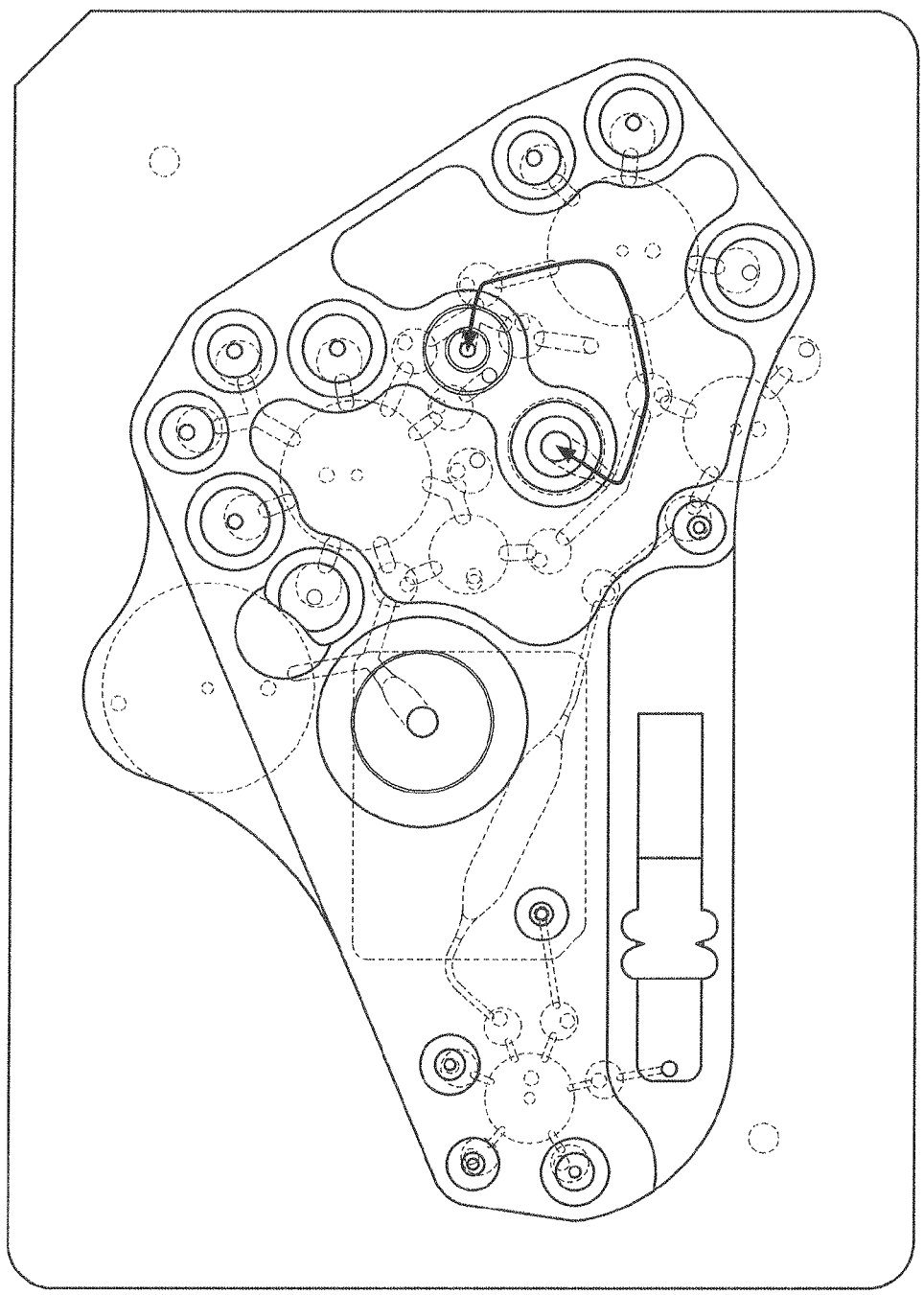
Figure 17J:
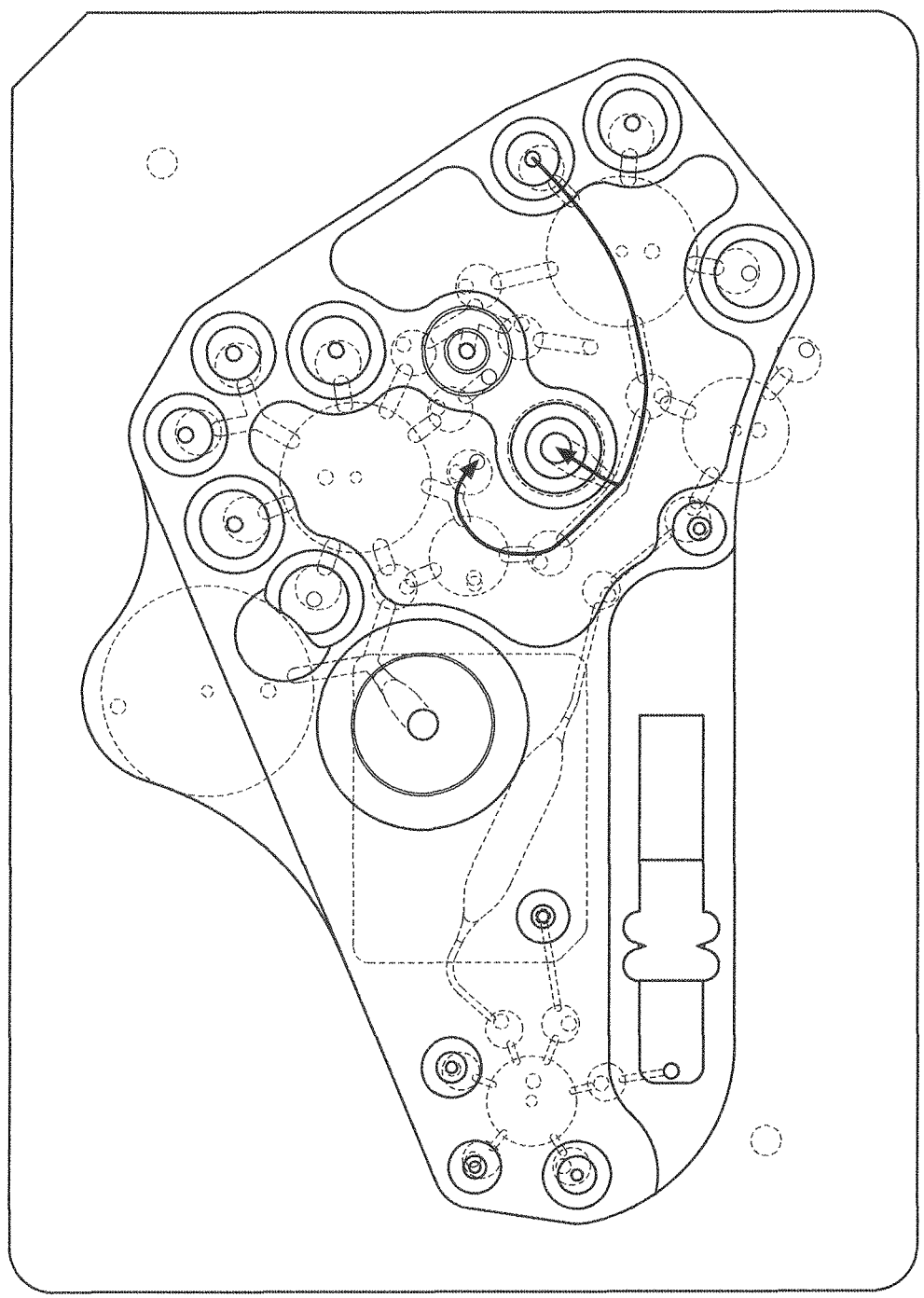
Figure 17K:
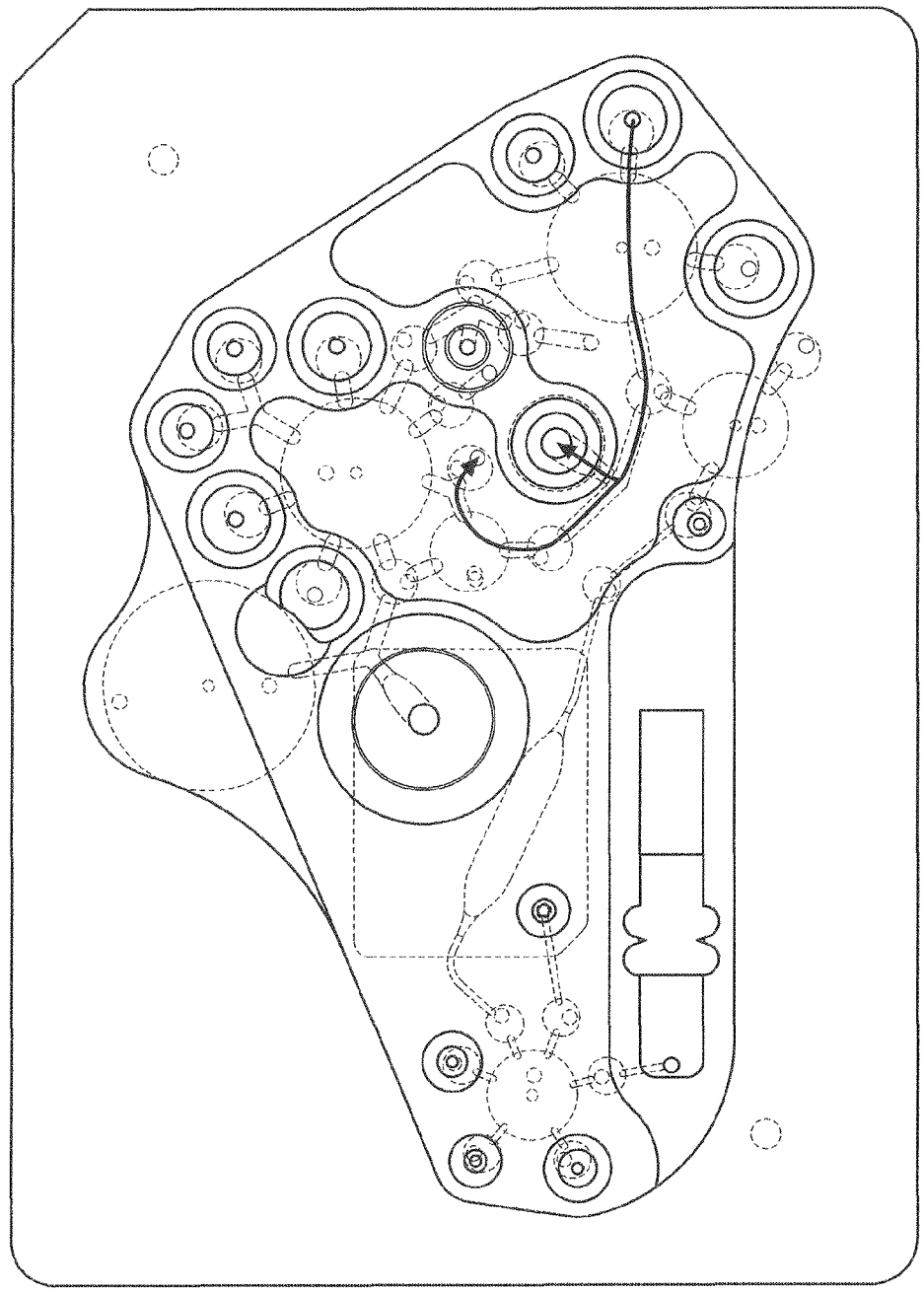
Figure 17L:
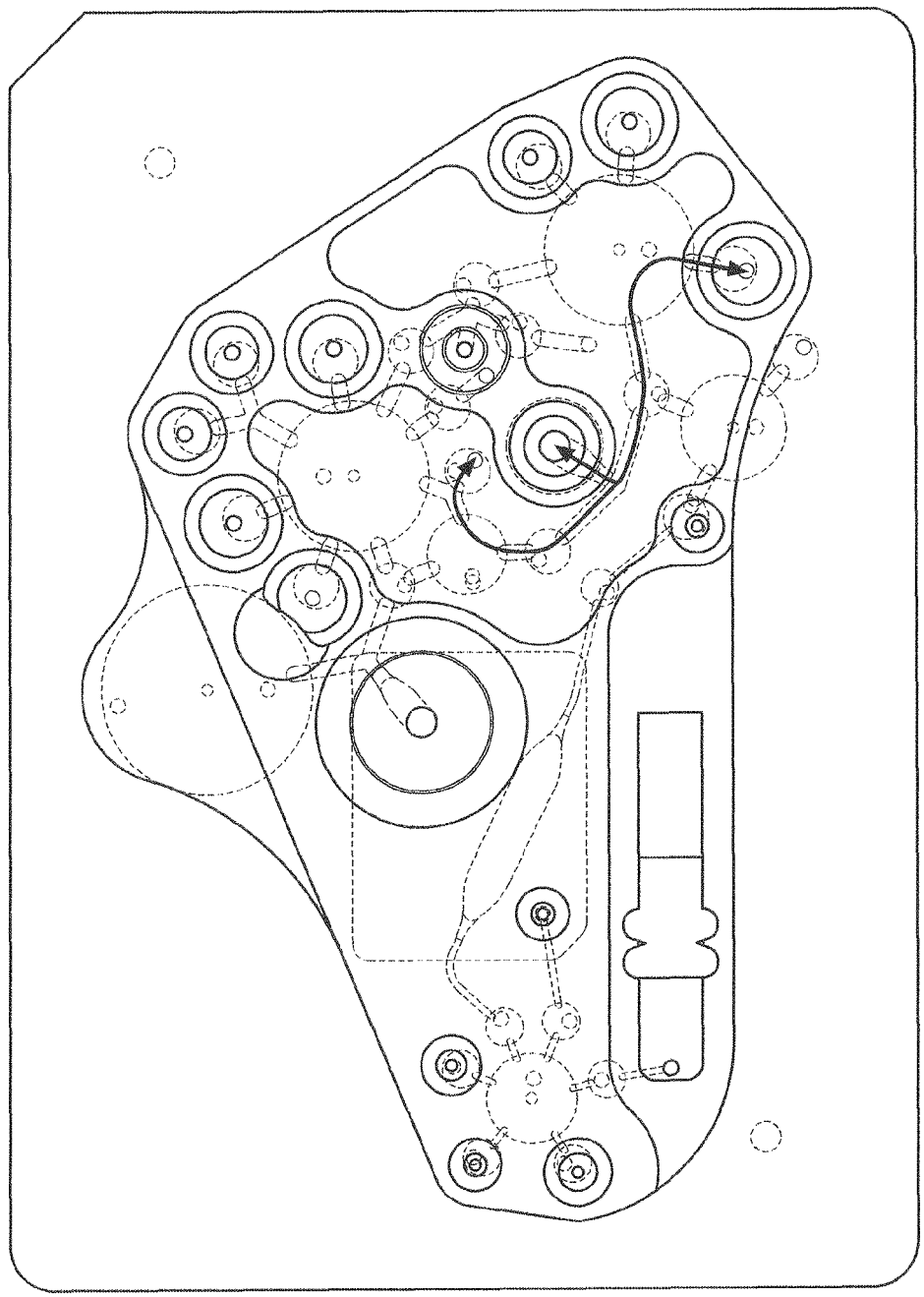
Figure 17M:
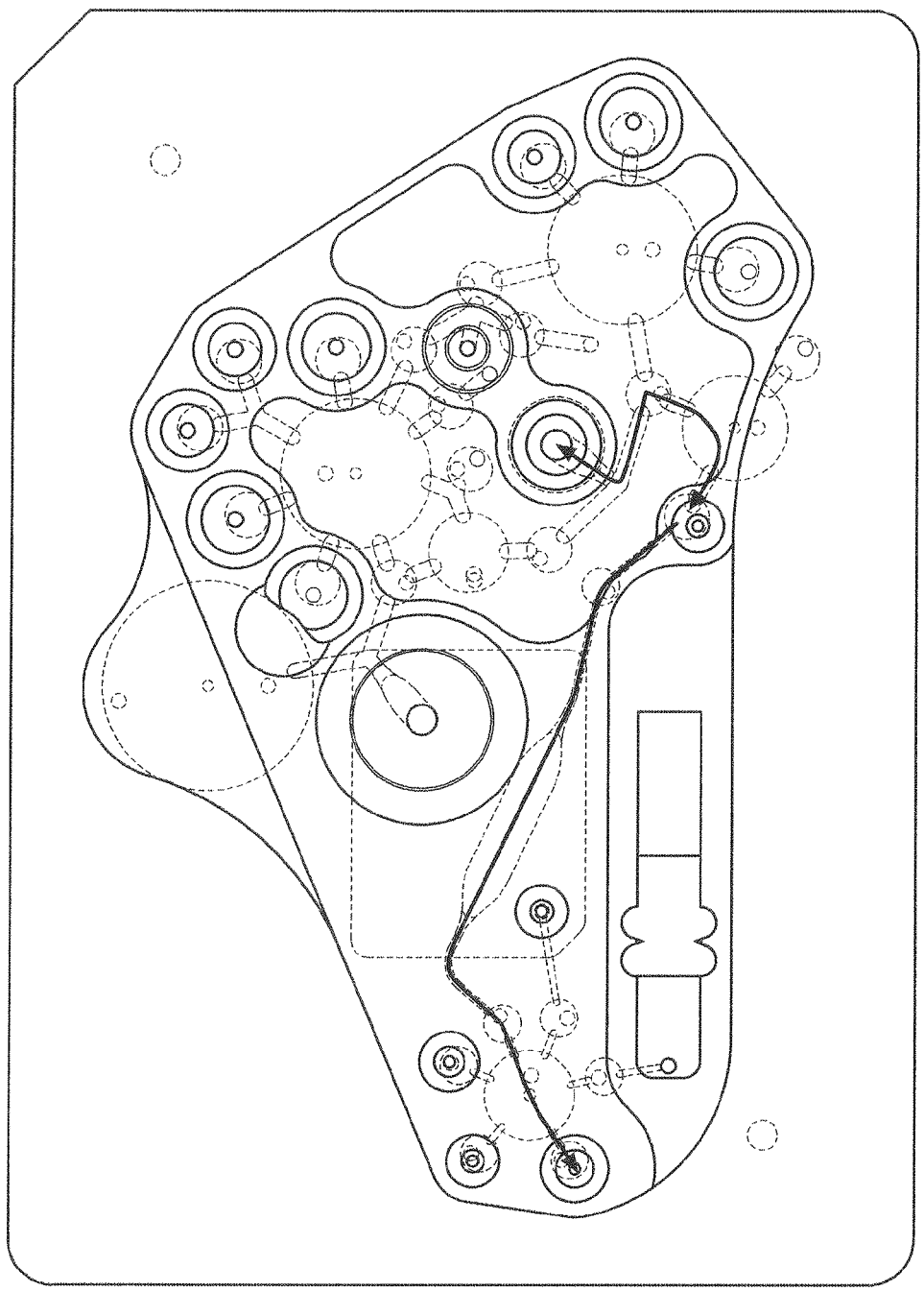
Figure 17N:
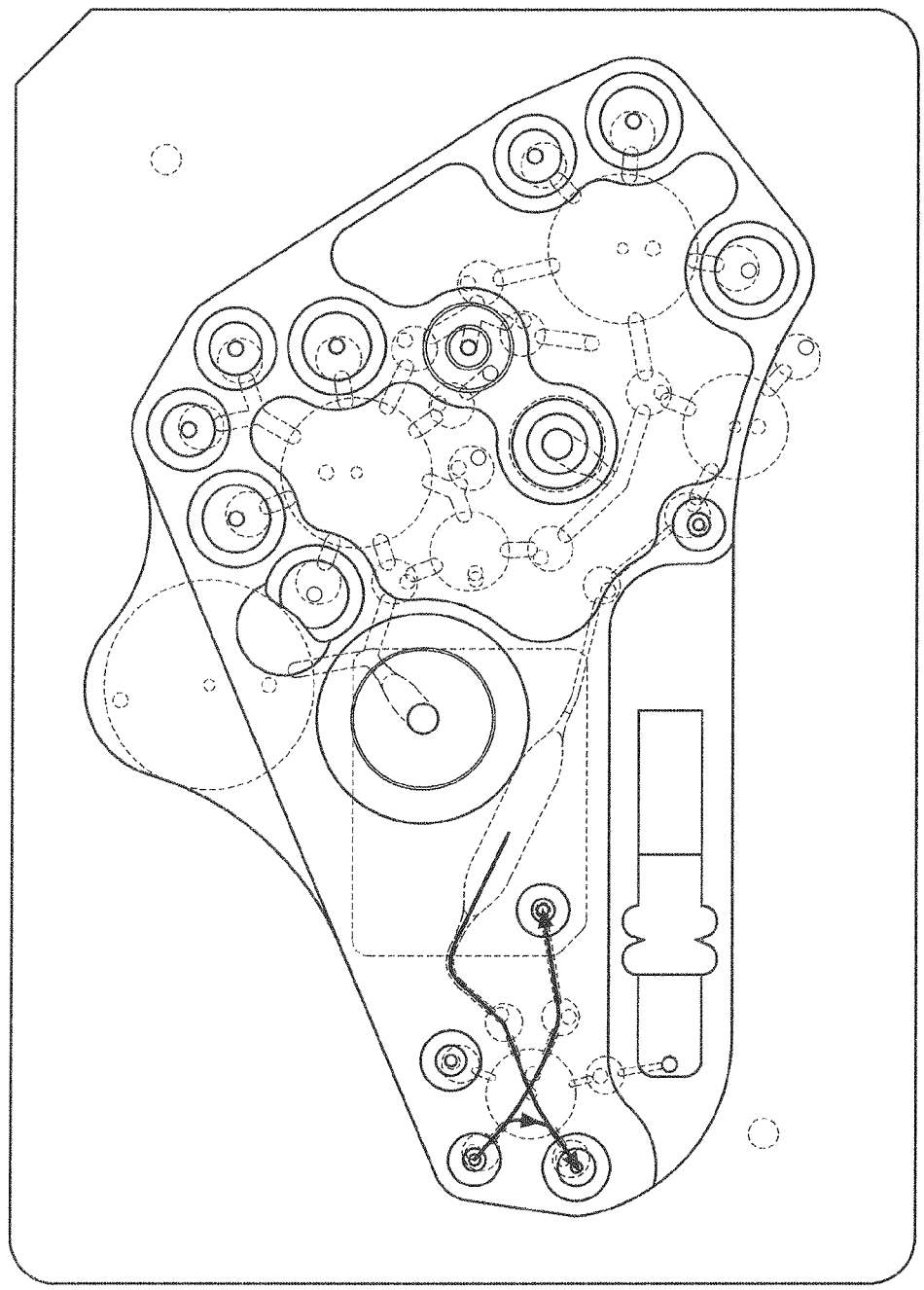
Figure 17O:
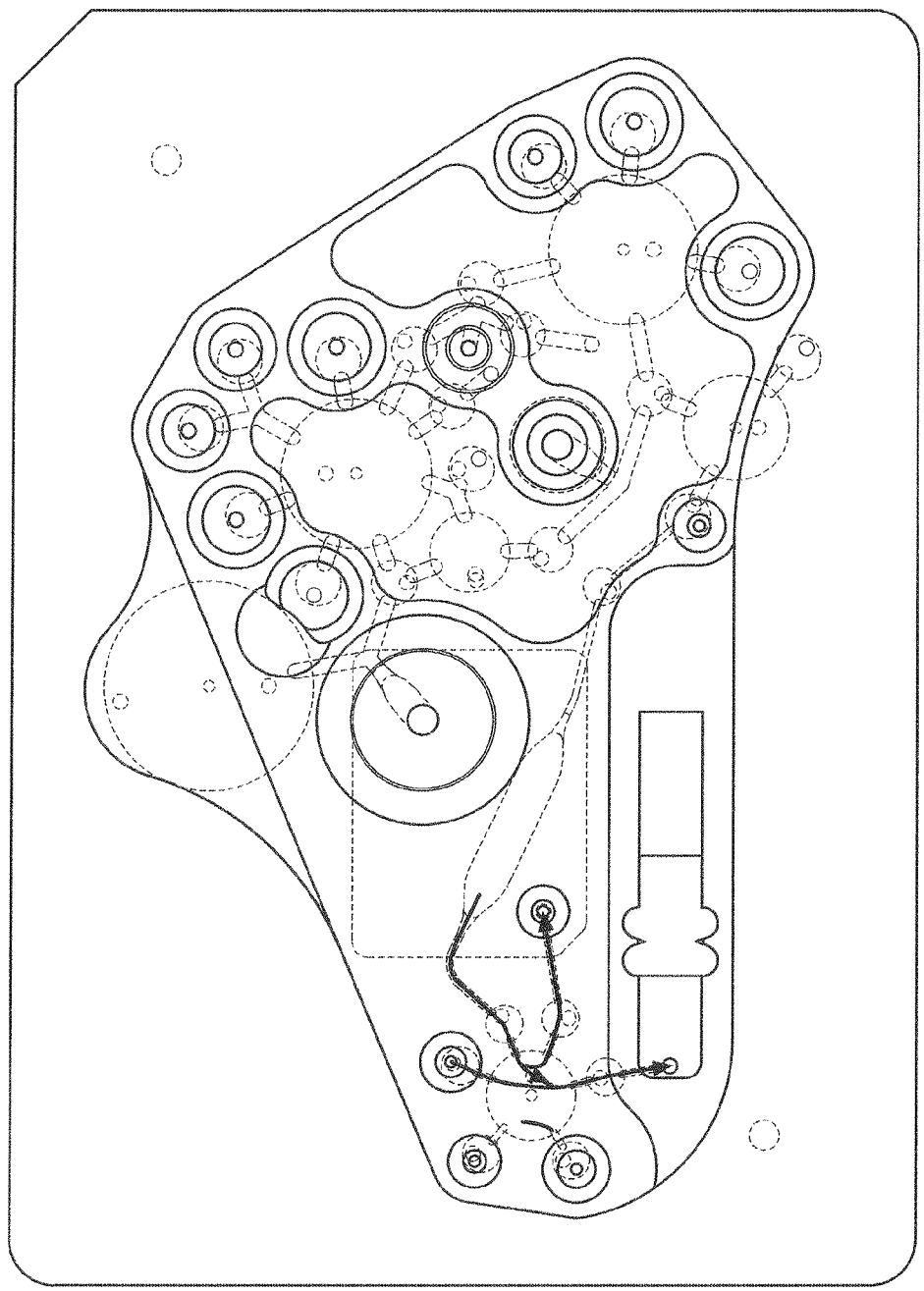

FIGS. 17A-O further illustrate the exemplary analysis processes as follows:

As illustrated in FIG. 17A, place sample into reservoir 33/55, dispense buffer and beads into reservoir 33/55 and incubate with gentle agitation by fluffing using the large diaphragm adjacent to reservoir 33/55. Choose temperature and incubation time appropriate for the assay. Raise magnet 49 into place under reservoir 33/55 and then pump contents to waste reservoir 35.

As illustrated in FIG. 17B, lower magnet 49 out of place under reservoir 33/55, dispense a wash buffer into common reservoir 34 (wash buffer 1), and pump wash buffer from common reservoir 34 (wash buffer 1) to reservoir 33/55 to re-suspend the beads. Gently agitate by fluffing as above, then raise magnet 49 into place under reservoir 33/55 and pump the contents to waste reservoir 35.

As illustrated in FIG. 17C, set multi-purpose heater 48 to the appropriate incubation temperature (if required by the particular assay) and, after an appropriate incubation, lower magnet 49 out of place under reservoir 33/55; dispense wash buffer into reservoir 37/56 and pump it to reservoir 33/55 to re-suspend the beads, gently agitate, and set multipurpose heater 48 to appropriate incubation temperature and time (as required by the particular assay); dispense lysis buffer into common reagent reservoir 34 (lysis buffer), pump the lysis buffer to reservoir 33/55, and agitate by fluffing as above and heat as required by the particular assay; dispense an organic alcohol (e.g., ethanol) into common reagent reservoir 34 (ethanol) and pump it to reservoir 33/55 and agitate by fluffing as above and heat as required by the particular assay.

As illustrated in FIG. 17D, pump the contents of reservoir 33/55 onto the top of the silica filter 36b in silica filter reservoir 36.

As illustrated in FIG. 17E, pull the contents of silica filter reservoir 36 through the silica filter 36b in the silica filter reservoir 36 and pump it to waste reservoir 35, followed (optionally) by pulling air through the filter by opening vacuum port 59.

As illustrated in FIG. 17F, dispense an organic alcohol (e.g., ethanol) into common reagent reservoir 34 (ethanol) and pump it to silica filter reservoir 36 onto the top of the silica filter 36b in silica filter reservoir 36; then repeat the steps illustrated in FIG. 17E.

As illustrated in FIG. 17G, dispense the same or another wash buffer into common reagent reservoir 34 (wash buffer 2) and pump it to silica filter reservoir 36 onto the top of the silica filter 36b in silica filter reservoir 36; then repeat the steps illustrated in FIG. 17E.

As illustrated in FIG. 17H, dispense the same or another wash buffer into common reagent reservoir 34 (wash buffer 3) and pump it to silica filter reservoir 36 onto the top of the silica filter 36b in silica filter reservoir 36; then repeat the steps illustrated in FIG. 17E.

Repeat the steps illustrated in FIGS. 17H and 17E; then, repeat the steps illustrated in FIGS. 17F and 17E.

As illustrated in FIG. 17I, dispense wash buffer into reservoir 37/56 and pump it to silica filter reservoir 36 onto the top of the silica filter 36b in silica filter reservoir 36. Incubate as appropriate and then pump it back to reservoir 37/56.

As illustrated in FIG. 17J, dispense a binding buffer into reservoir 37 (binding buffer) and pump it to reservoir 37/56; then dispense beads into reservoir 37/56; incubate and agitate as appropriate. Raise magnet 49 into place under reservoir 37/56 and pump the contents of reservoir 37/56 to waste reservoir 35.

As illustrated in FIG. 17K, lower magnet 49 out of place under reservoir 37/56. Dispense the same or another wash buffer into reservoir 37 (wash buffer A) and pump the contents of reservoir 37 (wash buffer A) into reservoir 37/56 to re-suspend the beads. Gently agitate and incubate as appropriate. Raise magnet 49 into place under reservoir 37/56 and pump the contents of reservoir 37/56 to waste reservoir 35. Repeat multiple times.

As illustrated in FIG. 17L, lower magnet 49 out of place under reservoir 37/56. Dispense the same or another wash buffer into reservoir 37 (wash buffer B) and pump the contents of reservoir 37 (wash buffer B) into reservoir 37/56 to re-suspend the beads. Gently agitate and incubate as appropriate. Raise magnet 49 into place under reservoir 37/56 and pump the contents of reservoir 37/56 to waste reservoir 35. Lower magnet 49 out of place under reservoir 37/56. Dispense the same or another wash buffer into reservoir 37 (wash buffer B) and pump the contents of reservoir 37 (wash buffer B) into reservoir 37/56 to re-suspend the beads. Gently agitate and incubate as appropriate. Raise magnet 49 into place under reservoir 37/56 and pump the contents of reservoir 37/56 to reservoir 37 (wash buffer B) to clear the channel and diaphragms between reservoir 37/56 and amplification master mix reservoir 38.

As illustrated in FIG. 17M, lower magnet 49 out of place under reservoir 37/56. Dispense amplification master mix into amplification master mix reservoir 38 and pump the contents of amplification master mix reservoir 38 into reservoir 37/56 to re-suspend beads. Gently agitate and incubate as appropriate. Pump the contents of reservoir 37/56 back into amplification master mix reservoir 38. Pump or pull the contents of amplification master mix reservoir 38 into the amplification reactor and through to waste to completely fill the amplification reactor. Incubate at appropriate temperatures and times for amplification.

As illustrated in FIG. 17N, dispense hybridization buffer into analysis reservoir 41 (hybridization buffer) and pump a portion to waste reservoir 42. Pump a portion of the contents of reservoir 41 (hybridization buffer) to reservoir 54 (the heated analysis reservoir). Pump a portion of the contents of the amplification reactor to waste reservoir 42. Pump a portion of the contents of the amplification reactor and another portion of the contents of reservoir 41 (hybridization buffer) into reservoir 54 (the heated analysis reservoir).

As illustrated in FIG. 17O, dispense any other required reagents into reservoir 54 (the heated analysis reservoir) as required. Agitate, heat and incubate the contents of reservoir 54 (the heated analysis reservoir) as required. Pump all or a portion of the contents of reservoir 54 (the heated analysis reservoir) into reservoir 41(analysis reservoir) to progress through an analysis of the contents of reservoir 54 (the heated analysis reservoir). Dispense running buffer into reservoir 41 (running buffer) and when all of the contents earlier pumped to reservoir 41(analysis reservoir) are consumed pump the contents of reservoir 41 (running buffer) into reservoir 41(analysis reservoir) to complete the assay. Finally, optically analyze the results displayed on the filter in reservoir 41(analysis reservoir).

FIG. 18 illustrates a side cross sectional view of the pneumatic manifold 15 with integrated pneumatic piston assemblies 51, one of which is located in the multi-purpose heater assembly 48 and one of which is located in the preparative area of the system. The figure specifically shows the internal components of the pneumatic piston assembly (alternatively the piston assembly may be motor or electromagnetically activated) 51 for the preparative area of the system.

Figure 19:
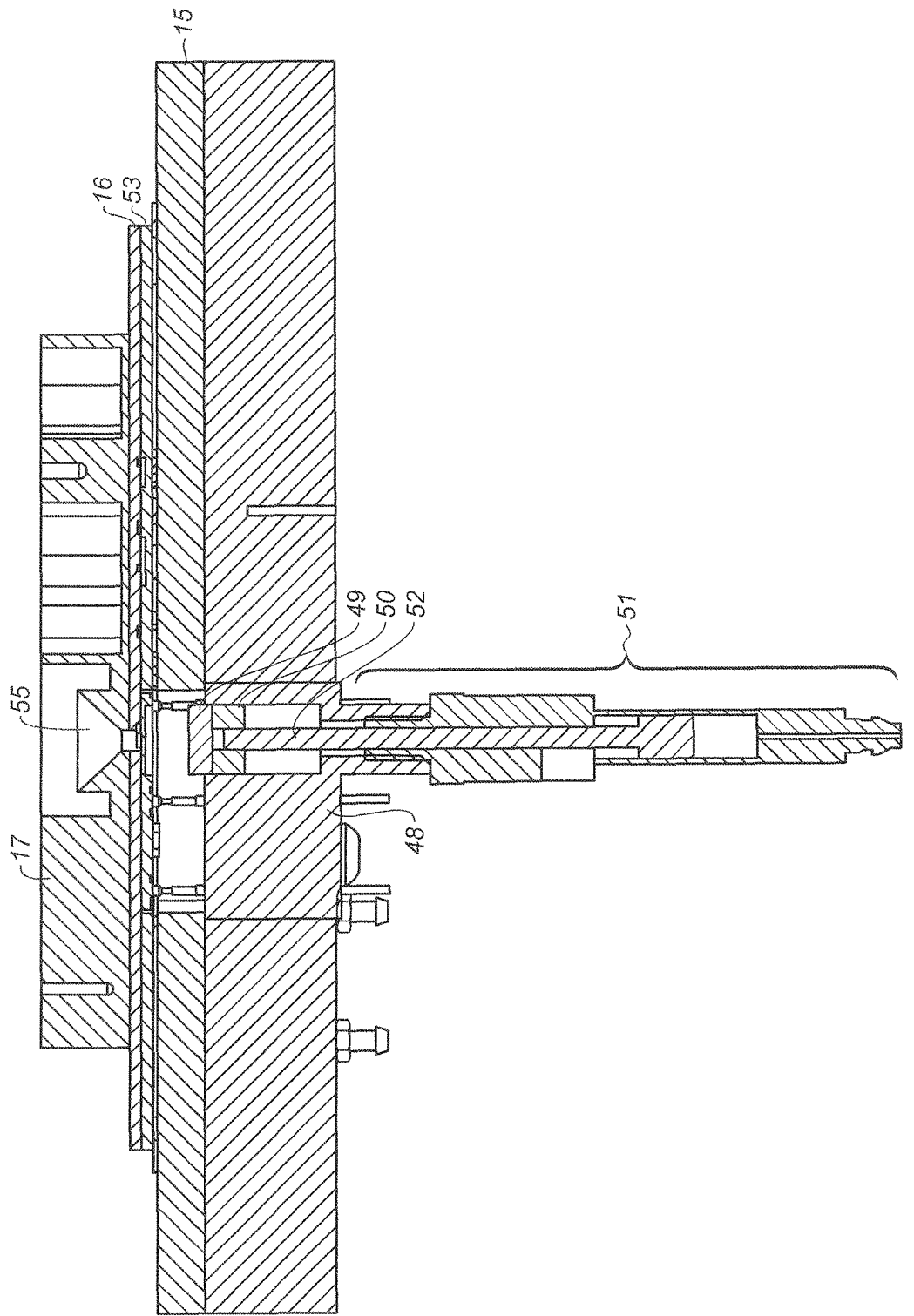
FIG. 19 shows a cross sectional side view of the pneumatic manifold and the microfluidic system of a single assay unit including functional features of the manifold incorporating pneumatically activated, heated magnet assembly and multiple heated reaction sites, according to an exemplary aspect of the invention.

FIG. 19 illustrates a side cross sectional view of the pneumatic manifold 15 with integrated pneumatic piston assembly (alternatively the piston assembly may be motor or electromagnetically activated) 51 located in the multipurpose heater assembly 48, and its internal components.

Figure 20:
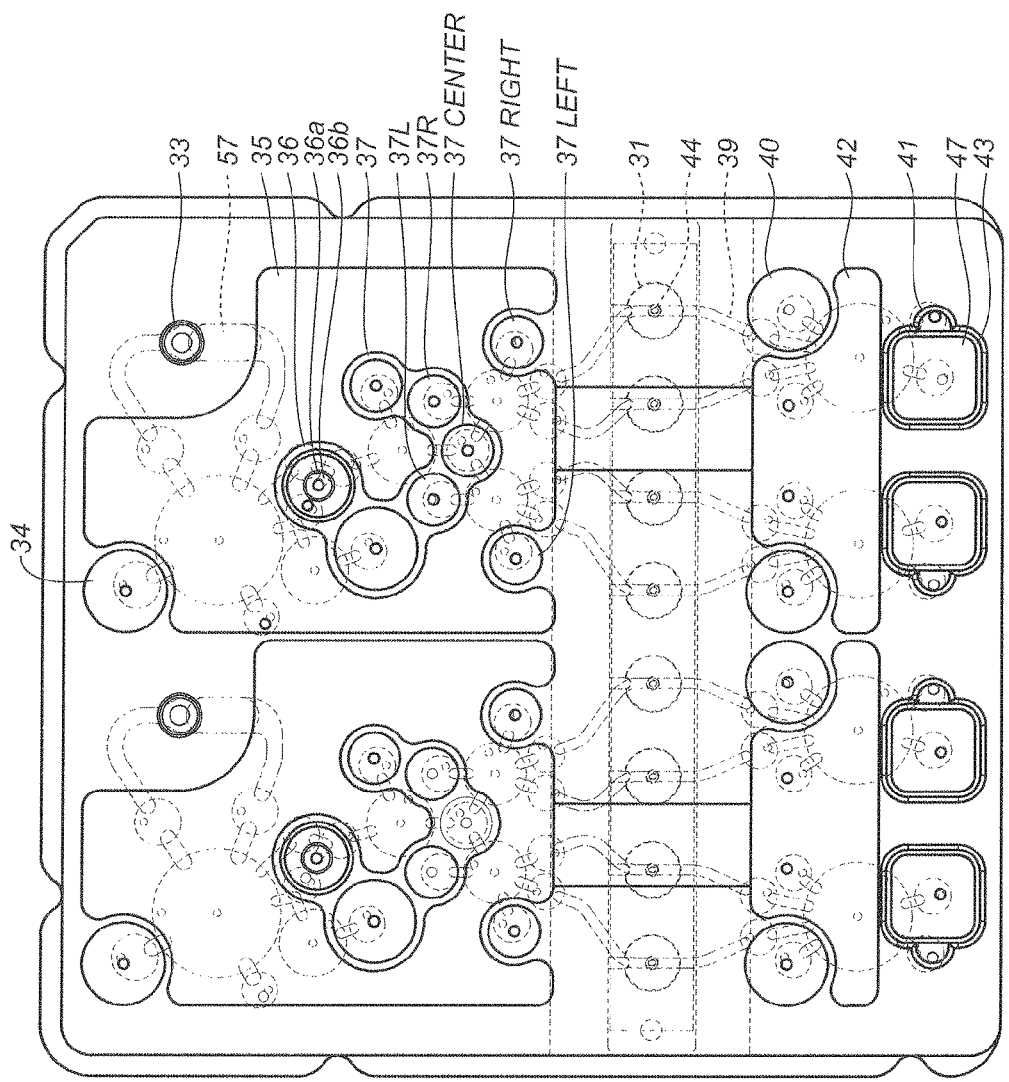
FIG. 20 shows a layered, cross sectional top plan view of a "double assay unit" arrangement of the reservoirs, fluidic channels and amplification reactors, which are a combination of the fluidic transport layer and the reservoir layer, according to an exemplary aspect of the invention.

FIG. 20 shows a layered top view of a double assay unit arrangement which shows exemplary alternative functions of the pneumatic manifold 15 incorporating a pneumatically activated magnet assembly 51 targeting a magnetic separation/concentration channel area 57 instead of a reservoir as described in FIGS. 17A-O, and including the arrangement of the reservoirs and channels employed by the system.

Figure 21A:
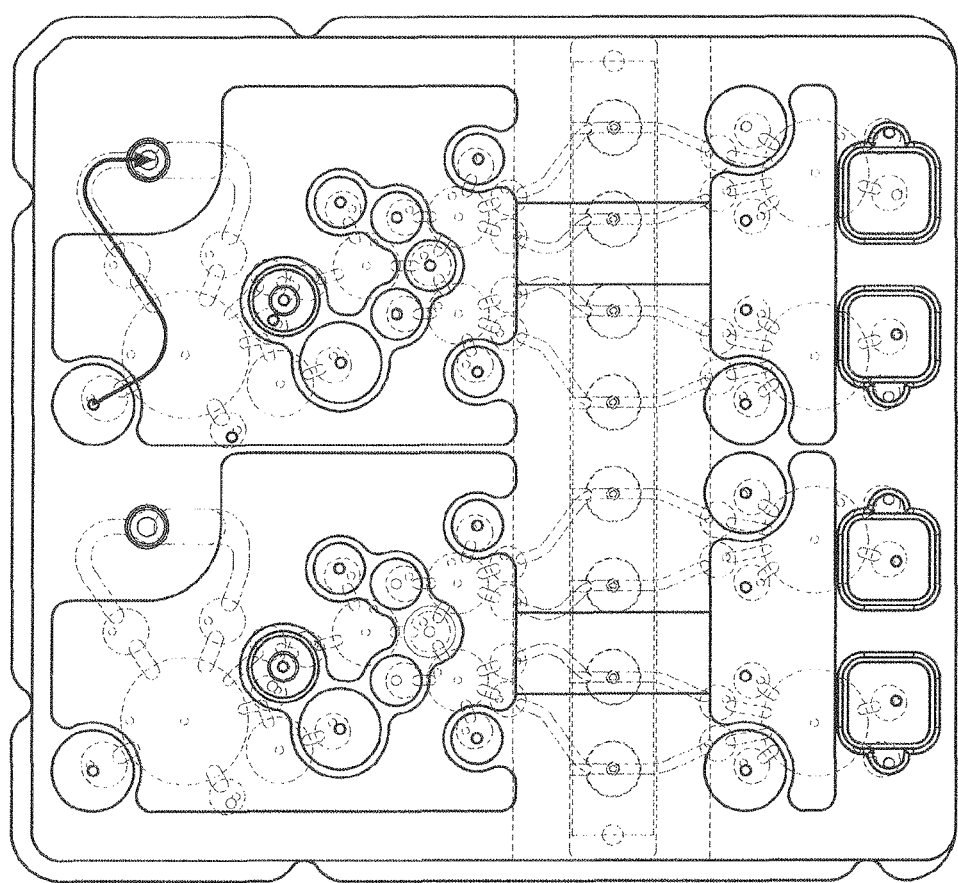

FIGS. 21A-K further illustrate the exemplary analysis processes as follows:

As illustrated in FIG. 21A, place sample into sample input reservoir 33, dispense enzyme into common reagent reservoir 34 and pump it to sample input reservoir 33. Incubate with gentle agitation. Dispense lysis buffer into common reagent reservoir 34 and pump it to sample input reservoir 33. Incubate with gentle agitation. Dispense beads into common reagent reservoir 34 and pump it to sample input reservoir 33. Incubate with gentle agitation. Dispense an organic alcohol (e.g. isopropanol) into common reagent reservoir 34 and pump it to sample input reservoir 33 and incubate it with gentle agitation.

Figure 21B:
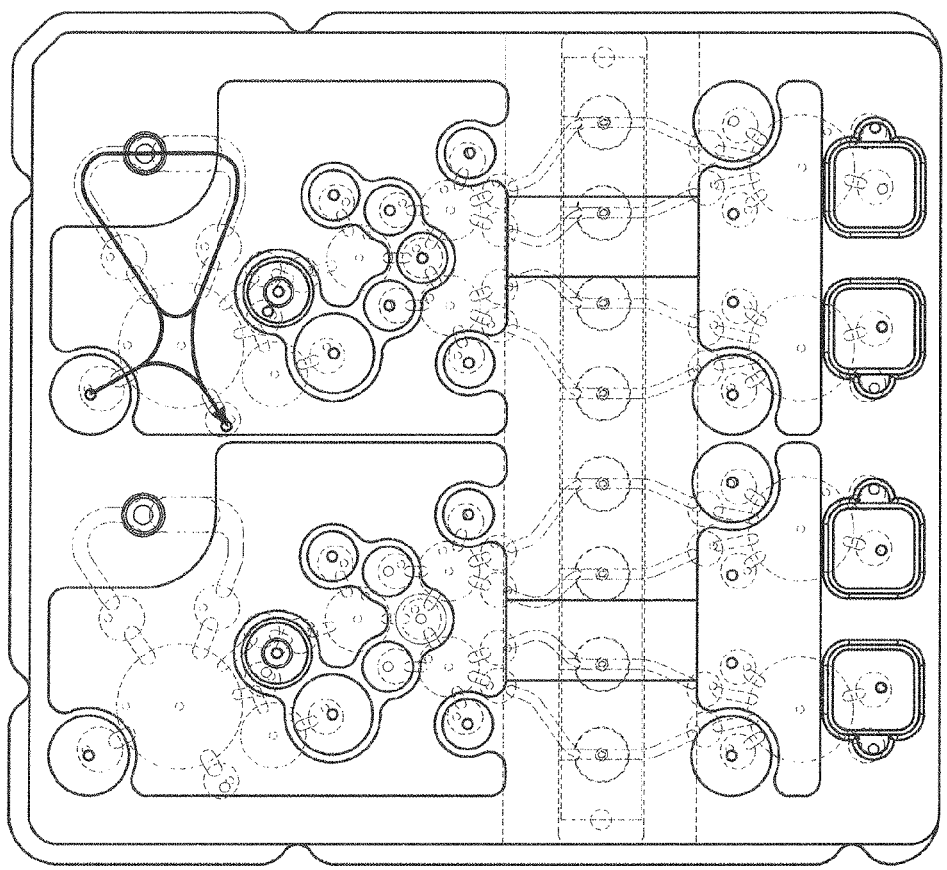

As illustrated in FIG. 21B, raise magnet 49 into place under separation/concentration channel 57 and pump the contents to waste reservoir 35. Lower magnet 49 out of place under separation/concentration channel 57. Dispense a wash buffer into common reagent reservoir 34 (preparation), pump to separation/concentration channel 57, and circulate alternatively clockwise and then counterclockwise multiple times through separation/concentration channel 57 to re-suspend and wash the beads. Raise magnet 49 into place under separation/concentration channel 57 and pump the contents to waste reservoir 35. Lower magnet 49 out of place under separation/concentration channel 57. Dispense the same or another wash buffer into common reagent reservoir 34 (preparation), pump to separation/concentration channel 57, and circulate alternatively clockwise and then counterclockwise multiple times through separation/concentration channel 57 to re-suspend and wash the beads. Raise magnet 49 into place under separation/concentration channel 57 and pump the contents to waste reservoir 35. Continue the above wash steps as required by the assay. Dispense wash buffer into common reagent reservoir 34 (preparation) and pump it to waste reservoir 35 to clear any residual reagents from the reservoir, channels, and diaphragms of the preparation area.

Figure 21C:
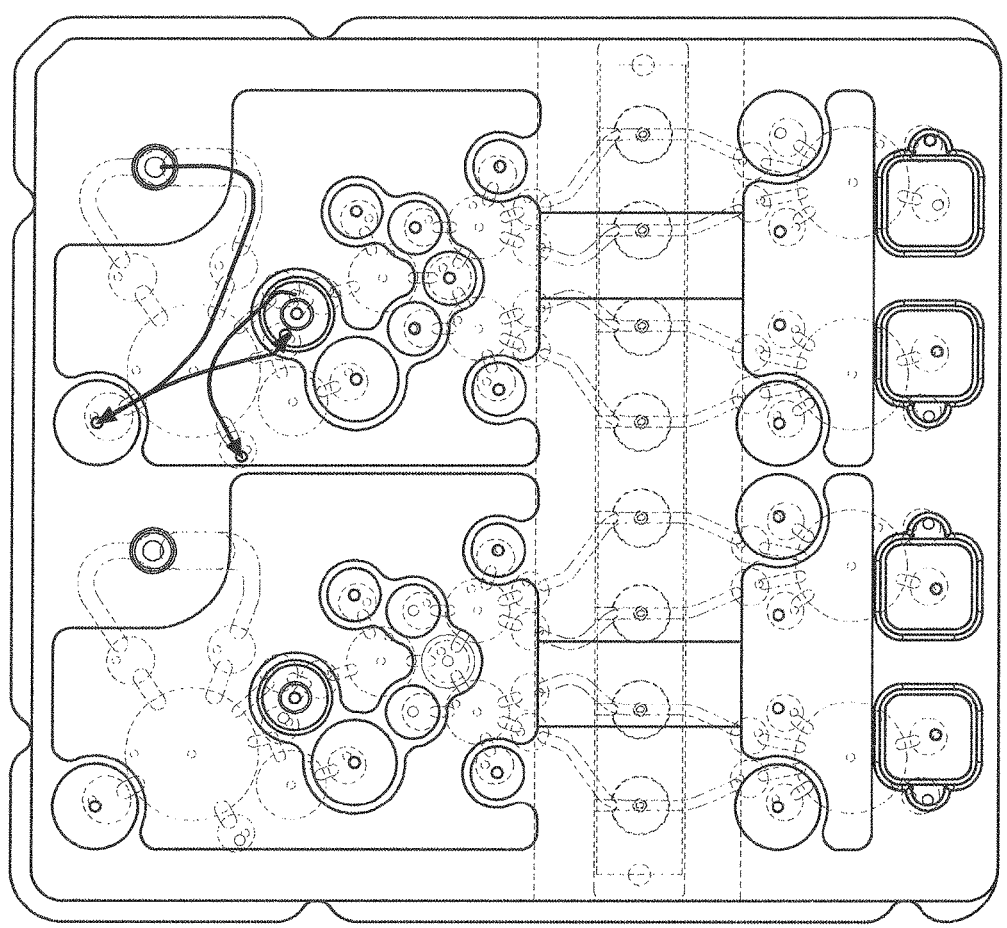

As illustrated in FIG. 21C, pump the solution from separation/concentration channel 57 to common reagent reservoir 34 (preparation). Dispense a high salt buffer into common reagent reservoir 34 (preparation). Dispense an organic alcohol (e.g., ethanol) into common reagent reservoir 34 (preparation). Pump the contents of common reagent reservoir 34 (preparation) onto the top of the silica filter 36b in silica filter reservoir 36, pull the contents through silica filter 36b in silica filter reservoir 36, and pump to waste reservoir 35.

Figure 21D:
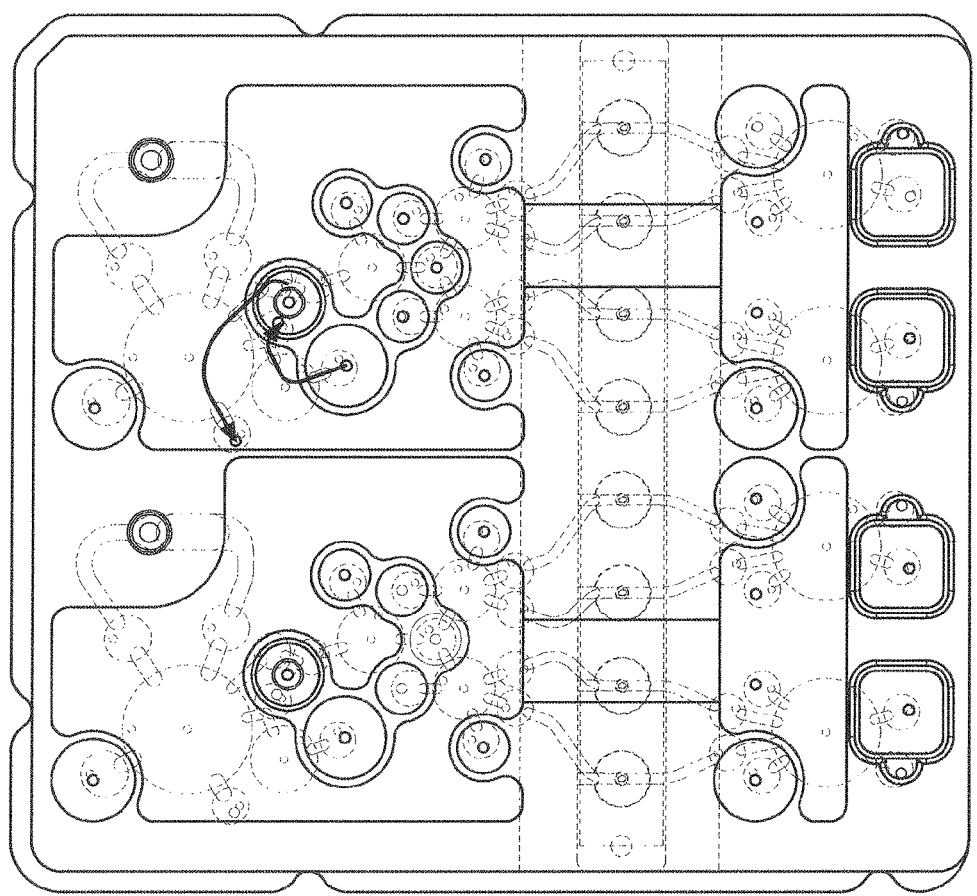

As illustrated in FIG. 21D, dispense the same or another wash buffer into common reagent reservoir 34 (elution), pump onto the top of the silica filter 36b in silica filter reservoir 36, pull the contents through silica filter 36b in silica filter reservoir 36, and pump to waste reservoir 35. Repeat with the same or an alternative wash buffer as required by the assay.

Figure 21E:
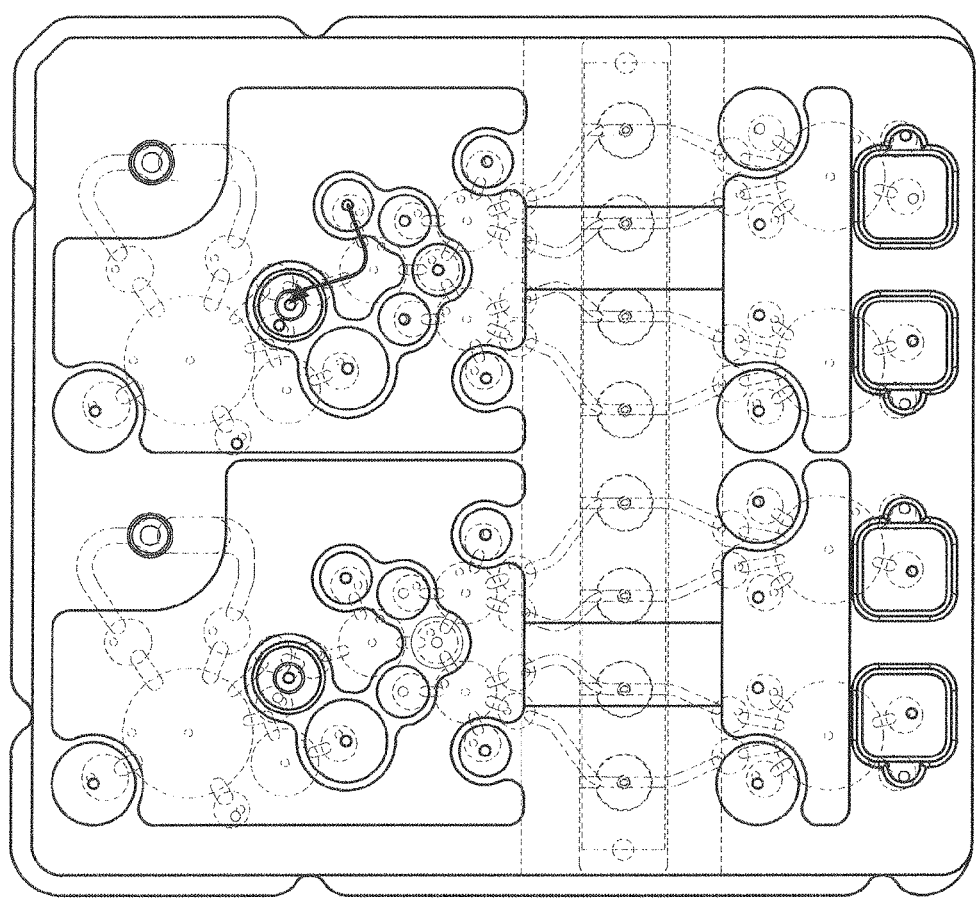

As illustrated in FIG. 21E, dispense elution buffer into reservoir 37 (elution) and pump it up through the bottom of the silica filter 36b in silica filter reservoir 36.

As illustrated in FIG. 21F, pull the contents of silica filter reservoir 36 through the silica filter, pump it to elution reservoir 37 (center), and then equally to elution reservoir 37L and 37R; or pump it directly in equal amounts to reservoir 37L and 37R by bypassing elution reservoir 37 (center).

Figure 21G:
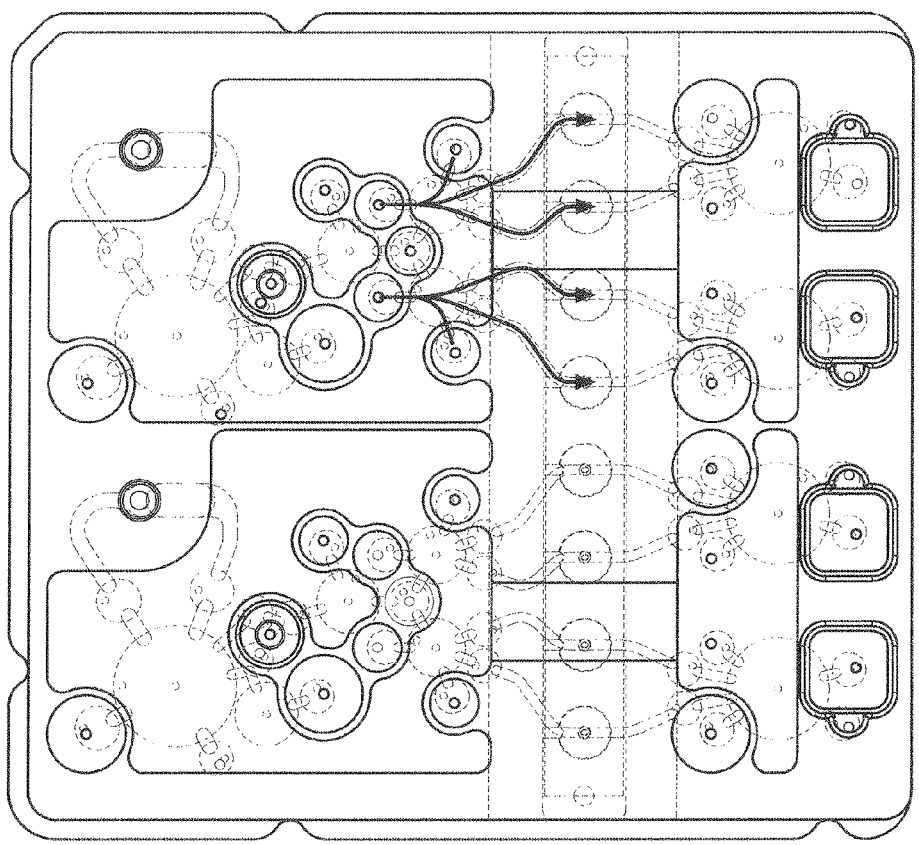

As illustrated in FIG. 21G, dispense amplification master mix into reservoirs 38L and 38R. The master mix dispensed into the separate reservoirs may or may not contain the same primers depending upon the assay. In the depiction, the original sample is now split into two aliquots. The sample may remain as a single aliquot or be split into more than two aliquots depending on the assay in particular and the layout of available reservoirs, channels, and amplification reactors to accommodate further splitting of the sample. Pump the solution in reservoir 37L and amplification master mix reservoir 38L into the amplification reactors 31L and 31R (two are depicted for the left side of the assay unit though only a single amplification reactor is necessary and more than two are possible). Repeat for the right side of the assay unit. Incubate at appropriate temperatures and times for amplification.

Figure 21H:
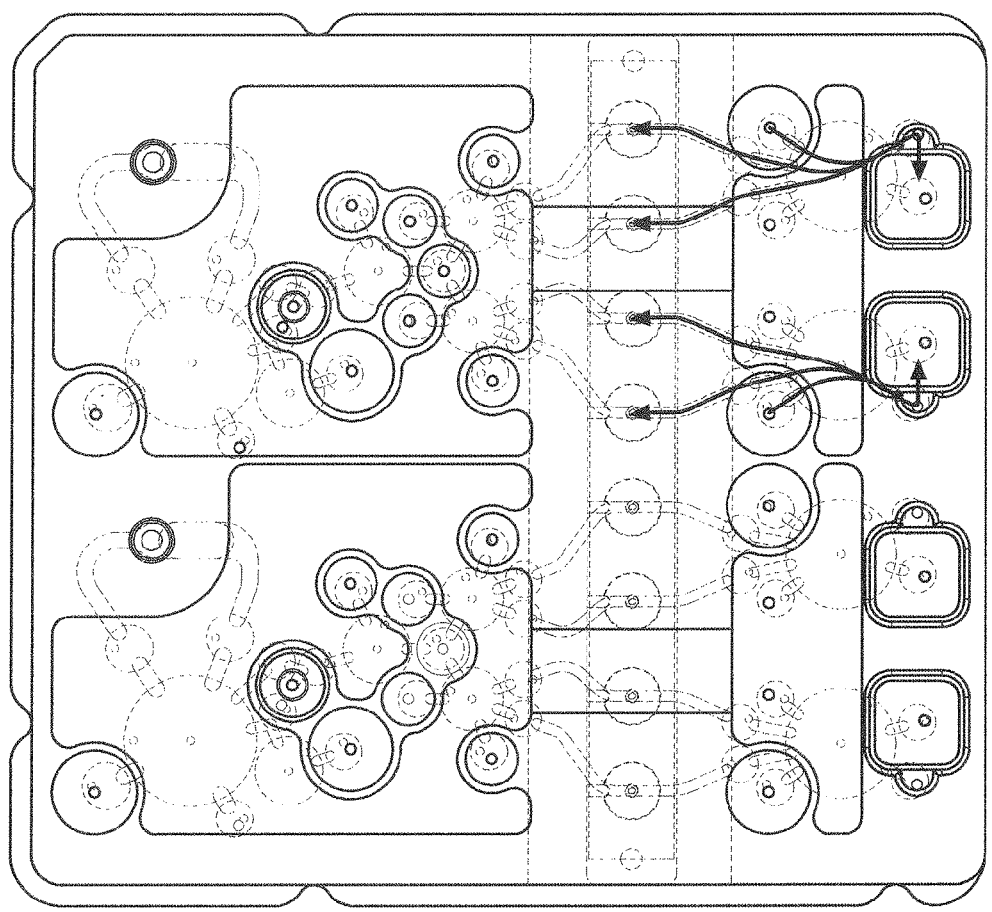

As illustrated in FIG. 21H, dispense pre-hybridization buffer into common reagent reservoir 40 (left and right) and from there into amplification reactors 31 (left and right) and on top of the analysis membrane 47 (left and right) in analysis reservoir 41(left and right).

Figure 21I:
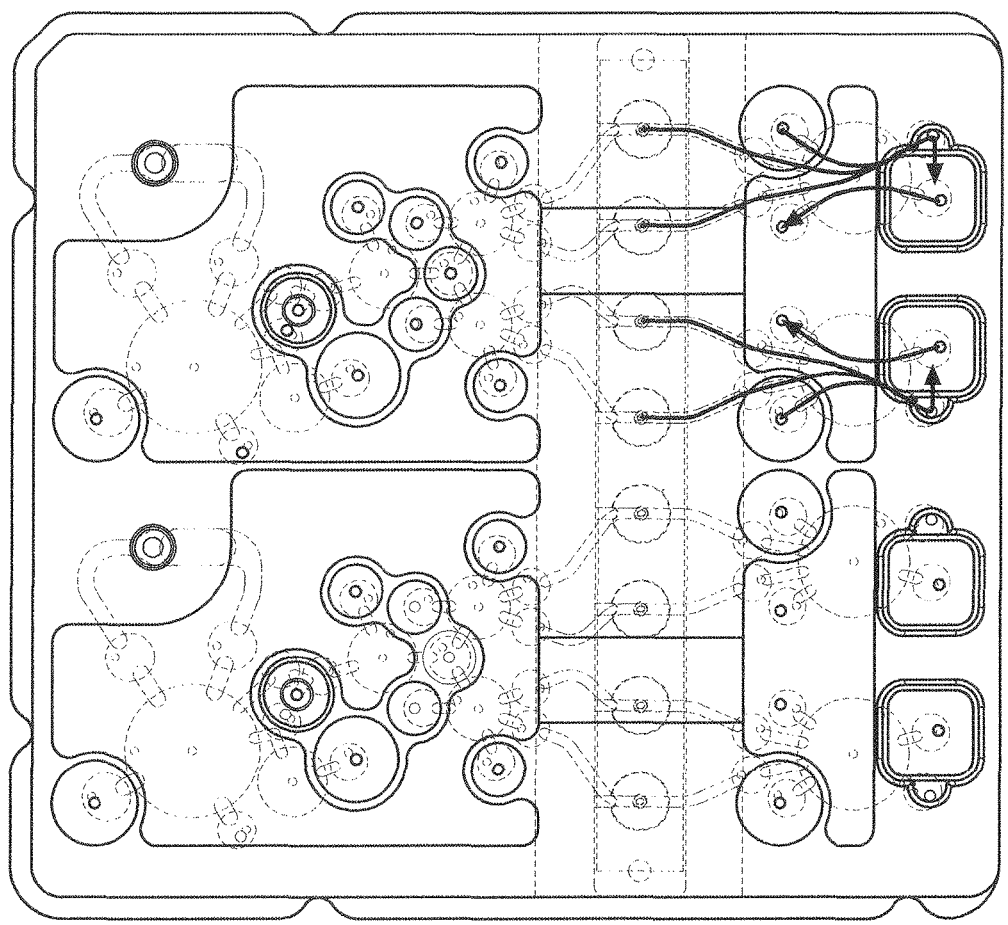

As illustrated in FIG. 21I, pump the contents of amplification reactors 31 (left and right) on top of the analysis membrane 47 (left and right) in analysis reservoir 41(left and right) and circulate it multiple times which provides enough contact between the amplicons and the targets attached to the analysis membrane 47(left and right). When satisfactory hybridization has occurred, pump the contents to waste reservoir 42. Dispense wash buffer into common reagent reservoir 40 (left and right) and pump on top of the analysis membrane 47 (left and right) suspended in analysis reservoir 41 (left and right) and pump to waste reservoir 42 (repeat multiple times).

As illustrated in FIG. 21J, dispense an appropriate amplicon visualization reagent (e.g., horseradish peroxidase ("HRP")) into common reagent reservoir 40 (left and right), pump on top of analysis membrane 47 (left and right) suspended in analysis reservoir 41 (left and right), and circulate until the reaction is satisfactorily complete, then pump the contents to waste reservoir 42. Dispense wash buffer into common reagent reservoir 40 (left and right), pump on top of the analysis membrane 47 (left and right) suspended in analysis reservoir 41 (left and right), and then pump the contents to waste reservoir 42. Repeat multiple times.

Figure 21K:
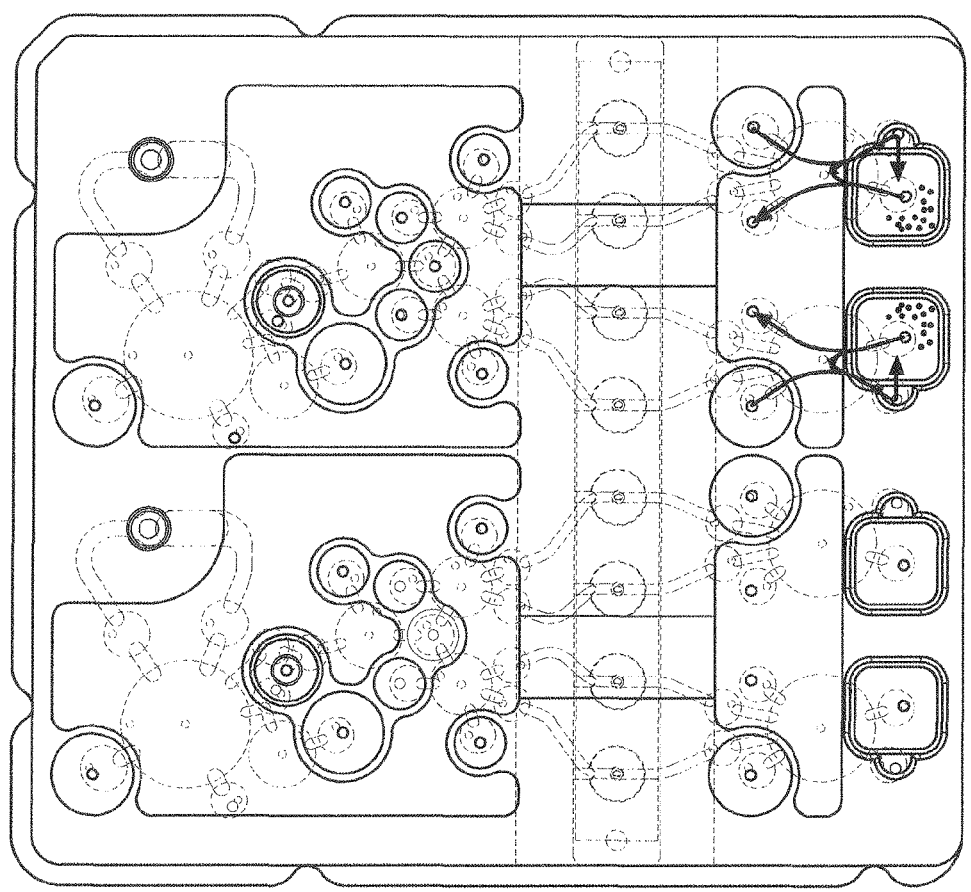
Figure 24:
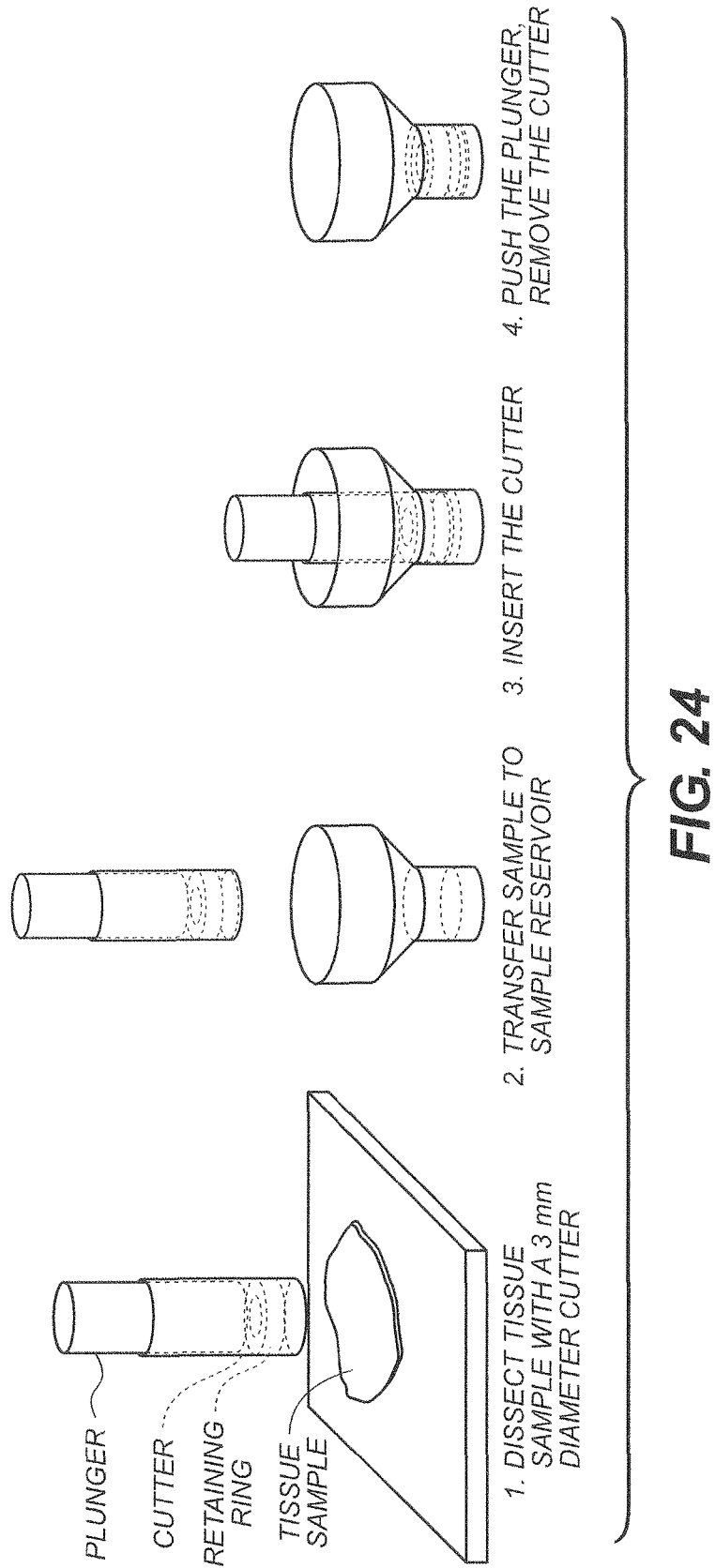
FIG. 24 schematically illustrates a process for fixing a tissue sample for on-CARD processing, according to a non-limiting, illustrative aspect of the invention.
Figure 45:
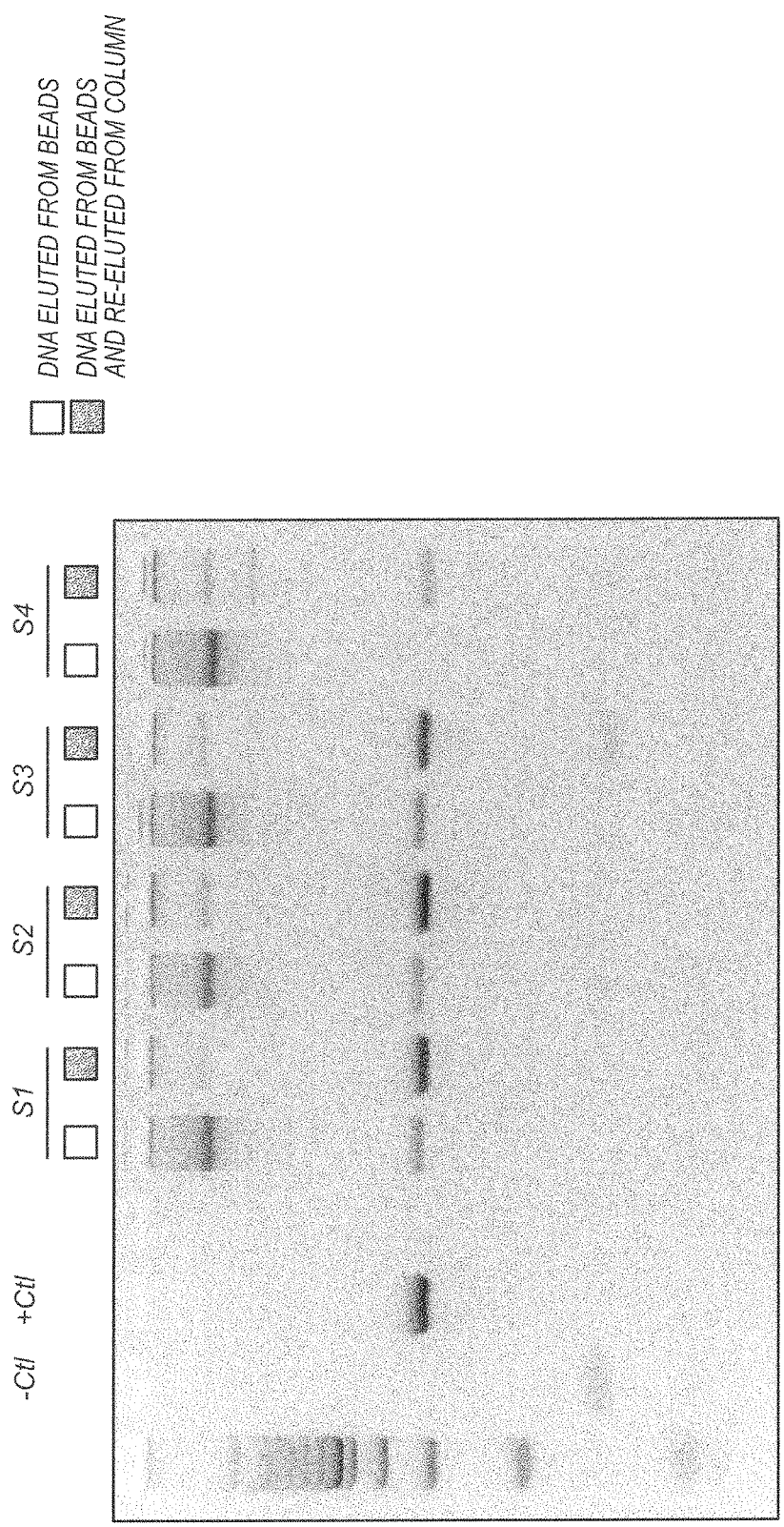
FIG. 45 shows that using the CARD configuration shown in FIG. 20, and according to the process shown in FIGS. 21-22, DNA was successfully purified, eluted and amplified.

As illustrated in FIG. 21K, dispense a visualization reagent reactant (e.g., tetramethyl benzidine "TMB") into common reagent reservoir 40 (left and right), pump on top of the analysis membrane 47 (left and right) suspended in analysis reservoir 41(left and right), circulate as described above to completely react the reagents (e.g., TMB with the HRP), and pump the contents to waste reservoir 42. Dispense wash buffer into common reagent reservoir 40 (left and right), pump on top of the analysis membrane 47 (left and right) suspended in analysis reservoir 41 (left and right), and pump to waste reservoir 42 (repeat multiple times). Finally, position the camera 27 on dispensing system 13 over the analysis membrane 47 (left and right) suspended in analysis reservoir 41 (left and right) and record the image. The image data is then processed by control system 19 and the results communicated to the operator. FIGS. 24-25 illustrate a non-limiting, exemplary process for automatically analyzing a tissue specimen using a CARD apparatus as described herein. FIG. 45 shows that using the CARD configuration shown in FIG. 20, and according to the process shown in FIGS. 21-22, DNA was successfully purified, eluted and amplified. The bands shown on the gel are amplified 25S rRNA from *Candida*. The column headings are –Ctl which denotes a benchtop negative control. +Ctl is the benchtop positive control. S1-S4 are four CARD runs. The white box results for each S1-S4 are from an aliquot removed from the CARD and amplified prior to the second step of the purification. In this embodiment, the nucleic acid was first purified, then eluted (there were 2 stages to the purification and 2 elutions: one from the first stage to the second stage and then elution from the second stage) then amplified, then run on a gel. The results confirm that the second stage of the purification provides a marked improvement of the target's amplification. In this case, the primer amplified the 25S rRNA from *Candida* which was spiked into a whole blood sample.

Referring to FIG. 24, rather than blending the specimen as is typically done, the tissue sample is dissected with a 3 mm diameter cutter. The cutter is then inserted into a sample reservoir whereupon operating the cutter plunger, the dissected sample is transferred to the analysis chamber. More specifically, with reference to FIG. 25, the sample is loaded as described immediately above; a controller dispenses lysis buffer/proteinase K into the reagent reservoir; the lysis buffer/proteinase K is pumped into the sample reservoir; the mixture is circulated; the controller dispenses ethanol into the reagent reservoir; ethanol is mixed with the reaction solution; the reaction solution is pumped into the purifier on top of the silica filter; and the reaction solution is pumped through the silica filter into the waste reservoir via the silica membrane. Additionally, a screen may be inserted into the reservoir prior to the insertion of the sample so that the tissue passes through the screen in order to increase the surface area of the specimen for the reagents to react more efficiently with the specimen.

Figure 22:
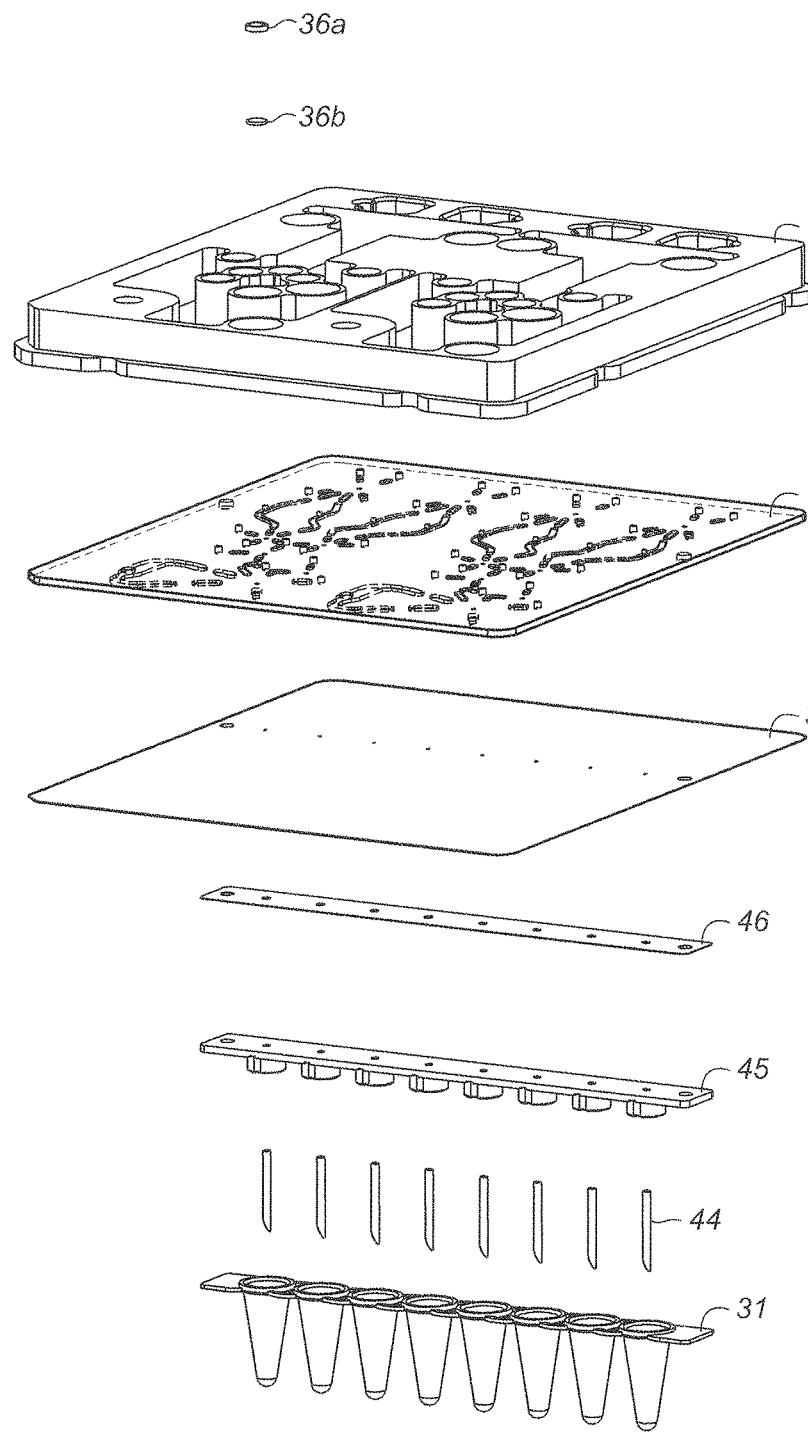
FIG. 22 shows an exploded view of a double assay unit arrangement, which shows the reservoir layer, the fluidic layer, the film layer, and the amplification reactors including the lumens used to fill and empty the amplification reactors, according to an exemplary aspect of the invention.

FIG. 22 illustrates an exploded view of a double assay unit arrangement of a channel style magnetic separation/concentration system showing the reservoir layer 17, the fluidic transport layer 16, the film layer 30, and the out of plane amplification reactors 31 showing their component parts. FIG. 22 also includes the silica filter system 36a and 36b.

Nucleic Acids

In certain embodiments, the invention provides a method of amplifying and/or isolating nucleic acid molecules of interest (also referred to herein as "nucleic acids of interest," "target nucleic acids," "target polynucleotides"). An isolated nucleic acid molecule (or "isolated nucleic acid") is a nucleic acid molecule (or "nucleic acid") that is separated from other nucleic acid molecules that are present in the natural source of the nucleic acid molecule. Preferably, an "isolated" nucleic acid is free of nucleic acid sequences (e.g., protein encoding sequences) that naturally flank the nucleic acid (i.e., sequences located at the 5' and 3' ends of the nucleic acid) in the genomic DNA of the organism from which the nucleic acid is derived. In other embodiments, the isolated nucleic acid is free of intron sequences.

"Nucleic acids of interest," "target nucleic acids" or "target polynucleotides" refer to molecules of a particular polynucleotide sequence of interest. Such nucleic acids of interest that may be analyzed by the methods of the present invention include, but are not limited to DNA molecules such as genomic DNA molecules, cDNA molecules and fragments thereof, including oligonucleotides, expressed sequence tags ("ESTs"), sequence tag sites ("STSs"), etc. Nucleic acids of interest that may be analyzed by the methods of the invention also include RNA molecules such as, but by no means limited to messenger RNA (mRNA) molecules, ribosomal RNA (rRNA) molecules, cRNA (i.e., RNA molecules prepared from cDNA molecules that are transcribed in vivo) and fragments thereof. In various embodiments, the isolated nucleic acid molecule can contain less than about 5 kb, 4 kb, 3 kb, 2 kb, 1 kb, 0.5 kb or 0.1 kb of nucleotide sequences that naturally flank the nucleic acid molecule in genomic DNA of the cell from which the nucleic acid is derived. Moreover, an isolated nucleic acid molecule, such as a cDNA molecule, can be substantially free of other cellular material, of culture medium when produced by recombinant techniques, or of chemical precursors or other chemicals when chemically synthesized.

The nucleic acids of interest can be DNA or RNA or chimeric mixtures or derivatives or modified versions thereof. The nucleic acid can be modified at the base moiety, sugar moiety, or phosphate backbone, and may include other appending groups or labels.

For example, in some embodiments the nucleic acid can comprise at least one modified base moiety which is selected from the group including but not limited to 5-fluorouracil, 5-bromouracil, 5-chlorouracil, 5-iodouracil, hypoxanthine, xanthine, 4 acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

In another embodiment, the nucleic acid can comprise at least one modified sugar moiety selected from the group including but not limited to arabinose, 2-fluoroarabinose, xylulose, and hexose.

In yet another embodiment, the nucleic acid can comprise at least one modified phosphate backbone selected from the group including but not limited to a phosphorothioate, a phosphorodithioate, a phosphoramidothioate, a phosphoramidate, a phosphordiamidate, a methylphosphonate, an alkyl phosphotriester, and a formacetal or analog thereof.

Nucleic acids for use as primers, probes, or templates may be obtained commercially or derived by standard methods known in the art, e.g., by use of an automated DNA synthesizer (such as those commercially available from Biosearch Technologies, Inc., Novato, Calif.; Applied Biosystems, Foster City, Calif., etc.) and standard phosphoramidite chemistry; or by cleavage of a larger nucleic acid fragment using non-specific nucleic acid cleaving chemicals or enzymes or site-specific restriction endonucleases.

If the sequence of a nucleic acid of interest from one species is known and the counterpart gene from another species is desired, it is routine in the art to design probes based upon the known sequence. The probes hybridize to nucleic acids from the species from which the sequence is desired, for example, hybridization to nucleic acids from genomic or DNA libraries from the species of interest.

In one embodiment, a nucleic acid molecule is used as a probe that is complementary to, or hybridizable under moderately stringent conditions to, an amplified, isolated nucleic acid of interest.

In another embodiment, a nucleic acid molecule is used as a probe that hybridizes under moderately stringent conditions to, and is at least 95% complementary to, an amplified nucleic acid of interest.

In another embodiment, a nucleic acid molecule is used as a probe that is at least 45% (or 55%, 65%, 75%, 85%, 95%, 98%, or 99%) identical to a nucleotide sequence of interest or a complement thereof.

In another embodiment, a nucleic acid molecule is used as a probe that comprises a fragment of at least 25 (50, 75, 100, 125, 150, 175, 200, 225, 250, 275, 300, 325, 350, 375, 400, 425, 450, 500, 550, 600, 650, 700, 800, 900, 1000, 1200, 1400, 1600, 1800, 2000, 2400, 2600, 2800, 3000, 3200, 3400, 3600, 3800, or 4000) nucleotides of a nucleic acid of interest or a complement thereof.

In another embodiment, a nucleic acid molecule is used as a probe that hybridizes under moderately stringent conditions to an amplified nucleic acid molecule having a nucleotide sequence of interest, or a complement thereof. In other embodiments, a nucleic acid molecule is used as a probe that can be at least 25, 50, 75, 100, 125, 150, 175, 200, 225, 250, 275, 300, 325, 350, 375, 400, 425, 450, 500, 550, 600, 650, 700, 800, 900, 1000, 1200, 1400, 1600, 1800, 2000, 2200, 2400, 2600, 2800, 3000, 3200, 3400, 3600, 3800, or 4000 nucleotides in length and hybridize under moderately stringent conditions to an amplified nucleic acid molecule of interest or a complement thereof.

Nucleic acids that can be used as probes (or templates) for detecting an amplified nucleic acid of interest can be obtained by any method known in the art, e.g., from a plasmid, by polymerase chain reaction (PCR) using synthetic primers hybridizable to the 3' and 5' ends of the nucleotide sequence of interest and/or by cloning from a cDNA or genomic library using an oligonucleotide probe specific for the nucleotide sequence. Genomic clones can be identified by probing a genomic DNA library under appropriate hybridization conditions, e.g., high stringency conditions, low stringency conditions or moderate stringency conditions, depending on the relatedness of the probe to the genomic DNA being probed. For example, if the probe for the nucleotide sequence of interest and the genomic DNA are from the same species, then high stringency hybridization conditions may be used; however, if the probe and the genomic DNA are from different species, then low stringency hybridization conditions may be used. High, low and moderate stringency conditions are all well known in the art.

Amplified nucleic acids of interest can be detectably labeled using standard methods known in the art.

The detectable label can be a fluorescent label, e.g., by incorporation of nucleotide analogs. Other labels suitable for use in the present invention include, but are not limited to, biotin, iminobiotin, antigens, cofactors, dinitrophenol, lipoic acid, olefinic compounds, detectable polypeptides, electron rich molecules, enzymes capable of generating a detectable signal by action upon a substrate, and radioactive isotopes. Preferred radioactive isotopes include, 32P, 0.35S, 14C, 15N and 125I, to name a few. Fluorescent molecules suitable for the present invention include, but are not limited to, fluorescein and its derivatives, rhodamine and its derivatives, texas red, 5'-carboxy-fluorescein ("FMA"), 2',7'-dimethoxy-4',5'-dichloro-6-carboxy-fluorescein ("JOE"), N,N,N',N'-tetramethyl-6-carboxy-rhodamine ("TAMRA"), 6'-carboxy-X-rhodamine ("ROX"), HEX, TET, IRD40 and IRD41. Fluorescent molecules that are suitable for the invention further include: cyamine dyes, including but not limited to Cy2, Cy3, Cy3.5, Cy5, Cy5.5, Cy7 and Fluor X; BODIPY dyes, including but not limited to BODIPY-FL, BODIPY-TR, BODIPY-TMR, BODIPY-630/650, and BODIPY-650/670; and ALEXA dyes, including but not limited to ALEXA-488, ALEXA-532, ALEXA-546, ALEXA-568, and ALEXA-594; as well as other fluorescent dyes known to those skilled in the art. Electron rich indicator molecules suitable for the present invention include, but are not limited to, aferritin, hemocyanin, and colloidal gold. Alternatively, an amplified nucleic acid of interest (target polynucleotide) may be labeled by specifically complexing a first group to it. A second group, covalently linked to an indicator molecule and which has an affinity for the first group, can be used to indirectly detect the target polynucleotide. In such an embodiment, compounds suitable for use as a first group include, but are not limited to, biotin and iminobiotin.

The nucleic acids of interest that are amplified and analyzed (e.g., detected) by the methods of the invention can be contacted to a probe or to a plurality of probes under conditions such that polynucleotide molecules having sequences complementary to the probe hybridize thereto. As used herein, a "probe" refers to polynucleotide molecules of a particular sequence to which nucleic acid molecules of interest having a particular sequence (generally a sequence complementary to the probe sequence) are capable of hybridizing so that hybridization of the target polynucleotide molecules to the probe can be detected. The polynucleotide sequences of the probes may be, e.g., DNA sequences, RNA sequences or sequences of a copolymer of DNA and RNA. For example, the polynucleotide sequences of the probes may be full or partial sequences of genomic DNA, cDNA, mRNA or cRNA sequences extracted from cells. The polynucleotide sequences of the probes may also be synthesized, e.g., by oligonucleotide synthesis techniques known to those skilled in the art. The probe sequences can also be synthesized enzymatically in vivo, enzymatically in vitro (e.g., by PCR) or non-enzymatically in vitro.

Preferably, the probes used in the methods of the present invention are immobilized to a solid support or surface such that polynucleotide sequences that are not hybridized or bound to the probe or probes may be washed off and removed without removing the probe or probes and any polynucleotide sequence bound or hybridized thereto. Methods of immobilizing probes to solid supports or surfaces are well known in the art. In one particular embodiment, the probes will comprise an array of distinct polynucleotide sequences bound to a solid (or semi-solid) support or surface such as a glass surface or a nylon or nitrocellulose membrane. Most preferably, the array is an addressable array wherein each different probe is located at a specific known location on the support or surface such that the identity of a particular probe can be determined from its location on the support or surface. In a specific embodiment, the method described in WO 2009/049268 A1 by Zhou et al. (published Apr. 16, 2009) can be used to immobilize nucleic acid probes to a solid support or surface.

Although the probes used in the invention can comprise any type of polynucleotide, in preferred embodiments the probes comprise oligonucleotide sequences (i.e., polynucleotide sequences that are between about 4 and about 200 bases in length, and are more preferably between about 15 and about 150 bases in length). In one embodiment, shorter oligonucleotide sequences are used that are between about 4 and about 40 bases in length, and are more preferably between about 15 and about 30 bases in length. However, a more preferred embodiment of the invention uses longer oligonucleotide probes that are between about 40 and about 80 bases in length, with oligonucleotide sequences between about 50 and about 70 bases in length (e.g., oligonucleotide sequences of about 60 bases in length) being particularly preferred.

Uses of the CARD

It will be apparent to the skilled artisan that CARD-based diagnostic assays, as disclosed herein, can be used for many different applications in which bench-top based assays are currently used. The design of the plastic CARD permits the incorporation of all necessary microfluidic networks, valves, pumps and reservoirs on a simple, inexpensive disposable microfluidic device. Since all assay functions (i.e., flow and mixing rates, temperature control, including thermocycling, resident times, etc.) are easily controlled by software, sophisticated multiplex PCR assays can be easily performed by individuals of varying skill level. Furthermore, CARDs can be inserted in either a portable, battery operated POC controller or into a higher throughput EncompassMDx™ workstation. Regardless of the format selected, however, ease-of-performance is achieved.

The CARD can be adapted by the skilled artisan to assay for any nucleic acid sequence of interest through choice of primer for amplification and choice of probe for detection.

In one embodiment, the CARD can be used for conducting molecular diagnostics assays, which can provide a basis for the management of potential disease states based upon an individual's genomic background.

In another embodiment, the CARD can be used for conducting screens for pharmacogenomic sensitivity, e.g., genetic predisposition for sensitivity to a drug, pharmaceutical composition, chemical or compound of interest.

In another embodiment, the CARD can be used for conducting oncogenic screening assays, i.e., screening for a nucleic acid of interest that is associated with predisposition for cancer.

In another embodiment, the CARD can be used for conducting screening assays for infectious disease agents, pathogens or sepsis.

In another embodiment, the CARD can be used for analysis of single nucleotide polymorphisms (SNPs) for oncology purposes, pharmacogenomic purposes, companion diagnostics (dosing or other needs specific to a particular pharmaceutical compound) or to detect communicable or noncommunicable infectious diseases.

In another embodiment, the CARD can be used for industrial or environmental assays for organisms of interest that are infectious to humans, animals or plants or for spoilage organisms in processed foods or non-processed foods.

In another embodiment, the CARD can be used industrially for conducting assays for monitoring recreational water (beaches, pools water parks, etc.) or water treatment systems for drinking water, ballast water or treated waste water.

In another embodiment, the CARD can be used for conducting screening assays for sparse target nucleic acids distributed in a large volume of liquid.

In another embodiment, the CARD can be used for conducting screening assays for sparse target nucleic acids wherein the sparse targets are to be distinguished from a high background of non-target nucleic acids in a sample.

In certain embodiments, the CARD can be easily adapted to have multiple amplification reactors (e.g., 31, FIGS. 11, 12) that sequester competing primers and that feed into a single analysis reservoir 41, so that multiple amplification reactions can be conducted concurrently on nucleic acids from a single sample.

The CARD can be adapted by the skilled artisan to perform any thermally mediated nucleic acid amplification known in the art including but not limited to: polymerase chain reaction (PCR), reverse-transcriptase (RT-) PCR, Rapid Amplification of cDNA Ends (RACE), rolling circle amplification, Nucleic Acid Sequence Based Amplification (NASBA), Transcript Mediated Amplification (TMA), Ligase Chain Reaction, transcription-associated amplification (TAA), Cold PCR and non-enzymatic amplification technology. (NEAT).

In addition to heating the CARD for nucleic acid amplification, the CARD can be heated to test for viability of a detected organism (e.g., the presence of heat-shock associated RNA expressed by the organism). Heating can also be used to regulate the stringency of hybridization in analyses such as the detection of single nucleotide polymorphisms (SNPs).

The CARD can be adapted by the skilled artisan to accommodate any analytic or detection method for amplicons known in the art, including but not limited to: colorimetric, fluorescent colorimetric, chemiluminescence, electrochemical, electrophoretic, lateral flow, protein microarray, nucleic acid microarray, fluorescence detection methods or various combinations of the detection methods listed above.

The following examples are offered by way of illustration and not by way of limitation.

EXAMPLES

Example 1

Pharmacogenomic Assay for Warfarin Sensitivity

This example demonstrates a specific embodiment of a pharmacogenomic assay for warfarin sensitivity that has been fully integrated and automated on the CARD. Reverse dot blot (RDB) was conducted to analyze the results, although as indicated below, the primer extension method can also be used. The protocol described below can be easily adapted by the skilled practitioner to assay for any single nucleotide polymorphism (SNP) of interest through choice of primers and probes, and can be used for other assays, e.g., oncogenic screening assays.

In general, assays conducted on the CARD comprise the following steps:
1. Direct application of a raw specimen to the CARD (the only operator step).
2. Chemical cell lysis.

Figure 29:
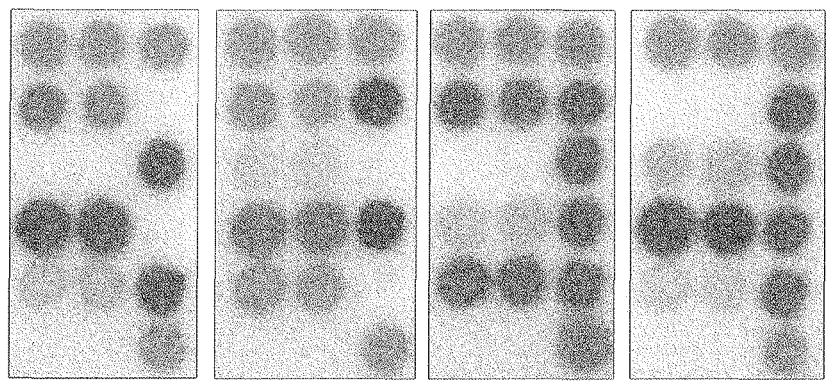
FIG. 29: Results of individual genotypes obtained using the Warfarin SNP assay in conjunction with RDB on an embodiment of the CARD. Filter results from buccal swabs of four individuals are shown in the upper portion of the figure. The table below the filters indicates the genotypes read from the filters. The filter key at the bottom of the figure shows the spotting system within each of the four microarrays.

3. Nucleic acid extraction and purification via binding to a silica column contained in the CARD.
4. Elution of purified nucleic acids from the silica column
5. Mixing of an aliquot of the purified nucleic acids with a PCR master mixture containing all of the reagents needed to perform PCR amplification including buffer, primers, nucleotide triphosphates, magnesium chloride, Taq DNA polymerase and Uracil-DNA Glycosylase, which is used to insure against the unlikely event of amplicon cross-over contamination.
6. Introduction of the complete mixture into the PCR thermocycler chambers located directly above the resistive heaters embedded in the manifold, followed by initiation of the thermocycling program.
7. Following completion of the thermocycling program, introduction of the amplicons into the detection module where they are subjected to an assay, e.g., by the primer extension method (FIGS. 26A-B) or a reverse dot blot (RDB) assay (FIG. 29).
8. Imaging and analysis of the detected spots on analysis membrane, e.g., via the primer extension method or RDB membrane.
9. Objective results provided to the user.

Although PCR amplification is employed in this embodiment, any thermally mediated nucleic acid amplification known in the art can be performed using the above approach, including but not limited to: polymerase chain reaction (PCR), reverse-transcriptase (RT-) PCR, Rapid Amplification of cDNA Ends (RACE), rolling circle amplification, Nucleic Acid Sequence Based Amplification (NASBA), Transcript Mediated Amplification (TMA), Ligase Chain Reaction, transcription-associated amplification (TAA), Cold PCR and non-enzymatic amplification technology. (NEAT).

In reference to FIGS. 14A-14L and the reservoir variation in FIG. 18, the following operations and reagents were used to perform pharmacogenomic studies pertaining to single nucleotide polymorphisms ("SNPs") of three individual SNPs known to be indicators of warfarin sensitivity: CYP2C9*2, CYP2C9*3, and VKORC1*2.

Probe Set
The following set of probes was used for detecting CYP2C9*2, CYP2C9*3, and VKORC1*2:

```
CYP2C9*2_WT
                                    (SEQ ID NO: 113)
/5AmMC6/ TGAGGACCGTGTTCA

CYP2C9*2_MUT
                                    (SEQ ID NO: 114)
/5AmMC6/ TGAGGACTGTGTTCA

CYP2C9*3_WT
                                    (SEQ ID NO: 115)
/5AmMC6/ A AGG TCA ATG TAT CTC T

CYP2C9*3_MUT
                                    (SEQ ID NO: 116)
/5AmMC6/ AGG TCA AGG TAT CTC

VKORC1_WT
                                    (SEQ ID NO: 117)
/5AmMC6/ CAT CGA CCC TTG GAC

VKORC1_MUT
                                    (SEQ ID NO: 118)
/5AmMC6/GTC CAA GAG TCG ATG A
```

Sample Addition and Cell Lysis
a. An operator adds a 5 µl sample of either blood or suspended buccal swabs into the sample input reservoir.
b. Dispense 30 µl of a cell storage buffer into the reagent input reservoir and pump it into the sample input reservoir.
c. Dispense 30 µl of a mixture of Proteinase K and lysis buffer into the reagent input reservoir and pump it into the sample input reservoir and incubate for 5 minutes.
d. Dispense 30 µl of ethanol into the reagent input reservoir and pump it into the sample input reservoir.
e. Pump the entire contents of the sample input reservoir on top of the filter in the purification reservoir and then pull the contents through the filter and pump it to waste.
f. Dispense 40 µl of ethanol into the reagent input reservoir and pump it onto the top of the filter in the purification reservoir and then pull the contents through the filter and pump it to waste.
g. Dispense 70 µl of wash buffer 1 into the reagent input reservoir and pump it onto the top of the filter in the purification reservoir and then pull the contents through the filter and pump it to waste.
h. Dispense 70 µl of wash buffer 2 into the reagent input reservoir and pump it onto the top of the filter in the purification reservoir and then pull the contents through the filter and pump it to waste.
i. Dispense 90 µl of water into the reagent input reservoir and pump it to waste.
j. Dispense 70 µl of elution buffer into the reagent input reservoir and pump it onto the top of the filter in the purification reservoir and then pump it to waste back through the channel it came from. Then pull any remaining fluid through the filter and pump it to waste.

Elution
a. Dispense 50 µl of elution buffer into one of the elution reservoirs and pump a portion of it to the other elution reservoir then pump the remainder up through the bottom of the filter in the purification reservoir and then fluff it by alternatively filling and emptying the purification reservoir at least 2 times.

PCR Loading
a. Dispense 12 µl of PCR master mix 1 into one of the master mix reservoirs and then repeat with 12 µl of PCR master mix 2 into the other master mix reservoir.
b. Pump a small amount (3 flexes of the diaphragm) of the contents of the purification reservoir to the second elution reservoir to which elution buffer was pumped.
c. Pump a single flex of the diaphragm to move a small amount of the material from the purification reservoir to one of amplification reservoirs then fill that same amplification reservoir with the master mix from the master mix reservoir on the same side as the amplification reservoir. Repeat to fill the second amplification reservoir.

PCR
a. 10 minutes at 37° C.
b. 2 minutes at 95° C.
c. Cycle 40×
  i. 30 seconds at 95° C.
  ii. 30 seconds at 45° C.
  iii. 30 seconds at 72° C.
  iv. 3 minutes at 72° C.

Reverse Dot Blot (RDB) Filter Blocking
RDB filter blocking is performed during thermocycling so that the two steps are coordinated with the completion of the amplification.
a. Dispense 80 µl of water into the analysis reagent reservoir and pump it to the analysis filter and then circulate alternatively clockwise and counterclockwise 15 times each to waste.

b. Dispense 80 μl of 0.1N NaOH into the analysis reagent reservoir and pump it to the analysis filter and circulate it alternatively clockwise and counterclockwise 15 times and then pump to waste.

c. Dispense 80 μl of water into the analysis reagent reservoir and pump it to the analysis filter and then circulate alternatively clockwise and counterclockwise 15 times each to waste. Repeat this step 2 more times.

Pre-Hybridization a. Dispense 80 μl of SS buffer (0.15M NaCl+0.01M Sodium Phosphate+0.001M EDTA+0.1% SDS with final pH 7.25-7.50) into the analysis reagent reservoir and pump it to the analysis filter and circulate it Dispense 80 μl of water into the analysis reagent reservoir and pump it to the analysis filter and then circulate alternatively clockwise and counterclockwise 5 times and then incubate without circulation for 10 minutes.

Amplicon Withdrawal

During the 10 minute incubation for pre-hybridization, these processes may begin.

a. Increase temperature in the amplification reactors to 95° C. for 30 seconds just prior to adding the SS buffer.

b. Concurrently dispense 80 μl of SS buffer into the analysis reagent reservoir and pump it into one of the amplification reactors. Repeat for the other amplification reactor. Incubate each amplification reactor for 3 minutes.

c. Turn off the amplification heaters and cool the amplification reactors allowing the wax/silicone to harden the sealing layer so that when removing the amplicons the liquid phase wax/silicone layer is not removed with the amplicons.

Hybridization a. Concurrently with the amplicon withdrawal steps a-c, empty the analysis reservoir and increase the temperature of the heater under the analysis reservoir to 50° C. to heat the membrane.

b. Pump 3 strokes each for each amplification reactor to pump some of the contents of each of the reactors to the analysis membrane.

c. Incubate by circulating alternatively clockwise and counterclockwise the contents of the analysis reservoir for fifteen minutes. It is best to use the covered analysis reservoir variation to improve the reaction. Then empty the contents to waste.

d. Dispense 80 μl of SS buffer into the analysis reagent reservoir and pump it to the analysis filter and then circulate alternatively clockwise and counterclockwise 15 times each then pump to waste. Repeat 2 times.

e. Decrease the temperature of the analysis reservoir to less than 30° C.

f. Dispense 80 μl of SS buffer into the analysis reagent reservoir and pump it to the analysis filter and then circulate it once then incubate it for 5 minutes circulating it once per minute and then pump it to waste.

Conjugation a. Dispense 80 μl of HRP into the analysis reagent reservoir and pump it to the analysis membrane circulate it alternatively clockwise and counterclockwise for 10 minutes then pump to waste.

b. Dispense 80 μl of SS buffer into the analysis reagent reservoir and pump it to the analysis filter and then circulate alternatively clockwise and counterclockwise 15 times each then pump to waste. Repeat 3 times.

Substrate Addition a. Dispense 80 μl of TMB into the analysis reagent reservoir and pump it to the analysis membrane circulate alternatively clockwise and counterclockwise for 5 minutes then pump to waste.

b. Dispense 80 μl of water into the analysis reagent reservoir and pump it to the analysis membrane circulate alternatively clockwise and counterclockwise 15 times then pump to waste. Repeat 2 times.

Image Analysis a. Position the camera over the analysis membrane and record the image.

b. Send the image to the control system for processing.

c. Report the results.

Example 2

CARD-Based Methods for Rapid and Automatic Detection of Single Nucleotide Polymorphisms (SNPs)

Introduction

This example demonstrates use of the CARD for the evolving molecular diagnostics industry that incorporates low cost, CARD technology to analyze clinical raw samples. Once a raw specimen is introduced into the CARD, all assay functions, including cell lysis, nucleic acid purification, multiplex PCR, and end-point analysis, are automatically performed.

The CARD was used in a pharmacogenomic assay to detect single nucleotide polymorphisms (SNPs) associated with warfarin sensitivity. Raw buccal swab samples from twenty individual volunteers were analyzed and the SNP profiles, identified by the warfarin sensitivity assay carried out on the CARD, were confirmed via bi-directional DNA sequencing. The pharmacogenomics protocol described below, however, can be easily adapted by the skilled practitioner to assay for any nucleic acid sequence or SNP of interest through choice of primers and probes. Such an assay could be used, for example, to screen for viral pathogens, for oncogenes or other genetic mutations, variants or markers of interest, and virtually any cell or tissue can be assayed.

Background

The use of molecular diagnostics has expanded greatly since its inception in the early 1980s, particularly as a means to permit the detection of slow growing or fastidious bacteria responsible for infectious diseases. The detection of viral pathogens, including viral load testing has also been significantly improved by molecular diagnostics. As more data have become available regarding the human genome, the use of molecular diagnostics in pharmacogenomic, companion diagnostics, and other personalized medicine applications continues to gain momentum. Despite its power and versatility, however, the need for highly trained personnel and expensive capital equipment has restricted the use of molecular diagnostics to specialized laboratories or central labs suitably equipped and staffed.

While many effective "point-of-care" (POC) diagnostics have been developed that rely upon immunological assays in a lateral flow assay format (e.g., pregnancy tests), the ability to perform the more complex molecular assays has not yet been fully achieved in an easy-to-use and inexpensive POC format. Before molecular diagnostics can be more broadly used in various POC settings, the assays need to be simplified and equipment requirements reduced. Currently, "bench top" molecular assays require significant effort by highly trained personnel to prepare the samples for analysis, starting with raw clinical specimens. Subsequently, the gene amplification and detection steps also require significant skill and expensive equipment. Moreover, while lateral flow POC assays frequently rely upon subjective interpretation of color intensity on test strips, results from more sophisticated molecular assays would be more meaningful if unambiguous and objective digital results can be provided. If all of these processes could be integrated in a seamless, fully automated manner, individuals of varying skill level could perform a range of POC molecular assays and achieve objective, clear-cut interpretation of results in an economical assay format.

The challenges posed by the molecular POC markets have led to the introduction of several "sample-to-results" platforms, but most still require either separate "sample preparation" steps and/or equipment or considerable "pre-preparation" of the sample prior to introduction into the system to achieve gene amplification and detection. To achieve true "sample-to-results" simplicity a platform has been developed that integrates all required sample preparation, assay, and detection steps into a single, inexpensive disposable plastic device capable of achieving fully automated molecular diagnostic testing. The CARD demonstrated in this example requires only the introduction of a raw specimen, with all subsequent steps performed automatically. The device's low cost of both capital equipment and disposables, as well as the absence of any "hands on" efforts, will help make molecular diagnostics a reality in the entire spectrum of critical and point-of-care testing.

Materials and Methods

Assays

"Bench top" assays were optimized to establish various parameters that were then converted to the fully automated platform of the CARD. Primers and probes were designed, using methods known in the art, for amplification and capture, respectively. This could also involve optimization of standard chemical lysis and nucleic acid purification protocol if any of the organisms being analyzed were too tough to be lysed.

All sequences were obtained from the National Center for Biotechnology (NCBI) information (www.ncbi.nlm.nih.gov). Primers and probes were designed using CLC Sequence Viewer (www.clcbio.com), Integrated DNA Technologies SciTools, (www.idtdna.com/scitools/) and NCBI Primer Blast (www.ncbi.nlm.nih.gov/tools/primer-blast) using standard methods known in the art. All primers and probes were synthesized at Integrated DNA Technologies (Coralville, Iowa). All microbial and viral DNAs were purchased from the American Type Culture Collection (ATCC, Manassas, Va.).

Warfarin Sensitivity Assay

De-identified buccal swabs were obtained from volunteers following informed consent and cells were lysed and DNA extracted. DNA was subjected to amplification on the CARD using primers designed to amplify the regions surrounding three individual SNPs known to inform warfarin sensitivity CYP2C9*2, CYP2C9*3, and VKORC1*2 (27-32). The CYP2C9*2 and CYP2C9*3 SNPs correspond to mutations in the cytochrome P450 gene, and the VKORC1*2 corresponds to a mutation in the vitamin K epoxide reductase complex subunit 1 gene.

Following purification, the DNA was separated into two distinct PCR reactions; one mix contained primers to amplify the regions surrounding both CYP2C9 mutations and the other mix contained primers to amplify the region surrounding the VKORC1*2 mutation. Following PCR, the amplicons from both reaction mixes were mixed, denatured, and then moved to a chamber containing probes covalently linked to the membrane filters. The denatured amplicons were annealed to the capture probes in the presence of buffer, dNTPs including biotinylated dUTP, magnesium ions, and DNA polymerase lacking the 3'-5' exonuclease proof-reading function (e.g., Vent Polymerase, New England Biolabs, Ipswich, Mass.).

For the primer extension assay, the immobilized probes, approximately 20 nucleotides long, contained the informative nucleotide at their 3' termini. Under these conditions the denatured and annealed amplicon strand behaves as the template, while the solid-phase probe represents the "primer" to be extended. When an exact match is present between the template and the primer, DNA synthesis occurs incorporating dNTPs including biotinylated dUTP. However, if there is a single mismatch between the terminal base of the immobilized "primer" and the template, elongation, and thus biotin incorporation does not occur (FIGS. 26A-B).

As conducted on the CARD, the thermocycling step of the primer extension assay is performed in the analysis reservoir 41 (see FIGS. 14A-C).

Following one round of elongation, extended products were then detected following incubation with streptavidin conjugated HRP and TMB substrate.

Digitally captured images were subjected to analysis with Image J software (rsb.info.nih.gov/ij). The mean intensities of the spots were measured and the averages of the wild-type spots divided by the average of the mutant probes. Ratios greater than, equal to, or less than 1 correspond to a homozygous wild-type, heterozygous, or homozygous mutant genotypes, respectively.

Confirmation of primer extended genotypes was achieved via bi-directional sequencing performed at the Cornell University Life Sciences Core Laboratories Center (Cornell University, Ithaca, N.Y.) using an Applied Biosystems Automated 3730DNA Analyzer with Big Dye Terminator chemistry (Rosenblum, B B, Lee, L G, Spurgeon, S L, et al. New dye-labeled terminators for improved DNA sequencing patterns. Nucleic Acid Res. 1997; 25: 4500-4504; Heiner, C R., Kunkapiller, K L, Chen, S-M., et al. Sequencing Multimegabase-Template DNA with BigDye Terminator Chemistry. Genome Research 1998; 8: 557-561) and Ampli-Taq-FS DNA Polymerase (Applied Biosystems, Inc., Foster City, Calif.).

Results

This assay run on the CARD was designed to perform genotyping analysis (warfarin sensitivity assay) by identifying three separate SNPs known to influence the metabolism of warfarin. This single (VKORC1*2) and multiplex (CYP2C9*2 and CYP2C9*3) PCR assays were designed to amplify the regions surrounding each SNP and then the denatured amplicons were subjected to primer extension assay to genotype each allele.

To evaluate the SNP assay on the CARD, buccal swabs from a total of 20 volunteers were analyzed. Each sample was evaluated using (1) the warfarin SNP assay run on the CARD and (2) bi-directional DNA sequencing. Using the primer extension assay, the warfarin sensitivity assay distinguishes between the various alleles found across the three distinct warfarin-related SNPs. As shown in FIGS. 26A-B, PCR-amplified DNA sequences were denatured and allowed to hybridize to specific capture probes immobilized on membrane filters. In this assay, the capture probes ultimately served as the primers to be extended using the amplicons as templates. Incorporation of biotinylated dUTP along the primer extended sequences results in streptavidinylated HRP binding and color detection as described in the Materials and Methods.

Figure 27:
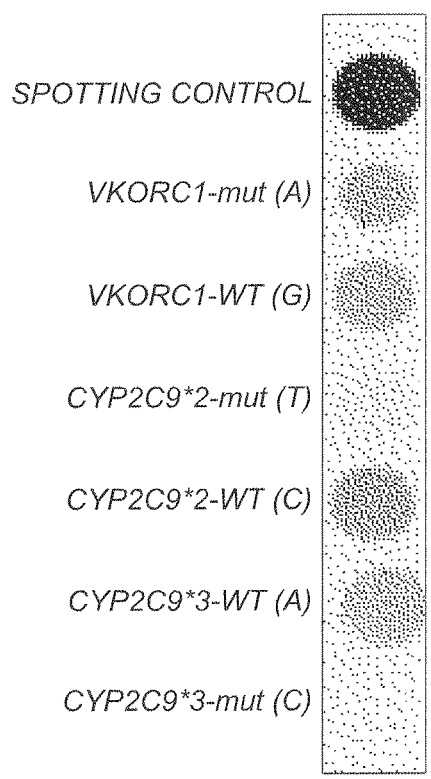
FIG. 27: Representative image derived from the primer extension component of the Warfarin SNP assay on an embodiment of the CARD. Colored precipitates are detected following hybridization of denatured amplicons with solid-phase capture probes, followed by incorporation of biotinylated dUTP and non-labeled dCTP, dATP, and dGTP in the presence of DNA polymerase, and finally incubation with streptavidinylated HRP and substrate. The key indicates the allele targeted by the capture probe. Following imaging, the number of pixels detected on the WT spot is divided by the number of pixels detected on the mutant spot. WT pixels/mut pixels>1 indicates a homozygous WT; WT pixels/mut pixels=1 indicates a heterozygous; and WT pixels/mut pixels<1 indicates a homozygous mutant. The resulting genotype indicated on the filter is: VKORC1—heterozygote; CYP2C9*2—homozygous WT; and CYP2C9*3—homozygous WT.
Figure 28:
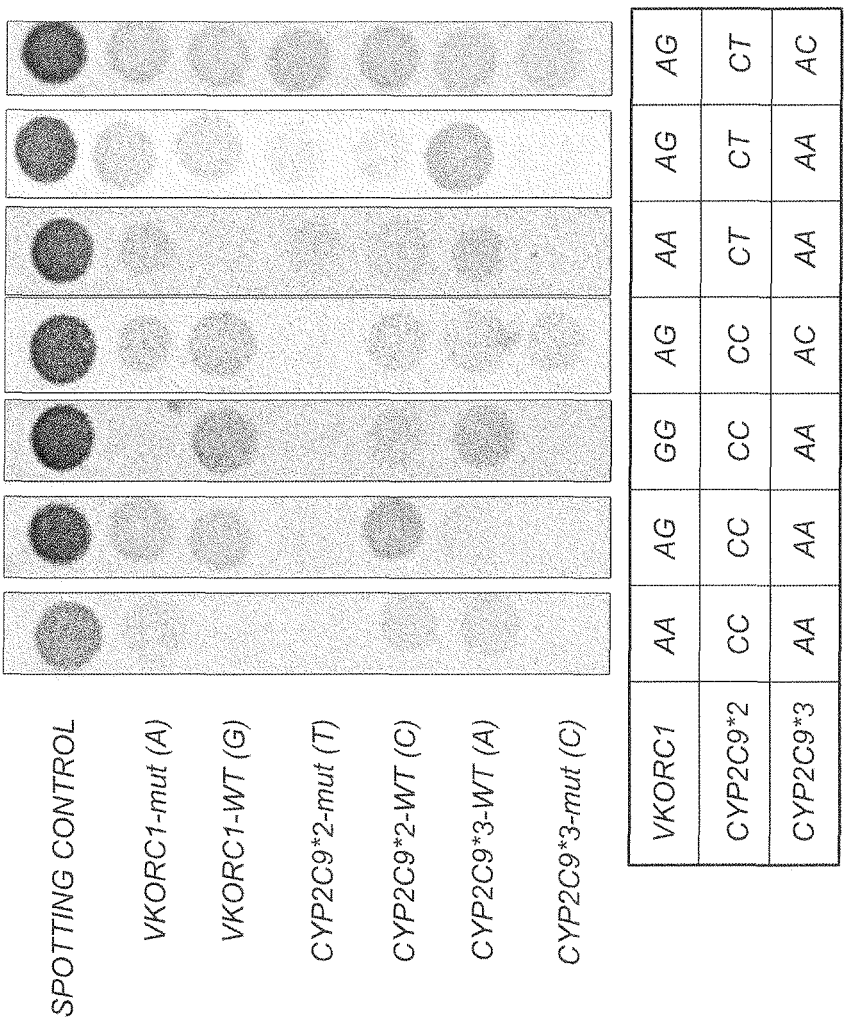
FIG. 28: Results of seven individual genotypes obtained using the Warfarin SNP assay in conjunction with primer extension on an embodiment of the CARD. Filter results from buccal swabs of seven individuals are shown in the upper portion of the figure. The lower portion of the figure indicates the genotypes read from these filters. In addition, all genotypes were verified via bi-directional sequencing. These genotypes were represented within the 20 individuals tested. The more rare combinations of genotypes were not expected in this small sample set.

FIG. 27 is a representative image demonstrating how the genotypes were read off of the primer extension filters, and FIG. 28 shows the 7 different genotypes that were obtained from the 20 individuals. The three possible genotypes that exist for each of the three SNPs identified can be detected by eye and/or established by determining the ratio of signal intensity of the individual spots. When each of the buccal swab samples from the 20 volunteers was evaluated on the warfarin sensitivity assay, the genotypes were originally read by at least two different individuals. These results were confirmed with bi-directional sequencing as well as with image analysis as described in Materials and Methods above.

The warfarin sensitivity assay in this example demonstrates the versatility of the CARD. Regardless of the assay(s) performed, only one "manual" (user conducted) step is required (i.e., initial introduction of the "raw" sample), with all subsequent steps computer automated. Owing to its ease of performance and interpretation of results, this assay will be useful in POC settings in which physicians wish to use genomic data, along with other clinical information, to help establish the correct initial dosing of warfarin. Therefore instead of relying upon time consuming and potentially dangerous "trial and error" dosing that relies upon repetitive PT/INR testing to finally achieve proper therapeutic doses of warfarin, physicians could initially start warfarin at more appropriate doses, based upon several art-known warfarin dosing algorithms (Daly, A K and King, B P. Pharmacogenetics of oral anticoagulants. Pharmacogenetics 2003; 13:247-252; Takahashi, H. and Eschizen, H. Pharmacogenetics of warfarin elimination and its clinical implications. Clin. Pharmacokinet 2001; 40: 587-603; Schwarz, U I, Ritchie, M D, Bradford, Y, et al. Genetic determinants of response to warfarin during initial anticoagulation. N. Eng. J. Med 2008; 358: 999-1008; Osinbowale, O., Al Malki, M., Schade, A., et al. An algorithm for managing warfarin resistance. Clev. Clinic J. of Med. 2009; 76: 724-730).

Assays run on the CARD provide a convenient, cost-effective means to perform sophisticated molecular assays in a completely "hands off" manner. Furthermore, the low capital costs of the equipment required to run the assays and the low disposable costs allows this platform to bring true "sample-to-results" molecular testing the point-of-care settings.

Example 3

CARD-Based Automated Human Papilloma Virus (HPV) Assay

This example demonstrates a specific embodiment of a human papilloma virus (HPV) assay that has been fully integrated and automated on the CARD. The protocol described below can be easily adapted by the skilled practitioner to assay for other nucleic acid sequences of interest through choice of primer for amplification and choice of probe for the array.

A vaginal swab is collected in a suitable transport media, which allows for extended room temperature storage, if necessary. The transport media can be, e.g., PBS buffer, in which the sample will be immediately introduced into the CARD for analysis. The transport media can also be is any type of solution known in the art that prevents DNA degradation so that the sample can be held for later use.

An aliquot is applied to the CARD and the run initiated as described in the protocol below. Without any further intervention by the operator, all the following steps are automatically performed: cell lysis, nucleic acid purification, PCR amplification and multiplexed end-point detection on a low density microarray. The following operations and reagents were used to perform the HPV assay on the CARD. See FIGS. 14A-14L.

Sample Addition and Cell Lysis
a. Operator inserts a sample (e.g., a vaginal swab) into the sample input reservoir.
b. Dispense 30 µl of a mixture of Proteinase K and lysis buffer into the reagent input reservoir and pump it into the sample input reservoir and incubate for 5 minutes.
c. Dispense 30 µl of ethanol into the reagent input reservoir and pump it into the sample input reservoir.
d. Pump the entire contents of the sample input reservoir on top of the filter in the purification reservoir and then pull the contents through the filter and pump it to waste.
e. Dispense 40 µl of ethanol into the reagent input reservoir and pump it onto the top of the filter in the purification reservoir and then pull the contents through the filter and pump it to waste.
f. Dispense 70 µl of wash buffer 1 into the reagent input reservoir and pump it onto the top of the filter in the purification reservoir and then pull the contents through the filter and pump it to waste.
g. Dispense 70 µl of wash buffer 2 into the reagent input reservoir and pump it onto the top of the filter in the purification reservoir and then pull the contents through the filter and pump it to waste.
h. Dispense 90 µl of water into the reagent input reservoir and pump it to waste.
i. Dispense 70 µl of elution buffer into the reagent input reservoir and pump it onto the top of the filter in the purification reservoir and then pump it to waste back through the channel it came from. Then pull any remaining fluid through the filter and pump it to waste.

Elution
a. Dispense 50 µl of elution buffer into one of the elution reservoirs and pump a portion of it to the other elution reservoir then pump the remainder up through the bottom of the filter in the purification reservoir and then fluff it by alternatively filling and emptying the purification reservoir at least 2 times.

Polymerase Chain Reaction (PCR) Loading
a. Dispense 12 µl of PCR master mix 1 into one of the master mix reservoirs and then repeat with 12 µl of PCR master mix 2 into the other master mix reservoir.
b. Pump a small amount (3 flexes of the diaphragm) of the contents of the purification reservoir to the second elution reservoir to which elution buffer was pumped.
c. Pump a single flex of the diaphragm to move a small amount of the material from the purification reservoir to one of amplification reservoirs then fill that same amplification reservoir with the master mix from the master mix reservoir on the same side as the amplification reservoir. Repeat to fill the second amplification reservoir.

Polymerase Chain Reaction (PCR)
a. 10 minutes at 37° C.
b. 2 minutes at 95° C.
c. Cycle 10×
 i. 30 seconds at 95° C.
 ii. 30 seconds at 46° C.
 iii. 30 seconds at 72° C.
d. Cycle 30×
 i. 15 seconds at 95° C.
 ii. 30 seconds at 49° C.
 iii. 30 seconds at 72° C.
 iv. 3 minutes at 72° C.

Reverse Dot Blot (RDB) Filter Blocking
a. Begin reverse dot blot (RDB) filter blocking during the above PCR thermocycling so that the two steps are coordinated with the completion of the amplification.
b. Dispense 150 µl of 0.1N NaOH into the analysis reagent reservoir and pump it on top of the analysis filter and circulate it from the top of the membrane through the perforated ring and back to the top of the membrane 5 times and then pump to waste.
c. Dispense 90 µl of water into the analysis reagent reservoir and pump it on top of the analysis filter and then circulate from the top of the membrane through the perforated ring and back to the top of the membrane 3 times each then pump to waste. Repeat this step 1 more time.

Pre-Hybridization
a. Dispense 70 µl of hybridization buffer (0.15M NaCl+ 0.01M Sodium Phosphate+0.001M EDTA+0.1% SDS+15% formamide with final pH 7.25-7.50) into the analysis reagent reservoir and pump it on top of the analysis filter and circulate it from the top of the membrane through the perforated ring and back to the top of the membrane 5 times then pump it to waste.

Amplicon Withdrawal
a. Dispense 70 µl of hybridization buffer into the analysis reagent reservoir and pump it onto the top of the analysis filter.
b. Dispense 70 µl of hybridization buffer into the analysis reagent reservoir and pump it into one of the amplification reactors. Repeat for the other amplification reactor.
c. Turn off the amplification heaters and cool the amplification reactors allowing the wax/silicone to harden the sealing layer so that when removing the amplicons the liquid phase wax/silicone layer is not removed with the amplicons.

Hybridization
a. Pump the contents of each amplification reactor to the top of the analysis membrane.
b. Incubate by circulating (from the top of the analysis membrane through the perforated ring and back to the top of the analysis membrane) the contents of the analysis reservoir for 12.5 minutes. Then empty the contents to waste.
c. Dispense 90 µl of wash buffer into the analysis reagent reservoir and pump it to the top of the analysis filter and then circulate from the top of the analysis membrane through the perforated ring and back to the top of the analysis membrane 3 times each then pump to waste. Repeat 2 times.

Conjugation
a. Dispense 120 µl of HRP into the analysis reagent reservoir and pump it to the top of the analysis membrane. Circulate it from the top of the analysis membrane through the perforated ring and back to the top of the analysis membrane for 4 minutes then pump to waste.
b. Dispense 90 µl of wash buffer into the analysis reagent reservoir and pump it to the top of the analysis filter. Then circulate from the top of the analysis membrane through the perforated ring and back to the top of the analysis membrane 3 times each then pump to waste. Repeat 3 times.

Substrate Addition
a. Dispense 120 µl of TMB into the analysis reagent reservoir and pump it to the top of the analysis membrane circulate from the top of the analysis membrane through the perforated ring and back to the top of the analysis membrane for 10 minutes then pump to waste.
b. Dispense 90 µl of water into the analysis reagent reservoir and pump it to the top of the analysis membrane. Then circulate from the top of the analysis membrane through the perforated ring and back to the top of the analysis membrane 15 times then pump to waste. Repeat 3 times.

Image Analysis
a. Position the camera over the analysis membrane and record the image.
b. Send the image to the control system for processing.
c. Report the results.

Example 4

CARD-Based Rapid Molecular Detection and Identification of 20 Clinically Relevant HPV Types This example demonstrates a method for rapidly, easily and automatically detecting and distinguishing at least 20 types of clinically relevant human papilloma virus (HPV) directly from clinical samples on the CARD, using the protocol discussed above in Example 3.

Introduction

Cervical cancer is the leading cause of cancer-related deaths among women in low-income countries and is the second leading cause of cancer-related deaths for women on a worldwide basis. Among currently FDA-approved molecular diagnostics, none are capable of distinguishing the various HPVs other than to classify them as "high" or "low" risk types.

Currently, two FDA approved molecular diagnostic tests are available in the United States for the direct detection of HPV DNA. The Hybrid Capture test (Digene HC2, Qiagen, Valencia, Calif.) and the Cervista HPV test (Hologic, Bedford Mass.). Both tests rely on signal amplification rather than target amplification. However, both FDA approved kits do not identify individual HR HPV, but rather the presence of a single or multiple HR HPVs will be read as the same positive result. In addition, there is a hybrid capture kit for detecting LR HPVs as a group and a Cervista kit specifically for the detection of only HPV 16 and 18.

Despite the availability of two highly predictive tests for determining probability of cervical cancer, the disparity of cervical cancer mortality between low income and industrialized regions still remains significant. Cultural, socio-economic, and logistical bathers prevent women in impoverished regions from benefiting from the predictive value of these tests. The design of an inexpensive point-of-care device for the molecular testing of HPV should significantly improve cervical cancer detection world-wide. Such a test would provide immediate and unequivocal results regarding HPV status, and inform either the need for further treatment or the time to next check-up. The HPV nucleic acid test demonstrated in this example is accessible to different populations regardless of these aforementioned barriers.

Materials and Methods

Preparation, Dilution and Storage of Genomic DNA

The C-33A human cervical carcinoma cell line, purchased from the American Type Culture Collection (ATCC, Manassas, Va.), was grown, and maintained in Eagles Minimal Essential Media containing 10% fetal bovine serum at 37° C. in a CO2 water-jacketed incubated. Cells were grown to confluence, collected either via scraping directly into PBS, or through trypsinization followed by counting of cells. Approximately 5 million cells (equivalent to 10 million genomes) were harvested and lysed followed by purification of genomic DNA using a Qiagen DNeasy kit (Qiagen, Valencia, Calif.). Concentration of nucleic acids was determined via absorbance at 260 nm Purified nucleic acids were stored at −20° C.

Preparation, Dilution and Storage of HPV Plasmid DNA

Chimeric plasmid DNA containing HPV genomes were purchased from American Type Culture Collection (ATCC, Manassas, Va.) and transformed into DH5 α*E. coli* bacteria. Cultures were expanded, and plasmid DNA was purified using Qiagen Plasmid Mini Kit (Qiagen, Valencia, Calif.).

Concentration of DNA was determined via absorbance at 260 nm, and DNA was diluted to 1E6 copies per µl. Plasmid DNA stocks were stored at −20° C.

Preparation of DNA from Clinical Samples

All samples were originally collected as vaginal swabs in Digene storage transport medium. A portion of the samples were also pre-treated with Digene denaturing solution. Two hundred µl of sample was subjected to nucleic acid purification with Qiagen DNAeasy or in-house purification reagents which will be described elsewhere. Purified nucleic acid was stored at −20° C.

Design of HPV Primers and Probes

The HPV L1 gene primer set was designed based on the HPV region corresponding to the 3' end of the L2 gene and the 5' end of the L1 gene, originally described by Yoshikawa, and then further elaborated on by others (Yoshikawa H, Kawana T, Kitagawa K, Mizuno M, Yoshikura H, Iwamoto A: Detection and typing of multiple genital human papillomaviruses by DNA amplification with consensus primers. Jpn J Cancer Res 1991, 82(5):524-531; Jeney C, Takacs T, Sebe A, Schaff Z: Detection and typing of 46 genital human papillomaviruses by the L1F/L1R primer system based multiplex PCR and hybridization. J Virol Methods 2007, 140(1-2):32-42; Takacs T, Jeney C, Kovacs L, Mozes J, Benczik M, Sebe A: Molecular beacon-based real-time PCR method for detection of 15 high-risk and 5 low-risk HPV types. J Virol Methods 2008, 149(1):153-162). The sequence for each specific HPV type was obtained from the National Center for Biotechnology information (www.ncbi.nlm.nih.gov). The HPV type and corresponding accession number were as follows: 6:NC_000904; 11:M14119; 16:NC_001526; 18:NC_001357; 31:J04353; 33:M12732; 35:M74117; 39:M62849 M38185; 42:M73236; 43:AJ620205; 44:U31788; 45:X74479; 51:M62877; 52:X74481; 53:NC_001593; 56:EF177177; 58:D90400; 59:X77858; 66:U31794; 68:DQ080079.

Based on the primers described in Jeney et al. (Jeney C, Takacs T, Sebe A, Schaff Z: Detection and typing of 46 genital human papillomaviruses by the L1F/L1R primer system based multiplex PCR and hybridization. J Virol Methods 2007, 140(1-2):32-42), the forward or reverse primer region of the HPV genomes of interest were aligned using CLC Sequence Viewer (www.clcbio.com). Primers were grouped into the most similar sequences. Mismatches were not allowed within the 10 most 3' nucleotides to have the best base-pairing directly upstream of where the polymerase catalyzes incorporation of nucleotides. Once the sequences were aligned, they were grouped such that no more than two degenerate nucleotides would be included in a single primer.

The sequences for the capture-specific probes were described in Jeney et al. except for slight modifications of HPV 6, 11, 16, and 18. The capture probe sequences are shown in FIG. 30 (Table 1, SEQ ID NOS: 1-20). Probes were 5' modified with a primary amine linked through a 6 Carbon spacer arm.

All primers and probes were synthesized at Integrated DNA Technologies (Coralville, Iowa).

Design of Globin Primers and Probe

The human beta-globin gene was chosen as an internal positive control necessary to confirm successful nucleic acid purification from clinical samples. The forward and reverse primers were designed as follows: 5'-GAA TAA CAG TGA TAA TTT CTG GG-3' and 5'-GAA GAT AAG AGG TAT GAA CAT GA-3' (SEQ ID NO:21), respectively. The amino-terminated beta-globin capture probe was: 5'-ATC GAG CTG AAG GGC ATC GAC TTC AA-3' (SEQ ID NO:22).

Polymerase Chain Reaction (PCR)

An extensive PCR optimization protocol was performed using plasmids containing full-length viral DNA for HPV 16 and HPV 18 based on their prominence as high risk HPV subtypes. Preliminary experiments demonstrated that HPV 16 was more challenging to amplify than 18, and thus optimization was focused on HPV 16 amplification. Thermocycling conditions similar to those described in Jeney et al. (Jeney C, Takacs T, Sebe A, Schaff Z: Detection and typing of 46 genital human papillomaviruses by the L1F/L1R primer system based multiplex PCR and hybridization. J Virol Methods 2007, 140(1-2):32-42) were performed in which PCR was performed for 10 cycles annealing at a lower temperature, and the for the remaining 25-35 cycles, annealing is performed at a higher temperature. PCR was performed using 1000 copies of HPV 16 containing plasmid over a background of 32 ng C33A purified nucleic acid and optimized for MgCl2 concentration, primer concentration, buffer constituents, and annealing temperatures for each of the two annealing temperatures. PCR was ultimately optimized under the following conditions: 10 mM Tris-HCl, pH 9, 50 mM KCl, 100 µg/ml BSA, 1.5 mM MgCl2, 0.2 mM dATP, 0.2 mM dGTP, 0.2 mM dCTP, 0.075 mM dTTP, 0.125 mM dUTP, 0.2 µM of each individual primer, 0.002 units/µl heat stable uracil-DNA glycosylase, UDG, (USB Corp., Cleveland, Ohio) and 0.05 units/µl GoTaq Hot Start Polymerase (Promega Corp., Madison Wis.). Thermocycling conditions were as follows: 37° C. 10 mM (UDG activation), 95° C., 2 mM, 10 cycles of 95° C. 30 sec, 46° C. 30 sec, 72° 30 sec, 25-35 cycles of 95° C. 30 sec, 49° C. 30 sec, 72° 30 sec, and a final extension at 72° C. for 3 min. These same conditions were verified useful for beta-globin amplification. PCR optimization was performed on an MJ Mini Gradient Thermal Cycler (Biorad, Hercules, Calif.) and further confirmed on a Multigene II Thermal Cycler (Labnet, Woodbridge, N.J.).

Electrophoresis and Image Analysis

Following amplification, 2 µl 6× dye was added to 10 µl for a final volume of 12 µl. Samples were analyzed on 3% agarose gels melted in 0.5×TAE (50×TAE is 2 M Tris acetate, 100 mM EDTA; 0.5×TAE is 20 mM Tris acetate, 1 mM EDTA) buffer to which 1/10,000 volume of GelGreen (Biotium, Hayward, Calif.) was added. Samples were electrophoresed for 30-60 mM at 100 Volts using a VWR mini Electrophoresis System (VWR, West Chester, Pa.). Wells were generated with 17 lane (4 mm wide) or 24 lane (3 mm wide) combs to which 5 µl or 3 µl, respectively, of samples containing dye were loaded.

Gel bands were illuminated using a Dark Reader Transilluminator (Clare Chemical Research, Delores, Colo.) and images were captured using a Sony Cyber-shot DSCH2 Digital camera, ISO set to 80, F=3.5, shutter speed=3 sec and timer=2 sec. Bands were quantitated using ImageJ software (http://rsb.info.nih.gov/ij/). Background was subtracted using a rolling ball radius set to 50 pixels and the area under the peaks measuring the bands was collected.

Cloning of L1 Fragment from Clinical Samples

The HPV L1 amplified regions were cloned for specific types from DNA purified from clinical samples. To do this, specific HPV types were identified via amplification and reverse dot blot hybridization. HPV L1 regions were cloned from samples containing single infections. Forward and reverse primers were designed with type specific L1 sequences (see FIG. 31, Table 2 (SEQ ID NOS: 23-46) flanked with Bam H1 and EcoR1 restriction sites, respectively. The digested fragment was subsequently gel purified and ligated into Bam H1/Eco R1 digested and gel purified pBS II KS+(Bluescript) cloning vector. Successful amplification of the HPV insert was confirmed using the HPV primer mix, and specific type was confirmed via RDB and sequencing using an Applied Biosystems Automated 3730 DNA Analyzer with Big Dye Terminator chemistry and Ampli-Taq-FS DNA Polymerase (Applied Biosystems, Inc., Foster City, Calif.).

Design of Spotting Control and Positive Control

A spotting control for the RDB filters was designed as follows: /5AmMC6/AAA AAA AAA AAA AAA AAA /3Bio/ (SEQ ID NO:47).

A positive control was designed that contained the forward primer sequence to HPV 6/11, and the reverse primer sequence to HPV 42, flanking a non-HPV related sequence derived from the green fluorescent protein, plasmid, pEGFP-C2. To do this, primers were designed with Bam H1 and EcoR1 restriction sites flanking the forward and reverse primer sequences, respectively, which in turn flanked GFP specific sequences allowing for the amplification of a 258 bp GFP insert. The resulting forward and reverse primer sequences were 5'-GCT TGG ATC CCG TAA ACG TAT TCC CTT ATT TTT TTA AAC GGC CAC AAG TTC AGC GTG-3' (SEQ ID NO:48) and 5'-AAG CGA ATT CAC TCT AAA TAC TCT GTA CTG TCT TGT AGT TGC CGT CGT CCT TGA-3' (SEQ ID NO:49), respectively. Following amplification, the PCR product was purified and restricted with Bam H1 and Eco R1. The digested fragment was subsequently gel purified and ligated into Bam H1/Eco R1 digested and gel purified pBS II KS+(Bluescript) cloning vector. Successful amplification of the GFP fragment was confirmed using the HPV primer mix.

Reverse Dot Blot (RDB)

Membrane filters were prepared following the method described in Zhang et al. (Zhang Y, Coyne M Y, Will S G, Levenson C H, Kawasaki E S: Single-base mutational analysis of cancer and genetic diseases using membrane bound modified oligonucleotides. Nucleic Acids Res 1991, 19(14): 3929-3933). Briefly, negatively charged nylon, 0.45 um, Biodyne C membranes (Pall Corporation, city, state) were pre-wet in 0.1 N HCl followed by activation in 10% N-Ethyl-N'-(3-dimethylaminopropyl)carbodiimide hydrochloride (EDC) for 15 min Membranes were rinsed in water and air-dried Amino-terminated nucleic acid probes were resuspended in 0.5 M Sodium Bicarbonate containing 0.1% Tween, and spotted on the membranes using a BioRobotics Biogrid (Boston, Mass.). Membranes were air-dried and dessicated until use. Immediately prior to use, membranes were incubated with 0.1 N NaOH to quench any remaining un-bound activated sites.

Amplicons, 5 µl, were mixed with 50 µl hybridization buffer (3×SSPE, 0.1% SDS, 25% formamide), heated at 95° C. for 5 minutes, and immediately placed on ice to prevent re-annealing. All membrane manipulations were performed at room temperature with gentle agitation. Membranes were prehybridized in 250 µl hybridization buffer for 15 min followed by the addition of denatured amplicon and hybridization for 1-3 h. Following hybridization, filters were washed in 1.5 ml 0.1% SDS, twice for 10-15 min Membranes were incubated with a 1:500 dilution of horseradish peroxidase conjugated streptavidin (Thermo Fisher Scientific, Inc., Waltham, Mass.) in 1×SSPE/0.1% SDS for 30 min followed by 3 rinses for 10 min each in 0.5×SSPE/0.3% SDS. One-Step TMB-Blotting Solution (Thermo Fisher Scientific, Inc.), 750 µl, was added to the membranes and color development performed for 10 min. Membranes were washed for 10 min with 5 ml of water. Developed filters were scanned using a Hewlett Packard Scanjet 4850 and/or photographed for documentation.

Results

Design of PCR Primers

FIG. 32 (Table 3A, SEQ ID NOS:50-77) and FIG. 33 (Table 3B, SEQ ID NOS:78-105) show the primers for amplifying the HPV L1 gene that were designed following the rules described in Materials and Methods. Following alignment starting at the 3' ends, not allowing any mismatches within the 10 most 3' nucleotides, and using a maximum of 2 degenerate nucleotides per primer, a total of 8 forward and 8 reverse primer sequences were designed. This reduces by half the number of individual primers synthesized by Jeney et al. (Jeney C, Takacs T, Sebe A, Schaff Z: Detection and typing of 46 genital human papillomaviruses by the L1F/L1R primer system based multiplex PCR and hybridization. J Virol Methods 2007, 140(1-2):32-42) and thus reduces the overall costs of the PCR assay. In total, there were 13 forward and 21 reverse primers produced from these degenerate sequences. Following this strategy, the mix of primers contained within it an exact match for 16 of the 20 HPV targets including all but one of the high risk types. Furthermore, although attempts were made to cover as much of the primer sequences as possible, mismatches were not as much of a concern in the low risk types. It was reasoned that although it is expected that all the relevant types will be amplified with these primers, in the unlikely event that a low risk is not amplified, a false negative under these conditions is not as critical as a false negative for a high risk. Mismatches in the forward primer set included single mismatches for low risk 42 and 43, and 3 mismatches for low risk 44. Mismatches in the reverse primer set included single mismatches for low risk 11 and 44, and high risk 66. All mismatches, except one in the HPV 44 forward sequence were within the 5' end of the primer.

Validation of HPV Amplification

Figure 34:
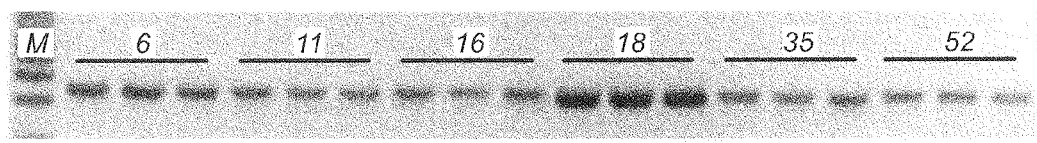
FIG. 34: Validation of HPV amplification with L1 primer mix. Full length HPV containing plasmids, types 6, 11, 16, 18, and 52, and partial HPV type 35 containing plasmid were subjected to amplification with the L1 primer mix. PCR was performed for 40 cycles on 1000 copies of plasmid DNA on a background of 16 ng C33A nucleic acid. M=100 bp DNA. See Example 4 for details.

The HPV L1 primer set was initially tested on chimeric plasmids containing full-length or partial HPV sequences. FIG. 34 shows the results of amplification of plasmid DNA for the various HPV types. Reaction mixtures containing 100 copies/µl of either full-length DNA sequence containing plasmids for HPV 6, 11, 16, 18, 52, or partial sequence for HPV 35 were subjected to 40 cycles of amplification. In all cases, HPV was amplified in the presence of 1.6 ng/µl C33A nucleic acids. All plasmids amplified with the primer set. There were differences among the plasmids with respect to how well each behaved as a template, with HPV 18 being a markedly better template than the others.

Figure 35A:
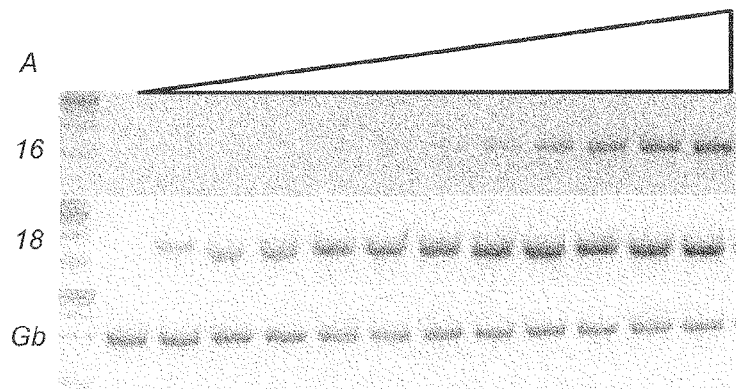
FIGS. 35A-D: PCR amplification of serially diluted HPV clones. A) Representative images of gels used to separate products resulting from amplification of 2 fold increasing amounts of full-length HPV 16 and HPV-18 containing plasmids; Lanes are as follows, Marker (100 bp DNA Ladder), 0, 122, 244, 488, 977, 1,953, 3,906, 7,813, 15,625, 31,250, 62,500, 125,000 copies of HPV plasmids. Lower image in A is a representative gel showing the separation of products resulting from the amplification of globin in the equivalent samples shown in the upper images. Specifically, this is the companion gel to the HPV 16 image shown above. B) Image analysis of gels separating PCR products of full-length (6, 11, 16, 18, 52) or partial (35) HPV containing plasmids. C) Image analysis of gels separating PCR products of HPV L1 clones generated from clinical samples. D) Image analysis of the companion globin gel for each of the curves shown in A. The bars represent the average and standard deviation of globin amplification in the presence of the different number of input HPV molecules. See Example 4 for details.
Figure 35B:
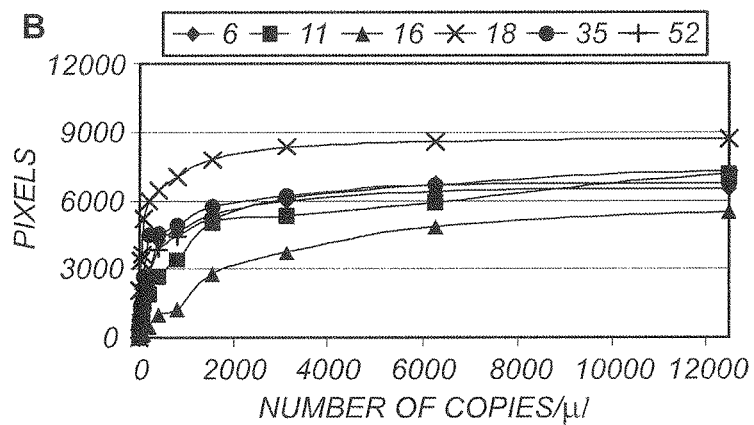
Figure 35C:
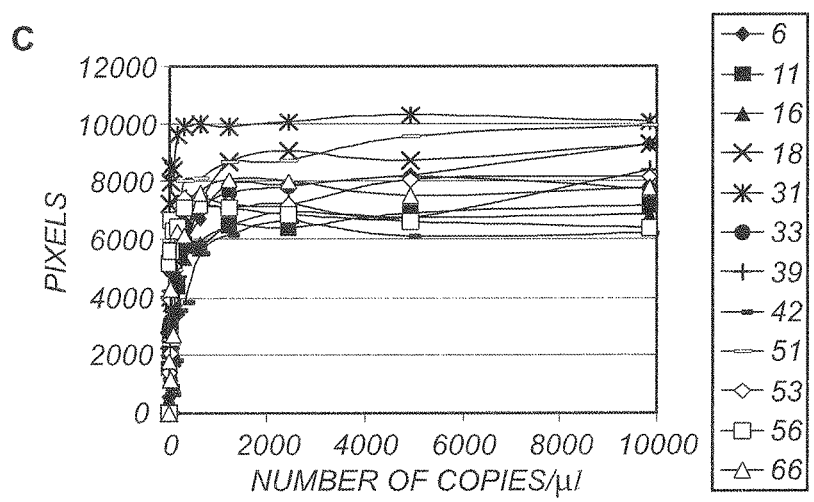

To demonstrate more clearly the differences between the behaviors of each plasmid as a template for the L1 primer set, amplification was performed on two-fold serially diluted plasmid DNA. FIGS. 35A-D show results of representative experiments in which HPV plasmid DNA was amplified at 12 to 12,500 copies/µl of DNA over a background of 1.6 ng/µl genomic nucleic acid per reaction. The upper images are of the gels used to separate the products of amplification of HPV 16 and HPV 18 containing plasmids, and similar to what is seen in FIG. 34, HPV 18 demonstrates better amplification at lower copy number than HPV 16. The data resulting from image analysis of these gels as well as similar gels analyzing products of amplification for the remaining plasmids are shown in FIG. 35B. The data from these graphs confirm the markedly better amplification of HPV 18 compared to the other plasmids and similarly that HPV 16 was less sensitive to amplification under these conditions. Amplification of HPV 18 began to plateau at approximately 200 copies/µl, amplification of HPV 11, 35 and 52 began to plateau at approximately 800 copies/µl and amplification of HPV 16, the weakest template, began to plateau at approximately 1500 copies/µl.

Figure 35D:
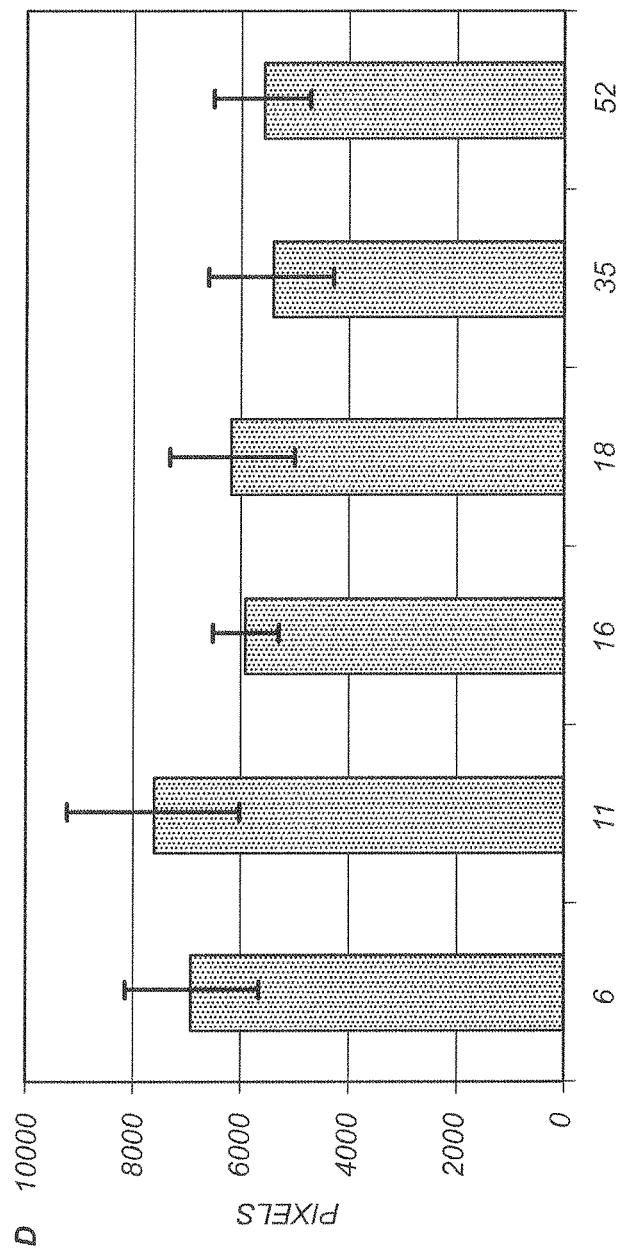

In addition to the full-length and partial HPV clones, L1 target regions cloned directly from clinical samples were also subjected to amplification with the L1 primers. The graph in FIG. 35D shows the results of image analysis of PCR of 10 copies/μl through 10,000 copies/μl of 12 type-specific HPV clones. Similar to what was seen with the full-length plasmids, some templates were more sensitive than others. Amplification of the most sensitive templates, HPV 18, 31, 33, 51, 56, and 66 began to plateau at <150 copies/μl. Amplification of the more challenging templates began to plateau at >300 copies/μl with 16 being the most challenging at 1500 copies/μl. The remaining templates show amplification plateaus between these lower and upper ranges. Taken together, these data demonstrate that all targets of HPV tested were suitable templates for amplification with the L1 primer set.

Preliminary experiments (data not shown) demonstrated that HPV and beta-globin could not be amplified simultaneously in the same reaction mix without adversely affecting one another. Typically, if one template was in significant excess of the other template, competition for PCR reactants would occur making this a poor assay design for the ultimate product. Therefore, an assay was designed such that beta-globin and HPV could be amplified in separate chambers, but would need to follow the same thermal cycling conditions. For the experiments shown in FIGS. 35A and 35B, the same samples were subjected to amplification with beta-globin primers. The lower image in FIG. 35A shows a representative gel of globin amplified products. The samples for these experiments contained the same input HPV and genomic DNA as with the HPV amplification curves. HPV input was increased whereas the genomic input nucleic acid stayed constant at 1.6 ng/μl. As can be seen in the image, the level of input HPV had little or no effect on globin amplification. FIG. 35D shows the results of image analysis of the companion globin gels run for each of the plasmid HPVs shown in FIG. 35B. These data demonstrate that regardless of the input of HPV, beta globin amplification remains relatively constant. Thus, whereas co-amplification of HPV and globin results in competition, the presence of either template without the specific primers did not adversely affect amplification of the specific target.

Globin Curve

Figure 36:
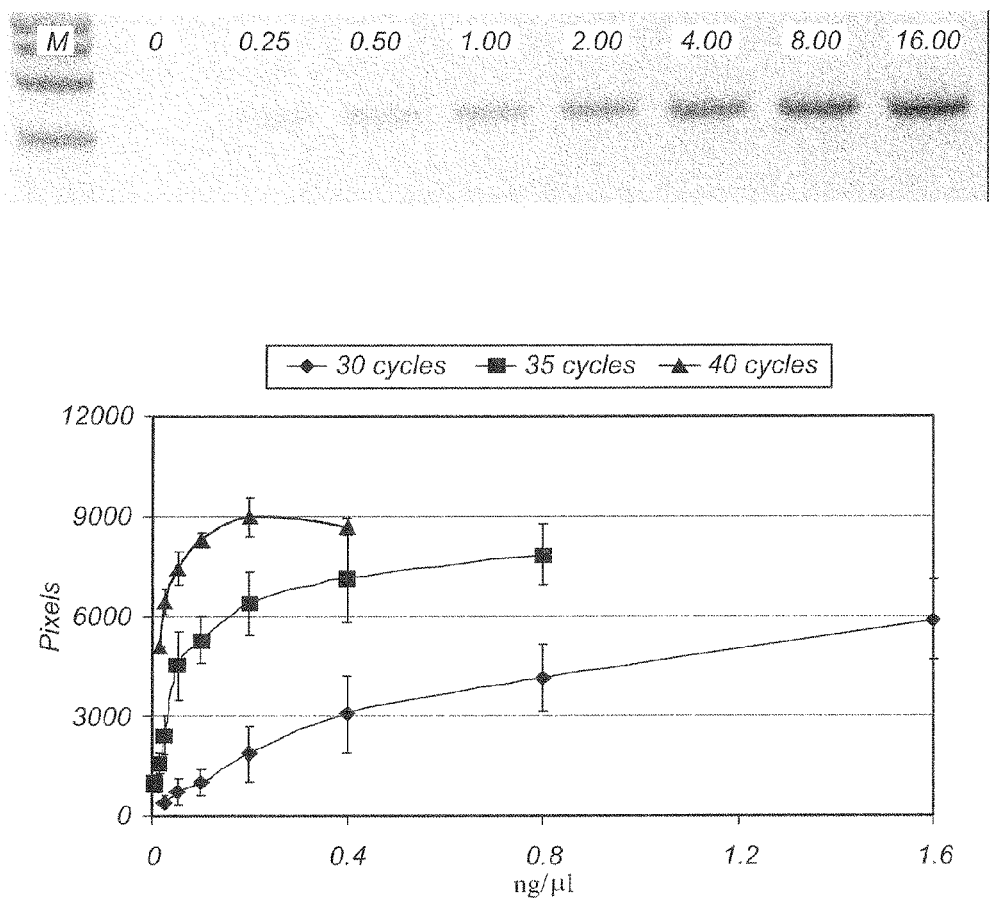
FIG. 36: PCR amplification of beta-globin in serially diluted C33A purified nucleic acid. Upper panel: Representative image of gels used to separate products resulting from amplification of beta-globin in 2 fold increasing amounts of C33A purified nucleic acid. M=Marker (100 bp DNA Ladder), 0, 0.025, 0.5, 1, 2, 4, 8, and 16 correspond to total input nucleic acid in ng. Lower panel: Image analysis of gels separating products following amplification for 30 (N=4), 35 (N=3) or 40 (N=2) cycles of PCR. Data points are average+/−standard deviation. See Example 4 for details.

The internal control beta-globin was amplified in a separate chamber from HPV, but was subjected to the same temperature and cycling conditions as HPV. Therefore, it was important to establish how beta-globin amplification would behave under these conditions. To address this question, serially diluted nucleic acid purified from C33A cells was subjected to amplification with beta-globin primers. Amplification was performed on 0.025-1.6 ng/μl of purified nucleic acid for 30, 35, or 40 cycles. The results from these experiments are shown in FIG. 36. When PCR was performed for 40 cycles, amplicon production was completely saturated at <0.2 ng/μl input nucleic acid. In contrast, when performed for 30 or 35 cycles, amplification of globin began to plateau at 0.4 or 0.1 ng/μl, respectively, and did not saturate until >1.6 or >0.8 ng/μl, respectively. These data were generated on various days using C33A nucleic acid purified at different times, demonstrating the highly reproducible nature of this assay.

In the experiments in FIG. 36, template was presented in the context of total nucleic acid purified form C33 A cells, rather than purified DNA. Because the ultimate goal of these experiments was to design a point-of-care microfluidic molecular diagnostic tool for HPV detection, each step of the assay was designed with manufacture of the end-product in mind. The use of ribonuclease treated nucleic acid resulting in RNA-free purified DNA was therefore considered. In experiments, ribonuclease in the purification module was determined unnecessary and possibly detrimental to the actual recovery of nucleic acids from low cell concentrations. That is, under conditions of limiting DNA, RNA may act as a carrier to aid purification. Several purification experiments were performed comparing the yields plus/minus ribonuclease treatment, and in the case of C33A cells, yields of nucleic acid were generally 4-fold higher in the absence of ribonuclease treatment, suggesting that the actual amount of genomic DNA is approximately one quarter the actual yields determined via absorbance at 260 nm.

RDB HPV/Globin

Figure 37A:
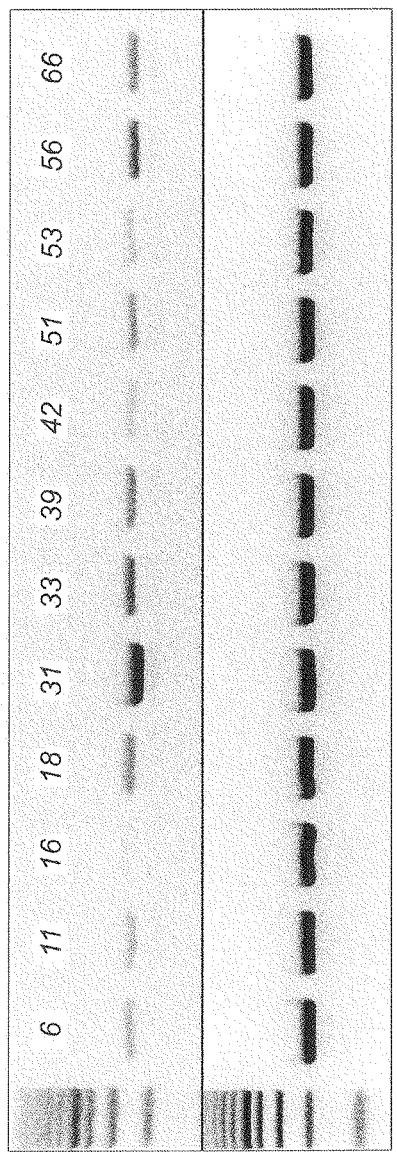
FIGS. 37A-B: A. Results of amplification of 10 copies/μl of HPV over a background of 1.6 ng/μl genomic nucleic acid. The upper image shows the gel image of HPV amplicons, and the bottom image shows the corresponding globin amplicons. B. Results of RDB of each combination of HPV and globin amplicon. See Example 4 for details.
Figure 37B:
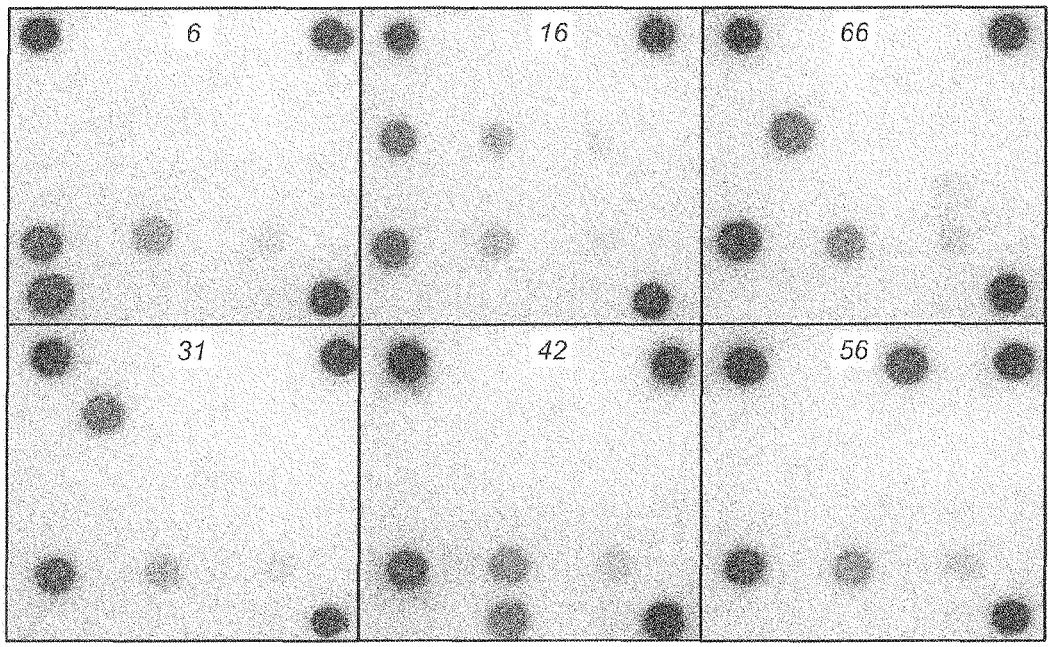

Following PCR amplification of genomic and HPV DNA in separate vessels, the amplicons were combined and subjected to RDB on a single membrane filter. FIG. 37A shows the results of amplification of 10 copies/μl of HPV over a background of 1.6 ng/μl genomic nucleic acid. The upper image shows the gel image of HPV amplicons, and the bottom image shows the corresponding globin amplicons. The relative intensities indicating the behavior of each clone as a template is consistent with what was seen previously for 10 copies/μl (FIG. 37B and data not shown). FIG. 37B shows the results of RDB of each combination of HPV and globin amplicon. Each clone was captured by its specific membrane bound probe and generated an unequivocal spot. In all but one instance the RDB spot was strong regardless of the intensity of the amplicon image. On the other hand, the intensity of HPV 53 capture appeared to mimic low intensity amplification, but could still be identified.

Clinical Samples-Determination of Cell Numbers

Figure 38:
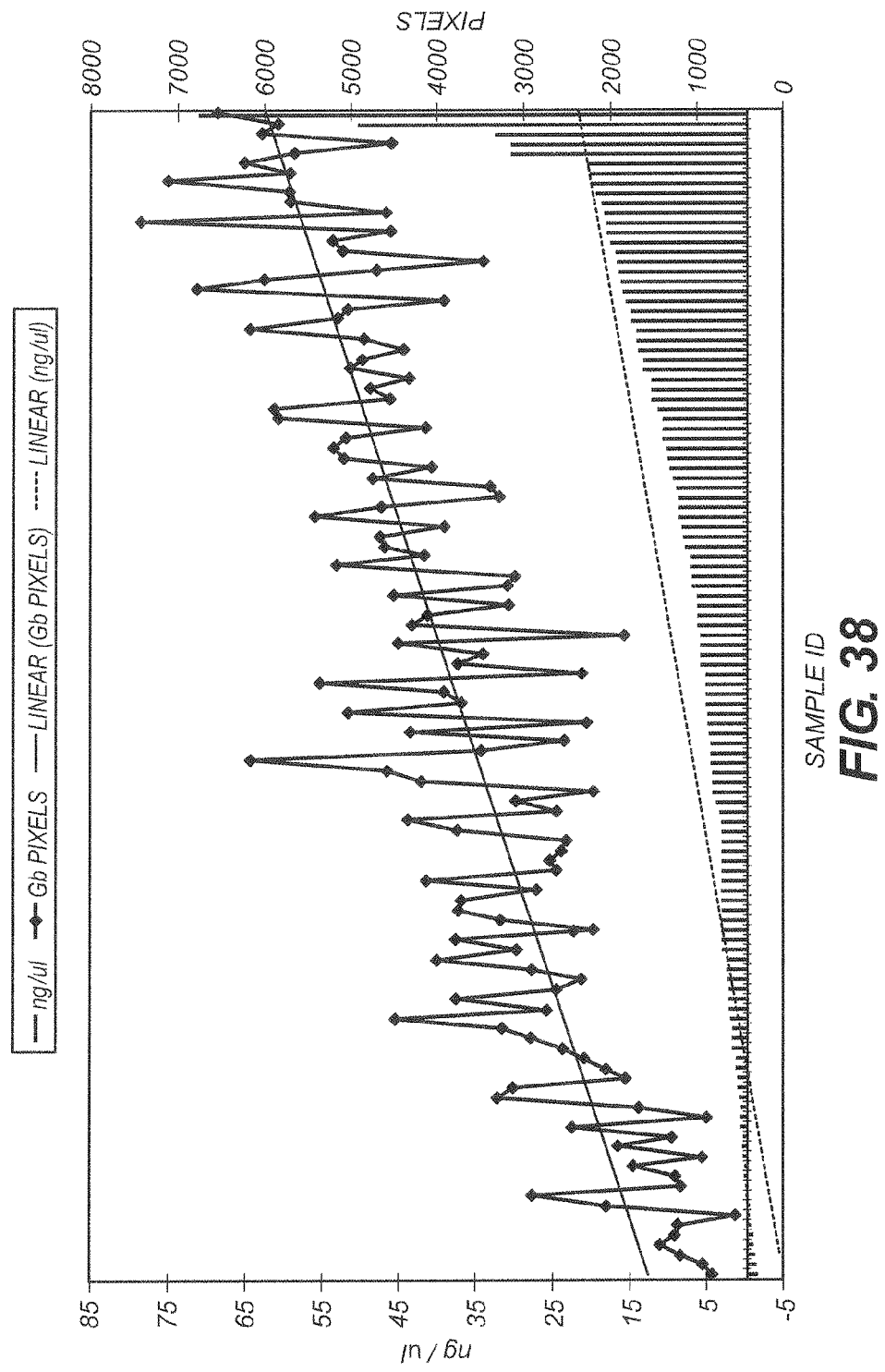
FIG. 38: Nucleic acids purified from clinical samples. Red bars, ng/ul DNA yields based on absorbance at 260 nm (left Y-axis). Blue curve: pixel intensity obtained from image analysis of gels separating products of PCR amplification of beta-globin (right Y-axis). Amplification was carried out on 1 μl of purified nucleic acid, regardless of concentration, for 30 cycles. Linear trendlines for both data sets are also shown. See Example 4 for details.

Having established robust and reproducible conditions for HPV and globin amplification followed by specific detection on RDB, the assay was validated using bona fide biological specimens. 117 clinical samples were obtained, subjected to nucleic acid purification, amplification of both HPV and globin, and final detection via RDB. All 117 samples were collected and stored in storage transport medium (STM, Qiagen). A portion of the samples were also treated with alkali denaturation reagent (Qiagen) prior to storage. Samples were frozen and stored for several weeks prior to nucleic acid purification. On average, the nucleic acids purified from samples stored with the addition of denaturant reagent gave slightly higher yields and purity when compared to samples stored in STM alone. The average yield from the denaturant/STM containing solutions versus STM alone was 11 and 4.6 ng/μl respectively and the ratio of absorbance at 260/280 nm was 1.8 and 1.6, respectively. Initially, 0.5 μl of each of these samples were analyzed for the presence of globin via PCR for 30 cycles, and each sample, regardless of the concentration of nucleic acid generated, a detectable amplicon band measurable by pixel intensity and confirmed via RDB detection. As seen in FIG. 38, although not directly correlated under these conditions, the trend of increasing pixel intensity followed the trend of increasing ng/μl yields. Thus even in the absence of detectable nucleic acids (via absorbance, Nanodrop limitation ~1 ng/μl), the assay produced a detectable globin amplicon following 30 cycles of PCR, and thereby validated the sensitivity and usefulness of the assay for clinical development.

Figure 39A:
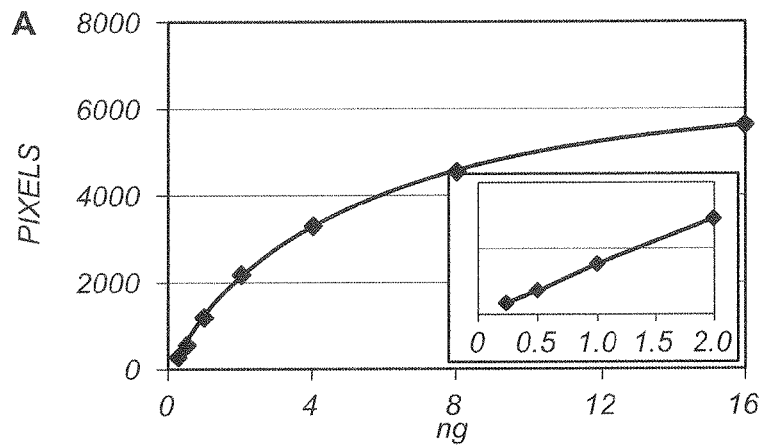
FIGS. 39A-C: Estimation of genomic equivalents in clinical samples. Amplification of beta-globin was carried out on diluted purified nucleic acid from selected clinical samples. A) Standard curve was generated using RNA free C33A DNA RNA-DNA. B) and C) Image analysis was used to calculate the equivalent "genome" based on the line equation shown in the inset in A (rear bars). Actual input nucleic acid based on absorbance at 260 nm (front bars) is also shown. See Example 4 for details.

Semi-quantitative PCR amplification of globin was used to calculate the number of genomes in the clinical samples. Reports suggest that a vaginal swab contains ~1-5 million cells (Depuydt C E, Benoy I H, Bailleul E J, Vandepitte J, Vereecken A J, Bogers J J. Improved endocervical sampling and HPV viral load detection by Cervex-Brush Combi. Cytopathology 2006, 17(6):374-381; Quint W G, Pagliusi S R, Lelie N, de Villiers E M, Wheeler C M: Results of the first World Health Organization international collaborative study of detection of human papillomavirus DNA. J Clin Microbiol 2006, 44(2):571-579; Schellenberg J, Blake Ball T, Lane M, Cheang M, Plummer F: Flow cytometric quantification of bacteria in vaginal swab samples self-collected by adolescents attending a gynecology clinic. J Microbiol Methods 2008, 73(3):216-226) equivalent to 6.4×10−6-3.2×10−5 g of pure DNA. Using RNA-free DNA from C33A cells, and performing 30 cycles of PCR, a curve of pixel intensity versus ng input was generated (FIG. 39A). This was similar to the curve generated in FIG. 36, however, in this case the total input nucleic acid was genomic DNA and therefore directly correlated to the number of genomes.

To convert from ng/μl to # genomes the following equation was used: $((ng/\mu l)/1E9)/3.2E-12$ g/genome To convert genomes to cells, divide the results from the above equation by 2.

Figure 39B:
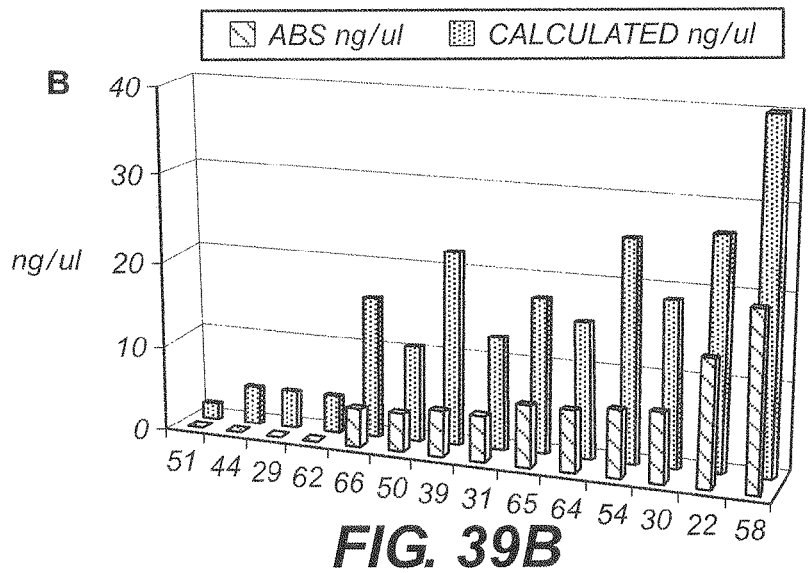

To determine the number of genomes present in the clinical samples, various low, medium, and high yielding samples (FIG. 38) were analyzed by dilutions such that the resulting intensity of the amplicons would fall within the linear range of the assay. The results in FIG. 39B show that the calculated range for samples stored in STM alone ranged from 1-40 ng/μl. These numbers were approximately 2-7 fold higher than the ng/μl obtained from absorbance at 260 nm. This was not surprising, since as described above, total nucleic acid purified in the absence of ribonuclease was, on average, 4-times greater than DNA purified following ribonuclease treatment. Using the equation above, this range corresponded to 312.5-12,500 genomes/μl, or 156.25-6,250 cell/μl. The original volume of these samples was 1 ml. Therefore, the number of cells found in these samples ranged from 156,250-6,250,000.

Figure 39C:
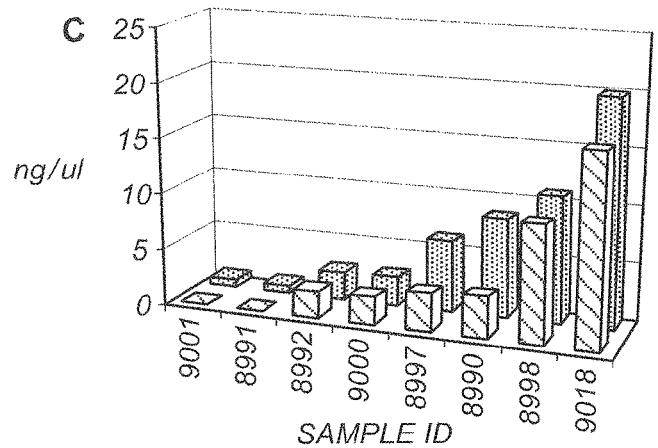

FIG. 39C shows the calculated ng/μl for samples that were stored in STM and denaturant. Under these conditions, the difference between calculated ng/μl and ng/μl obtained from absorbance at 260 nm was not as great consistent with the hydrolysis of RNA in the presence of alkali. The calculated DNA range under these conditions was between 0.6-20 ng/μl. This corresponded to 187.5-6250 genomes/μl or 93.75-3125 cells/μl. The original volume of these samples was 1.5 ml. Therefore, the number of cells found in these samples ranged from 140,625-4,687,500.

Taken together, these data demonstrate that using the semi-quantitative system, the number of cells from samples stored under different conditions could be estimated, and that regardless of the storage, the range of cells calculated was consistent with previous reports. These data provided a lower (~150,000 cells) and higher (~5,000,000 cells) limit on what to expect in vaginal samples and demonstrated that the assay was compatible with the full range expected in the samples.

Clinical Samples and Demonstration of HPV

To demonstrate that the system could detect and distinguish HPV as well as, or better than, the current accepted method of HPV detection, PCR was performed on nucleic acid purified from all 117 clinical samples using the L1 primer set followed by RDB of the resulting amplicons.

FIG. 40 (Table 4) is the summary of results of PCR and RDB of the clinical samples. As shown in the table, 75% (88/117) of the samples demonstrated an HPV amplified band following PCR and 45% (40/88) of the HPV amplicon positives were captured by an HPV-specific probe on RDB. The most likely explanation for non-detection of the remaining was absence of specific capture probes for the HPV types. Of the HPV RDB positive spots, 31/40 contained a high risk HPV type, present either as a single infection (21) multiple high risk infection (5) or combined low and high risk infection (5). The remaining 9 RDB positive samples were due to low risk single (7) or multiple (2) infections.

Figure 41A:
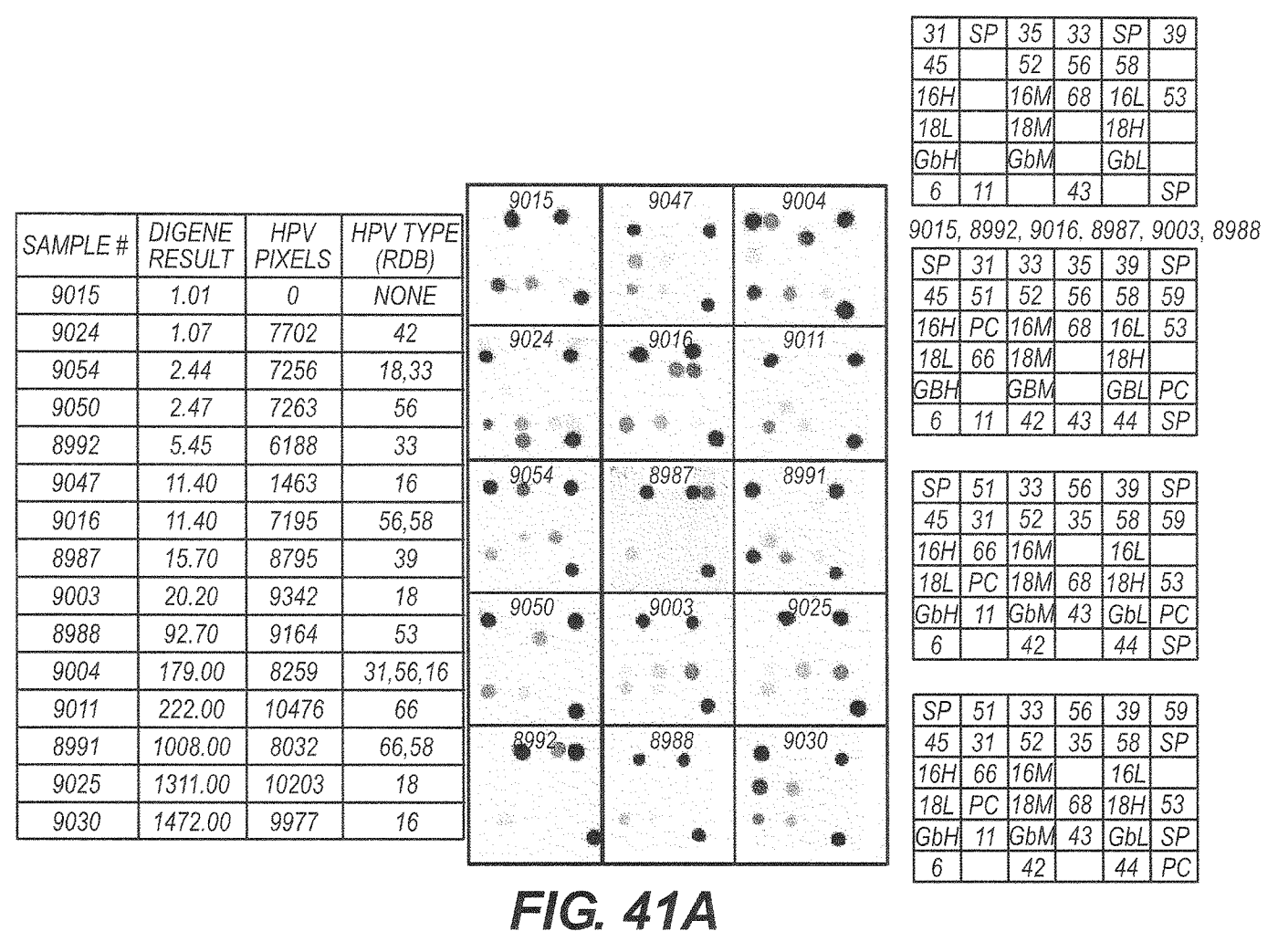

It was determined how well the assay compared with Digene HC2 (Qiagen, Valencia, Calif.) data in detecting high risk HPV. The data in FIG. 41A show the comparison of samples positive for HPV high risk using the Digene system versus the HPV result obtained with the system described in this example. The assay confirmed high risk infectivity in all but 1 of the Digene high risk samples. This sample (data not shown) resulted in Digene positive of 1.01, just barely considered Digene-positive for high risk. However, in multiple repeats of this sample, an HPV amplicon was never detected. This suggests that this would have been read as a false positive, albeit a very low positive. On the other hand, the assay system demonstrated in this example picked up several other high risk samples that were not detected using the Digene HC2 kit. As can be seen in FIG. 41B, the present assay system picked up 6 high risk samples that were read as negative by the Digene system, demonstrating the superiority sensitivity and specificity of the assay demonstrated in this example.

Discussion

This example demonstrates the development of a HPV molecular diagnostic test that detects and distinguishes individual low and high risk HPV subtypes. The method was developed for use on a fully automated microfluidic (CARD) platform that required only the input of a biological specimen on the part of the user. The automated protocol releases nucleic acids from the sample, subjects them to amplification with globin and HPV specific primers, and identifies specific subtypes of HPV via a reverse dot blot hybridization and detection. The example demonstrates the ability of the HPV assay to identify 20 different infectious HPV types as well as beta-globin from human epithelial cells. In addition, both the sensitivity of this assay as well as its reproducibility was been demonstrated.

Preliminary studies (not shown) were aimed at testing previously known PCR-based methods for the identification of HPV specific subtypes in biological samples and determining if any of these methods were suitable for use with the HPV assay, and/or if any could be improved upon. Criteria for a good target selection to be used on the CARD included:

1. The amplification of a short amplicon that would not require substantial elongation time during PCR and thus result in decreased overall time for PCR.
2. The targeting of a hypervariable region to design specific capture probes for all targets of interest and that could be expanded to include new HPV subtypes as they become relevant.
3. Significant homology in the flanking regions of the target site to minimize the number of primers required to amplify all HPV targets of interest Although many PCR-based methods known in the art rely on the amplification of a distinct nucleic acid sequence within the L1 gene, there do exist methods that rely on alternative genes within the HPV genome (Josefsson A, Livak K, Gyllensten U: Detection and quantitation of human papillomavirus by using the fluorescent 5' exonuclease assay. J Clin Microbiol 1999, 37(3):490-496). FIG. 42 (SEQ ID NO:106) shows the sequence of the L1 gene of HPV 16 containing highlighted sequences (SEQ ID NOS:107-112) corresponding to the various target regions for amplification. SEQ ID NO:107 and SEQ ID NO:108 are L1 forward and reverse primers, respectively; SEQ ID NO:109 and SEQ ID NO:110 are SPF primers; SEQ ID NO:110 and SEQ ID NO:111 are GP5/GP6; SEQ ID NO:109 and SEQ ID NO:112 are PGMY11/09.

Three of the established systems amplified all or part of a 450 bp region residing within the middle of the L1 gene. The MY09/MY11 system was originally described in the early 1990s as a set of degenerative primers that could detect multiple HPV types (Hildesheim A, Schiffman M H, Gravitt P E, Glass A G, Greer C E, Zhang T, Scott D R, Rush B B, Lawler P, Sherman M E et al: Persistence of type-specific human papillomavirus infection among cytologically normal women. J Infect Dis 1994, 169(2):235-240) resulting in an amplicon of approximately 450 bp. To avoid some of the problems that may arise with the use of degenerative primers, Gravitt et al. (Gravitt P E, Peyton C L, Alessi T Q, Wheeler C M, Coutlee F, Hildesheim A, Schiffman M H, Scott D R, Apple R J: Improved amplification of genital human papillomaviruses. J Clin Microbiol 2000, 38(1):357-361) modified the MY09/MY11 system and designed a pool of 5 forward and 13 reverse primers. Individual combinations of these primers would allow amplification of any of the target HPV types. Targeting the same region, Snijders et al. (Snijders P J, van den Brule A J, Schrijnemakers H F, Snow G, Meijer C J, Walboomers J M: The use of general primers in the polymerase chain reaction permits the detection of a broad spectrum of human papillomavirus genotypes. J Gen Virol 1990, 71 (Pt 1):173-181) identified single sequence primers which were further modified by elongation at the 3' ends (de Roda Husman A M, Walboomers J M, van den Brule A J, Meijer C J, Snijders P J: The use of general primers GP5 and GP6 elongated at their 3' ends with adjacent highly conserved sequences improves human papillomavirus detection by PCR. J Gen Virol 1995, 76 (Pt 4):1057-1062) and expanded to cover a broader range of HPV types (Schmitt M, Dondog B, Waterboer T, Pawlita M: Homogeneous amplification of genital human alpha papillomaviruses by PCR using novel broad-spectrum GP5+ and GP6+ primers. J Clin Microbiol 2008, 46(3):1050-1059). The size of the amplicon generated by this "general primer" system was 150 bp.

Targeting the same region of the L1 gene, Kleter and colleagues (Kleter B, van Doom L J, Schrauwen L, Molijn A, Sastrowijoto S, ter Schegget J, Lindeman J, ter Harmsel B, Burger M, Quint W: Development and clinical evaluation of a highly sensitive PCR-reverse hybridization line probe assay for detection and identification of anogenital human papillomavirus. J Clin Microbiol 1999, 37(8):2508-2517; Kleter B, van Doom L J, ter Schegget J, Schrauwen L, van Krimpen K, Burger M, ter Harmsel B, Quint W: Novel short-fragment PCR assay for highly sensitive broad-spectrum detection of anogenital human papillomaviruses. Am J Pathol 1998, 153 (6):1731-1739) designed a system of 4 forward and 2 reverse primers capable of recognizing all HPV types by the incorporation of the "universal base", inosine. These primers amplified a 65 bp region that included within the amplicon a hypervariable region that could be targeted directly for type-specific capture. Focusing on the upstream L1 sequence, Yoshikawa, et al. (Yoshikawa H, Kawana T, Kitagawa K, Mizuno M, Yoshikura H, Iwamoto A: Detection and typing of multiple genital human papillomaviruses by DNA amplification with consensus primers. Jpn J Cancer Res 1991, 82(5): 524-531) describes the L1C1/L1C2 primers that were later modified to include up to 46 distinct types of HPV (Jeney C, Takacs T, Sebe A, Schaff Z: Detection and typing of 46 genital human papillomaviruses by the L1F/L1R primer system based multiplex PCR and hybridization. J Virol Methods 2007, 140(1-2):32-42; Takacs T, Jeney C, Kovacs L, Mozes J, Benczik M, Sebe A: Molecular beacon-based real-time PCR method for detection of 15 high-risk and 5 low-risk HPV types. J Virol Methods 2008, 149(1):153-162). The study undertaken by Jeney (Jeney C, Takacs T, Sebe A, Schaff Z: Detection and typing of 46 genital human papillomaviruses by the L1F/L1R primer system based multiplex PCR and hybridization. J Virol Methods 2007, 140(1-2):32-42; Takacs T, Jeney C, Kovacs L, Mozes J, Benczik M, Sebe A: Molecular beacon-based real-time PCR method for detection of 15 high-risk and 5 low-risk HPV types. J Virol Methods 2008, 149(1):153-162) to identify novel regions that would allow for more sensitive detection of more types, identified a region within the HPV L1 sequence that was consistent with one of the hypervariable regions of the proteins identified by X-ray crystallographic studies (Chen X S, Garcea R L, Goldberg I, Casini G, Harrison S C: Structure of small virus-like particles assembled from the L1 protein of human papillomavirus 16. Mol Cell 2000, 5(3):557-567) and further confirmed by domain swapping experiments (Olcese V A, Chen Y, Schlegel R, Yuan H: Characterization of HPV16 L1 loop domains in the formation of a type-specific, conformational epitope. BMC Microbiol 2004, 4:29). Use of the primers described in Jeney C, Takacs T, Sebe A, Schaff Z (Detection and typing of 46 genital human papillomaviruses by the L1F/L1R primer system based multiplex PCR and hybridization. J Virol Methods 2007, 140(1-2):32-42) and Takacs T, Jeney C, Kovacs L, Mozes J, Benczik M, Sebe A (Molecular beacon-based real-time PCR method for detection of 15 high-risk and 5 low-risk HPV types. J Virol Methods 2008, 149(1):153-162) results in a ~250 bp amplicon.

Testing of each of these aforementioned L1 amplification methods was performed. Success was achieved with each system. Targeting the upstream L1 250 bp region was chosen for further studies owing to its amplicon size and hypervariability within the capture probe region, which allowed for better design of capture probes that could be hybridized at room temperature.

Figure 43A:
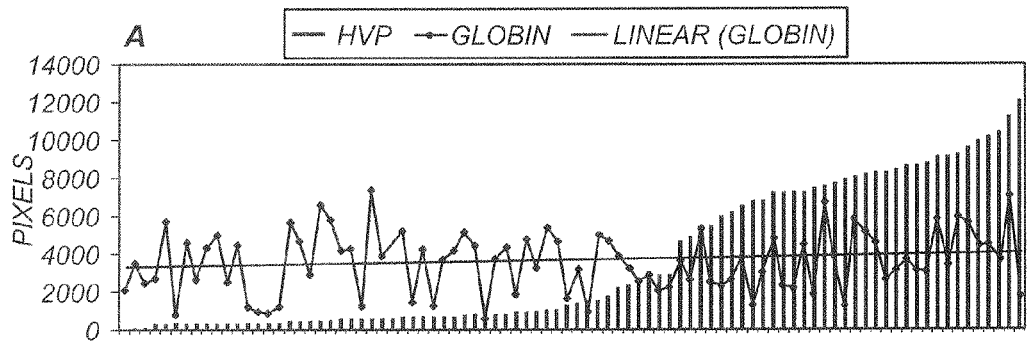
FIGS. 43A-C: A: Results of plotting increasing HPV pixel intensity with the corresponding globin pixel intensity; B: The ratio of HPV to globin pixels plotted versus low to high risk HPV types; C: The ratio of HPV to globin pixels plotted versus low to high risk HPV types. The "Digene" series plots the numbers which are the results of the commercially available Digene assay in comparison to with the present assay. The inset chart shows the Digene assay results (with a different scale Y-axis) that were then scaled and incorporated in the main graph. See Example 4 for details.

As more becomes known regarding HPV infections and the potential development of cervical cancer, it is becoming clear that in addition to demonstrating the presence of high risk HPV types, understanding the viral load, or number of HPV particles per cell, will also contribute to diagnosis. To examine this using the assay, the pixel intensity of HPV and globin from the same samples was evaluated. FIG. 43A shows the results of plotting increasing HPV pixel intensity with the corresponding globin pixel intensity. As shown in FIG. 43A, there is no correlation between globin pixel intensity and increasing HPV pixel intensity.

Figure 43B:
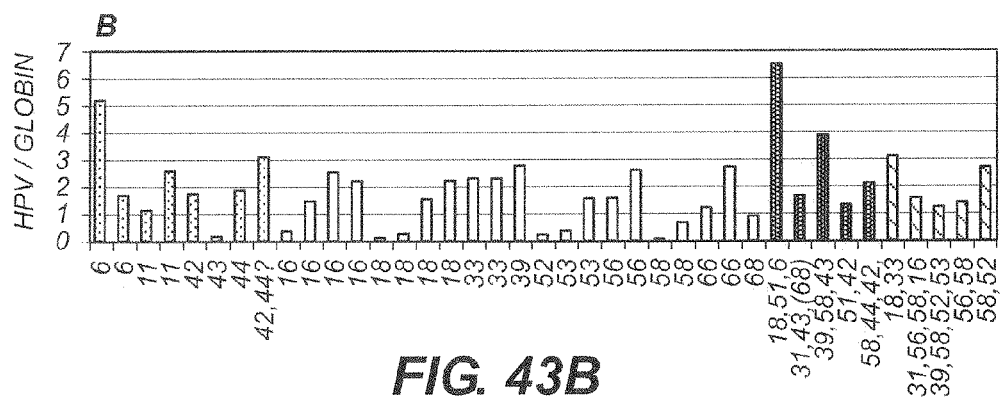
Figure 43C:
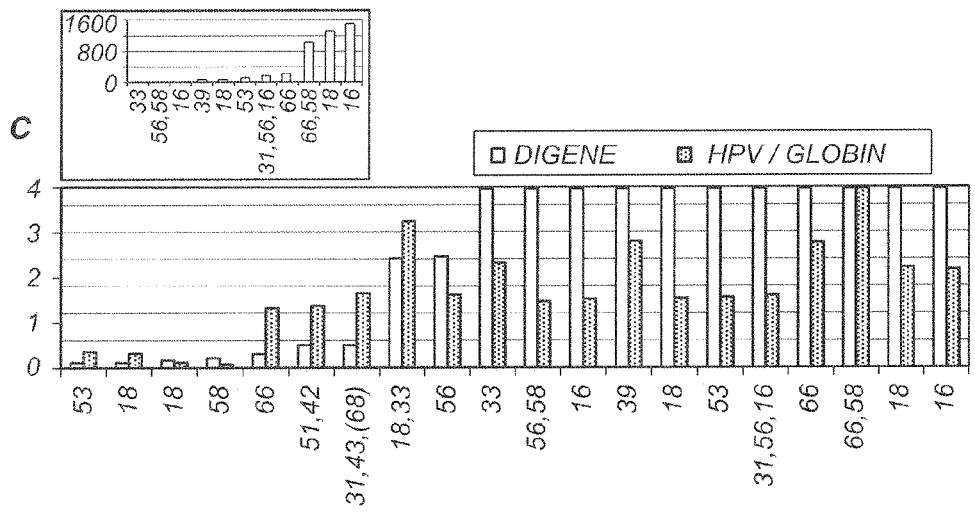

The ratio of HPV to globin pixels was then compared to the presence of high risk HPV types. FIG. 43B shows the ratio of HPV to globin pixels and was plotted versus low to high risk HPV types. These ratios varied from <1 to >6, but there did not appear to be any obvious correlation with the presence of HPV types. FIG. 43C shows the ratio of HPV to globin pixels plotted versus low to high risk HPV types. The "Digene" series plots the numbers which are the results of the commercially available Digene assay in comparison to with the present assay. The inset chart shows the Digene assay results (with a different scale Y-axis) that were then scaled and incorporated in the main graph.

In summary, the HPV assay conducted on the CARD provides a fully automated system for the rapid and reliable molecular detection of clinically relevant HPV types. Furthermore, owing to the portability of the CARD, the methods demonstrated in this example have widespread application in both industrialized and developing nations.

Example 5

CARD-Based Detection of a Sparse Target

This example demonstrates the detection of a sparse target. In this example, the sparse target nucleic acid is associated with a waterborne pathogen. Detection of the sparse target nucleic acid is indicative of its presence in a water supply. Such an assay can be used to detect sparse targets (from small numbers of organisms or cell nuclei) in a large liquid sample volume.

In reference to FIGS. 20A-20P the following operations and reagents were used to perform an assay for a live waterborne pathogen, *Cryptosporidium parvum*.

Sample Addition and Immunomagnetic Separation

All reagents are commercially available from Dynal for immunomagnetic capture of *Cryptosporidium parvum*. Volumes were adjusted for automated operation on the CARD.

a. An operator adds 1 ml of a pre-concentrated water sample into the sample input reservoir.
b. Dispense 100 µl of buffer 1, 100 µl of buffer 2 and 10 µl of beads into the same tube as the sample. Incubate for 30 minutes with gentle agitation or fluffing.
c. Raise the magnet under the sample input reservoir and pump the contents of the reservoir to waste.
d. Dispense 200 µl of buffer 1 into the buffer 1 reservoir and after lowering the magnet pump it to the sample input reservoir to re-suspend the beads.
e. Raise the magnet under the sample input reservoir and pump the contents of the reservoir to waste.

Heat Shock

Heat shock is optionally carried out to test for live organisms captured in the immunomagnetic separation step described above. (Otherwise, proceed to DNA amplification with standard PCR methods as detailed below.)

Amplification is conducted using RNA amplification reagents and an RNA amplification technique (e.g., RT-PCR or NASBA or art-known equivalents).

a. Lower the magnet.
b. Dispense 40 µl of nuclease free water into the non-heated magnetic separation reservoir and pump the entire contents into the heated magnetic separation reservoir and gently fluff to re-suspend the beads.
c. Turn on the heater to 42° C. for 5 minutes. Living Crypto will begin to express an RNA coding for a heat shock protein.

Lysis and Purification

All reagents are commercially available from Qiagen. Volumes were adjusted for automated operation on the CARD.

a. Dispense 100 µl of Qiagen lysis buffer RLT into the lysis buffer reservoir and pump it to the sample input reservoir and agitate by fluffing 6 times. Then increase the temperature of the heater to 60° C. and incubate for 10 minutes. Fluff twice during the minutes once at 5 minutes and then just prior to 10 minutes.
b. Dispense 100 µl of ethanol into the ethanol reservoir and pump it to the sample input reservoir and fluff 6 times.
c. Pump the entire contents of the sample input reservoir to the top of the silica filter and then pull the contents through the filter and pump it to waste. Pull air through the filter by opening the valves connected to the vacuum port and applying a vacuum for 30 seconds.
d. Dispense 100 µl of ethanol into the ethanol reservoir and pump it to the top of the silica filter and then pull the contents through the filter and pump it to waste. Pull air through the filter by opening the valves connected to the vacuum port and applying a vacuum for 30 seconds.
e. Dispense 100 µl of buffer 2 into the buffer 2 reservoir and pump it to the top of the silica filter and then pull the contents through the filter and pump it to waste. Pull air through the filter by opening the valves connected to the vacuum port and applying a vacuum for 30 seconds.
f. Dispense 100 µl of buffer 3 into the buffer 3 reservoir and pump it to the top of the silica filter and then pull the contents through the filter and pump it to waste. Pull air through the filter by opening the valves connected to the vacuum port and applying a vacuum for 30 seconds and repeat once.
g. Dispense 100 µl of ethanol into the ethanol reservoir and pump it to the top of the silica filter and then pull the contents through the filter and pump it to waste. Pull air through the filter by opening the valves connected to the vacuum port and applying a vacuum for 30 seconds.
h. Dispense 40 µl of nuclease free water into the non-heated magnetic separation reservoir and pump the entire contents up through the bottom of the silica filter and incubate for 2 minutes then pump the entire contents back to the non-heated magnetic separation reservoir.

mRNA Separation

All reagents are commercially available from Dynal volumes were adjusted for automated operation on the CARD.

a. Dispense 100 µl of binding buffer and then dispense 20 µl of beads into the non-heated magnetic separation reservoir then pump the binding buffer into the non-heated magnetic separation reservoir. Incubate for 5 minutes with gentle fluffing.
b. Raise magnet under the non-heated magnetic separation reservoir and pump the contents to waste.
c. Dispense 100 µl of wash buffer A into the wash buffer A reservoir and pump it into the non-heated magnetic separation reservoir. Lower the magnet and re-suspend the beads with gentle fluffing.
d. Raise magnet under the non-heated magnetic separation reservoir and pump the contents to waste.
e. Repeat steps c and d again.
f. Dispense 100 µl of wash buffer B into the wash buffer B reservoir and pump it into the non-heated magnetic separation reservoir. Lower the magnet and re-suspend the beads with gentle fluffing.
g. Raise magnet under the non-heated magnetic separation reservoir and pump the contents to waste.
h. Repeat steps f and g again.
i. While the non-heated magnetic separation reservoir is empty (except for the beads) back pump air to the wash buffer B reservoir to clear the channels and diaphragms of any residual fluids.

NASBA Amplification a. Lower the magnet under the non-heated magnetic separation reservoir.
b. Dispense 30 µl of NASBA master mix amplification master mix reservoir and pump it to the non-heated magnetic separation reservoir. Fluff the contents of the non-heated magnetic separation reservoir to re-suspend the beads.
c. Pump the contents of the non-heated magnetic separation reservoir back into the amplification master mix reservoir
d. Increase the temperature of the multipurpose heater to 41° C.
e. Pull the contents of the amplification master mix reservoir through the amplification reactor and pump a small amount into waste. This process completely fills the amplification reactor with fluid (no air bubbles).
f. Incubate the contents of the amplification reactor for 90 minutes at 41° C.

Lateral Flow Analysis a. Dispense 20 µl of hybridization buffer into the hybridization buffer reservoir and pump an initial 4 µl portion of it to waste to clear the channel and the diaphragm.
b. Pump 4 µl to the hybridization buffer to the heated analysis reservoir.

c. Pump an initial volume of 14 μl from the amplification reactor to waste to clear the channel and the diaphragm.
d. Then pump 2 μl from the amplification reactor into the heated analysis reservoir and then 6 μl from the hybridization buffer reservoir into the heated analysis reservoir.
e. Dispense 4 μl of marker (in this case liposomes tagged with an oligonucleotide homologous to the amplicons and filled with a marker that will be visible at the end point of the lateral flow analysis) into the heated analysis reservoir. Incubate with gentle agitation at 41° C. for 5 minutes.
f. Pump 8 μl of the contents of the heated analysis reservoir to the lateral flow strip in the analysis reservoir.
g. Concurrently dispense 35 μl of running buffer into the running buffer reservoir and pump it to the lateral flow strip after the initial volume of 8 μl or solution from the heated analysis reservoir is pumped to the lateral flow strip.
h. The tagged liposomes if they hybridized with the amplicons will be captured by another complimentary oligonucleotide attached to the lateral flow test strip and the internal die contained in the lipsome will be visible at the same point.

Image Analysis
a. Position the camera over the analysis membrane and record the image.
b. Send the image to the control system for processing.
c. Report the results.

FIG. 44 shows results obtained from the CARD-based detection. Heat shock mRNA from *Cryptosporidium parvum* was detected. IMS=immunomagnetic separation. HS=heat shock.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening.

The recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not impose a limitation on the scope of the invention unless otherwise claimed.

No language in the specification should be construed as indicating any non-claimed element as essential to the practice of the invention.

It will be apparent to those skilled in the art that various modifications and variations can be made to the present invention without departing from the spirit and scope of the invention. There is no intention to limit the invention to the specific form or forms disclosed, but on the contrary, the intention is to cover all modifications, alternative constructions, and equivalents falling within the spirit and scope of the invention, as defined in the appended claims. Thus, it is intended that the present invention cover the modifications and variations of this invention provided they come within the scope of the appended claims and their equivalents.

We claim:

1. An automated process for isolating, amplifying, and analyzing a target nucleic acid sequence that may be present in a fluid test sample, comprising:
  providing a dispensing system;
  providing a pneumatic manifold that operates a microfluidic system having a fluidic transport layer and at least one fluidic channel disposed in the fluidic transport layer; at least one sample input reservoir, at least one reagent reservoir, at least one analysis reservoir, and at least one temperature-controlled amplification/reaction reactor attached to the fluidic transport layer;
  introducing the fluid test sample into the at least one fluidic channel;
  providing at least one reagent to the at least one fluidic channel from at least one reagent reservoir that is in fluid connection with the fluidic transport layer;
  combining the fluid test sample and the at least one reagent in the at least one fluidic channel, the at least one sample input reservoir, or the at least one temperature-controlled amplification/reaction reactor;
  transporting the fluid test sample to the at least one temperature-controlled amplification/reaction reactor that is in operative communication with the fluidic transport layer;
  incubating the fluid test sample in the temperature-controlled amplification/reaction reactor under conditions sufficient to permit the target nucleic acid sequence to be amplified;
  transporting the incubated fluid test sample to the at least one analysis reservoir; and
  analyzing the amplified target nucleic acid sequence from the incubated test sample,
  wherein the test sample is transported from a starting location in the fluidic transport layer to the at least one analysis reservoir separately from the pneumatic manifold and the dispensing system.

2. The automated process of claim 1, wherein the transporting and combining steps are accomplished by pumping the fluid test sample and the volume of the at least one reagent through the fluidic transport layer via at least one multi-valve diaphragm pump that is operated by the pneumatic manifold.

3. The automated process of claim 1, wherein the analyzing step further comprises performing a microarray analysis on a microarray in the at least one analysis reservoir in the microfluidic system.

4. The automated process of claim 3, further comprising providing a microarray analysis membrane in the at least one analysis reservoir; flowing a fluid over a top surface of the microarray analysis membrane; and removing the fluid substantially through a fluid exit route along a periphery of the analysis membrane.

5. The automated process of claim 3, further comprising providing a microarray analysis membrane in the at least one analysis reservoir; and, flowing a fluid alternatively back and forth over a top surface of the microarray analysis membrane.

6. The automated process of claim 3, further comprising providing heat to the at least one analysis reservoir.

7. The automated process of claim 1, wherein analysis of the target nucleic acid sequence indicates the presence of an infectious agent.

8. The automated process of claim 1, wherein the target nucleic acid sequence comprises a SNP.

9. The automated process of claim 1, wherein the analyzing step comprises detecting an interaction between the amplified target nucleic acid sequence and a probe for the target nucleic acid sequence.

10. The automated process of claim 9, wherein the analyzing step comprises determining presence of, or predisposition for:
  the disease or disorder of interest,
  the infectious agent,
  the pathogen,
  cancer, or
  sensitivity to the drug, pharmaceutical composition, chemical or compound of interest.

11. The automated process of claim 1, wherein the analyzing step comprises determining an amount or level of the amplified target nucleic acid sequence and wherein the method further comprises comparing the amount or level with a preselected amount or level of the target nucleic acid sequence.

12. The automated process of claim 11 wherein a difference between the amount or level and the preselected amount or level is indicative of presence of, or predisposition for:
  a disease or disorder of interest,
  an infectious agent,
  a pathogen,
  cancer, or
  sensitivity to a drug, pharmaceutical composition, chemical or compound of interest.

13. The automated process of claim 1, comprising providing the at least one reagent via a pipette tip, incorporated into the dispensing system.

* * * * *

SEQUENCE LISTING

```
<160> NUMBER OF SEQ ID NOS: 118

<210> SEQ ID NO 1
<211> LENGTH: 22
<212> TYPE: DNA
<213> ORGANISM: Artificial Sequence
<220> FEATURE:
<223> OTHER INFORMATION: synthesized

<400> SEQUENCE: 1
ttccataaaa cgggctaaca aa                                              22

<210> SEQ ID NO 2
<211> LENGTH: 22
<212> TYPE: DNA
<213> ORGANISM: Artificial Sequence
<220> FEATURE:
<223> OTHER INFORMATION: synthesized

<400> SEQUENCE: 2
actctatcaa aaaagttaac aa                                              22

<210> SEQ ID NO 3
<211> LENGTH: 24
<212> TYPE: DNA
<213> ORGANISM: Artificial Sequence
<220> FEATURE:
```

```
<223> OTHER INFORMATION: synthesized

<400> SEQUENCE: 3
aaacctaaca ataacaaaat atta                                              24

<210> SEQ ID NO 4
<211> LENGTH: 19
<212> TYPE: DNA
<213> ORGANISM: Artificial Sequence
<220> FEATURE:
<223> OTHER INFORMATION: synthesized

<400> SEQUENCE: 4
ggtggcaata agcaggata                                                    19

<210> SEQ ID NO 5
<211> LENGTH: 20
<212> TYPE: DNA
<213> ORGANISM: Artificial Sequence
<220> FEATURE:
<223> OTHER INFORMATION: synthesized

<400> SEQUENCE: 5
aaatctgaca atcctaaaaa                                                   20

<210> SEQ ID NO 6
<211> LENGTH: 24
<212> TYPE: DNA
<213> ORGANISM: Artificial Sequence
<220> FEATURE:
<223> OTHER INFORMATION: synthesized

<400> SEQUENCE: 6
aaaaatccta ctaacgctaa aaaa                                              24

<210> SEQ ID NO 7
<211> LENGTH: 25
<212> TYPE: DNA
<213> ORGANISM: Artificial Sequence
<220> FEATURE:
<223> OTHER INFORMATION: synthesized

<400> SEQUENCE: 7
aaaacaagat tctaataaaa tagca                                             25

<210> SEQ ID NO 8
<211> LENGTH: 22
<212> TYPE: DNA
<213> ORGANISM: Artificial Sequence
<220> FEATURE:
<223> OTHER INFORMATION: synthesized

<400> SEQUENCE: 8
taaagtgggt atgaatggtg gt                                                22

<210> SEQ ID NO 9
<211> LENGTH: 20
<212> TYPE: DNA
<213> ORGANISM: Artificial Sequence
<220> FEATURE:
<223> OTHER INFORMATION: synthesized

<400> SEQUENCE: 9
caaaaaggcc aaataagaca                                                   20
```

```
<210> SEQ ID NO 10
<211> LENGTH: 23
<212> TYPE: DNA
<213> ORGANISM: Artificial Sequence
<220> FEATURE:
<223> OTHER INFORMATION: synthesized

<400> SEQUENCE: 10
ccttaaaaat tcctctggta aaa                                                 23

<210> SEQ ID NO 11
<211> LENGTH: 20
<212> TYPE: DNA
<213> ORGANISM: Artificial Sequence
<220> FEATURE:
<223> OTHER INFORMATION: synthesized

<400> SEQUENCE: 11
atacgaccag caaacaagac                                                     20

<210> SEQ ID NO 12
<211> LENGTH: 20
<212> TYPE: DNA
<213> ORGANISM: Artificial Sequence
<220> FEATURE:
<223> OTHER INFORMATION: synthesized

<400> SEQUENCE: 12
acctaatggt gcaggtaata                                                     20

<210> SEQ ID NO 13
<211> LENGTH: 19
<212> TYPE: DNA
<213> ORGANISM: Artificial Sequence
<220> FEATURE:
<223> OTHER INFORMATION: synthesized

<400> SEQUENCE: 13
taaaacctca acgcgtgct                                                      19

<210> SEQ ID NO 14
<211> LENGTH: 22
<212> TYPE: DNA
<213> ORGANISM: Artificial Sequence
<220> FEATURE:
<223> OTHER INFORMATION: synthesized

<400> SEQUENCE: 14
aaaacaccag tagtggtaat gg                                                  22

<210> SEQ ID NO 15
<211> LENGTH: 22
<212> TYPE: DNA
<213> ORGANISM: Artificial Sequence
<220> FEATURE:
<223> OTHER INFORMATION: synthesized

<400> SEQUENCE: 15
catttctaaa tctggtaaag ca                                                  22

<210> SEQ ID NO 16
<211> LENGTH: 22
<212> TYPE: DNA
<213> ORGANISM: Artificial Sequence
<220> FEATURE:
<223> OTHER INFORMATION: synthesized
```

<400> SEQUENCE: 16
aaggacaata ccaaaacaaa ca                                              22

<210> SEQ ID NO 17
<211> LENGTH: 20
<212> TYPE: DNA
<213> ORGANISM: Artificial Sequence
<220> FEATURE:
<223> OTHER INFORMATION: synthesized

<400> SEQUENCE: 17
ccatcaaaag tcccaataac                                                 20

<210> SEQ ID NO 18
<211> LENGTH: 20
<212> TYPE: DNA
<213> ORGANISM: Artificial Sequence
<220> FEATURE:
<223> OTHER INFORMATION: synthesized

<400> SEQUENCE: 18
ggtggtaatg gtagacagga                                                 20

<210> SEQ ID NO 19
<211> LENGTH: 21
<212> TYPE: DNA
<213> ORGANISM: Artificial Sequence
<220> FEATURE:
<223> OTHER INFORMATION: synthesized

<400> SEQUENCE: 19
caaatctggt accaaaacaa a                                               21

<210> SEQ ID NO 20
<211> LENGTH: 20
<212> TYPE: DNA
<213> ORGANISM: Artificial Sequence
<220> FEATURE:
<223> OTHER INFORMATION: synthesized

<400> SEQUENCE: 20
ttaaggttcc tatgtctggg                                                 20

<210> SEQ ID NO 21
<211> LENGTH: 23
<212> TYPE: DNA
<213> ORGANISM: Artificial Sequence
<220> FEATURE:
<223> OTHER INFORMATION: synthesized

<400> SEQUENCE: 21
gaataacagt gataatttct ggg                                             23

<210> SEQ ID NO 22
<211> LENGTH: 26
<212> TYPE: DNA
<213> ORGANISM: Artificial Sequence
<220> FEATURE:
<223> OTHER INFORMATION: synthesized

<400> SEQUENCE: 22
atcgagctga agggcatcga cttcaa                                          26

<210> SEQ ID NO 23
<211> LENGTH: 34

<212> TYPE: DNA
<213> ORGANISM: Artificial Sequence
<220> FEATURE:
<223> OTHER INFORMATION: synthesized

<400> SEQUENCE: 23
gcttggatcc cgtaaacgta ttcccttatt tttt        34

<210> SEQ ID NO 24
<211> LENGTH: 34
<212> TYPE: DNA
<213> ORGANISM: Artificial Sequence
<220> FEATURE:
<223> OTHER INFORMATION: synthesized

<400> SEQUENCE: 24
gcttggatcc cgtaaacgta ttcccttatt tttt        34

<210> SEQ ID NO 25
<211> LENGTH: 34
<212> TYPE: DNA
<213> ORGANISM: Artificial Sequence
<220> FEATURE:
<223> OTHER INFORMATION: synthesized

<400> SEQUENCE: 25
gcttggatcc cgtaaacgtt taccatattt tttt        34

<210> SEQ ID NO 26
<211> LENGTH: 34
<212> TYPE: DNA
<213> ORGANISM: Artificial Sequence
<220> FEATURE:
<223> OTHER INFORMATION: synthesized

<400> SEQUENCE: 26
gcttggatcc cgtaaacgtg ttccctattt tttt        34

<210> SEQ ID NO 27
<211> LENGTH: 34
<212> TYPE: DNA
<213> ORGANISM: Artificial Sequence
<220> FEATURE:
<223> OTHER INFORMATION: synthesized

<400> SEQUENCE: 27
gcttggatcc cgtaaacgtg tatcatattt tttt        34

<210> SEQ ID NO 28
<211> LENGTH: 34
<212> TYPE: DNA
<213> ORGANISM: Artificial Sequence
<220> FEATURE:
<223> OTHER INFORMATION: synthesized

<400> SEQUENCE: 28
gcttggatcc cgtaaacgtt ttccatattt tttt        34

<210> SEQ ID NO 29
<211> LENGTH: 34
<212> TYPE: DNA
<213> ORGANISM: Artificial Sequence
<220> FEATURE:
<223> OTHER INFORMATION: synthesized

<400> SEQUENCE: 29
gcttggatcc cgtaaacgta ttccctattt tttt              34

<210> SEQ ID NO 30
<211> LENGTH: 34
<212> TYPE: DNA
<213> ORGANISM: Artificial Sequence
<220> FEATURE:
<223> OTHER INFORMATION: synthesized

<400> SEQUENCE: 30
gcttggatcc cgtaaacctg taccatattt tttt              34

<210> SEQ ID NO 31
<211> LENGTH: 34
<212> TYPE: DNA
<213> ORGANISM: Artificial Sequence
<220> FEATURE:
<223> OTHER INFORMATION: synthesized

<400> SEQUENCE: 31
gcttggatcc cgtaaacgta tacccctattt tttt              34

<210> SEQ ID NO 32
<211> LENGTH: 34
<212> TYPE: DNA
<213> ORGANISM: Artificial Sequence
<220> FEATURE:
<223> OTHER INFORMATION: synthesized

<400> SEQUENCE: 32
gcttggatcc cgtaaacgta ttccctattt tctt              34

<210> SEQ ID NO 33
<211> LENGTH: 34
<212> TYPE: DNA
<213> ORGANISM: Artificial Sequence
<220> FEATURE:
<223> OTHER INFORMATION: synthesized

<400> SEQUENCE: 33
gcttggatcc cgtaaacgta ttccctattt tttt              34

<210> SEQ ID NO 34
<211> LENGTH: 34
<212> TYPE: DNA
<213> ORGANISM: Artificial Sequence
<220> FEATURE:
<223> OTHER INFORMATION: synthesized

<400> SEQUENCE: 34
gcttggatcc cgtaaacgta ttccctattt tttt              34

<210> SEQ ID NO 35
<211> LENGTH: 30
<212> TYPE: DNA
<213> ORGANISM: Artificial Sequence
<220> FEATURE:
<223> OTHER INFORMATION: synthesized

<400> SEQUENCE: 35
aagcgaattc accttaaata ccctgtattg              30

<210> SEQ ID NO 36
<211> LENGTH: 30
<212> TYPE: DNA
<213> ORGANISM: Artificial Sequence

```
<220> FEATURE:
<223> OTHER INFORMATION: synthesized

<400> SEQUENCE: 36
aagcgaattc accttaaaca ctctatattg                                    30

<210> SEQ ID NO 37
<211> LENGTH: 30
<212> TYPE: DNA
<213> ORGANISM: Artificial Sequence
<220> FEATURE:
<223> OTHER INFORMATION: synthesized

<400> SEQUENCE: 37
aagcgaattc attctaaata ccctgtattg                                    30

<210> SEQ ID NO 38
<211> LENGTH: 30
<212> TYPE: DNA
<213> ORGANISM: Artificial Sequence
<220> FEATURE:
<223> OTHER INFORMATION: synthesized

<400> SEQUENCE: 38
aagcgaattc accctaaata ctctatattg                                    30

<210> SEQ ID NO 39
<211> LENGTH: 30
<212> TYPE: DNA
<213> ORGANISM: Artificial Sequence
<220> FEATURE:
<223> OTHER INFORMATION: synthesized

<400> SEQUENCE: 39
aagcgaattc accctaaata ccctatattg                                    30

<210> SEQ ID NO 40
<211> LENGTH: 30
<212> TYPE: DNA
<213> ORGANISM: Artificial Sequence
<220> FEATURE:
<223> OTHER INFORMATION: synthesized

<400> SEQUENCE: 40
aagcgaattc accctaaaaa ccctatattg                                    30

<210> SEQ ID NO 41
<211> LENGTH: 30
<212> TYPE: DNA
<213> ORGANISM: Artificial Sequence
<220> FEATURE:
<223> OTHER INFORMATION: synthesized

<400> SEQUENCE: 41
aagcgaattc acgcgaaata ccctatattg                                    30

<210> SEQ ID NO 42
<211> LENGTH: 30
<212> TYPE: DNA
<213> ORGANISM: Artificial Sequence
<220> FEATURE:
<223> OTHER INFORMATION: synthesized

<400> SEQUENCE: 42
aagcgaattc actctaaata ctctgtactg                                    30
```

<210> SEQ ID NO 43
<211> LENGTH: 30
<212> TYPE: DNA
<213> ORGANISM: Artificial Sequence
<220> FEATURE:
<223> OTHER INFORMATION: synthesized

<400> SEQUENCE: 43
aagcgaattc accctaaata ccctgtattg                                30

<210> SEQ ID NO 44
<211> LENGTH: 30
<212> TYPE: DNA
<213> ORGANISM: Artificial Sequence
<220> FEATURE:
<223> OTHER INFORMATION: synthesized

<400> SEQUENCE: 44
aagcgaattc actctaaaca ccctatactg                                30

<210> SEQ ID NO 45
<211> LENGTH: 30
<212> TYPE: DNA
<213> ORGANISM: Artificial Sequence
<220> FEATURE:
<223> OTHER INFORMATION: synthesized

<400> SEQUENCE: 45
aagcgaattc accctaaata ccctatattg                                30

<210> SEQ ID NO 46
<211> LENGTH: 30
<212> TYPE: DNA
<213> ORGANISM: Artificial Sequence
<220> FEATURE:
<223> OTHER INFORMATION: synthesized

<400> SEQUENCE: 46
aagcgaattc accctaaaca ctctatactg                                30

<210> SEQ ID NO 47
<211> LENGTH: 18
<212> TYPE: DNA
<213> ORGANISM: Artificial Sequence
<220> FEATURE:
<223> OTHER INFORMATION: synthesized

<400> SEQUENCE: 47
aaaaaaaaaa aaaaaaaa                                             18

<210> SEQ ID NO 48
<211> LENGTH: 57
<212> TYPE: DNA
<213> ORGANISM: Artificial Sequence
<220> FEATURE:
<223> OTHER INFORMATION: synthesized

<400> SEQUENCE: 48
gcttggatcc cgtaaacgta ttcccttatt ttttaaacg gccacaagtt cagcgtg     57

<210> SEQ ID NO 49
<211> LENGTH: 54
<212> TYPE: DNA
<213> ORGANISM: Artificial Sequence
<220> FEATURE:
<223> OTHER INFORMATION: synthesized

```
<400> SEQUENCE: 49
aagcgaattc actctaaata ctctgtactg tcttgtagtt gccgtcgtcc ttga        54

<210> SEQ ID NO 50
<211> LENGTH: 24
<212> TYPE: DNA
<213> ORGANISM: Artificial Sequence
<220> FEATURE:
<223> OTHER INFORMATION: synthesized

<400> SEQUENCE: 50
cgtaaacgtt ttccatattt tttt                                        24

<210> SEQ ID NO 51
<211> LENGTH: 24
<212> TYPE: DNA
<213> ORGANISM: Artificial Sequence
<220> FEATURE:
<223> OTHER INFORMATION: synthesized

<400> SEQUENCE: 51
cgtaaacgtt ttccatattt tttt                                        24

<210> SEQ ID NO 52
<211> LENGTH: 24
<212> TYPE: DNA
<213> ORGANISM: Artificial Sequence
<220> FEATURE:
<223> OTHER INFORMATION: synthesized

<400> SEQUENCE: 52
cgtaaacgtt ttccatattt tttt                                        24

<210> SEQ ID NO 53
<211> LENGTH: 24
<212> TYPE: DNA
<213> ORGANISM: Artificial Sequence
<220> FEATURE:
<223> OTHER INFORMATION: synthesized

<400> SEQUENCE: 53
cgtaaacgtt taccatattt tttt                                        24

<210> SEQ ID NO 54
<211> LENGTH: 24
<212> TYPE: DNA
<213> ORGANISM: Artificial Sequence
<220> FEATURE:
<223> OTHER INFORMATION: synthesized

<400> SEQUENCE: 54
cgtaaacgtt twccatattt tttt                                        24

<210> SEQ ID NO 55
<211> LENGTH: 24
<212> TYPE: DNA
<213> ORGANISM: Artificial Sequence
<220> FEATURE:
<223> OTHER INFORMATION: synthesized

<400> SEQUENCE: 55
cgtaaacgta ttccctattt tttt                                        24

<210> SEQ ID NO 56
```

```
<211> LENGTH: 24
<212> TYPE: DNA
<213> ORGANISM: Artificial Sequence
<220> FEATURE:
<223> OTHER INFORMATION: synthesized

<400> SEQUENCE: 56
cgtaaacgta ttccctattt tttt                                              24

<210> SEQ ID NO 57
<211> LENGTH: 24
<212> TYPE: DNA
<213> ORGANISM: Artificial Sequence
<220> FEATURE:
<223> OTHER INFORMATION: synthesized

<400> SEQUENCE: 57
cgtaaacgta ttccctattt tttt                                              24

<210> SEQ ID NO 58
<211> LENGTH: 24
<212> TYPE: DNA
<213> ORGANISM: Artificial Sequence
<220> FEATURE:
<223> OTHER INFORMATION: synthesized

<400> SEQUENCE: 58
cgtaaacgta ttccctattt tttt                                              24

<210> SEQ ID NO 59
<211> LENGTH: 24
<212> TYPE: DNA
<213> ORGANISM: Artificial Sequence
<220> FEATURE:
<223> OTHER INFORMATION: synthesized

<400> SEQUENCE: 59
cgtaaacgta taccctattt tttt                                              24

<210> SEQ ID NO 60
<211> LENGTH: 24
<212> TYPE: DNA
<213> ORGANISM: Artificial Sequence
<220> FEATURE:
<223> OTHER INFORMATION: synthesized

<400> SEQUENCE: 60
cgtaaacgta twccctattt tttt                                              24

<210> SEQ ID NO 61
<211> LENGTH: 24
<212> TYPE: DNA
<213> ORGANISM: Artificial Sequence
<220> FEATURE:
<223> OTHER INFORMATION: synthesized

<400> SEQUENCE: 61
cgtaaacgtg tatcatattt tttt                                              24

<210> SEQ ID NO 62
<211> LENGTH: 24
<212> TYPE: DNA
<213> ORGANISM: Artificial Sequence
<220> FEATURE:
<223> OTHER INFORMATION: synthesized

<400> SEQUENCE: 62
```

```
cgtaaacgct ttcatattt tttt                                          24
```

<210> SEQ ID NO 63
<211> LENGTH: 24
<212> TYPE: DNA
<213> ORGANISM: Artificial Sequence
<220> FEATURE:
<223> OTHER INFORMATION: synthesized

<400> SEQUENCE: 63

```
cgtaaacctg taccatattt tttt                                         24
```

<210> SEQ ID NO 64
<211> LENGTH: 24
<212> TYPE: DNA
<213> ORGANISM: Artificial Sequence
<220> FEATURE:
<223> OTHER INFORMATION: synthesized

<400> SEQUENCE: 64

```
cgtaaacgyg twtcatattt tttt                                         24
```

<210> SEQ ID NO 65
<211> LENGTH: 24
<212> TYPE: DNA
<213> ORGANISM: Artificial Sequence
<220> FEATURE:
<223> OTHER INFORMATION: synthesized

<400> SEQUENCE: 65

```
cgtaaacgtg ttccctattt tttt                                         24
```

<210> SEQ ID NO 66
<211> LENGTH: 24
<212> TYPE: DNA
<213> ORGANISM: Artificial Sequence
<220> FEATURE:
<223> OTHER INFORMATION: synthesized

<400> SEQUENCE: 66

```
cgtaaacgtg ttccctattt tttt                                         24
```

<210> SEQ ID NO 67
<211> LENGTH: 24
<212> TYPE: DNA
<213> ORGANISM: Artificial Sequence
<220> FEATURE:
<223> OTHER INFORMATION: synthesized

<400> SEQUENCE: 67

```
cgtaaacgtg ttccctattt tttt                                         24
```

<210> SEQ ID NO 68
<211> LENGTH: 24
<212> TYPE: DNA
<213> ORGANISM: Artificial Sequence
<220> FEATURE:
<223> OTHER INFORMATION: synthesized

<400> SEQUENCE: 68

```
cgtaaacgtg tttccttgtt tttt                                         24
```

<210> SEQ ID NO 69
<211> LENGTH: 24
<212> TYPE: DNA

<213> ORGANISM: Artificial Sequence
<220> FEATURE:
<223> OTHER INFORMATION: synthesized

<400> SEQUENCE: 69
cgtaaacgta ttcccttatt tttt                                          24

<210> SEQ ID NO 70
<211> LENGTH: 24
<212> TYPE: DNA
<213> ORGANISM: Artificial Sequence
<220> FEATURE:
<223> OTHER INFORMATION: synthesized

<400> SEQUENCE: 70
cgtaaacgta ttcccttatt tttt                                          24

<210> SEQ ID NO 71
<211> LENGTH: 24
<212> TYPE: DNA
<213> ORGANISM: Artificial Sequence
<220> FEATURE:
<223> OTHER INFORMATION: synthesized

<400> SEQUENCE: 71
cgtaaacgta ttcccttatt tttt                                          24

<210> SEQ ID NO 72
<211> LENGTH: 24
<212> TYPE: DNA
<213> ORGANISM: Artificial Sequence
<220> FEATURE:
<223> OTHER INFORMATION: synthesized

<400> SEQUENCE: 72
cgtaaacacc ttccttattt tttt                                          24

<210> SEQ ID NO 73
<211> LENGTH: 24
<212> TYPE: DNA
<213> ORGANISM: Artificial Sequence
<220> FEATURE:
<223> OTHER INFORMATION: synthesized

<400> SEQUENCE: 73
cgtaaacacc ttccttattt tttt                                          24

<210> SEQ ID NO 74
<211> LENGTH: 24
<212> TYPE: DNA
<213> ORGANISM: Artificial Sequence
<220> FEATURE:
<223> OTHER INFORMATION: synthesized

<400> SEQUENCE: 74
cgtaaagcta tcccatattt tttt                                          24

<210> SEQ ID NO 75
<211> LENGTH: 24
<212> TYPE: DNA
<213> ORGANISM: Artificial Sequence
<220> FEATURE:
<223> OTHER INFORMATION: synthesized

<400> SEQUENCE: 75
cgtaaagcta tcccatattt tttt                                          24

<210> SEQ ID NO 76
<211> LENGTH: 24
<212> TYPE: DNA
<213> ORGANISM: Artificial Sequence
<220> FEATURE:
<223> OTHER INFORMATION: synthesized

<400> SEQUENCE: 76
cgtaaacgta ttccctattt tctt                                              24

<210> SEQ ID NO 77
<211> LENGTH: 24
<212> TYPE: DNA
<213> ORGANISM: Artificial Sequence
<220> FEATURE:
<223> OTHER INFORMATION: synthesized

<400> SEQUENCE: 77
cgtaaacgta ttccctattt tctt                                              24

<210> SEQ ID NO 78
<211> LENGTH: 20
<212> TYPE: DNA
<213> ORGANISM: Artificial Sequence
<220> FEATURE:
<223> OTHER INFORMATION: synthesized

<400> SEQUENCE: 78
accctaaata ccctatattg                                                   20

<210> SEQ ID NO 79
<211> LENGTH: 20
<212> TYPE: DNA
<213> ORGANISM: Artificial Sequence
<220> FEATURE:
<223> OTHER INFORMATION: synthesized

<400> SEQUENCE: 79
acgcgaaata ccctatattg                                                   20

<210> SEQ ID NO 80
<211> LENGTH: 20
<212> TYPE: DNA
<213> ORGANISM: Artificial Sequence
<220> FEATURE:
<223> OTHER INFORMATION: synthesized

<400> SEQUENCE: 80
acsckaaata ccctatattg                                                   20

<210> SEQ ID NO 81
<211> LENGTH: 20
<212> TYPE: DNA
<213> ORGANISM: Artificial Sequence
<220> FEATURE:
<223> OTHER INFORMATION: synthesized

<400> SEQUENCE: 81
atcttaaaaa ccctatattg                                                   20

<210> SEQ ID NO 82
<211> LENGTH: 20
<212> TYPE: DNA
<213> ORGANISM: Artificial Sequence
<220> FEATURE:

-continued

<223> OTHER INFORMATION: synthesized

<400> SEQUENCE: 82
accctaaata ccctatattg                    20

<210> SEQ ID NO 83
<211> LENGTH: 20
<212> TYPE: DNA
<213> ORGANISM: Artificial Sequence
<220> FEATURE:
<223> OTHER INFORMATION: synthesized

<400> SEQUENCE: 83
accctaaata ctctatattg                    20

<210> SEQ ID NO 84
<211> LENGTH: 20
<212> TYPE: DNA
<213> ORGANISM: Artificial Sequence
<220> FEATURE:
<223> OTHER INFORMATION: synthesized

<400> SEQUENCE: 84
accttaaaca ctctatattg                    20

<210> SEQ ID NO 85
<211> LENGTH: 20
<212> TYPE: DNA
<213> ORGANISM: Artificial Sequence
<220> FEATURE:
<223> OTHER INFORMATION: synthesized

<400> SEQUENCE: 85
accctaaaaa ccctatattg                    20

<210> SEQ ID NO 86
<211> LENGTH: 20
<212> TYPE: DNA
<213> ORGANISM: Artificial Sequence
<220> FEATURE:
<223> OTHER INFORMATION: synthesized

<400> SEQUENCE: 86
accctaaaha cyctatattg                    20

<210> SEQ ID NO 87
<211> LENGTH: 20
<212> TYPE: DNA
<213> ORGANISM: Artificial Sequence
<220> FEATURE:
<223> OTHER INFORMATION: synthesized

<400> SEQUENCE: 87
attctaaata ccctgtattg                    20

<210> SEQ ID NO 88
<211> LENGTH: 20
<212> TYPE: DNA
<213> ORGANISM: Artificial Sequence
<220> FEATURE:
<223> OTHER INFORMATION: synthesized

<400> SEQUENCE: 88
attctaaata ccctgtattg                    20

<210> SEQ ID NO 89
<211> LENGTH: 20
<212> TYPE: DNA
<213> ORGANISM: Artificial Sequence
<220> FEATURE:
<223> OTHER INFORMATION: synthesized

<400> SEQUENCE: 89
attctaaata ccctgtattg                                              20

<210> SEQ ID NO 90
<211> LENGTH: 20
<212> TYPE: DNA
<213> ORGANISM: Artificial Sequence
<220> FEATURE:
<223> OTHER INFORMATION: synthesized

<400> SEQUENCE: 90
accctaaata ccctgtattg                                              20

<210> SEQ ID NO 91
<211> LENGTH: 20
<212> TYPE: DNA
<213> ORGANISM: Artificial Sequence
<220> FEATURE:
<223> OTHER INFORMATION: synthesized

<400> SEQUENCE: 91
accttaaata ccctgtattg                                              20

<210> SEQ ID NO 92
<211> LENGTH: 20
<212> TYPE: DNA
<213> ORGANISM: Artificial Sequence
<220> FEATURE:
<223> OTHER INFORMATION: synthesized

<400> SEQUENCE: 92
accytaaata ccctgtattg                                              20

<210> SEQ ID NO 93
<211> LENGTH: 20
<212> TYPE: DNA
<213> ORGANISM: Artificial Sequence
<220> FEATURE:
<223> OTHER INFORMATION: synthesized

<400> SEQUENCE: 93
accctaaaca ctctgtattg                                              20

<210> SEQ ID NO 94
<211> LENGTH: 20
<212> TYPE: DNA
<213> ORGANISM: Artificial Sequence
<220> FEATURE:
<223> OTHER INFORMATION: synthesized

<400> SEQUENCE: 94
accctaaata ctctgtattg                                              20

<210> SEQ ID NO 95
<211> LENGTH: 20
<212> TYPE: DNA
<213> ORGANISM: Artificial Sequence
<220> FEATURE:
<223> OTHER INFORMATION: synthesized

```
<400> SEQUENCE: 95
actctaaata ctctgtattg                                              20

<210> SEQ ID NO 96
<211> LENGTH: 20
<212> TYPE: DNA
<213> ORGANISM: Artificial Sequence
<220> FEATURE:
<223> OTHER INFORMATION: synthesized

<400> SEQUENCE: 96
actctaaata ctctgtattg                                              20

<210> SEQ ID NO 97
<211> LENGTH: 20
<212> TYPE: DNA
<213> ORGANISM: Artificial Sequence
<220> FEATURE:
<223> OTHER INFORMATION: synthesized

<400> SEQUENCE: 97
acyctaaaya ctctgtattg                                              20

<210> SEQ ID NO 98
<211> LENGTH: 20
<212> TYPE: DNA
<213> ORGANISM: Artificial Sequence
<220> FEATURE:
<223> OTHER INFORMATION: synthesized

<400> SEQUENCE: 98
accctaaaca ctctatactg                                              20

<210> SEQ ID NO 99
<211> LENGTH: 20
<212> TYPE: DNA
<213> ORGANISM: Artificial Sequence
<220> FEATURE:
<223> OTHER INFORMATION: synthesized

<400> SEQUENCE: 99
actctaaaca ccctatactg                                              20

<210> SEQ ID NO 100
<211> LENGTH: 20
<212> TYPE: DNA
<213> ORGANISM: Artificial Sequence
<220> FEATURE:
<223> OTHER INFORMATION: synthesized

<400> SEQUENCE: 100
actctaaaca ccctatactg                                              20

<210> SEQ ID NO 101
<211> LENGTH: 20
<212> TYPE: DNA
<213> ORGANISM: Artificial Sequence
<220> FEATURE:
<223> OTHER INFORMATION: synthesized

<400> SEQUENCE: 101
actctaaaca cyctatactg                                              20

<210> SEQ ID NO 102
<211> LENGTH: 20
```

```
<212> TYPE: DNA
<213> ORGANISM: Artificial Sequence
<220> FEATURE:
<223> OTHER INFORMATION: synthesized

<400> SEQUENCE: 102
accctaaaga ccctatactg                                                   20

<210> SEQ ID NO 103
<211> LENGTH: 20
<212> TYPE: DNA
<213> ORGANISM: Artificial Sequence
<220> FEATURE:
<223> OTHER INFORMATION: synthesized

<400> SEQUENCE: 103
accctaaaga ccctatactg                                                   20

<210> SEQ ID NO 104
<211> LENGTH: 20
<212> TYPE: DNA
<213> ORGANISM: Artificial Sequence
<220> FEATURE:
<223> OTHER INFORMATION: synthesized

<400> SEQUENCE: 104
actctaaata ctctgtactg                                                   20

<210> SEQ ID NO 105
<211> LENGTH: 20
<212> TYPE: DNA
<213> ORGANISM: Artificial Sequence
<220> FEATURE:
<223> OTHER INFORMATION: synthesized

<400> SEQUENCE: 105
actctaaata ctctgtactg                                                   20

<210> SEQ ID NO 106
<211> LENGTH: 1722
<212> TYPE: DNA
<213> ORGANISM: Human papillomavirus type 16

<400> SEQUENCE: 106
agtatcaggt cctgatatac ccattaatat aactgaccaa gctccttcat taattcctat        60
agttccaggg tctccacaat atacaattat tgctgatgca ggtgactttt atttacatcc       120
tagttattac atgttacgaa aacgacgtaa acgttaccta tatttttttt cagatgtctc       180
tttggctgcc tagtgaggcc actgtctact tgcctcctgt cccagtatct aaggttgtaa       240
gcacggatga atatgttgca cgcacaaaca tatattatca tgcaggaaca tccagactac       300
ttgcagttgg acatccctat tttcctatta aaaaacctaa caataacaaa atattagttc       360
ctaaagtatc aggattacaa tacagggtat ttagaataca tttacctgac cccaataagt       420 ttggtttttcc tgacacctca tttataatc cagatacaca gcggctggtt tgggcctgtg       480
taggtgttga ggtaggtcgt ggtcagccat taggtgtggg cattagtggc catcctttat       540
taaataaatt ggatgacaca gaaaatgcta gtgcttatgc agcaaatgca ggtgtggata       600
atagagaatg tatctctatg gattacaaac aaacacaatt gtgtttaatt ggttgcaaac       660
cacctatagg ggaacactgg ggcaaaggat cccatgtac caatgttgca gtaaatccag       720
gtgattgtcc accattagag ttaataaaca cagttattca ggatggtgat atggttcata       780
```

```
ctggctttgg tgctatggac tttactacat tacaggctaa caaaagtgaa gttccactgg      840
atatttgtac atctatttgc aaatatccag attatattaa aatggtgtca gaaccatatg      900
gcgacagctt attttttttat ttacgaaggg aacaaatgtt tgttagacat ttatttaata      960
gggctggtac tgttggtgaa aatgtaccag acgatttata cattaaaggc tctgggtcta     1020
ctgcaaattt agccagttca aattattttc ctacacctag tggttctatg gttacctctg     1080
atgcccaaat attcaataaa ccttattggt tacaacgagc acagggccac aataatggca     1140
tttgttgggg taaccaacta tttgttactg ttgttgatac tacacgcagt acaaatatgt     1200
cattatgtgc tgccatatct acttcagaaa ctacatataa aaatactaac tttaaggagt     1260
acctacgaca tgggggaggaa tatgatttac agtttatttt tcaactgtgc aaaataaccct     1320 taactgcaga cgttatgaca tacatacatt ctatgaattc cactattttg gaggactgga     1380
attttggtct acaacctccc ccaggaggca cactagaaga tacttatagg tttgtaaccc     1440
aggcaattgc ttgtcaaaaa catacacctc cagcacctaa agaagatgat ccccttaaaa     1500
aatacacttt tgggaagta aatttaaagg aaaagttttc tgcagaccta gatcagtttc     1560
ctttaggacg caaattttta ctacaagcag gattgaaggc caaaccaaaa tttacattag     1620
gaaaacgaaa agctacaccc accacctcat ctacctctac aactgctaaa cgcaaaaaac     1680
gtaagctgta agtattgtat gtatgttgaa ttagtgttgt tt                         1722
```

<210> SEQ ID NO 107
<211> LENGTH: 24
<212> TYPE: DNA
<213> ORGANISM: Human papillomavirus type 16

<400> SEQUENCE: 107
cgtaaacgtt taccatattt tttt                                             24

<210> SEQ ID NO 108
<211> LENGTH: 21
<212> TYPE: DNA
<213> ORGANISM: Human papillomavirus type 16

<400> SEQUENCE: 108
caatacaggg tatttagaat a                                                21

<210> SEQ ID NO 109
<211> LENGTH: 20
<212> TYPE: DNA
<213> ORGANISM: Human papillomavirus type 16

<400> SEQUENCE: 109
gcacagggcc acaataatgg                                                  20

<210> SEQ ID NO 110
<211> LENGTH: 23
<212> TYPE: DNA
<213> ORGANISM: Human papillomavirus type 16

<400> SEQUENCE: 110
tttgttactg ttgttgatac tac                                              23

<210> SEQ ID NO 111
<211> LENGTH: 25
<212> TYPE: DNA
<213> ORGANISM: Human papillomavirus type 16

<400> SEQUENCE: 111

```
gaatatgatt tacagtttat ttttc                                              25

<210> SEQ ID NO 112
<211> LENGTH: 20
<212> TYPE: DNA
<213> ORGANISM: Human papillomavirus type 16

<400> SEQUENCE: 112
gatcagtttc ctttaggacg                                                    20

<210> SEQ ID NO 113
<211> LENGTH: 15
<212> TYPE: DNA
<213> ORGANISM: Artificial Sequence
<220> FEATURE:
<223> OTHER INFORMATION: synthesized

<400> SEQUENCE: 113
tgaggaccgt gttca                                                         15

<210> SEQ ID NO 114
<211> LENGTH: 15
<212> TYPE: DNA
<213> ORGANISM: Artificial Sequence
<220> FEATURE:
<223> OTHER INFORMATION: synthesized

<400> SEQUENCE: 114
tgaggactgt gttca                                                         15

<210> SEQ ID NO 115
<211> LENGTH: 17
<212> TYPE: DNA
<213> ORGANISM: Artificial Sequence
<220> FEATURE:
<223> OTHER INFORMATION: synthesized

<400> SEQUENCE: 115
aaggtcaatg tatctct                                                       17

<210> SEQ ID NO 116
<211> LENGTH: 15
<212> TYPE: DNA
<213> ORGANISM: Artificial Sequence
<220> FEATURE:
<223> OTHER INFORMATION: synthesized

<400> SEQUENCE: 116
aggtcaaggt atctc                                                         15

<210> SEQ ID NO 117
<211> LENGTH: 15
<212> TYPE: DNA
<213> ORGANISM: Artificial Sequence
<220> FEATURE:
<223> OTHER INFORMATION: synthesized

<400> SEQUENCE: 117
catcgaccct tggac                                                         15

<210> SEQ ID NO 118
<211> LENGTH: 16
<212> TYPE: DNA
<213> ORGANISM: Artificial Sequence
<220> FEATURE:
```

-continued

<223> OTHER INFORMATION: synthesized

<400> SEQUENCE: 118
gtccaagagt cgatga                                                        16